United States Patent [19]
Wexler

[11] Patent Number: 4,846,878
[45] Date of Patent: Jul. 11, 1989

[54] HERBICIDAL PYRAZOLE SULFONAMIDES

[75] Inventor: Barry A. Wexler, Wilmington, Del.

[73] Assignee: E. I. Du Pont de Nemours and Company, Wilmington, Del.

[21] Appl. No.: 159,288

[22] Filed: Feb. 23, 1988

Related U.S. Application Data

[60] Division of Ser. No. 22,365, Mar. 13, 1987, Pat. No. 4,747,870, which is a continuation-in-part of Ser. No. 859,275, May 2, 1986, abandoned.

[51] Int. Cl.$^4$ .................. C07D 403/12; C07D 403/14; A01N 43/66; A01N 43/70
[52] U.S. Cl. ........................................ 71/93; 544/212; 544/219; 544/207; 544/209; 544/198; 544/113; 71/90

[58] Field of Search ...................... 71/93, 90; 544/212, 544/219, 207, 209, 198, 113

[56] References Cited

U.S. PATENT DOCUMENTS 4,370,480  1/1983  Levitt et al. ...................... 544/320

FOREIGN PATENT DOCUMENTS 87780    9/1983   European Pat. Off. .
95925   12/1983   European Pat. Off. .
5870407 12/1984   Japan .
833850  12/1983   South Africa .

*Primary Examiner*—John M. Ford

[57] ABSTRACT

This invention relates to certain pyrazole sulfonylurea herbicidal compounds, agriculturally suitable compositions thereof and a method of their use.

33 Claims, No Drawings

HERBICIDAL PYRAZOLE SULFONAMIDES

RELATED APPLICATIONS

This is a division of application Ser. No. 022,365, filed Mar. 13, 1987 now U.S. Pat. No. 4,747,870, which is a continuation-in-part of U.S. Ser. No. 859,275 filed May 2, 1986, now abandoned.

BACKGROUND OF THE INVENTION

This invention relates to novel pyrazole sulfonylurea herbicidal compounds, agriculturally suitable compositions thereof and a method of using them to control the growth of undesired vegetation.

New compounds effective for controlling the growth of undesired vegetation are in constant demand. In the most common situation, such compounds are sought to selectively control the growth of weeds in useful crops such as cotton, rice, corn, wheat and soybeans, to name a few. Unchecked weed growth in such crops can cause significant losses, reducing profit to the farmer and increasing costs to the consumer. In other situations, herbicides are desired which will control all plant growth. Examples of areas in which complete control of all vegetation is desired are areas around fuel shortage tanks, ammunition depots and industrial storage areas. There are many products commercially available for these purposes, but the search continues for products which are more effective, less costly and environmentally safe.

The "sulfonylurea" herbicides are an extremely potent class of herbicides discovered within the last few years. A multitude of structural variations exist within the class of herbicides, but they generally consist of a sulfonylurea bridge, —$SO_2NHCONH$—, linking two aromatic or heteroaromatic rings.

EP-A No. 95,925 which was published 12/7/83 discloses herbicidal sulfonylureas of formula $$Q-SO_2NHCN-A$$
$$\underset{R}{|}$$

I wherein
Q is, in part,

Q-4, Q-5, Q-6

$R_{10}$ is H, $C_1$–$C_4$ alkyl, $C_3$–$C_4$ alkenyl, $C_3$–$C_4$ alkynyl, $CO_2R_{24}$, $SO_2NR_{20}R_{21}$ or $SO_2R_{22}$;
$R_{11}$ is H, $C_1$–$C_3$ alkyl, F, Cl, Br, $NO_2$, $OR_{16}$, $CO_2R_{24}$, $S(O)_mR_{25}$ or $SO_2NR_{20}R_{21}$;
provided that when $R_{10}$ is other than $C_1$–$C_3$ alkyl, then $R_{11}$ is H, Cl, $OCH_3$, $NO_2$, or $CH_3$;
$R_{12}$ is H or $CH_3$;
$R_{13}$ and $R_{14}$ are independently H, $C_1$–$C_3$ alkyl, $OR_{16}$, F, Cl, Br, $NO_2$, $CO_2R_{24}$, $S(O)_mR_{25}$ or $SO_2NR_{20}R_{21}$;
provided that, when either of $R_{13}$ or $R_{14}$ is $CO_2R_{24}$, $S(O)_mR_{25}$ or $SO_2NR_{20}R_{21}$, then the other is H, Cl, $CH_3$, $OCH_3$ or $NO_2$; and
$R_{15}$ is H or $CH_3$.

EP-A-No. 87,780 which was published 9/7/83 discloses herbicidal sulfonylureas of formula wherein
A is H, $C_1$–$C_8$ alkyl or optionally substituted phenyl;
B and C are independently H, halogen, $NO_2$, $C_1$–$C_8$ alkyl, arylalkyl, $C_1$–$C_8$ alkoxy, haloalkyl, $CO_2R$, $CONR_1R_2$, $S(O)_nR_3$, $SO_2NR_4R_5$, or optionally substituted phenyl.

ZA 83/3850 which was published 11/28/83 discloses compounds of formula wherein
Q is a five-membered, heterocyclic radical which is bound by way of a carbon atom and contains 2 or 3 heteroatoms and which may be optionally substituted by halogen, pseudohalogen, nitro, alkyl, hydroxyl, haloalkyl, alkoxy, alkylthio, haloalkoxy, haloalkylthio, amino, alkylamino, dialkylamino, alkylcarbonylamino, alkylcarbonyl, alkoxycarbonyl, alkoxyalkyl, alkylthiocarbonyl, carbamoyl, alkylaminocarbonyl, dialkylaminocarbonyl, alkylsulfinyl, alkylsulfonyl, alkenyloxy or alkynyloxy; and groups such as phenyl, phenoxy or phenylthio, which are unsubstituted or substituted by halogen, nitro, cyano, alkyl, alkoxy, haloalkyl, alkylcarbonyl, alkoxycarbonyl or haloalkoxy; and also benzyl unsubstituted or substituted by halogen and/or alkyl.

Japanese Patent Application Number 58-70407 (SHO No. 59-219,218, laid open 12/10/84) discloses pyrazole-5-sulfonylureas of formula wherein
A is H, lower alkyl or phenyl;
B is H or lower alkyl;
D is H, $CO_2R$ or $COAr$, halogen, $NO_2$ or $SO_2NR^1R^2$; and
Ar is phenyl optionally substituted with halogen.

U.S. Pat. No. 4,370,480 discloses herbicidal sulfonylureas of formula

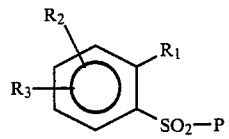

wherein
$R_1$ is

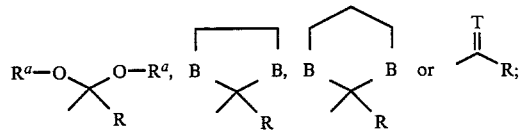

R is H; $C_1$-$C_2$ alkyl; $C_2$-$C_6$ alkenyl; $C_2$-$C_6$ alkynyl; $C_1$-$C_4$ alkyl substituted with one to four substituents selected from 0-3 F, 0-3 Cl, 0-3 Br, 0-2 $OCH_3$, 0-1 cyano, 0-1 $CO_2R_1$ where $R_1$ is $C_1$-$C_3$ alkyl; $CO_2R_1$, $C_2$-$C_4$ alkenyl substituted with 1-3 Cl; $C_3$-$C_6$ cycloalkyl; $C_5$-$C_6$ cycloalkenyl; $C_5$-$C_6$ cycloalkyl substituted with substituents selected from 1-3 $CH_3$ or one of $CH_3CH_2$, Cl, $OCH_3$; $C_4$-$C_7$ cycloalkylalkyl;

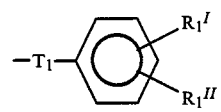

where $T_1$ is

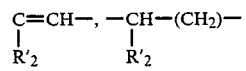

or a single bond; and
T is O or $NOR_1^{III}$

SUMMARY

The compounds of this invention are compounds of Formula I.

wherein
J is

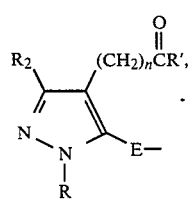

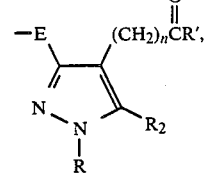

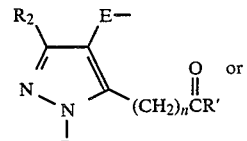

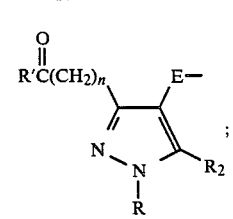

R is H, $C_1$-$C_3$ alkyl, phenyl, $SO_2NR_aR_b$, $C_1$-$C_2$ haloalkyl, $C_2$-$C_4$ alkoxyalkyl, $C_2$-$C_3$ cyanoalkyl, $C_2$-$C_4$ alkylthioalkyl, $C_2$-$C_4$ alkylsulfinylalkyl, $C_2$-$C_4$ alkylsulfonylalkyl, $CO_2C_1$-$C_2$ alkyl, $C_1$-$C_4$ alkylcarbonyl, $C_1$-$C_2$ alkylsulfonyl, $C_3$-$C_4$ alkenyl, $C_3$-$C_4$ alkynyl or $C_1$-$C_2$ alkyl substituted with $CO_2C_1$-$C_2$ alkyl;

$R_1$ is H or $CH_3$;

$R_2$ is H, $C_1$-$C_3$ alkyl, $C_1$-$C_3$ haloalkyl, halogen, nitro, $C_1$-$C_3$ alkoxy, $SO_2NR_cR_d$, $C_1$-$C_3$ alkylthio, $C_1$-$C_3$ alkylsulfinyl, $C_1$-$C_3$ alkylsulfonyl, CN, $CO_2R_e$, $C_1$-$C_3$ haloalkoxy, $C_1$-$C_3$ haloalkylthio, amino, $C_1$-$C_2$ alkylamino, di($C_1$-$C_3$ alkyl)amino or $C_1$-$C_2$ alkyl substituted with $C_1$-$C_2$ alkoxy, $C_1$-$C_2$ haloalkoxy, $C_1$-$C_2$ alkylthio, $C_1$-$C_2$ haloalkylthio, CN, OH or SH;

$R_a$ and $R_b$ are independently $C_1$-$C_2$ alkyl;

$R_c$ is H, $C_1$-$C_4$ alkyl, $C_2$-$C_3$ cyanoalkyl, methoxy or ethoxy;

$R_d$ is H, $C_1$-$C_4$ alkyl or $C_3$-$C_4$ alkenyl; or $R_c$ and $R_d$ may be taken together as —$(CH_2)_3$—, —$(CH_2)_4$—, —$(CH_2)_5$— or —$CH_2CH_2OCH_2CH_2$—;

$R_e$ is $C_1$-$C_4$ alkyl, $C_3$-$C_4$ alkenyl, $C_3$-$C_4$ alkynyl, $C_2$-$C_4$ haloalkyl, $C_2$-$C_3$ cyanoalkyl, $C_5$-$C_6$ cycloalkyl, $C_4$-$C_7$ cycloalkylalkyl or $C_2$-$C_4$ alkoxyalkyl;

R' is $C_3$-$C_5$ cycloalkyl;

E is a single bond or $CH_2$;

W is O or S;

n is 0 or 1;

A is

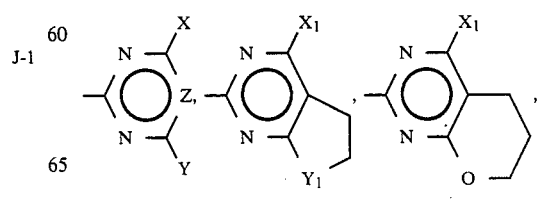

-continued

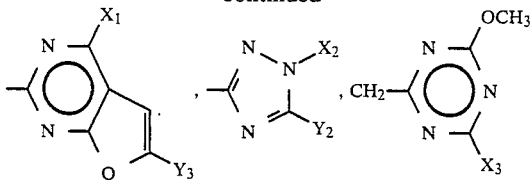

A-4    A-5    A-6

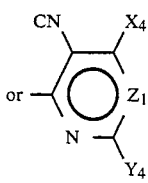

A-7

X is H, $C_1$-$C_4$ alkyl, $C_1$-$C_4$ alkoxy, $C_1$-$C_4$ haloalkoxy, $C_1$-$C_4$ haloalkyl, $C_1$-$C_4$ haloalkylthio, $C_1$-$C_4$ alkylthio, halogen, $C_2$-$C_5$ alkoxyalkyl, $C_2$-$C_5$ alkoxyalkoxy, amino, $C_1$-$C_3$ alkylamino, di($C_1$-$C_3$ alkyl)amino or $C_3$-$C_5$ cycloalkyl;

Y is H, $C_1$-$C_4$ alkyl, $C_1$-$C_4$ alkoxy, $C_1$-$C_4$ haloalkoxy, $C_1$-$C_4$ haloalkylthio, $C_1$-$C_4$ alkylthio, $C_2$-$C_5$ alkoxyalkyl, $C_2$-$C_5$ alkoxyalkoxy, amino, $C_1$-$C_3$ alkylamino, di($C_1$-$C_3$ alkyl)amino, $C_3$-$C_4$ alkenyloxy, $C_3$-$C_4$ alkynyloxy, $C_2$-$C_5$ alkylthioalkyl, $C_1$-$C_4$ haloalkyl, $C_2$-$C_4$ alkynyl, azido, cyano, $C_2$-$C_5$ alkylsulfinylalkyl, $C_2$-$C_5$ alkylsulfonylalkyl,

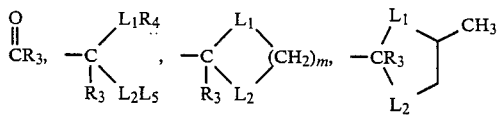

or $N(OCH_3)CH_3$;

m is 2 or 3;
$L_1$ and $L_2$ are independently O or S;
$R_3$ is H or $C_1$-$C_3$ alkyl;
$R_4$ and $R_5$ are independently $C_1$-$C_3$ alkyl;
Z is CH or N;
$Z_1$ is CH or N;
$Y_1$ is O or $CH_2$;
$X_1$ is $CH_3$, $OCH_3$, $OC_2H_5$ or $OCF_2H$;
$X_2$ is $CH_3$, $C_2H_5$ or $CH_2CF_3$;
$Y_2$ is $OCH_3$, $OC_2H_5$, $SCH_3$, $SC_2H_5$, $CH_3$ or $CH_2CH_3$;
$X_3$ is $CH_3$ or $OCH_3$;
$Y_3$ is H or $CH_3$;
$X_4$ is $CH_3$, $OCH_3$, $OC_2H_5$, $CH_2OCH_3$ or Cl; and
$Y_4$ is $CH_3$, $OCH_3$, $OC_2H_5$ or Cl;
and their agriculturally suitable salts; provided that
(a) when X is Cl, F, Br or I, then Z is CH and Y is $OCH_3$, $OC_2H_5$, $N(OCH_3)CH_3$, $NHCH_3$, $N(CH_3)_2$ or $OCF_2H$;
(b) when X or Y is $C_1$ haloalkoxy, then Z is CH;
(c) $X_4$ and $Y_4$ are not simultaneously Cl;
(d) when W is S, then $R_1$ is H, A is A-1 and Y is $CH_3$, $OCH_3$, $OC_2H_5$, $CH_2OCH_3$, $C_2H_5$, $CF_3$, $SCH_3$, $OCH_2CH=CH_2$, $OCH_2C\equiv CH$, $OCH_2CH_2OCH_3$, $CH(OCH_3)_2$ or 1,3-dioxolan-2-yl;
(e) when the total number of carbons of X and Y is greater than four, then the number of carbons of R must be less than or equal to two.

In the above definitions, the term "alkyl", used either alone or in compound words such as "alkylthio" or "haloalkyl", denotes straight chain or branched alkyl, e.g. methyl, ethyl, n-propyl, isopropyl or the different butyl isomers.

Alkoxy denotes methoxy, ethoxy, n-propyloxy, isopropyloxy and the different butyl isomers.

Alkenyl denotes straight chain or branched alkenes, e.g. 1-propenyl, 2-propenyl, 3-propenyl and the different butenyl isomers.

Alkynyl denotes straight chain or branched alkynes, e.g. ethynyl, 1-propynyl, 2-propynyl and the different butynyl isomers.

Alkylsulfonyl denotes methylsulfonyl, ethylsulfonyl and the different propylsulfonyl isomers.

Alkylthio, alkylsulfinyl, alkylamino, etc. are defined analogously to the above examples.

Cycloalkyl denotes cyclopropyl, cyclobutyl, and cyclopentyl.

The term "halogen", either alone or in compound words such as "haloalkyl", denotes fluorine, chlorine, bromine or iodine. Further, when used in compound words such as "haloalkyl" said alkyl may be partially halogenated or fully substituted with halogen atoms and said halogen atoms may be the same or different. Examples of haloalkyl include $CH_2CH_2F$, $CF_2CF_3$ and $CH_2CHFCl$.

The total number of carbon atoms in a substituent group is indicated by the $C_i$-$C_j$ prefix where i and j are numbers from 1 to 7. For example, $C_1$-$C_3$ alkylsulfonyl would designate methylsulfonyl through propylsulfonyl. $C_2$ alkoxyalkoxy would designate $OCH_2OCH_3$, $C_2$ cyanoalkyl would designate $CH_2CN$ and $C_3$ cyanoalkyl would designate $CH_2CH_2CN$ and $CH(CN)CH_3$.

Compounds of the Invention preferred for reasons of increased ease of synthesis and/or greater herbicidal efficacy are:

1. Compounds of Formula I where
   E is a single bond; and
   W is O.
2. Compounds of Formula I where
   E is $CH_2$; and
   W is O.
3. Compounds of Preferred 1 where
   $R_2$ is H, $C_1$-$C_3$ alkyl, halogen, $C_1$-$C_3$ alkyl substituted with 1 to 3 halogen atoms selected from 1 to 3 Cl, 1 to 3 F or 1 Br, $OCH_3$, $SO_2NHCH_3$, $SO_2N(CH_3)_2$, $S(O)_nCH_3$, $CO_2CH_3$, $CO_2CH_2CH_3$, $OCF_2H$, $CH_2OCH_3$ or $CH_2CN$;
   X is $C_1$-$C_2$ alkyl, $C_1$-$C_2$ alkoxy, Cl, F, Br, I, $OCF_2H$, $CH_2F$, $CF_3$, $OCH_2CH_2F$, $OCH_2CHF_2$, $OCH_2CF_3$, $CH_2Cl$ or $CH_2Br$; and
   Y is H, $C_1$-$C_2$ alkyl, $C_1$-$C_2$ alkoxy, $CH_2OCH_3$, $CH_2OCH_2CH_3$, $NHCH_3$, $N(OCH_3)CH_3$, $N(CH_3)_2$, $CF_3$, $SCH_3$, $OCH_2CH=CH_2$, $OCH_2C\equiv CH$, $OCH_2CH_2OCH_3$,

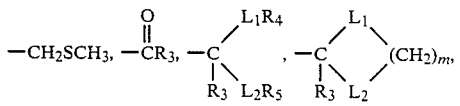

$OCF_2H$, $OCF_2Br$, $SCF_2H$, $C\equiv CH$ or $C\equiv CCH_3$;

4. Compounds of Preferred 3 where
   R is H, $C_1$-$C_3$ alkyl, phenyl, $CH_2CF_3$ or $CH_2CH=CH_2$;
   X is $CH_3$, $OCH_3$, $OCH_2CH_3$, Cl or $OCF_2H$; and
   Y is $CH_3$, $OCH_3$, $C_2H_5$, $CH_2OCH_3$, $NHCH_3$, or $CH(OCH_3)_2$
5. Compounds of Preferred 4 where
   A is A-1;
   $R_2$ is H, Cl, Br, $OCH_3$ or $CH_3$; and
   n is 0.
6. Compounds of Preferred 5 where J is J-1.
7. Compounds of Preferred 5 where J is J-2.
8. Compounds of Preferred 5 where J is J-3.
9. Compounds of Preferred 5 where J is J-4.
10. Compounds of Preferred 2 where
    R is H, $C_1$-$C_3$ alkyl, phenyl, $CH_2CF_3$ or $CH_2CH=CH_2$;
    $R_2$ is H, Cl, Br, $OCH_3$ or $CH_3$;
    n is 0;
    A is A-1;
    X is $CH_3$, $OCH_3$, $OCH_2CH_3$, Cl or $OCF_2H$; and
    Y is $CH_3$, $OCH_3$, $C_2H_5$, $CH_2OCH_3$, $NHCH_3$, or $CH(OCH_3)_2$.

A compound of the invention especially preferred for reasons of greatest ease of synthesis and/or greatest herbicidal efficacy is:
4-(Cyclopropylcarbonyl)-N-[(4,6-dimethoxypyrimidin-2-yl)aminocarbonyl]-1-methyl-1H-pyrazole-5-sulfonamide, m.p. 189°–192° C.(d).

The compounds of this invention are highly active as preemergent and/or postemergent herbicides or plant growth regulants with selectivity on rice, corn, wheat, soybeans and barley.

DETAILED DESCRIPTION OF THE INVENTION

Synthesis

Compounds of Formula I can be prepared by one or more of the procedures shown in Equations 1, 4, and 5. J, R, and A are as previously defined.

$$JSO_2N=C=W + \underset{\underset{R}{|}}{HNA} \longrightarrow I \qquad \text{Equation 1}$$

$$\text{II} \qquad \text{III}$$

The reaction of Equation 1 is best carried out in an inert aprotic organic solvent such as dichloromethane, 1,2-dichloroethane, tetrahydrofuran, or acetonitrile, at a temperature between 20° and 85° C. The order of addition is not critical; however, it is often convenient to add the sulfonyl isocyanate or a solution of it in the reaction solvent, to a stirred suspension of the amine.

In some cases, the desired product is insoluble in the reaction solvent at ambient temperature and crystallizes from it in pure form. Products soluble in the reaction solvent are isolated by evaporation of the solvent. Compounds of Formula I then may be purified by trituration of the evaporation residue with solvents such as 1-chlorobutane or ethyl ether and filtration, by recrystallization from mixtures of solvents such as 1,2-dichloroethane, 1-chlorobutane and heptane or by chromatography on silica gel.

Sulfonyl isocyanates (II, W is O) are known in the art and are prepared from the corresponding sulfonamides (IV) by one of the following two general methods.

$$JSO_2NH_2 \xrightarrow[COCl_2, cat.]{CH_3(CH_2)_3NCO} II, W \text{ is } O \qquad \text{Equation 2}$$

$$\text{IV}$$

The sulfonamide IV is reacted with an alkyl isocyanate (e.g., n-butyl isocyanate) in a solvent whose boiling point is above 135° C., such as xylene. The reaction can optionally be carried out in the presence of a catalytic amount of 1,4-diaza[2.2.2]bicyclooctane (DABCO). The reaction mixture is heated to 135°–140° C. and held at that temperature for 5–60 minutes, after which phosgene is slowly added at such a rate that the temperature remains between 133° and 135° C. When the consumption of phosgene has ceased, the mixture is cooled and filtered to remove insoluble material. Finally, the solvent, alkyl isocyanate, and excess phosgene are evaporated, leaving the sulfonyl isocyanate (II).

If desired, the alkyl isocyanate-sulfonamide adduct can be made and isolated before reaction with the phosgene. In this case the sulfonamide (IV), alkyl isocyanate, and anhydrous base (e.g, $K_2CO_3$) in a polar, aprotic solvent (e.g. acetone, butanone, or acetonitrile) are mixed and heated under reflux for 1 to 6 hours. The reaction mixture is then diluted with water, and the pH is adjusted to about 3 with acid (e.g. HCl, $H_2SO_4$). The adduct is filtered out and dried, and then reacted with phosgene as described above. This procedure modification is especially useful when sulfonamide (IV) is high melting and has low solubility in the phosgenation solvent.

Sulfonyl isocyanates (II, W is O) can also be prepared by the following method.

$$\text{(a) IV} \xrightarrow{SOCl_2} JSO_2NSO$$

$$\text{V}$$

$$\text{(b) V} \xrightarrow[\text{pyridine cat.}]{COCl_2,} II, W \text{ is } O \qquad \text{Equation 3}$$

The sulfonamide (IV) is heated at reflux in an excess of thionyl chloride. The reaction is continued until the sulfonamide protons are no longer detectable in the proton magnetic resonance spectrum. From 16 hours to 5 days is typically sufficient for complete conversion to the thionylamide (V) (Equation 3a).

The thionyl chloride is evaporated and the residue is treated with an inert solvent (e.g. toluene) containing at least one equivalent (typically 2-3 equivalents) of phosgene. A catalytic amount of pyridine (typically 0.1 equivalent) is added, and the mixture is heated to about 60°–140° C., with 80°–100° C. preferred. Conversion to the isocyanate (II, W is O) is usually substantially complete within 15 minutes to 3 hours (Equation 3b). The mixture is then cooled and filtered, and the solvent is evaporated, leaving the sulfonyl isocyanate (II, W is O).

Sulfonyl isothiocyanates (II, W is S) are known in the art and are prepared from the corresponding sulfonamides (IV) by reaction with carbon disulfide and potassium hydroxide followed by treatment of the resulting dipotassium salt VI with phosgene. Such a procedure is described in *Arch. Pharm.* 299, 174 (1966).

Many of the compounds of Formula I can be prepared by the procedure shown in Equation 4.

Equation 4

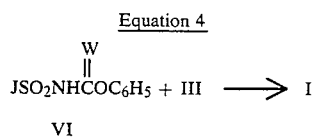

The reaction of Equation 4 is carried out by contacting phenylcarbamates or phenylthiocarbamates of Formula VI with aminoheterocycles of Formula III in an inert organic solvent such as dioxane or tetrahydrofuran at temperatures of about 20°–100° C. for a period of about one-half to twenty-four hours. The product can be isolated by evaporation of the reaction solvent and purified by methods previously described.

Phenylcarbamates and phenylthiocarbamates of Formula VI can be prepared by the methods described, or modifications thereof known to those skilled in the art, in U.S. Pat. No. 4,443,243.

Alternatively, many of the compounds of Formula I can be prepared by the method described in Equation 5.

Equation 5

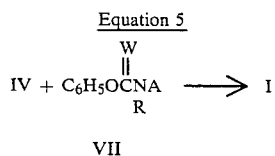

The reaction of Equation 5 can be carried out by contacting equimolar amounts of a sulfonamide of Formula IV with a heterocyclic phenylcarbamate or phenylthiocarbamate of Formula VII in the presence of a base such as 1,8-diazabicyclo[5.4.0]undec-7-ene (DBU), by methods analogous to those described in South African Patent Application No. 83/0441. The phenylcarbamates and phenylthiocarbamates of Formula VII can be prepared by methods, or modifications thereof known to those skilled in the art, described in South African Patent Application No. 82/5671 and South African Patent Application No. 82/5045.

The sulfonamides IV of this invention may be prepared in a variety of ways some of which are described in Equations 6 through 15.

For example, the 4-keto-5-sulfonamide isomer 1 may be prepared as outlined in Equation 6.

Equation 6

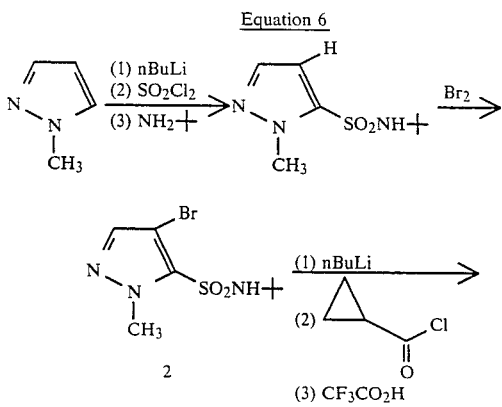

-continued
Equation 6

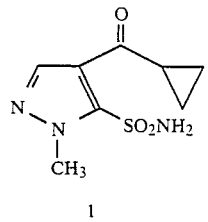

Preparation of the intermediates such as bromide 2 may be found in EPA-No. 95,925. Exposure of bromide 2 to nBuLi followed by addition of the resulting anion to cyclopropyl acid chloride affords the protected sulfonamide. Deprotection of the sulfonamide affords the desired sulfonamide 1.

Introduction of various R and $R_2$ groups to sulfonamides such as 1 may be accomplished in several ways. For example, the sequence in Equation 6 could also be performed on 3-chloro-1-methylpyrazole or 1,3-dimethylpyrazole affording 3 and 4 respectively. Chloride 3 may then be used to further elaborate

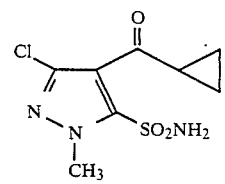

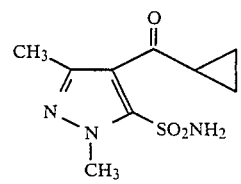

$R_2$ as outlined in Equation 7.

Equation 7

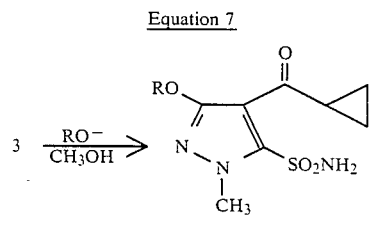

The N-substituent of compounds such as 1, 3, 4 and 5 may also be varied by applying the same sequence of reactions as outlined in Equation 6 to various N-substituted pyrazoles. For example, pyrazole may be alkylated with dimethylsulfamoylchloride to afford pyrazole 6. Pyrazole 6 is then converted to sulfonamide 7 as outlined in Equation 8.

Equation 8

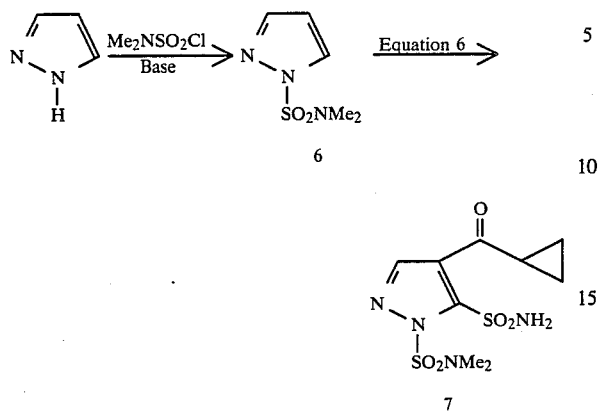

In the case where either R or $R_2$ are sensitive to nBuLi (i.e. $R_2$ is $CO_2CH_3$ or Br) then the lithiating reagent of choice is lithium diisopropylamide (LDA). Utilizing the same sequence as outlined in Equation 6 but substituting LDA for nBuLi affords sulfonamides such as 8. This is outlined in Equation 9.

Equation 9

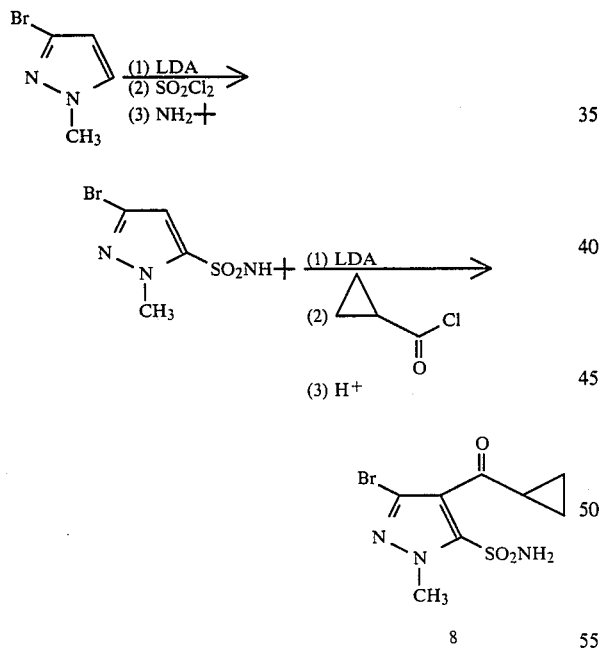

The isomeric 5-keto-4-sulfonamide pyrazoles may be prepared as outlined in Equations 10 and 11.

Equation 10

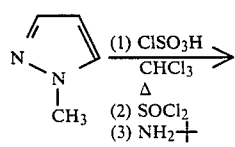

Equation 10 -continued

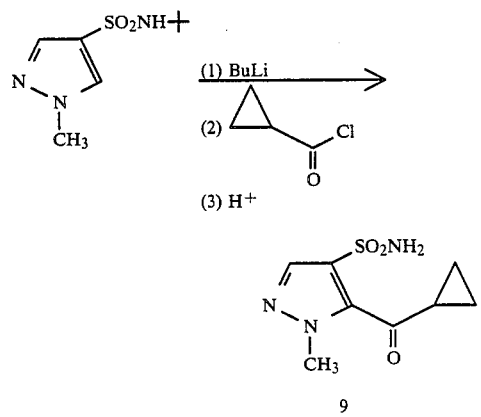

In Equation 10 the sequential order of group introduction is reversed to that of Equation 6. The introduction of various R and $R_2$ groups may be accomplished in the same manor as previously described for the 4-ketoisomer in Equations 7, 8 and 9.

An alternate synthesis of sulfonamides such as 9 is outlined in Equation 11.

Equation 11

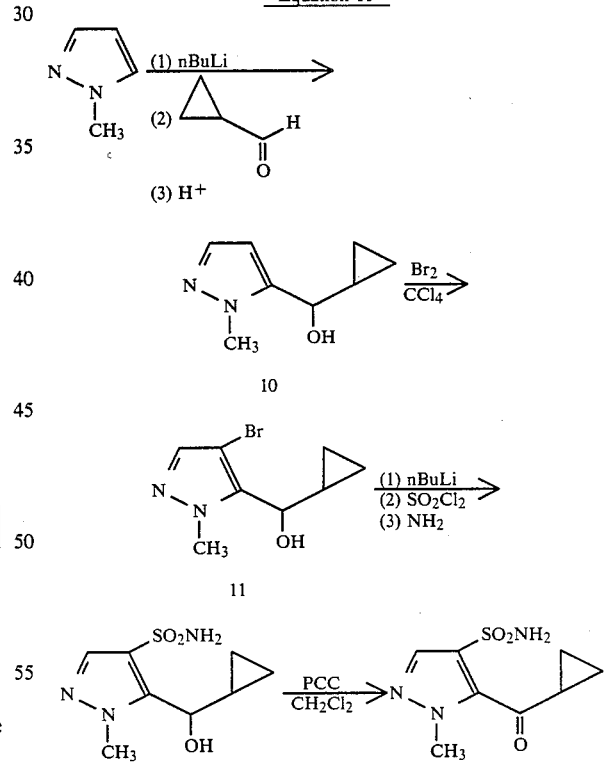

Oxidations of alcohols to ketones such as 12 to 9 are well known in the art. For further discussion pertaining to the oxidation of alcohols to ketones, see R. H. Cornforth, J. W. Cornforth and G. Popjak, *Tetrahedron*, 18, 1351 (1962).

The isomeric 3-keto-4-sulfonamide such as 13 may be prepared as outlined in Equation 12.

Equation 12

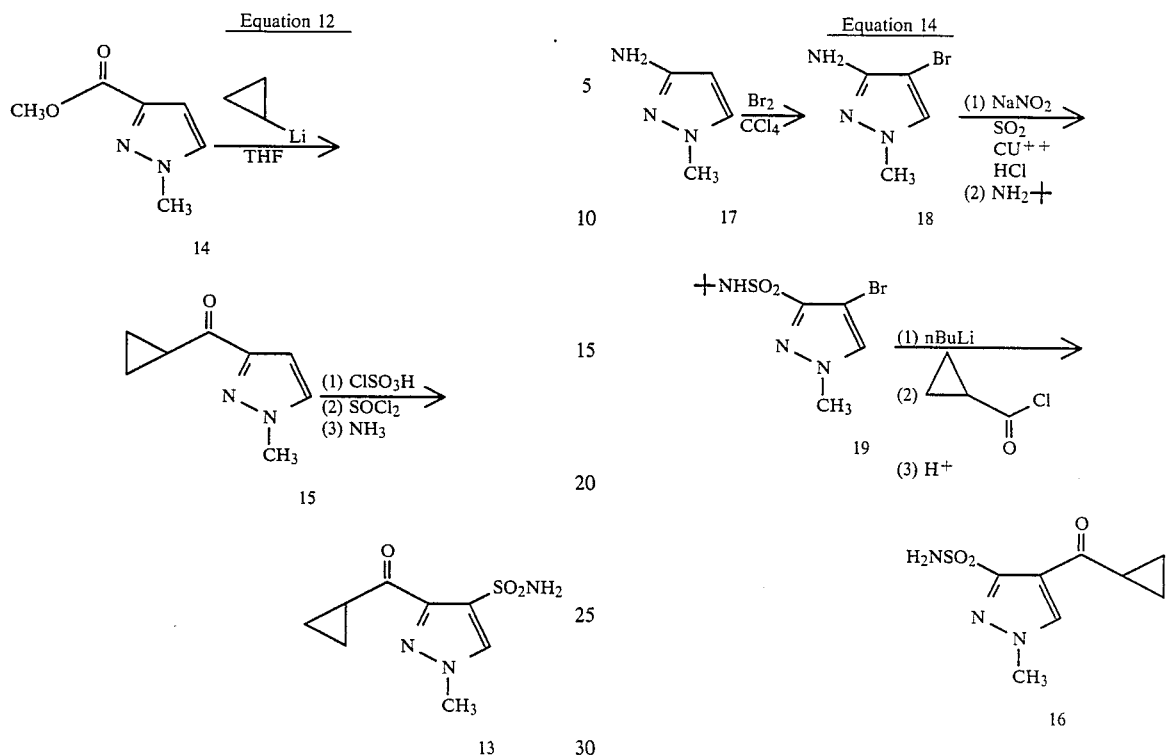

In the above example of Equation 12, as before, minor variations of starting material allows for the introduction of different R and $R_2$ groups. The starting pyrazoles 14 or 15 may be prepared via the condensation of a hydrazine with a triketo species as outlined in Equation 13.

Equation 13

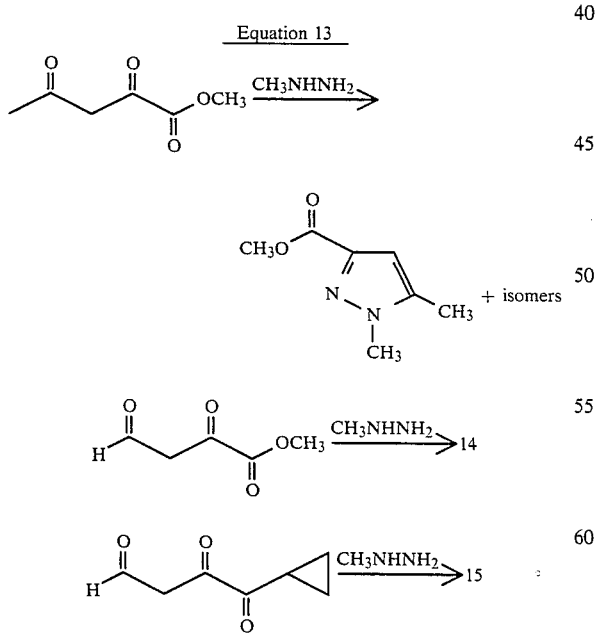

The final pyrazole isomer of the invention such as sulfonamide 16 may be prepared as outlined in Equation 14.

Again, as described previously, alteration of the starting material allows for the preparation of compounds such as 16 where R and/or $R_2$ may be varied. For example, utilizing phenylhydrazine and a chloronitrite results in pyrazole 20 and subsequently sulfonamide, 21. This is outlined in Equation 15.

Equation 15

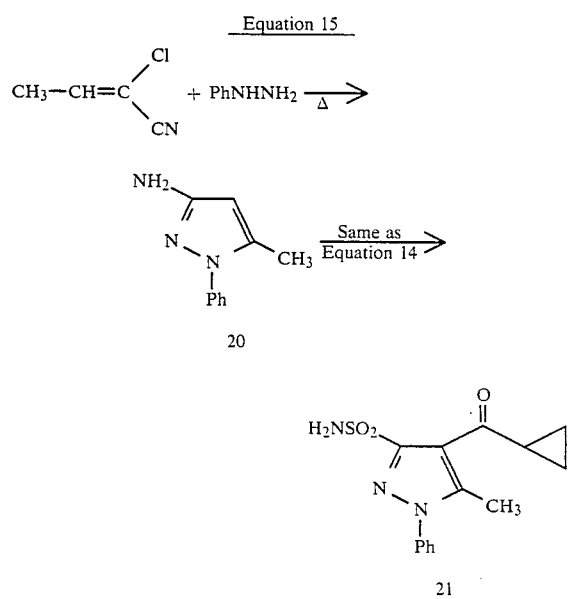

In all the above examples, substitution of cyclopropyl acid chloride with cyclobutyl or cyclopentyl acid chloride would result in the corresponding 4 or 5-membered ring analogs such as compounds 22, 23, 24, 25 and 26.

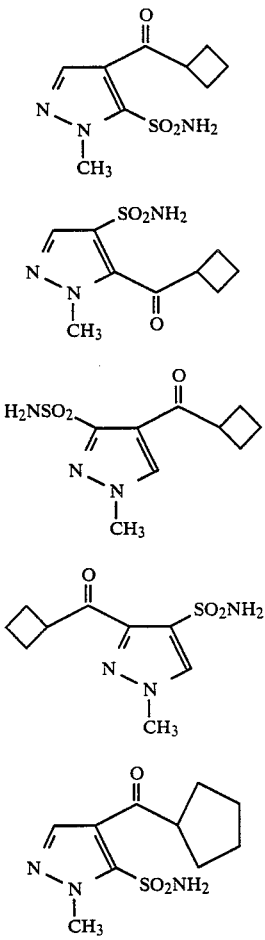

For further details pertaining to the synthesis of pyrazoles see EP-A-No. 87,780, South African Patent Application No. 833,350, EP-A-No. 95,925 and T. L. Jacobs, "Heterocyclic Compounds", R. C. Elderfield, ed., Vol. 5, pp. 45–161, Wiley, New York, 1957.

For further details pertaining to carbanions see J. Stowell, "Carbanions in Organic Synthesis", Wiley-Interscience, New York, 1979.

The synthesis of heterocyclic amines such as those represented by Formula III has been reviewed in "The Chemistry of Heterocyclic Compounds," a series published by Interscience Publ., New York and London. Aminopyrimidines are described by D. J. Brown in "The Pyrimidines," Vol. XVI of the series mentioned above which is herein incorporated by reference. The 2-amino-1,3,5-triazines of Formula III, where A is A-1 and Z is N, can be prepared according to methods described by E. M. Smolin and L. Rapaport in "s-Triazines and Derivatives," Vol. XIII.

Pyrimidines of Formula III, where A is A-1 and Y is an acetal or thioacetal substituent, can be prepared by methods taught in European Patent Application No. 84,224 (published July 27, 1983).

Pyrimidines of Formula III, where A is A-1 and Y is cyclopropyl or $OCF_2H$ can be synthesized according to the methods taught in U.S. Pat. No. 4,515,626 and U.S. Pat. No. 4,540,782, respectively.

Compounds of Formula III, where A is A-2 or A-3, can be prepared by procedures disclosed in U.S. Pat. No. 4,339,267.

Compounds of Formula III, where A is A-4, can be prepared by methods taught in U.S. Pat. No. 4,487,626.

Additional references dealing with the synthesis of bicyclic pyrimidines of Formula III, where A is A-2, A-3, or A-4 are Braker, Sheehan, Spitzmiller and Lott, *J. Am. Chem. Soc.*, 69, 3072 (1947); Mitler and Bhattachanya, *Quart. J. Indian Chem. Soc.*, 4, 152 (1927); Shrage and Hitchings, *J. Org. Chem.*, 16, 1153 (1951); Caldwell, Kornfeld and Donnell, *J. Am. Chem. Soc.*, 63, 2188 (1941); and Fissekis, Myles and Brown, *J. Org. Chem.*, 29, 2670 (1964).

Compounds of Formula III, where A is A-5, can be prepared by methods taught in U.S. Pat. No. 4,421,550.

Compounds of Formula III, where A is A-6, can be prepared by methods taught in the U.S. Pat. No. 4,496,392.

Compounds of Formula III, where A is A-7 can be prepared by methods taught in EP-A-No. 125,864.

Agriculturally suitable salts of compounds of Formula I are also useful herbicides and can be prepared in a number of ways known to the art. For example, metal salts can be made by contacting compounds of Formula I with a solution of an alkali or alkaline earth metal salt having a sufficiently basic anion (e.g., hydroxide, alkoxide, carbonate or hydroxide). Quaternary amine salts can be made by similar techniques.

Salts of compounds of Formula I can also be prepared by exchange of one cation for another. Cationic exchange can be effected by direct contact of an aqueous solution of a salt of a compound of Formula I (e.g., alkali or quaternary amine salt) with a solution containing the cation to be exchanged. This method is most effective when the desired salt containing the exchange cation is insoluble in water and can be separated by filtration.

Exchange may also be effected by passing an aqueous solution of a salt of a compound of formula I (e.g., an alkali metal or quaternary amine salt) through a column packed with a cation exchange resin containing the cation to be exchanged for that of the original salt and the desired product is eluted from the column. This method is particularly useful when the desired salt is water-soluble, e.g., a potassium sodium or calcium salt.

Acid addition salts, useful in this invention, can be obtained by reacting a compound of Formula I with a suitable acid, e.g., p-toluenesulfonic acid, trichloroacetic acid or the like.

The preparation of the compounds of this invention is further illustrated by the following specific examples. Unless otherwise indicated, temperatures are in degrees centigrade.

EXAMPLE 1

Preparation of 4-cyclopropylcarbonyl-1-methyl-5-pyrazole t-butyl sulfonamide

To a cooled −78° C., solution of n-BuLi (3.7 g, 57.2 mmol) in approximately 350 ml of tetrahydrofuran is added 1-methyl-4-bromo-5-pyrazole t-butylsulfonamide (7.5 g, 25.4 mmol) dropwise. The solution is stirred for 15 minutes and then added via cannula to freshly distilled cyclopropyl acid chloride (6 g, 57.2 mmol) cooled to −78° C. The resulting solution was quenched with brine, separated, dryed and concentrated in vaccuo. The resulting oil was flash chromatographed (50:50 (v/v)) ethylacetate-hexane to afford 2.7 g of a white solid, m.p. 113°–115° C.

EXAMPLE 2

Preparation of 4-cyclopropylcarbonyl-1-methyl-5-pyrazolesulfonamide

To a stirring solution of trifluoroacetic acid was added 4-cyclopropyl-1-methyl-5-pyrazole t-butylsulfonamide. The solution was stirred overnight at room temperature. The reaction mixture was concentrated in vaccuo and the resulting solids were triturated with n-butylchloride, m.p. 125°–127° C.; NMR (200 MHZ, CDCl$_3$) 1.1 (m, 2H), 1.3 (m, 2H), 2.4 (m, 1H), 4.2 (s, 3H), 6.4 (br. s, 2H), 8.07 (s, 1H).

EXAMPLE 3

Preparation of 4-(Cyclopropylcarbonyl)-N-[(4,6-dimethoxypyrimidin-2-yl)aminocarbonyl]-1-methyl-1H-pyrazole-5-sulfonamide To a stirring mixture of the sulfonamide from Example 2 (175 mg, 0.76 mmol) and the phenylcarbamate of 4,6-dimethoxy-2-aminopyrimidine (210 mg, 0.76 mmol) in 3 ml of acetonitrile was added diazobicycloundecane (116 mg, 0.76 mmol). The solution was stirred for approximately 10 minutes. Acidification of the reaction mixture and filtration of the resulting solids afforded 300 mg of the desired compound m.p. 189°–192° C. NMR (200 MHz, CDCl$_3$) 1.0 (m, 2H), 1.1 (m, 2H), 2.4 (m, 1H), 4.0 (s, 6H), 4.35 (s, 1H), 5.80 (s, 1H), 7.4 (br. s, 1H), 8.05 (s, 1H), 12.9 (s, 1H).

TABLES

Table I

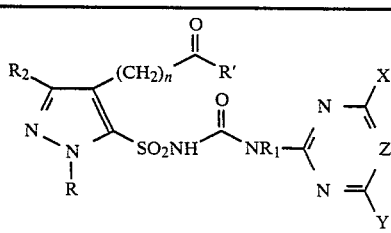

Table II

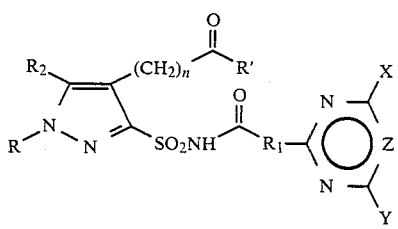

Table III

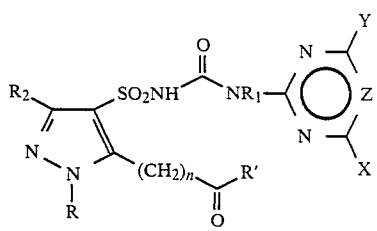

Table IV

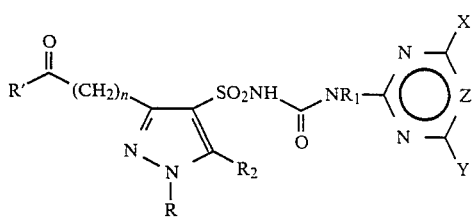

Table V

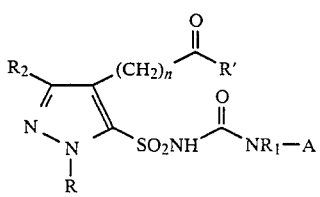

Table VI

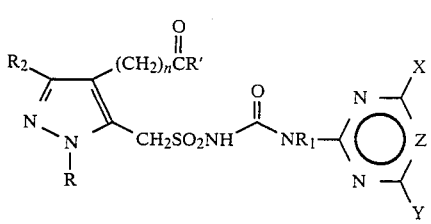

Table VII

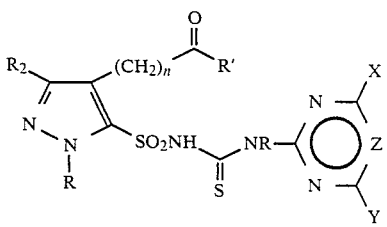

TABLE I

| R | R$_1$ | n | R$_2$ | R' | X | Y | Z | m.p. (°C.) |
|---|---|---|---|---|---|---|---|---|
| CH$_3$ | H | 0 | H | cyclopropyl | CH$_3$ | CH$_3$ | CH | 162–165 |
| CH$_3$ | H | 0 | H | cyclopropyl | CH$_3$ | OCH$_3$ | CH | 155–157 |
| CH$_3$ | H | 0 | H | cyclopropyl | OCH$_3$ | OCH$_3$ | CH | 189–192 |
| CH$_3$ | H | 0 | H | cyclopropyl | CH$_3$ | CH$_3$ | N | |
| CH$_3$ | H | 0 | H | cyclopropyl | CH$_3$ | OCH$_3$ | N | 134–136 |
| CH$_3$ | H | 0 | H | cyclopropyl | OCH$_3$ | OCH$_3$ | N | 164–166 |
| CH$_3$ | H | 0 | H | cyclopropyl | Cl | OCH$_3$ | CH | 197–199 |
| CH$_3$ | H | 0 | H | cyclobutyl | CH$_3$ | CH$_3$ | CH | 190–194 |
| CH$_3$ | H | 0 | H | cyclobutyl | CH$_3$ | OCH$_3$ | CH | 200–203 |
| CH$_3$ | H | 0 | H | cyclobutyl | OCH$_3$ | OCH$_3$ | CH | 196–199 |
| CH$_3$ | H | 0 | H | cyclobutyl | CH$_3$ | CH$_3$ | N | |
| CH$_3$ | H | 0 | H | cyclobutyl | CH$_3$ | OCH$_3$ | N | 175–178 |
| CH$_3$ | H | 0 | H | cyclobutyl | OCH$_3$ | OCH$_3$ | | 168–170 |
| CH$_3$ | H | 0 | H | cyclobutyl | Cl | OCH$_3$ | CH | 210–212 |
| CH$_3$ | H | 0 | H | cyclopentyl | CH$_3$ | CH$_3$ | CH | |
| CH$_3$ | H | 0 | H | cyclopentyl | CH$_3$ | OCH$_3$ | CH | |
| CH$_3$ | H | 0 | H | cyclopentyl | OCH$_3$ | OCH$_3$ | CH | |
| CH$_3$ | H | 0 | H | cyclopentyl | CH$_3$ | CH$_3$ | N | |

TABLE I-continued

| R | $R_1$ | n | $R_2$ | R' | X | Y | Z | m.p. (°C.) |
|---|---|---|---|---|---|---|---|---|
| $CH_3$ | H | 0 | H | cyclopentyl | $CH_3$ | $OCH_3$ | N | |
| $CH_3$ | H | 0 | H | cyclopentyl | $OCH_3$ | $OCH_3$ | N | |
| $CH_3$ | H | 0 | H | cyclopentyl | Cl | $OCH_3$ | CH | |
| $CH_3$ | H | 0 | H | cyclopropyl | $OCH_3$ | $OCH_2CH_3$ | CH | |
| $CH_3$ | H | 0 | H | cyclopropyl | cyclopropyl | $OCH_3$ | CH | |
| $CH_3$ | H | 0 | H | cyclopropyl | $OCH_3$ | $CH(OCH_3)_2$ | CH | |
| $CH_3$ | H | 0 | H | cyclopropyl | $NHCH_3$ | $OCH_2CH_3$ | N | |
| $CH_3$ | H | 0 | H | cyclopropyl | $NHCH_3$ | $OCH_3$ | N | |
| $CH_3$ | H | 0 | H | cyclopropyl | $OCH_3$ | $OCH_2CH_3$ | N | |
| $CH_3$ | H | 0 | H | cyclopropyl | $CH_2F$ | $CH_3$ | CH | |
| $CH_3$ | H | 0 | $CH_3$ | cyclopropyl | $CH_3$ | $CH_3$ | CH | |
| $CH_3$ | H | 0 | $CH_3$ | cyclopropyl | $CH_3$ | $OCH_3$ | CH | |
| $CH_3$ | H | 0 | $CH_3$ | cyclopropyl | $OCH_3$ | $OCH_3$ | CH | |
| $CH_3$ | H | 0 | $CH_3$ | cyclopropyl | $CH_3$ | $CH_3$ | N | |
| $CH_3$ | H | 0 | $CH_3$ | cyclopropyl | $CH_3$ | $OCH_3$ | N | |
| $CH_3$ | H | 0 | $CH_3$ | cyclopropyl | $OCH_3$ | $OCH_3$ | N | |
| $CH_3$ | H | 0 | $CH_3$ | cyclopropyl | Cl | $OCH_3$ | CH | |
| $CH_3$ | H | 0 | $CH_3$ | cyclobutyl | $CH_3$ | $CH_3$ | CH | |
| $CH_3$ | H | 0 | $CH_3$ | cyclobutyl | $CH_3$ | $OCH_3$ | CH | |
| $CH_3$ | H | 0 | $CH_3$ | cyclobutyl | $OCH_3$ | $OCH_3$ | CH | |
| $CH_3$ | H | 0 | $CH_3$ | cyclobutyl | $CH_3$ | $CH_3$ | N | |
| $CH_3$ | H | 0 | $CH_3$ | cyclobutyl | $CH_3$ | $OCH_3$ | N | |
| $CH_3$ | H | 0 | $CH_3$ | cyclobutyl | $OCH_3$ | $OCH_3$ | N | |
| $CH_3$ | H | 0 | $CH_3$ | cyclobutyl | Cl | $OCH_3$ | CH | |
| $CH_3$ | H | 0 | $CH_3$ | cyclopentyl | $CH_3$ | $CH_3$ | CH | |
| $CH_3$ | H | 0 | $CH_3$ | cyclopentyl | $CH_3$ | $OCH_3$ | CH | |
| $CH_3$ | H | 0 | $CH_3$ | cyclopentyl | $OCH_3$ | $OCH_3$ | CH | |
| $CH_3$ | H | 0 | $CH_3$ | cyclpentyl | $CH_3$ | $CH_3$ | N | |
| $CH_3$ | H | 0 | $CH_3$ | cyclopentyl | $CH_3$ | $OCH_3$ | N | |
| $CH_3$ | H | 0 | $CH_3$ | cyclopentyl | $OCH_3$ | $OCH_3$ | N | |
| $CH_3$ | H | 0 | $CH_3$ | cyclopentyl | Cl | $OCH_3$ | CH | |
| $CH_3$ | H | 0 | $CH_3$ | cyclopropyl | $OCH_3$ | $OCH_2CH_3$ | CH | |
| $CH_3$ | H | 0 | $CH_3$ | cyclopropyl | cyclopropyl | $OCH_3$ | CH | |
| $CH_3$ | H | 0 | $CH_3$ | cyclopropyl | $OCH_3$ | $CH(OCH_3)_2$ | CH | |
| $CH_3$ | H | 0 | $CH_3$ | cyclopropyl | $NHCH_3$ | $OCH_2CH_3$ | N | |
| $CH_3$ | H | 0 | $CH_3$ | cyclopropyl | $NHCH_3$ | $OCH_3$ | N | |
| $CH_3$ | H | 0 | $CH_3$ | cyclopropyl | $OCH_3$ | $OCH_2CH_3$ | N | |
| $CH_3$ | H | 0 | $CH_3$ | cyclopropyl | $CH_2F$ | $CH_3$ | CH | |
| $CH_3$ | H | 0 | Cl | cyclopropyl | $CH_3$ | $CH_3$ | CH | 167–169 |
| $CH_3$ | H | 0 | Cl | cyclopropyl | $CH_3$ | $OCH_3$ | CH | 178–180 |
| $CH_3$ | H | 0 | Cl | cyclopropyl | $OCH_3$ | $OCH_3$ | CH | 193–195 |
| $CH_3$ | H | 0 | Cl | cyclopropyl | $CH_3$ | $CH_3$ | N | |
| $CH_3$ | H | 0 | Cl | cyclopropyl | $CH_3$ | $OCH_3$ | N | |
| $CH_3$ | H | 0 | Cl | cyclopropyl | $OCH_3$ | $OCH_3$ | N | |
| $CH_3$ | H | 0 | Cl | cyclopropyl | Cl | $OCH_3$ | CH | |
| $CH_3$ | H | 0 | Cl | cyclobutyl | $CH_3$ | $CH_3$ | CH | |
| $CH_3$ | H | 0 | Cl | cyclobutyl | $CH_3$ | $OCH_3$ | CH | |
| $CH_3$ | H | 0 | Cl | cyclobutyl | $OCH_3$ | $OCH_3$ | CH | |
| $CH_3$ | H | 0 | Cl | cyclobutyl | $CH_3$ | $CH_3$ | N | |
| $CH_3$ | H | 0 | Cl | cyclobutyl | $CH_3$ | $OCH_3$ | N | |
| $CH_3$ | H | 0 | Cl | cyclobutyl | $OCH_3$ | $OCH_3$ | N | |
| $CH_3$ | H | 0 | Cl | cyclobutyl | Cl | $OCH_3$ | CH | |
| $CH_3$ | H | 0 | Cl | cyclopentyl | $CH_3$ | $CH_3$ | CH | |
| $CH_3$ | H | 0 | Cl | cyclopentyl | $CH_3$ | $OCH_3$ | CH | |
| $CH_3$ | H | 0 | Cl | cyclopentyl | $OCH_3$ | $OCH_3$ | CH | |
| $CH_3$ | H | 0 | Cl | cyclopentyl | $CH_3$ | $CH_3$ | N | |
| $CH_3$ | H | 0 | Cl | cyclopentyl | $CH_3$ | $OCH_3$ | N | |
| $CH_3$ | H | 0 | Cl | cyclopentyl | $OCH_3$ | $OCH_3$ | N | |
| $CH_3$ | H | 0 | Cl | cyclopentyl | Cl | $OCH_3$ | CH | |
| $CH_3$ | H | 0 | Cl | cyclopropyl | $OCH_3$ | $OCH_3CH_3$ | CH | |
| $CH_3$ | H | 0 | Cl | cyclopropyl | cyclopropyl | $OCH_3$ | CH | |
| $CH_3$ | H | 0 | Cl | cyclopropyl | $OCH_3$ | $CH(OCH_3)_2$ | CH | |
| $CH_3$ | H | 0 | Cl | cyclopropyl | $NHCH_3$ | $OCH_2CH_3$ | N | |
| $CH_3$ | H | 0 | Cl | cyclopropyl | $NHCH_3$ | $OCH_3$ | N | |
| $CH_3$ | H | 0 | Cl | cyclopropyl | $OCH_3$ | $OCH_2CH_3$ | N | |
| $CH_3$ | H | 0 | Cl | cyclopropyl | $CH_2F$ | $CH_3$ | CH | |
| $CH_3$ | H | 0 | Br | cyclopropyl | $CH_3$ | $CH_3$ | CH | |
| $CH_3$ | H | 0 | Br | cyclopropyl | $CH_3$ | $OCH_3$ | CH | |
| $CH_3$ | H | 0 | Br | cyclopropyl | $OCH_3$ | $OCH_3$ | CH | |
| $CH_3$ | H | 0 | Br | cyclopropyl | $CH_3$ | $CH_3$ | N | |
| $CH_3$ | H | 0 | Br | cyclopropyl | $CH_3$ | $OCH_3$ | N | |
| $CH_3$ | H | 0 | Br | cyclopropyl | $OCH_3$ | $OCH_3$ | N | |
| $CH_3$ | H | 0 | Br | cyclopropyl | Cl | $OCH_3$ | CH | |
| $CH_3$ | H | 0 | Br | cyclobutyl | $CH_3$ | $CH_3$ | CH | |
| $CH_3$ | H | 0 | Br | cyclobutyl | $CH_3$ | $OCH_3$ | CH | |
| $CH_3$ | H | 0 | Br | cyclobutyl | $OCH_3$ | $OCH_3$ | CH | |
| $CH_3$ | H | 0 | Br | cyclobutyl | $CH_3$ | $CH_3$ | N | |
| $CH_3$ | H | 0 | Br | cyclobutyl | $CH_3$ | $OCH_3$ | N | |

TABLE I-continued

| R | R₁ | n | R₂ | R' | X | Y | Z | m.p. (°C.) |
|---|---|---|---|---|---|---|---|---|
| CH₃ | H | 0 | Br | cyclobutyl | OCH₃ | OCH₃ | N | |
| CH₃ | H | 0 | Br | cyclobutyl | Cl | OCH₃ | CH | |
| CH₃ | H | 0 | Br | cyclopentyl | CH₃ | CH₃ | CH | |
| CH₃ | H | 0 | Br | cyclopentyl | CH₃ | OCH₃ | CH | |
| CH₃ | H | 0 | Br | cyclopentyl | OCH₃ | OCH₃ | CH | |
| CH₃ | H | 0 | Br | cyclopentyl | CH₃ | CH₃ | N | |
| CH₃ | H | 0 | Br | cyclopentyl | CH₃ | OCH₃ | N | |
| CH₃ | H | 0 | Br | cyclopentyl | OCH₃ | OCH₃ | N | |
| CH₃ | H | 0 | Br | cyclopentyl | Cl | OCH₃ | CH | |
| CH₃ | H | 0 | Br | cyclopropyl | OCH₃ | OCH₂C₃ | CH | |
| CH₃ | H | 0 | Br | cyclopropyl | cyclopropyl | OCH₃ | CH | |
| CH₃ | H | 0 | Br | cyclopropyl | OCH₃ | CH(OCH₃)₂ | CH | |
| CH₃ | H | 0 | Br | cyclopropyl | NHCH₃ | OCH₂CH₃ | N | |
| CH₃ | H | 0 | Br | cyclopropyl | NHCH₃ | OCH₃ | N | |
| CH₃ | H | 0 | Br | cyclopropyl | OCH₃ | OCH₂CH₃ | N | |
| CH₃ | H | 0 | Br | cyclopropyl | CH₂F | CH₃ | CH | |
| CH₃ | H | 0 | CH₂F | cyclopropyl | CH₃ | CH₃ | CH | |
| CH₃ | H | 0 | CH₂F | cyclopropyl | CH₃ | OCH₃ | CH | |
| CH₃ | H | 0 | CH₂F | cyclopropyl | OCH₃ | OCH₃ | CH | |
| CH₃ | H | 0 | CH₂F | cyclopropyl | CH₃ | CH₃ | N | |
| CH₃ | H | 0 | CH₂F | cyclopropyl | CH₃ | OCH₃ | N | |
| CH₃ | H | 0 | CH₂F | cyclopropyl | OCH₃ | OCH₃ | N | |
| CH₃ | H | 0 | CH₂F | cyclopropyl | Cl | OCH₃ | CH | |
| CH₃ | H | 0 | CH₂F | cyclobutyl | CH₃ | CH₃ | CH | |
| CH₃ | H | 0 | CH₂F | cyclobutyl | CH₃ | OCH₃ | CH | |
| CH₃ | H | 0 | CH₂F | cyclobutyl | OCH₃ | OCH₃ | CH | |
| CH₃ | H | 0 | CH₂F | cyclobutyl | CH₃ | CH₃ | N | |
| CH₃ | H | 0 | CH₂F | cyclobutyl | CH₃ | OCH₃ | N | |
| CH₃ | H | 0 | CH₂F | cyclobutyl | OCH₃ | OCH₃ | N | |
| CH₃ | H | 0 | CH₂F | cyclobutyl | Cl | OCH₃ | CH | |
| CH₃ | H | 0 | CH₂F | cyclopentyl | CH₃ | CH₃ | CH | |
| CH₃ | H | 0 | CH₂F | cyclopentyl | CH₃ | OCH₃ | CH | |
| CH₃ | H | 0 | CH₂F | cyclopentyl | OCH₃ | OCH₃ | CH | |
| CH₃ | H | 0 | CH₂F | cyclopentyl | CH₃ | CH₃ | N | |
| CH₃ | H | 0 | CH₂F | cyclopentyl | CH₃ | OCH₃ | N | |
| CH₃ | H | 0 | CH₂F | cyclopentyl | OCH₃ | OCH₃ | N | |
| CH₃ | H | 0 | CH₂F | cyclopentyl | Cl | OCH₃ | CH | |
| CH₃ | H | 0 | CH₂F | cyclopropyl | OCH₃ | OCH₂CH₃ | CH | |
| CH₃ | H | 0 | CH₂F | cyclopropyl | cyclopropyl | OCH₃ | CH | |
| CH₃ | H | 0 | CH₂F | cyclopropyl | OCH₃ | CH(OCH₃)₂ | CH | |
| CH₃ | H | 0 | CH₂F | cyclopropyl | NHCH₃ | OCH₂CH₃ | N | |
| CH₃ | H | 0 | CH₂F | cyclopropyl | NHCH₃ | OCH₃ | N | |
| CH₃ | H | 0 | CH₂F | cyclopropyl | OCH₃ | OCH₂CH₃ | N | |
| CH₃ | H | 0 | CH₂F | cyclopropyl | CH₂F | CH₃ | CH | |
| CH₃ | H | 0 | OCH₃ | cyclopropyl | CH₃ | CH₃ | CH | |
| CH₃ | H | 0 | OCH₃ | cyclopropyl | CH₃ | OCH₃ | CH | |
| CH₃ | H | 0 | OCH₃ | cyclopropyl | OCH₃ | OCH₃ | CH | |
| CH₃ | H | 0 | OCH₃ | cyclopropyl | CH₃ | CH₃ | N | |
| CH₃ | H | 0 | OCH₃ | cyclopropyl | CH₃ | OCH₃ | N | |
| CH₃ | H | 0 | OCH₃ | cyclopropyl | OCH₃ | OCH₃ | N | |
| CH₃ | H | 0 | OCH₃ | cyclopropyl | Cl | OCH₃ | CH | |
| CH₃ | H | 0 | CH₃ | cyclobutyl | CH₃ | CH₃ | CH | |
| CH₃ | H | 0 | OCH₃ | cyclobutyl | CH₃ | OCH₃ | CH | |
| CH₃ | H | 0 | OCH₃ | cyclobutyl | OCH₃ | OCH₃ | CH | |
| CH₃ | H | 0 | OCH₃ | cyclobutyl | CH₃ | CH₃ | N | |
| CH₃ | H | 0 | OCH₃ | cyclobutyl | CH₃ | OCH₃ | N | |
| CH₃ | H | 0 | OCH₃ | cyclobutyl | OCH₃ | OCH₃ | N | |
| CH₃ | H | 0 | OCH₃ | cyclobutyl | Cl | OCH₃ | CH | |
| CH₃ | H | 0 | OCH₃ | cyclopentyl | CH₃ | CH₃ | CH | |
| CH₃ | H | 0 | OCH₃ | cyclopentyl | CH₃ | OCH₃ | CH | |
| CH₃ | H | 0 | OCH₃ | cyclopentyl | OCH₃ | OCH₃ | CH | |
| CH₃ | H | 0 | OCH₃ | cyclopentyl | CH₃ | CH₃ | N | |
| CH₃ | H | 0 | OCH₃ | cyclopentyl | CH₃ | OCH₃ | N | |
| CH₃ | H | 0 | OCH₃ | cyclopentyl | OCH₃ | OCH₃ | N | |
| CH₃ | H | 0 | OCH₃ | cyclopentyl | Cl | OCH₃ | CH | |
| CH₃ | H | 0 | OCH₃ | cyclopropyl | OCH₃ | OCH₂CH₃ | CH | |
| CH₃ | H | 0 | OCH₃ | cyclopropyl | cyclopropyl | OCH₃ | CH | |
| CH₃ | H | 0 | OCH₃ | cyclopropyl | OCH₃ | CH(OCH₃)₂ | CH | |
| CH₃ | H | 0 | OCH₃ | cyclopropyl | NHCH₃ | OCH₂CH₃ | N | |
| CH₃ | H | 0 | OCH₃ | cyclopropyl | NHCH₃ | OCH₃ | N | |
| CH₃ | H | 0 | OCH₃ | cyclopropyl | OCH₃ | OCH₂CH₃ | N | |
| CH₃ | H | 0 | OCH₃ | cyclopropyl | CH₂F | CH₃ | CH | |
| CH₃ | H | 0 | SO₂N(CH₃)₂ | cyclopropyl | CH₃ | CH₃ | CH | |
| CH₃ | H | 0 | SO₂N(CH₃)₂ | cyclopropyl | CH₃ | OCH₃ | CH | |
| CH₃ | H | 0 | SO₂N(CH₃)₂ | cyclopropyl | OCH₃ | OCH₃ | CH | |
| CH₃ | H | 0 | SO₂N(CH₃)₂ | cyclopropyl | CH₃ | CH₃ | N | |
| CH₃ | H | 0 | SO₂N(CH₃)₂ | cyclopropyl | CH₃ | OCH₃ | N | |
| CH₃ | H | 0 | SO₂N(CH₃)₂ | cyclopropyl | OCH₃ | OCH₃ | N | |
| CH₃ | H | 0 | SO₂N(CH₃)₂ | cyclopropyl | Cl | OCH₃ | CH | |
| CH₃ | H | 0 | SO₂N(CH₃)₂ | cyclobutyl | CH₃ | CH₃ | CH | |
| CH₃ | H | 0 | SO₂N(CH₃)₂ | cyclobutyl | CH₃ | OCH₃ | CH | |

TABLE I-continued

| R | $R_1$ | n | $R_2$ | R' | X | Y | Z | m.p. (°C.) |
|---|---|---|---|---|---|---|---|---|
| $CH_3$ | H | 0 | $SO_2N(CH_3)_2$ | cyclobutyl | $OCH_3$ | $OCH_3$ | CH | |
| $CH_3$ | H | 0 | $SO_2N(CH_3)_2$ | cyclobutyl | $OCH_3$ | $OCH_3$ | CH | |
| $CH_3$ | H | 0 | $SO_2N(CH_3)_2$ | cyclobutyl | $CH_3$ | $CH_3$ | N | |
| $CH_3$ | H | 0 | $SO_2N(CH_3)_2$ | cyclobutyl | $CH_3$ | $OCH_3$ | N | |
| $CH_3$ | H | 0 | $SO_2N(CH_3)_2$ | cyclobutyl | $OCH_3$ | $OCH_3$ | N | |
| $CH_3$ | H | 0 | $SO_2N(CH_3)_2$ | cyclobutyl | Cl | $OCH_3$ | CH | |
| $CH_3$ | H | 0 | $SO_2N(CH_3)_2$ | cyclopentyl | $CH_3$ | $CH_3$ | CH | |
| $CH_3$ | H | 0 | $SO_2N(CH_3)_2$ | cyclopentyl | $CH_3$ | $OCH_3$ | CH | |
| $CH_3$ | H | 0 | $SO_2N(CH_3)_2$ | cyclopentyl | $OCH_3$ | $OCH_3$ | CH | |
| $CH_3$ | H | 0 | $SO_2N(CH_3)_2$ | cyclopentyl | $CH_3$ | $CH_3$ | N | |
| $CH_3$ | H | 0 | $SO_2N(CH_3)_2$ | cyclopentyl | $CH_3$ | $OCH_3$ | N | |
| $CH_3$ | H | 0 | $SO_2N(CH_3)_2$ | cyclopentyl | $OCH_3$ | $OCH_3$ | N | |
| $CH_3$ | H | 0 | $SO_2N(CH_3)_2$ | cyclopentyl | Cl | $OCH_3$ | CH | |
| $CH_3$ | H | 0 | $SO_2N(CH_3)_2$ | cyclopropyl | $OCH_3$ | $OCH_2CH_3$ | CH | |
| $CH_3$ | H | 0 | $SO_2N(CH_3)_2$ | cyclopropyl | cyclopropyl | $OCH_3$ | CH | |
| $CH_3$ | H | 0 | $SO_2N(CH_3)_2$ | cyclopropyl | $OCH_3$ | $CH(OCH_3)_2$ | CH | |
| $CH_3$ | H | 0 | $SO_2N(CH_3)_2$ | cyclopropyl | $NHCH_3$ | $OCH_2CH_3$ | N | |
| $CH_3$ | H | 0 | $SO_2N(CH_3)_2$ | cyclopropyl | $NHCH_3$ | $OCH_3$ | N | |
| $CH_3$ | H | 0 | $SO_2N(CH_3)_2$ | cyclopropyl | $OCH_3$ | $OCH_2CH_3$ | N | |
| $CH_3$ | H | 0 | $SO_2N(CH_3)_2$ | cyclopropyl | $CH_2F$ | $CH_3$ | CH | |
| $CH_3$ | H | 0 | $SCH_3$ | cyclopropyl | $CH_3$ | $CH_3$ | CH | |
| $CH_3$ | H | 0 | $SCH_3$ | cyclopropyl | $CH_3$ | $OCH_3$ | CH | |
| $CH_3$ | H | 0 | $SCH_3$ | cyclopropyl | $OCH_3$ | $OCH_3$ | CH | |
| $CH_3$ | H | 0 | $SCH_3$ | cyclopropyl | $CH_3$ | $CH_3$ | N | |
| $CH_3$ | H | 0 | $SCH_3$ | cyclopropyl | $CH_3$ | $OCH_3$ | N | |
| $CH_3$ | H | 0 | $SCH_3$ | cyclopropyl | $OCH_3$ | $OCH_3$ | N | |
| $CH_3$ | H | 0 | $SCH_3$ | cyclopropyl | Cl | $OCH_3$ | CH | |
| $CH_3$ | H | 0 | $SCH_3$ | cyclobutyl | $CH_3$ | $CH_3$ | CH | |
| $CH_3$ | H | 0 | $SCH_3$ | cyclobutyl | $CH_3$ | $OCH_3$ | CH | |
| $CH_3$ | H | 0 | $SCH_3$ | cyclobutyl | $OCH_3$ | $OCH_3$ | CH | |
| $CH_3$ | H | 0 | $SCH_3$ | cyclobutyl | $CH_3$ | $CH_3$ | N | |
| $CH_3$ | H | 0 | $SCH_3$ | cyclobutyl | $CH_3$ | $OCH_3$ | N | |
| $CH_3$ | H | 0 | $SCH_3$ | cyclobutyl | $OCH_3$ | $OCH_3$ | N | |
| $CH_3$ | H | 0 | $SCH_3$ | cyclobutyl | Cl | $OCH_3$ | CH | |
| $CH_3$ | H | 0 | $SCH_3$ | cyclopentyl | $CH_3$ | $CH_3$ | CH | |
| $CH_3$ | H | 0 | $SCH_3$ | cyclopentyl | $CH_3$ | $OCH_3$ | CH | |
| $CH_3$ | H | 0 | $SCH_3$ | cyclopentyl | $OCH_3$ | $OCH_3$ | CH | |
| $CH_3$ | H | 0 | $SCH_3$ | cyclopentyl | $CH_3$ $CH_3$ | N | | |
| $CH_3$ | H | 0 | $SCH_3$ | cyclopentyl | $CH_3$ | $OCH_3$ | N | |
| $CH_3$ | H | 0 | $SCH_3$ | cyclopentyl | $OCH_3$ | $OCH_3$ | N | |
| $CH_3$ | H | 0 | $SCH_3$ | cyclopentyl | Cl | $OCH_3$ | CH | |
| $CH_3$ | H | 0 | $SCH_3$ | cyclopropyl | $OCH_3$ | $OCH_3CH_3$ | CH | |
| $CH_3$ | H | 0 | $SCH_3$ | cyclopropyl | cyclopropyl | $OCH_3$ | CH | |
| $CH_3$ | H | 0 | $SCH_3$ | cyclopropyl | $OCH_3$ | $CH(OCH_3)_2$ | CH | |
| $CH_3$ | H | 0 | $SCH_3$ | cyclopropyl | $NHCH_3$ | $OCH_2CH_3$ | N | |
| $CH_3$ | H | 0 | $SCH_3$ | cyclopropyl | $NHCH_3$ | $OCH_3$ | N | |
| $CH_3$ | H | 0 | $SCH_3$ | cyclopropyl | $OCH_3$ | $OCH_2CH_3$ | N | |
| $CH_3$ | H | 0 | $SCH_3$ | cyclopropyl | $CH_2F$ | $CH_3$ | CH | |
| $CH_3$ | H | 0 | $SOCH_3$ | cyclopropyl | $CH_3$ | $CH_3$ | CH | |
| $CH_3$ | H | 0 | $SOCH_3$ | cyclopropyl | $CH_3$ | $OCH_3$ | CH | |
| $CH_3$ | H | 0 | $SOCH_3$ | cyclopropyl | $OCH_3$ | $OCH_3$ | CH | |
| $CH_3$ | H | 0 | $SOCH_3$ | cyclopropyl | $CH_3$ | $C_3$ | N | |
| $CH_3$ | H | 0 | $SOCH_3$ | cyclopropyl | $CH_3$ | $OCH_3$ | N | |
| $CH_3$ | H | 0 | $SOCH_3$ | cyclopropyl | $OCH_3$ $OCH_3$ | N | | |
| $CH_3$ | H | 0 | $SOCH_3$ | cyclopropyl | Cl | $OCH_3$ | CH | |
| $CH_3$ | H | 0 | $SOCH_3$ | cyclobutyl | $CH_3$ | $CH_3$ | CH | |
| $CH_3$ | H | 0 | $SOCH_3$ | cyclobutyl | $CH_3$ | $OCH_3$ | CH | |
| $CH_3$ | H | 0 | $SOCH_3$ | cyclobutyl | $OCH_3$ | $OCH_3$ | CH | |
| $CH_3$ | H | 0 | $SOCH_3$ | cyclobutyl | $CH_3$ | $CH_3$ | N | |
| $CH_3$ | H | 0 | $SOCH_3$ | cyclobutyl | $CH_3$ | $OCH_3$ | N | |
| $CH_3$ | H | 0 | $SOCH_3$ | cyclobutyl | $OCH_3$ | $OCH_3$ | N | |
| $CH_3$ | H | 0 | $SOCH_3$ | cyclobutyl | Cl | $OCH_3$ | CH | |
| $CH_3$ | H | 0 | $SOCH_3$ | cyclopentyl | $CH_3$ | $CH_3$ | CH | |
| $CH_3$ | H | 0 | $SOCH_3$ | cyclopentyl | $CH_3$ | $OCH_3$ | CH | |
| $CH_3$ | H | 0 | $SOCH_3$ | cyclopentyl | $OCH_3$ | $OCH_3$ | CH | |
| $CH_3$ | H | 0 | $SOCH_3$ | cyclopentyl | $CH_3$ | $CH_3$ | N | |
| $CH_3$ | H | 0 | $SOCH_3$ | cyclopentyl | $CH_3$ | $OCH_3$ | N | |
| $CH_3$ | H | 0 | $SOCH_3$ | cyclopentyl | $OCH_3$ | $OCH_3$ | N | |
| $CH_3$ | H | 0 | $SOCH_3$ | cyclopentyl | Cl | $OCH_3$ | CH | |
| $CH_3$ | H | 0 | $SOCH_3$ | cyclopropyl | $OCH_3$ | $OCH_2CH_3$ | CH | |
| $CH_3$ | H | 0 | $SOCH_3$ | cyclopropyl | cyclopropyl | $OCH_3$ | CH | |
| $CH_3$ | H | 0 | $SOCH_3$ | cyclopropyl | $OCH_3$ | $CH(OCH_3)_2$ | CH | |
| $CH_3$ | H | 0 | $SOCH_3$ | cyclopropyl | $NHCH_3$ | $OCH_2CH_3$ | N | |
| $CH_3$ | H | 0 | $SOCH_3$ | cyclopropyl | $NHCH_3$ | $OCH_3$ | N | |
| $CH_3$ | H | 0 | $SOCH_3$ | cyclopropyl | $OCH_3$ | $OCH_2CH_3$ | N | |
| $CH_3$ | H | 0 | $SOCH_3$ | cyclopropyl | $CH_2F$ | $CH_3$ | CH | |
| $CH_3$ | H | 0 | $SO_2CH_3$ | cyclopropyl | $CH_3$ | $CH_3$ | CH | |
| $CH_3$ | H | 0 | $SO_2CH_3$ | cyclopropyl | $CH_3$ | $OCH_3$ | CH | |
| $CH_3$ | H | 0 | $SO_2CH_3$ | cyclopropyl | $OCH_3$ | $OCH_3$ | CH | |

TABLE I-continued

| R | R₁ | n | R₂ | R' | X | Y | Z | m.p. (°C.) |
|---|---|---|---|---|---|---|---|---|
| CH₃ | H | 0 | SO₂CH₃ | cyclopropyl | CH₃ | CH₃ | N | |
| CH₃ | H | 0 | SO₂CH₃ | cyclopropyl | CH₃ | OCH₃ | N | |
| CH₃ | H | 0 | SO₂CH₃ | cyclopropyl | OCH₃ | OCH₃ | N | |
| CH₃ | H | 0 | SO₂CH₃ | cyclopropyl | OCH₃ | | CH | |
| | | | | Cl | | | | |
| CH₃ | H | 0 | SO₂CH₃ | cyclobutyl | CH₃ | CH₃ | CH | |
| CH₃ | H | 0 | SO₂CH₃ | cyclobutyl | CH₃ | OCH₃ | CH | |
| CH₃ | H | 0 | SO₂CH₃ | cyclobutyl | OCH₃ | OCH₃ | CH | |
| CH₃ | H | 0 | SO₂CH₃ | cyclobutyl | CH₃ | CH₃ | N | |
| CH₃ | H | 0 | SO₂CH₃ | cyclobutyl | CH₃ | OCH₃ | N | |
| CH₃ | H | 0 | SO₂CH₃ | cyclobutyl | OCH₃ | OCH₃ | N | |
| CH₃ | H | 0 | SO₂CH₃ | cyclobutyl | Cl | OCH₃ | CH | |
| CH₃ | H | 0 | SO₂CH₃ | cyclopentyl | CH₃ | CH₃ | CH | |
| CH₃ | H | 0 | SO₂CH₃ | cyclopentyl | CH₃ | OCH₃ | CH | |
| CH₃ | H | 0 | SO₂CH₃ | cyclopentyl | OCH₃ | OCH₃ | CH | |
| CH₃ | H | 0 | SO₂CH₃ | cyclopentyl | CH₃ | CH₃ | N | |
| CH₃ | H | 0 | SO₂CH₃ | cyclopentyl | CH₃ | OCH₃ | N | |
| CH₃ | H | 0 | SO₂CH₃ | cyclopentyl | OCH₃ | OCH₃ | N | |
| CH₃ | H | 0 | SO₂CH₃ | cyclopentyl | Cl | OCH₃ | CH | |
| CH₃ | H | 0 | SO₂CH₃ | cyclopropyl | OCH₃ | OCH₂CH₃ | CH | |
| CH₃ | H | 0 | SO₂CH₃ | cyclopropyl | cyclopropyl | OCH₃ | CH | |
| CH₃ | H | 0 | SO₂CH₃ | cyclopropyl | OCH₃ | CH(OCH₃)₂ | CH | |
| CH₃ | H | 0 | SO₂CH₃ | cyclopropyl | NHCH₃ | OCH₂CH₃ | N | |
| CH₃ | H | 0 | SO₂CH₃ | cyclopropyl | NHCH₃ | OCH₃ | N | |
| CH₃ | H | 0 | SO₂CH₃ | cyclopropyl | OCH₃ | OCH₂CH₃ | N | |
| CH₃ | H | 0 | SO₂CH₃ | cyclopropyl | CH₂F | CH₃ | CH | |
| CH₃ | H | 0 | CN | cyclopropyl | CH₃ | CH₃ | CH | |
| CH₃ | H | 0 | CN | cyclopropyl | CH₃ | OCH₃ | CH | |
| CH₃ | H | 0 | CN | cyclopropyl | OCH₃ | OCH₃ | CH | |
| CH₃ | H | 0 | CN | cyclopropyl | CH₃ | CH₃ | N | |
| CH₃ | H | 0 | CN | cyclopropyl | CH₃ | OCH₃ | N | |
| CH₃ | H | 0 | CN | cyclopropyl | OCH₃ | OCH₃ | N | |
| CH₃ | H | 0 | CN | cyclopropyl | Cl | OCH₃ | CH | |
| CH₃ | H | 0 | CN | cyclobutyl | CH₃ | CH₃ | CH | |
| CH₃ | H | 0 | CN | cyclobutyl | CH₃ | OCH₃ | CH | |
| CH₃ | H | 0 | CN | cyclobutyl | OCH₃ | OCH₃ | CH | |
| CH₃ | H | 0 | CN | cyclobutyl | CH₃ | CH₃ | N | |
| CH₃ | H | 0 | CN | cyclobutyl | CH₃ | OCH₃ | N | |
| CH₃ | H | 0 | CN | cyclobutyl | OCH₃ | OCH₃ | N | |
| CH₃ | H | 0 | CN | cyclobutyl | Cl | OCH₃ | CH | |
| CH₃ | H | 0 | CN | cyclopentyl | CH₃ | CH₃ | CH | |
| CH₃ | H | 0 | CN | cyclopentyl | CH₃ | OCH₃ | CH | |
| CH₃ | H | 0 | CN | cyclopentyl | OCH₃ | OCH₃ | CH | |
| CH₃ | H | 0 | CN | cyclopentyl | CH₃ | CH₃ | N | |
| CH₃ | H | 0 | CN | cyclopentyl | CH₃ | OCH₃ | N | |
| CH₃ | H | 0 | CN | cyclopentyl | OCH₃ | OCH₃ | N | |
| CH₃ | H | 0 | CN | cyclopentyl | Cl | OCH₃ | CH | |
| CH₃ | H | 0 | CN | cyclopropyl | OCH₃ | OCH₂CH₃ | CH | |
| CH₃ | H | 0 | CN | cyclopropyl | cyclopropyl | OCH₃ | CH | |
| CH₃ | H | 0 | CN | cyclopropyl | OCH₃ | CH(OCH₃)₂ | CH | |
| CH₃ | H | 0 | CN | cyclopropyl | NHCH₃ | OCH₂CH₃ | N | |
| CH₃ | H | 0 | CN | cyclopropyl | NHCH₃ | OCH₃ | N | |
| CH₃ | H | 0 | CN | cyclopropyl | OCH₃ | OCH₂CH₃ | N | |
| CH₃ | H | 0 | CN | cyclopropyl | CH₂F | CH₃ | CH | |
| CH₃ | H | 0 | CO₂CH₃ | cyclopropyl | CH₃ | CH₃ | CH | |
| CH₃ | H | 0 | CO₂CH₃ | cyclopropyl | CH₃ | OCH₃ | CH | |
| CH₃ | H | 0 | CO₂CH₃ | cyclopropyl | OCH₃ | OCH₃ | CH | |
| CH₃ | H | 0 | CO₂CH₃ | cyclopropyl | CH₃ | CH₃ | N | |
| CH₃ | H | 0 | CO₂CH₃ | cyclopropyl | CH₃ | OCH₃ | N | |
| CH₃ | H | 0 | CO₂CH₃ | cyclopropyl | OCH₃ | OCH₃ | N | |
| CH₃ | H | 0 | CO₂CH₃ | cyclopropyl | Cl | OCH₃ | CH | |
| CH₃ | H | 0 | CO₂CH₃ | cyclobutyl | CH₃ | CH₃ | CH | |
| CH₃ | H | 0 | CO₂CH₃ | cyclobutyl | CH₃ | OCH₃ | CH | |
| CH₃ | H | 0 | CO₂CH₃ | cyclobutyl | CH₃ | OCH₃ | N | |
| CH₃ | H | 0 | CO₂CH₃ | cyclobutyl | CH₃ | CH₃ | N | |
| CH₃ | H | 0 | CO₂CH₃ | cyclobutyl | OCH₃ | OCH₃ | N | |
| CH₃ | H | 0 | CO₂CH₃ | cyclobutyl | Cl | OCH₃ | CH | |
| CH₃ | H | 0 | CO₂CH₃ | cyclopentyl | CH₃ | CH₃ | CH | |
| CH₃ | H | 0 | CO₂CH₃ | cyclopentyl | CH₃ | OCH₃ | CH | |
| CH₃ | H | 0 | CO₂CH₃ | cyclopentyl | OCH₃ | OCH₃ | CH | |
| CH₃ | H | 0 | CO₂CH₃ | cyclopentyl | CH₃ | CH₃ | N | |
| CH₃ | H | 0 | CO₂CH₃ | cyclopentyl | CH₃ | OCH₃ | N | |
| CH₃ | H | 0 | CO₂CH₃ | cyclopentyl | OCH₃ | OCH₃ | N | |
| CH₃ | H | 0 | CO₂CH₃ | cyclopentyl | Cl | OCH₃ | CH | |
| CH₃ | H | 0 | CO₂CH₃ | cyclopropyl | OCH₃ | OCH₂CH₃ | CH | |
| CH₃ | H | 0 | CO₂CH₃ | cyclopropyl | cyclopropyl | OCH₃ | CH | |
| CH₃ | H | 0 | CO₂CH₃ | cyclopropyl | OCH₃ | CH(OCH₃)₂ | CH | |
| CH₃ | H | 0 | CO₂CH₃ | cyclopropyl | NHCH₃ | OCH₂CH₃ | N | |
| CH₃ | H | 0 | CO₂CH₃ | cyclopropyl | NHCH₃ | OCH₃ | N | |
| CH₃ | H | 0 | CO₂CH₃ | cyclopropyl | OCH₃ | OCH₂CH₃ | N | |
| CH₃ | H | 0 | CO₂CH₃ | cyclopropyl | CH₂F | CH₃ | CH | |

TABLE I-continued

| R | R₁ | n | R₂ | R' | X | Y | Z | m.p. (°C.) |
|---|----|---|----|----|---|---|---|-----------|
| CH₃ | H | 0 | N(CH₃)₂ | cyclopropyl | CH₃ | CH₃ | CH | |
| CH₃ | H | 0 | N(CH₃)₂ | cyclopropyl | CH₃ | OCH₃ | CH | |
| CH₃ | H | 0 | N(CH₃)₂ | cyclopropyl | OCH₃ | OCH₃ | CH | |
| CH₃ | H | 0 | N(CH₃)₂ | cyclopropyl | CH₃ | CH₃ | N | |
| CH₃ | H | 0 | N(CH₃)₂ | cyclopropyl | CH₃ | OCH | N | |
| CH₃ | H | 0 | N(CH₃)₂ | cyclopropyl | OCH₃ | OCH₃ | N | |
| CH₃ | H | 0 | N(CH₃)₂ | cyclopropyl | Cl | OCH₃ | CH | |
| CH₃ | H | 0 | N(CH₃)₂ | cyclobutyl | CH₃ | CH₃ | CH | |
| CH₃ | H | 0 | N(CH₃)₂ | cyclobutyl | CH₃ | OCH₃ | CH | |
| CH₃ | H | 0 | N(CH₃)₂ | cyclobutyl | OCH₃ | OCH₃ | CH | |
| CH₃ | H | 0 | N(CH₃)₂ | cyclobutyl | CH₃ | CH₃ | N | |
| CH₃ | H | 0 | N(CH₃)₂ | cyclobutyl | CH₃ | OCH₃ | N | |
| CH₃ | H | 0 | N(CH₃)₂ | cyclobutyl | OCH₃ | OCH₃ | N | |
| CH₃ | H | 0 | N(CH₃)₂ | cyclobutyl | Cl | OCH₃ | CH | |
| CH₃ | H | 0 | N(CH₃)₂ | cyclopentyl | CH₃ | CH₃ | CH | |
| CH₃ | H | 0 | N(CH₃)₂ | cyclopentyl | CH₃ | OCH₃ | CH | |
| CH₃ | H | 0 | N(CH₃)₂ | cyclopentyl | OCH₃ | OCH₃ | CH | |
| CH₃ | H | 0 | N(CH₃)₂ | cyclopentyl | CH₃ | CH₃ | N | |
| CH₃ | H | 0 | N(CH₃)₂ | cyclopentyl | CH₃ | OCH₃ | N | |
| CH₃ | H | 0 | N(CH₃)₂ | cyclopentyl | OCH₃ | OCH₃ | N | |
| CH₃ | H | 0 | N(CH₃)₂ | cyclopentyl | Cl | OCH₃ | CH | |
| CH₃ | H | 0 | N(CH₃)₂ | cyclopropyl | OCH₃ | OCH₂CH₃ | CH | |
| CH₃ | H | 0 | N(CH₃)₂ | cyclopropyl | cyclopropyl | OCH₃ | CH | |
| CH₃ | H | 0 | N(CH₃)₂ | cyclopropyl | OCH₃ | CH(OCH₃)₂ | CH | |
| CH₃ | H | 0 | N(CH₃)₂ | cyclopropyl | NHCH₃ | OCH₂CH₃ | N | |
| CH₃ | H | 0 | N(CH₃)₂ | cyclopropyl | NHCH₃ | OCH₃ | N | |
| CH₃ | H | 0 | N(CH₃)₂ | cyclopropyl | OCH₃ | OCH₂CH₃ | N | |
| CH₃ | H | 0 | N(CH₃)₂ | cyclopropyl | CH₂F | CH₃ | CH | |
| CH₃ | H | 0 | CH₂CN | cyclopropyl | CH₃ | CH₃ | CH | |
| CH₃ | H | 0 | CH₂CN | cyclopropyl | CH₃ | OCH₃ | CH | |
| CH₃ | H | 0 | CH₂CN | cyclopropyl | OCH₃ | OCH₃ | CH | |
| CH₃ | H | 0 | CH₂CN | cyclopropyl | CH₃ | CH₃ | N | |
| CH₃ | H | 0 | CH₂CN | cyclopropyl | CH₃ | OCH₃ | N | |
| CH₃ | H | 0 | CH₂CN | cyclopropyl | OCH₃ | OCH₃ | N | |
| CH₃ | H | 0 | CH₂CN | cyclopropyl | Cl | OCH₃ | CH | |
| CH₃ | H | 0 | CH₂CN | cyclobutyl | CH₃ | CH₃ | CH | |
| CH₃ | H | 0 | CH₂CN | cyclobutyl | CH₃ | OCH₃ | CH | |
| CH₃ | H | 0 | CH₂CN | cyclobutyl | OCH₃ | OCH₃ | CH | |
| CH₃ | H | 0 | CH₂CN | cyclobutyl | CH₃ | CH₃ | N | |
| CH₃ | H | 0 | CH₂CN | cyclobutyl | CH₃ | OCH₃ | N | |
| CH₃ | H | 0 | CH₂CN | cyclobutyl | OCH₃ | OCH₃ | N | |
| CH₃ | H | 0 | CH₂CN | cyclobutyl | Cl | OCH₃ | CH | |
| CH₃ | H | 0 | CH₂CN | cyclopentyl | CH₃ | CH₃ | CH | |
| CH₃ | H | 0 | CH₂CN | cyclopentyl | CH₃ | OCH₃ | CH | |
| CH₃ | H | 0 | CH₂CN | cyclopentyl | OCH₃ | OCH₃ | CH | |
| CH₃ | H | 0 | CH₂CN | cyclopentyl | CH₃ | CH₃ | N | |
| CH₃ | H | 0 | CH₂CN | cyclopentyl | CH₃ | OCH₃ | N | |
| CH₃ | H | 0 | CH₂CN | cyclopentyl | OCH₃ | OCH₃ | N | |
| CH₃ | H | 0 | CH₂CN | cyclopentyl | Cl | OCH₃ | CH | |
| CH₃ | H | 0 | CH₂CN | cyclopropyl | OCH₃ | OCH₂CH₃ | CH | |
| CH₃ | H | 0 | CH₂CN | cyclopropyl | cyclopropyl | OCH₃ | CH | |
| CH₃ | H | 0 | CH₂CN | cyclopropyl | OCH₃ | CH(OCH₃)₂ | CH | |
| CH₃ | H | 0 | CH₂CN | cyclopropyl | NHCH₃ | OCH₂CH₃ | N | |
| CH₃ | H | 0 | CH₂CN | cyclopropyl | NHCH₃ | OCH₃ | N | |
| CH₃ | H | 0 | CH₂CN | cyclopropyl | OCH₃ | OCH₂CH₃ | N | |
| CH₃ | H | 0 | CH₂CN | cyclopropyl | CH₂F | CH₃ | CH | |
| CH₃ | H | 0 | CH₂OCH₃ | cyclopropyl | CH₃ | CH₃ | CH | |
| CH₃ | H | 0 | CH₂OCH₃ | cyclopropyl | CH₃ | OCH₃ | CH | |
| CH₃ | H | 0 | CH₂OCH₃ | cyclopropyl | OCH₃ | OCH₃ | CH | |
| CH₃ | H | 0 | CH₂OCH₃ | cyclopropyl | CH₃ | CH₃ | N | |
| CH₃ | H | 0 | CH₂OCH₃ | cyclopropyl | CH₃ | OCH₃ | N | |
| CH₃ | H | 0 | CH₂OCH₃ | cyclopropyl | OCH₃ | OCH₃ | N | |
| CH₃ | H | 0 | CH₂OCH₃ | cyclopropyl | Cl | OCH₃ | CH | |
| CH₃ | H | 0 | CH₂OCH₃ | cyclobutyl | CH₃ | CH₃ | CH | |
| CH₃ | H | 0 | CH₂OCH₃ | cyclobutyl | CH₃ | OCH₃ | CH | |
| CH₃ | H | 0 | CH₂OCH₃ | cyclobutyl | OCH₃ | OCH₃ | CH | |
| CH₃ | H | 0 | CH₂OCH₃ | cyclobutyl | CH₃ | CH₃ | N | |
| CH₃ | H | 0 | CH₂OCH₃ | cyclobutyl | CH₃ | OCH₃ | N | |
| CH₃ | H | 0 | CH₂OCH₃ | cyclobutyl | OCH₃ | OCH₃ | N | |
| CH₃ | H | 0 | CH₂OCH₃ | cyclobutyl | Cl | OCH₃ | CH | |
| CH₃ | H | 0 | CH₂OCH₃ | cyclopentyl | CH₃ | CH₃ | CH | |
| CH₃ | H | 0 | CH₂OCH₃ | cyclopentyl | CH₃ | OCH₃ | CH | |
| CH₃ | H | 0 | CH₂OCH₃ | cyclopentyl | OCH₃ | OCH₃ | CH | |
| CH₃ | H | 0 | CH₂OCH₃ | cyclopentyl | CH₃ | CH₃ | N | |
| CH₃ | H | 0 | CH₂OCH₃ | cyclopentyl | CH₃ | OCH₃ | N | |
| CH₃ | H | 0 | CH₂OCH₃ | cyclopentyl | OCH₃ | OCH₃ | N | |
| CH₃ | H | 0 | CH₂OCH₃ | cyclopentyl | Cl | OCH₃ | CH | |
| CH₃ | H | 0 | CH₂OCH₃ | cyclopropyl | OCH₃ | OCH₂CH₃ | CH | |
| CH₃ | H | 0 | CH₂OCH₃ | cyclopropyl | cyclopropyl | OCH₃ | CH | |
| CH₃ | H | 0 | CH₂OCH₃ | cyclopropyl | OCH₃ | CH(OCH₃)₂ | CH | |
| CH₃ | H | 0 | CH₂OCH₃ | cyclopropyl | NHCH₃ | OCH₂CH₃ | N | |

TABLE I-continued

| R | R$_1$ | n | R$_2$ | R' | X | Y | Z | m.p. (°C.) |
|---|---|---|---|---|---|---|---|---|
| CH$_3$ | H | 0 | CH$_2$OCH$_3$ | cyclopropyl | NHCH$_3$ | OCH$_3$ | N | |
| CH$_3$ | H | 0 | CH$_2$OCH$_3$ | cyclopropyl | OCH$_3$ | OCH$_2$CH$_3$ | N | |
| CH$_3$ | H | 0 | CH$_2$OCH$_3$ | cyclopropyl | CH$_2$F | CH$_3$ | CH | |
| CH$_3$ | H | 0 | CH(OH)CH$_3$ | cyclopropyl | CH$_3$ | CH$_3$ | CH | |
| CH$_3$ | H | 0 | CH(OH)CH$_3$ | cyclopropyl | CH$_3$ | OCH$_3$ | CH | |
| CH$_3$ | H | 0 | CH(OH)CH$_3$ | cyclopropyl | OCH$_3$ | OCH$_3$ | CH | |
| CH$_3$ | H | 0 | CH(OH)CH$_3$ | cyclopropyl | CH$_3$ | CH$_3$ | N | |
| CH$_3$ | H | 0 | CH(OH)CH$_3$ | cyclopropyl | CH$_3$ | OCH$_3$ | N | |
| CH$_3$ | H | 0 | CH(OH)CH$_3$ | cyclopropyl | OCH$_3$ | OCH$_3$ | N | |
| CH$_3$ | H | 0 | CH(OH)CH$_3$ | cyclopropyl | Cl | OCH$_3$ | CH | |
| CH$_3$ | H | 0 | CH(OH)CH$_3$ | cyclobutyl | CH$_3$ | CH$_3$ | CH | |
| CH$_3$ | H | 0 | CH(OH)CH$_3$ | cyclobutyl | CH$_3$ | OCH$_3$ | CH | |
| CH$_3$ | H | 0 | CH(OH)CH$_3$ | cyclobutyl | OCH$_3$ | OCH$_3$ | CH | |
| CH$_3$ | H | 0 | CH(OH)CH$_3$ | cyclobutyl | CH$_3$ | CH$_3$ | N | |
| CH$_3$ | H | 0 | CH(OH)CH$_3$ | cyclobutyl | CH$_3$ | OCH$_3$ | N | |
| CH$_3$ | H | 0 | CH(OH)CH$_3$ | cyclobutyl | OCH$_3$ | OCH$_3$ | N | |
| CH$_3$ | H | 0 | CH(OH)CH$_3$ | cyclobutyl | Cl | OCH$_3$ | CH | |
| CH$_3$ | H | 0 | CH(OH)CH$_3$ | cyclopentyl | CH$_3$ | CH$_3$ | CH | |
| CH$_3$ | H | 0 | CH(OH)CH$_3$ | cyclopentyl | CH$_3$ | OCH$_3$ | CH | |
| CH$_3$ | H | 0 | CH(OH)CH$_3$ | cyclopentyl | OCH$_3$ | OCH$_3$ | CH | |
| CH$_3$ | H | 0 | CH(OH)CH$_3$ | cyclopentyl | CH$_3$ | CH$_3$ | N | |
| CH$_3$ | H | 0 | CH(OH)CH$_3$ | cyclopentyl | CH$_3$ | OCH$_3$ | N | |
| CH$_3$ | H | 0 | CH(OH)CH$_3$ | cyclopentyl | OCH$_3$ | OCH$_3$ | N | |
| CH$_3$ | H | 0 | CH(OH)CH$_3$ | cyclopentyl | Cl | OCH$_3$ | CH | |
| CH$_3$ | H | 0 | CH(OH)CH$_3$ | cyclopropyl | OCH$_3$ | OCH$_2$CH$_3$ | CH | |
| CH$_3$ | H | 0 | CH(OH)CH$_3$ | cyclopropyl | cyclopropyl | OCH$_3$ | CH | |
| CH$_3$ | H | 0 | CH(OH)CH$_3$ | cyclopropyl | OCH$_3$ | CH(OCH$_3$)$_2$ | CH | |
| CH$_3$ | H | 0 | CH(OH)CH$_3$ | cyclopropyl | NHCH$_3$ | OCH$_2$CH$_3$ | N | |
| CH$_3$ | H | 0 | CH(OH)CH$_3$ | cyclopropyl | NHCH$_3$ | OCH$_3$ | N | |
| CH$_3$ | H | 0 | CH(OH)CH$_3$ | cyclopropyl | OCH$_3$ | OCH$_2$CH$_3$ | N | |
| CH$_3$ | H | 0 | CH(OH)CH$_3$ | cyclopropyl | CH$_2$F | CH$_3$ | CH | |
| CH$_2$CH$_3$ | H | 0 | H | cyclopropyl | CH$_3$ | CH$_3$ | CH | |
| CH$_2$CH$_3$ | H | 0 | H | cyclopropyl | CH$_3$ | OCH$_3$ | CH | |
| CH$_2$CH$_3$ | H | 0 | H | cyclopropyl | OCH$_3$ | OCH$_3$ | CH | |
| CH$_2$CH$_3$ | H | 0 | H | cyclopropyl | CH$_3$ | CH$_3$ | N | |
| CH$_2$CH$_3$ | H | 0 | H | cyclopropyl | CH$_3$ | OCH$_3$ | N | |
| CH$_2$CH$_3$ | H | 0 | H | cyclopropyl | OCH$_3$ | OCH$_3$ | N | |
| CH$_2$CH$_3$ | H | 0 | H | cyclopropyl | Cl | OCH$_3$ | CH | |
| CH$_2$CH$_3$ | H | 0 | H | cyclobutyl | CH$_3$ | CH$_3$ | CH | |
| CH$_2$CH$_3$ | H | 0 | H | cyclobutyl | CH$_3$ | OCH$_3$ | CH | |
| CH$_2$CH$_3$ | H | 0 | H | cyclobutyl | OCH$_3$ | OCH$_3$ | CH | |
| CH$_2$CH$_3$ | H | 0 | H | cyclobutyl | CH$_3$ | CH$_3$ | N | |
| CH$_2$CH$_3$ | H | 0 | H | cyclobutyl | CH$_3$ | OCH$_3$ | N | |
| CH$_2$CH$_3$ | H | 0 | H | cyclobutyl | OCH$_3$ | OCH$_3$ | N | |
| CH$_2$CH$_3$ | H | 0 | H | cyclobutyl | Cl | OCH$_3$ | CH | |
| CH$_2$CH$_3$ | H | 0 | H | cyclopentyl | CH$_3$ | CH$_3$ | CH | |
| CH$_2$CH$_3$ | H | 0 | H | cyclopentyl | CH$_3$ | OCH$_3$ | CH | |
| CH$_2$CH$_3$ | H | 0 | H | cyclopentyl | OCH$_3$ | OCH$_3$ | CH | |
| CH$_2$CH$_3$ | H | 0 | H | cyclopentyl | CH$_3$ | CH$_3$ | N | |
| CH$_2$CH$_3$ | H | 0 | H | cyclopentyl | CH$_3$ | OCH$_3$ | N | |
| CH$_2$CH$_3$ | H | 0 | H | cyclopentyl | OCH$_3$ | OCH$_3$ | N | |
| CH$_2$CH$_3$ | H | 0 | H | cyclopentyl | Cl | OCH$_3$ | CH | |
| CH$_2$CH$_3$ | H | 0 | H | cyclopropyl | OCH$_3$ | OCH$_2$CH$_3$ | CH | |
| CH$_2$CH$_3$ | H | 0 | H | cyclopropyl | cyclopropyl | OCH$_3$ | CH | |
| CH$_2$CH$_3$ | H | 0 | H | cyclopropyl | OCH$_3$ | CH(OCH$_3$)$_2$ | CH | |
| CH$_2$CH$_3$ | H | 0 | H | cyclopropyl | NHCH$_3$ | OCH$_2$CH$_3$ | N | |
| CH$_2$CH$_3$ | H | 0 | H | cyclopropyl | NHCH$_3$ | OCH$_3$ | N | |
| CH$_2$CH$_3$ | H | 0 | H | cyclopropyl | OCH$_3$ | OCH$_2$CH$_3$ | N | |
| CH$_2$CH$_3$ | H | 0 | H | cyclopropyl | CH$_2$F | CH$_3$ | CH | |
| Ph | H | 0 | H | cyclopropyl | CH$_3$ | CH$_3$ | CH | |
| Ph | H | 0 | H | cyclopropyl | CH$_3$ | OCH$_3$ | CH | |
| Ph | H | 0 | H | cyclopropyl | OCH$_3$ | OCH$_3$ | CH | |
| Ph | H | 0 | H | cyclopropyl | CH$_3$ | CH$_3$ | N | |
| Ph | H | 0 | H | cyclopropyl | CH$_3$ | OCH$_3$ | N | |
| Ph | H | 0 | H | cyclopropyl | OCH$_3$ | OCH$_3$ | N | |
| Ph | H | 0 | H | cyclopropyl | Cl | OCH$_3$ | CH | |
| Ph | H | 0 | H | cyclobutyl | CH$_3$ | CH$_3$ | CH | |
| Ph | H | 0 | H | cyclobutyl | CH$_3$ | OCH$_3$ | CH | |
| Ph | H | 0 | H | cyclobutyl | OCH$_3$ | OCH$_3$ | CH | |
| Ph | H | 0 | H | cyclobutyl | CH$_3$ | CH$_3$ | N | |
| Ph | H | 0 | H | cyclobutyl | CH$_3$ | OCH$_3$ | N | |
| Ph | H | 0 | H | cyclobutyl | OCH$_3$ | OCH$_3$ | N | |
| Ph | H | 0 | H | cyclobutyl | Cl | OCH$_3$ | CH | |
| Ph | H | 0 | H | cyclopentyl | CH$_3$ | CH$_3$ | CH | |
| Ph | H | 0 | H | cyclopentyl | CH$_3$ | OCH$_3$ | CH | |
| Ph | H | 0 | H | cyclopentyl | OCH$_3$ | OCH$_3$ | CH | |
| Ph | H | 0 | H | cyclopentyl | CH$_3$ | CH$_3$ | N | |
| Ph | H | 0 | H | cyclopentyl | CH$_3$ | OCH$_3$ | N | |
| Ph | H | 0 | H | cyclopentyl | OCH$_3$ | OCH$_3$ | N | |
| Ph | H | 0 | H | cyclopentyl | Cl | OCH$_3$ | CH | |
| Ph | H | 0 | H | cyclopropyl | OCH$_3$ | OCH$_2$CH$_3$ | CH | |

TABLE I-continued

| R | $R_1$ | n | $R_2$ | R' | X | Y | Z | m.p. (°C.) |
|---|---|---|---|---|---|---|---|---|
| Ph | H | 0 | H | cyclopropyl | cyclopropyl | $OCH_3$ | CH | |
| Ph | H | 0 | H | cyclopropyl | $OCH_3$ | $CH(OCH_3)_2$ | CH | |
| Ph | H | 0 | H | cyclopropyl | $NHCH_3$ | $OCH_2CH_3$ | N | |
| Ph | H | 0 | H | cyclopropyl | $NHCH_3$ | $OCH_3$ | N | |
| Ph | H | 0 | H | cyclopropyl | $OCH_3$ | $OCH_2CH_3$ | N | |
| Ph | H | 0 | H | cyclopropyl | $CH_2F$ | $CH_3$ | CH | |
| $CO_2CH_3$ | H | 0 | H | cyclopropyl | $CH_3$ | $CH_3$ | CH | |
| $CO_2CH_3$ | H | 0 | H | cyclopropyl | $CH_3$ | $OCH_3$ | CH | |
| $CO_2CH_3$ | H | 0 | H | cyclopropyl | $OCH_3$ | $OCH_3$ | CH | |
| $CO_2CH_3$ | H | 0 | H | cyclopropyl | $CH_3$ | $CH_3$ | N | |
| $CO_2CH_3$ | H | 0 | H | cyclopropyl | $CH_3$ | $OCH_3$ | N | |
| $CO_2CH_3$ | H | 0 | H | cyclopropyl | $OCH_3$ | $OCH_3$ | N | |
| $CO_2CH_3$ | H | 0 | H | cyclopropyl | Cl | $OCH_3$ | CH | |
| $CO_2CH_3$ | H | 0 | H | cyclobutyl | $CH_3$ | $CH_3$ | CH | |
| $CO_2CH_3$ | H | 0 | H | cyclobutyl | $CH_3$ | $OCH_3$ | CH | |
| $CO_2CH_3$ | H | 0 | H | cyclobutyl | $OCH_3$ | $OCH_3$ | CH | |
| $CO_2CH_3$ | H | 0 | H | cyclobutyl | $CH_3$ | $CH_3$ | N | |
| $CO_2CH_3$ | H | 0 | H | cyclobutyl | $CH_3$ | $OCH_3$ | N | |
| $CO_2CH_3$ | H | 0 | H | cyclobutyl | $OCH_3$ | $OCH_3$ | N | |
| $CO_2CH_3$ | H | 0 | H | cyclobutyl | Cl | $OCH_3$ | CH | |
| $CO_2CH_3$ | H | 0 | H | cyclopentyl | $CH_3$ | $CH_3$ | CH | |
| $CO_2CH_3$ | H | 0 | H | cyclopentyl | $CH_3$ | $OCH_3$ | CH | |
| $CO_2CH_3$ | H | 0 | H | cyclopentyl | $OCH_3$ | $OCH_3$ | CH | |
| $CO_2CH_3$ | H | 0 | H | cyclopentyl | $CH_3$ | $CH_3$ | N | |
| $CO_2CH_3$ | H | 0 | H | cyclopentyl | $CH_3$ | $OCH_3$ | N | |
| $CO_2CH_3$ | H | 0 | H | cyclopentyl | $OCH_3$ | $OCH_3$ | N | |
| $CO_2CH_3$ | H | 0 | H | cyclopentyl | Cl | $OCH_3$ | CH | |
| $CO_2CH_3$ | H | 0 | H | cyclopropyl | $OCH_3$ | $OCH_2CH_3$ | CH | |
| $CO_2CH_3$ | H | 0 | H | cyclopropyl | cyclopropyl | $OCH_3$ | CH | |
| $CO_2CH_3$ | H | 0 | H | cyclopropyl | $OCH_3$ | $CH(OCH_3)_2$ | CH | |
| $CO_2CH_3$ | H | 0 | H | cyclopropyl | $NHCH_3$ | $OCH_2CH_3$ | N | |
| $CO_2CH_3$ | H | 0 | H | cyclopropyl | $NHCH_3$ | $OCH_3$ | N | |
| $CO_2CH_3$ | H | 0 | H | cyclopropyl | $OCH_3$ | $OCH_2CH_3$ | N | |
| $CO_2CH_3$ | H | 0 | H | cyclopropyl | $CH_2F$ | $CH_3$ | CH | |
| $SO_2N(CH_3)_2$ | H | 0 | H | cyclopropyl | $CH_3$ | $CH_3$ | CH | |
| $SO_2N(CH_3)_2$ | H | 0 | H | cyclopropyl | $CH_3$ | $OCH_3$ | CH | |
| $SO_2N(CH_3)_2$ | H | 0 | H | cyclopropyl | $OCH_3$ | $OCH_3$ | CH | |
| $SO_2N(CH_3)_2$ | H | 0 | H | cyclopropyl | $CH_3$ | $CH_3$ | N | |
| $SO_2N(CH_3)_2$ | H | 0 | H | cyclopropyl | $CH_3$ | $OCH_3$ | N | |
| $SO_2N(CH_3)_2$ | H | 0 | H | cyclopropyl | $OCH_3$ | $OCH_3$ | N | |
| $SO_2N(CH_3)_2$ | H | 0 | H | cyclopropyl | Cl | $OCH_3$ | CH | |
| $SO_2N(CH_3)_2$ | H | 0 | H | cyclobutyl | $CH_3$ | $CH_3$ | CH | |
| $SO_2N(CH_3)_2$ | H | 0 | H | cyclobutyl | $CH_3$ | $OCH_3$ | CH | |
| $SO_2N(CH_3)_2$ | H | 0 | H | cyclobutyl | $OCH_3$ | $OCH_3$ | CH | |
| $SO_2N(CH_3)_2$ | H | 0 | H | cyclobutyl | $CH_3$ | $CH_3$ | N | |
| $SO_2N(CH_3)_2$ | H | 0 | H | cyclobutyl | $CH_3$ | $OCH_3$ | N | |
| $SO_2N(CH_3)_2$ | H | 0 | H | cyclobutyl | $OCH_3$ | $OCH_3$ | N | |
| $SO_2N(CH_3)_2$ | H | 0 | H | cyclobutyl | Cl | $OCH_3$ | CH | |
| $SO_2N(CH_3)_2$ | H | 0 | H | cyclopentyl | $CH_3$ | $CH_3$ | CH | |
| $SO_2N(CH_3)_2$ | H | 0 | H | cyclopentyl | $CH_3$ | $OCH_3$ | CH | |
| $SO_2N(CH_3)_2$ | H | 0 | H | cyclopentyl | $OCH_3$ | $OCH_3$ | CH | |
| $SO_2N(CH_3)_2$ | H | 0 | H | cyclopentyl | $CH_3$ | $CH_3$ | N | |
| $SO_2N(CH_3)_2$ | H | 0 | H | cyclopentyl | $CH_3$ | $OCH_3$ | N | |
| $SO_2N(CH_3)_2$ | H | 0 | H | cyclopentyl | $OCH_3$ | $OCH_3$ | N | |
| $SO_2N(CH_3)_2$ | H | 0 | H | cyclopentyl | Cl | $OCH_3$ | CH | |
| $SO_2N(CH_3)_2$ | H | 0 | H | cyclopropyl | $OCH_3$ | $OCH_2CH_3$ | CH | |
| $SO_2N(CH_3)_2$ | H | 0 | H | cyclopropyl | cyclopropyl | $OCH_3$ | CH | |
| $SO_2N(CH_3)_2$ | H | 0 | H | cyclopropyl | $OCH_3$ | $CH(OCH_3)_2$ | CH | |
| $SO_2N(CH_3)_2$ | H | 0 | H | cyclopropyl | $NHCH_3$ | $OCH_2CH_3$ | N | |
| $SO_2N(CH_3)_2$ | H | 0 | H | cyclopropyl | $NHCH_3$ | $OCH_3$ | N | |
| $SO_2N(CH_3)_2$ | H | 0 | H | cyclopropyl | $OCH_3$ | $OCH_2CH_3$ | N | |
| $SO_2N(CH_3)_2$ | H | 0 | H | cyclopropyl | $CH_2F$ | $CH_3$ | CH | |
| $CH_2F$ | H | 0 | H | cyclopropyl | $CH_3$ | $CH_3$ | CH | |
| $CH_2F$ | H | 0 | H | cyclopropyl | $CH_3$ | $OCH_3$ | CH | |
| $CH_2F$ | H | 0 | H | cyclopropyl | $OCH_3$ | $OCH_3$ | CH | |
| $CH_2F$ | H | 0 | H | cyclopropyl | $CH_3$ | $CH_3$ | N | |
| $CH_2F$ | H | 0 | H | cyclopropyl | $CH_3$ | $OCH_3$ | N | |
| $CH_2F$ | H | 0 | H | cyclopropyl | $OCH_3$ | $OCH_3$ | N | |
| $CH_2F$ | H | 0 | H | cyclopropyl | Cl | $OCH_3$ | CH | |
| $CH_2F$ | H | 0 | H | cyclobutyl | $CH_3$ | $CH_3$ | CH | |
| $CH_2F$ | H | 0 | H | cyclobutyl | $CH_3$ | $OCH_3$ | CH | |
| $CH_2F$ | H | 0 | H | cyclobutyl | $OCH_3$ | $OCH_3$ | CH | |
| $CH_2F$ | H | 0 | H | cyclobutyl | $CH_3$ | $CH_3$ | N | |
| $CH_2F$ | H | 0 | H | cyclobutyl | $CH_3$ | $OCH_3$ | N | |
| $CH_2F$ | H | 0 | H | cyclobutyl | $OCH_3$ | $OCH_3$ | N | |
| $CH_2F$ | H | 0 | H | cyclobutyl | Cl | $OCH_3$ | CH | |
| $CH_2F$ | H | 0 | H | cyclopentyl | $CH_3$ | $CH_3$ | CH | |
| $CH_2F$ | H | 0 | H | cyclopentyl | $CH_3$ | $OCH_3$ | CH | |
| $CH_2F$ | H | 0 | H | cyclopentyl | $OCH_3$ | $OCH_3$ | CH | |
| $CH_2F$ | H | 0 | H | cyclopentyl | $CH_3$ | $CH_3$ | N | |
| $CH_2F$ | H | 0 | H | cyclopentyl | $CH_3$ | $OCH_3$ | N | |

TABLE I-continued

| R | R₁ | n | R₂ | R' | X | Y | Z | m.p. (°C.) |
|---|---|---|---|---|---|---|---|---|
| CH₂F | H | 0 | H | cyclopentyl | OCH₃ | OCH₃ | N | |
| CH₂F | H | 0 | H | cyclopentyl | Cl | OCH₃ | CH | |
| CH₂F | H | 0 | H | cyclopropyl | OCH₃ | OCH₂CH₃ | CH | |
| CH₂F | H | 0 | H | cyclopropyl | cyclopropyl | OCH₃ | CH | |
| CH₂F | H | 0 | H | cyclopropyl | OCH₃ | CH(OCH₃)₂ | CH | |
| CH₂F | H | 0 | H | cyclopropyl | NHCH₃ | OCH₂CH₃ | N | |
| CH₂F | H | 0 | H | cyclopropyl | NHCH₃ | OCH₃ | N | |
| CH₂F | H | 0 | H | cyclopropyl | OCH₃ | OCH₂CH₃ | N | |
| CH₂F | H | 0 | H | cyclopropyl | CH₂F | CH₃ | CH | |
| CH₂CH=CH₂ | H | 0 | H | cyclopropyl | CH₃ | CH₃ | CH | |
| CH₂CH=CH₂ | H | 0 | H | cyclopropyl | CH₃ | OCH₃ | CH | |
| CH₂CH=CH₂ | H | 0 | H | cyclopropyl | OCH₃ | OCH₃ | CH | |
| CH₂CH=CH₂ | H | 0 | H | cyclopropyl | CH₃ | CH₃ | N | |
| CH₂CH=CH₂ | H | 0 | H | cyclopropyl | CH₃ | OCH₃ | N | |
| CH₂CH=CH₂ | H | 0 | H | cyclopropyl | OCH₃ | OCH₃ | N | |
| CH₂CH=CH₂ | H | 0 | H | cyclopropyl | Cl | OCH₃ | CH | |
| CH₂CH=CH₂ | H | 0 | H | cyclobutyl | CH₃ | CH₃ | CH | |
| CH₂CH=CH₂ | H | 0 | H | cyclobutyl | CH₃ | OCH₃ | CH | |
| CH₂CH=CH₂ | H | 0 | H | cyclobutyl | OCH₃ | OCH₃ | CH | |
| CH₂CH=CH₂ | H | 0 | H | cyclobutyl | CH₃ | CH₃ | N | |
| CH₂CH=CH₂ | H | 0 | H | cyclobutyl | CH₃ | OCH₃ | N | |
| CH₂CH=CH₂ | H | 0 | H | cyclobutyl | OCH₃ | OCH₃ | N | |
| CH₂CH=CH₂ | H | 0 | H | cyclobutyl | Cl | OCH₃ | CH | |
| CH₂CH=CH₂ | H | 0 | H | cyclopentyl | CH₃ | CH₃ | CH | |
| CH₂CH=CH₂ | H | 0 | H | cyclopentyl | CH₃ | OCH₃ | CH | |
| CH₂CH=CH₂ | H | 0 | H | cyclopentyl | OCH₃ | OCH₃ | CH | |
| CH₂CH=CH₂ | H | 0 | H | cyclopentyl | CH₃ | CH₃ | N | |
| CH₂CH=CH₂ | H | 0 | H | cyclopentyl | CH₃ | OCH₃ | N | |
| CH₂CH=CH₂ | H | 0 | H | cyclopentyl | OCH₃ | OCH₃ | N | |
| CH₂CH=CH₂ | H | 0 | H | cyclopentyl | Cl | OCH₃ | CH | |
| CH₂CH=CH₂ | H | 0 | H | cyclopropyl | OCH₃ | OCH₂CH₃ | CH | |
| CH₂CH=CH₂ | H | 0 | H | cyclopropyl | cyclopropyl | OCH₃ | CH | |
| CH₂CH=CH₂ | H | 0 | H | cyclopropyl | OCH₃ | CH(OCH₃)₂ | CH | |
| CH₂CH=CH₂ | H | 0 | H | cyclopropyl | NHCH₃ | OCH₂CH₃ | N | |
| CH₂CH=CH₂ | H | 0 | H | cyclopropyl | NHCH₃ | OCH₃ | N | |
| CH₂CH=CH₂ | H | 0 | H | cyclopropyl | OCH₃ | OCH₂CH₃ | N | |
| CH₂CH=CH₂ | H | 0 | H | cyclopropyl | CH₂F | CH₃ | CH | |
| CH₂C≡CH | H | 0 | H | cyclopropyl | CH₃ | CH₃ | CH | |
| CH₂C≡CH | H | 0 | H | cyclopropyl | CH₃ | OCH₃ | CH | |
| CH₂C≡CH | H | 0 | H | cyclopropyl | OCH₃ | OCH₃ | CH | |
| CH₂C≡CH | H | 0 | H | cyclopropyl | CH₃ | CH₃ | N | |
| CH₂C≡CH | H | 0 | H | cyclopropyl | CH₃ | OCH₃ | N | |
| CH₂C≡CH | H | 0 | H | cyclopropyl | OCH₃ | OCH₃ | N | |
| CH₂C≡CH | H | 0 | H | cyclopropyl | Cl | OCH₃ | CH | |
| CH₂C≡CH | H | 0 | H | cyclobutyl | CH₃ | CH₃ | CH | |
| CH₂C≡CH | H | 0 | H | cyclobutyl | CH₃ | OCH₃ | CH | |
| CH₂C≡CH | H | 0 | H | cyclobutyl | OCH₃ | OCH₃ | CH | |
| CH₂C≡CH | H | 0 | H | cyclobutyl | CH₃ | CH₃ | N | |
| CH₂C≡CH | H | 0 | H | cyclobutyl | CH₃ | OCH₃ | N | |
| CH₂C≡CH | H | 0 | H | cyclobutyl | OCH₃ | OCH₃ | N | |
| CH₂C≡CH | H | 0 | H | cyclobutyl | Cl | OCH₃ | CH | |
| CH₂=CH | H | 0 | H | cyclopentyl | CH₃ | CH₃ | CH | |
| CH₂C≡CH | H | 0 | H | cyclopentyl | CH₃ | OCH₃ | CH | |
| CH₂C≡CH | H | 0 | H | cyclopentyl | OCH₃ | OCH₃ | CH | |
| CH₂C≡CH | H | 0 | H | cyclopentyl | CH₃ | CH₃ | N | |
| CH₂C≡CH | H | 0 | H | cyclopentyl | CH₃ | OCH₃ | N | |
| CH₂C≡CH | H | 0 | H | cyclopentyl | OCH₃ | OCH₃ | N | |
| CH₂C≡CH | H | 0 | H | cyclopentyl | Cl | OCH₃ | CH | |
| CH₂C≡CH | H | 0 | H | cyclopropyl | OCH₃ | OCH₂CH₃ | CH | |
| CH₂C≡CH | H | 0 | H | cyclopropyl | cyclopropyl | OCH₃ | CH | |
| CH₂C≡CH | H | 0 | H | cyclopropyl | OCH₃ | CH(OCH₃)₂ | CH | |
| CH₂C≡CH | H | 0 | H | cyclopropyl | NHCH₃ | OCH₂CH₃ | N | |
| CH₂C≡CH | H | 0 | H | cyclopropyl | NHCH₃ | OCH₃ | N | |
| CH₂C≡CH | H | 0 | H | cyclopropyl | OCH₃ | OCH₂CH₃ | N | |
| CH₂C≡CH | H | 0 | H | cyclopropyl | CH₂F | CH₃ | CH | |
| H | H | 0 | Cl | cyclopropyl | CH₃ | CH₃ | CH | |
| H | H | 0 | Cl | cyclopropyl | CH₃ | OCH₃ | CH | |
| H | H | 0 | Cl | cyclopropyl | OCH₃ | OCH₃ | CH | |
| H | H | 0 | Cl | cyclopropyl | CH₃ | CH₃ | N | |
| H | H | 0 | Cl | cyclopropyl | CH₃ | OCH₃ | N | |
| H | H | 0 | Cl | cyclopropyl | OCH₃ | OCH₃ | N | |
| H | H | 0 | Cl | cyclopropyl | Cl | OCH₃ | CH | |
| H | H | 0 | Cl | cyclobutyl | CH₃ | CH₃ | CH | |
| H | H | 0 | Cl | cyclobutyl | CH₃ | OCH₃ | CH | |
| H | H | 0 | Cl | cyclobutyl | OCH₃ | OCH₃ | CH | |
| H | H | 0 | Cl | cyclobutyl | CH₃ | CH₃ | N | |
| H | H | 0 | Cl | cyclobutyl | CH₃ | OCH₃ | N | |
| H | H | 0 | Cl | cyclobutyl | OCH₃ | OCH₃ | N | |
| H | H | 0 | Cl | cyclobutyl | Cl | OCH₃ | CH | |
| H | H | 0 | Cl | cyclopentyl | CH₃ | CH₃ | CH | |
| H | H | 0 | Cl | cyclopentyl | CH₃ | OCH₃ | CH | |

TABLE I-continued

| R | R$_1$ | n | R$_2$ | R' | X | Y | Z | m.p. (°C.) |
|---|---|---|---|---|---|---|---|---|
| H | H | 0 | Cl | cyclopentyl | OCH$_3$ | OCH$_3$ | CH | |
| H | H | 0 | Cl | cyclopentyl | CH$_3$ | CH$_3$ | N | |
| H | H | 0 | Cl | cyclopentyl | CH$_3$ | OCH$_3$ | N | |
| H | H | 0 | Cl | cyclopentyl | OCH$_3$ | OCH$_3$ | N | |
| H | H | 0 | Cl | cyclopentyl | Cl | OCH$_3$ | CH | |
| H | H | 0 | Cl | cyclopropyl | OCH$_3$ | OCH$_2$CH$_3$ | CH | |
| H | H | 0 | Cl | cyclopropyl | cyclopropyl | OCH$_3$ | CH | |
| H | H | 0 | Cl | cyclopropyl | OCH$_3$ | CH(OCH$_3$)$_2$ | CH | |
| H | H | 0 | Cl | cyclopropyl | NHCH$_3$ | OCH$_2$CH$_3$ | N | |
| H | H | 0 | Cl | cyclopropyl | NHCH$_3$ | OCH$_3$ | N | |
| H | H | 0 | Cl | cyclopropyl | OCH$_3$ | OCH$_2$CH$_3$ | N | |
| H | H | 0 | Cl | cyclopropyl | CH$_2$F | CH$_3$ | CH | |
| CH$_2$CH$_3$ | H | 0 | Cl | cyclopropyl | CH$_3$ | CH$_3$ | CH | |
| CH$_2$CH$_3$ | H | 0 | Cl | cyclopropyl | CH$_3$ | OCH$_3$ | CH | |
| CH$_2$CH$_3$ | H | 0 | Cl | cyclopropyl | OCH$_3$ | OCH$_3$ | CH | |
| CH$_2$CH$_3$ | H | 0 | Cl | cyclopropyl | CH$_3$ | CH$_3$ | N | |
| CH$_2$CH$_3$ | H | 0 | Cl | cyclopropyl | CH$_3$ | OCH$_3$ | N | |
| CH$_2$CH$_3$ | H | 0 | Cl | cyclopropyl | OCH$_3$ | OCH$_3$ | N | |
| CH$_2$CH$_3$ | H | 0 | Cl | cyclopropyl | Cl | OCH$_3$ | CH | |
| CH$_2$CH$_3$ | H | 0 | Cl | cyclobutyl | CH$_3$ | CH$_3$ | CH | |
| CH$_2$CH$_3$ | H | 0 | Cl | cyclobutyl | CH$_3$ | Og$_3$ | CH | |
| CH$_2$CH$_3$ | H | 0 | Cl | cyclobutyl | OCH$_3$ | OCH$_3$ | CH | |
| CH$_2$CH$_3$ | H | 0 | Cl | cyclobutyl | CH$_3$ | CH$_3$ | N | |
| CH$_2$CH$_3$ | H | 0 | Cl | cyclobutyl | CH$_3$ | OCH$_3$ | N | |
| CH$_2$CH$_3$ | H | 0 | Cl | cyclobutyl | OCH$_3$ | OCH$_3$ | N | |
| CH$_2$CH$_3$ | H | 0 | Cl | cyclobutyl | Cl | OCH$_3$ | CH | |
| CH$_2$CH$_3$ | H | 0 | Cl | cyclopentyl | CH$_3$ | CH$_3$ | CH | |
| CH$_2$CH$_3$ | H | 0 | Cl | cyclopentyl | CH$_3$ | OCH$_3$ | CH | |
| CH$_2$CH$_3$ | H | 0 | Cl | cyclopentyl | OCH$_3$ | OCH$_3$ | CH | |
| CH$_2$CH$_3$ | H | 0 | Cl | cyclopentyl | CH$_3$ | CH$_3$ | N | |
| CH$_2$CH$_3$ | H | 0 | Cl | cyclopentyl | CH$_3$ | OCH$_3$ | N | |
| CH$_2$CH$_3$ | H | 0 | Cl | cyclopentyl | OCH$_3$ | OCH$_3$ | N | |
| CH$_2$CH$_3$ | H | 0 | Cl | cyclopentyl | Cl | OCH$_3$ | CH | |
| CH$_2$CH$_3$ | H | 0 | Cl | cyclopropyl | OCH$_3$ | OCH$_2$CH$_3$ | CH | |
| CH$_2$CH$_3$ | H | 0 | Cl | cyclopropyl | cyclopropyl | OCH$_3$ | CH | |
| CH$_2$CH$_3$ | H | 0 | Cl | cyclopropyl | OCH$_3$ | CH(OCH$_3$)$_2$ | CH | |
| CH$_2$CH$_3$ | H | 0 | Cl | cyclopropyl | NHCH$_3$ | OCH$_2$CH$_3$ | N | |
| CH$_2$CH$_3$ | H | 0 | Cl | cyclopropyl | NHCH$_3$ | OCH$_3$ | N | |
| CH$_2$CH$_3$ | H | 0 | Cl | cyclopropyl | OCH$_3$ | OCH$_2$CH$_3$ | N | |
| CH$_2$CH$_3$ | H | 0 | Cl | cyclopropyl | CH$_2$F | CH$_3$ | CH | |
| CH$_2$CH$_2$CH$_3$ | H | 0 | Cl | cyclopropyl | CH$_3$ | CH$_3$ | CH | |
| CH$_2$CH$_2$CH$_3$ | H | 0 | Cl | cyclopropyl | CH$_3$ | OCH$_3$ | CH | |
| CH$_2$CH$_2$CH$_3$ | H | 0 | Cl | cyclopropyl | OCH$_3$ | OCH$_3$ | CH | |
| CH$_2$CH$_2$CH$_3$ | H | 0 | Cl | cyclopropyl | CH$_3$ | CH$_3$ | N | |
| CH$_2$CH$_2$CH$_3$ | H | 0 | Cl | cyclopropyl | CH$_3$ | OCH$_3$ | N | |
| CH$_2$CH$_2$CH$_3$ | H | 0 | Cl | cyclopropyl | OCH$_3$ | OCH$_3$ | N | |
| CH$_2$CH$_2$CH$_3$ | H | 0 | Cl | cyclopropyl | Cl | OCH$_3$ | CH | |
| CH$_2$CH$_2$CH$_3$ | H | 0 | Cl | cyclobutyl | CH$_3$ | CH$_3$ | CH | |
| CH$_2$CH$_2$CH$_3$ | H | 0 | Cl | cyclobutyl | CH$_3$ | OCH$_3$ | CH | |
| CH$_2$CH$_2$CH$_3$ | H | 0 | Cl | cyclobutyl | OCH$_3$ | OCH$_3$ | CH | |
| CH$_2$CH$_2$CH$_3$ | H | 0 | Cl | cyclobutyl | CH$_3$ | CH$_3$ | N | |
| CH$_2$CH$_2$CH$_3$ | H | 0 | Cl | cyclobutyl | CH$_3$ | OCH$_3$ | N | |
| CH$_2$CH$_2$CH$_3$ | H | 0 | Cl | cyclobutyl | OCH$_3$ | OCH$_3$ | N | |
| CH$_2$CH$_2$CH$_3$ | H | 0 | Cl | cyclobutyl | Cl | OCH$_3$ | CH | |
| CH$_2$CH$_2$CH$_3$ | H | 0 | Cl | cyclopentyl | CH$_3$ | CH$_3$ | CH | |
| CH$_2$CH$_2$CH$_3$ | H | 0 | Cl | cyclopentyl | CH$_3$ | OCH$_3$ | CH | |
| CH$_2$CH$_2$CH$_3$ | H | 0 | Cl | cyclopentyl | OCH$_3$ | OCH$_3$ | CH | |
| CH$_2$CH$_2$CH$_3$ | H | 0 | Cl | cyclopentyl | CH$_3$ | CH$_3$ | N | |
| CH$_2$CH$_2$CH$_3$ | H | 0 | Cl | cyclopentyl | CH$_3$ | OCH$_3$ | N | |
| CH$_2$CH$_2$CH$_3$ | H | 0 | Cl | cyclopentyl | OCH$_3$ | OCH$_3$ | N | |
| CH$_2$CH$_2$CH$_3$ | H | 0 | Cl | cyclopentyl | Cl | OCH$_3$ | CH | |
| CH$_2$CH$_2$CH$_3$ | H | 0 | Cl | cyclopropyl | OCH$_3$ | OCH$_2$CH$_3$ | CH | |
| CH$_2$CH$_2$CH$_3$ | H | 0 | Cl | cyclopropyl | cyclopropyl | OCH$_3$ | CH | |
| CH$_2$CH$_2$CH$_3$ | H | 0 | Cl | cyclopropyl | OCH$_3$ | CH(OCH$_3$)$_2$ | CH | |
| CH$_2$CH$_2$CH$_3$ | H | 0 | Cl | cyclopropyl | NHCH$_3$ | OCH$_2$CH$_3$ | N | |
| CH$_2$CH$_2$CH$_3$ | H | 0 | Cl | cyclopropyl | NHCH$_3$ | OCH$_3$ | N | |
| CH$_2$CH$_2$CH$_3$ | H | 0 | Cl | cyclopropyl | OCH$_3$ | OCH$_2$CH$_3$ | N | |
| CH$_2$CH$_2$CH$_3$ | H | 0 | Cl | cyclopropyl | CH$_2$F | CH$_3$ | CH | |
| CH$_2$SO$_2$CH$_3$ | H | 0 | Cl | cyclopropyl | CH$_3$ | CH$_3$ | CH | |
| CH$_2$SO$_2$CH$_3$ | H | 0 | Cl | cyclopropyl | CH$_3$ | OCH$_3$ | CH | |
| CH$_2$SO$_2$CH$_3$ | H | 0 | Cl | cyclopropyl | OCH$_3$ | OH$_3$ | CH | |
| CH$_2$SO$_2$CH$_3$ | H | 0 | Cl | cyclopropyl | CH$_3$ | CH$_3$ | N | |
| CH$_2$SO$_2$CH$_3$ | H | 0 | Cl | cyclopropyl | CH$_3$ | OCH$_3$ | N | |
| CH$_2$SO$_2$CH$_3$ | H | 0 | Cl | cyclopropyl | OCH$_3$ | OCH$_3$ | N | |
| CH$_2$SO$_2$CH$_3$ | H | 0 | Cl | cyclopropyl | Cl | OCH$_3$ | CH | |
| CH$_2$SO$_2$CH$_3$ | H | 0 | Cl | cyclobutyl | CH$_3$ | CH$_3$ | CH | |
| CH$_2$SO$_2$CH$_3$ | H | 0 | Cl | cyclobutyl | CH$_3$ | OCH$_3$ | CH | |
| CH$_2$SO$_2$CH$_3$ | H | 0 | Cl | cyclobutyl | OCH$_3$ | OCH$_3$ | CH | |
| CH$_2$SO$_2$CH$_3$ | H | 0 | Cl | cyclobutyl | CH$_3$ | CH$_3$ | N | |
| CH$_2$SO$_2$CH$_3$ | H | 0 | Cl | cyclobutyl | CH$_3$ | OCH$_3$ | N | |
| CH$_2$SO$_2$CH$_3$ | H | 0 | Cl | cyclobutyl | OCH$_3$ | OCH$_3$ | N | |

TABLE I-continued

| R | R₁ | n | R₂ | R' | X | Y | Z | m.p. (°C.) |
|---|---|---|---|---|---|---|---|---|
| CH₂SO₂CH₃ | H | 0 | Cl | cyclobutyl | Cl | OCH₃ | CH | |
| CH₂SO₂CH₃ | H | 0 | Cl | cyclopentyl | CH₃ | CH₃ | CH | |
| CH₂SO₂CH₃ | H | 0 | Cl | cyclopentyl | CH₃ | OCH₃ | CH | |
| CH₂SO₂CH₃ | H | 0 | Cl | cyclopentyl | OCH₃ | OCH₃ | CH | |
| CH₂SO₂CH₃ | H | 0 | Cl | cyclopentyl | CH₃ | CH₃ | N | |
| CH₂SO₂Ch₃ | H | 0 | Cl | cyclopentyl | CH₃ | OCH₃ | N | |
| CH₂SO₂CH₃ | H | 0 | Cl | cyclopentyl | OCH₃ | OCH₃ | N | |
| CH₂SO₂CH₃ | H | 0 | Cl | cyclopentyl | Cl | OCH₃ | CH | |
| CH₂SO₂CH₃ | H | 0 | Cl | cyclopropyl | OCH₃ | OCH₂CH₃ | CH | |
| CH₂SO₂CH₃ | H | 0 | Cl | cyclopropyl | cyclopropyl | OCH₃ | CH | |
| CH₂SO₂CH₃ | H | 0 | Cl | cyclopropyl | OCH₃ | CH(OCH₃)₂ | CH | |
| CH₂SO₂CH₃ | H | 0 | Cl | cyclopropyl | NHCH₃ | OCH₂CH₃ | N | |
| CH₂SO₂CH₃ | H | 0 | Cl | cyclopropyl | NHCH₃ | OCH₃ | N | |
| CH₂SO₂CH₃ | H | 0 | Cl | cyclopropyl | OCH₃ | OCH₂CH₃ | N | |
| CH₂SO₂CH₃ | H | 0 | Cl | cyclopropyl | CH₂F | CH₃ | CH | |
| Ph | H | 0 | Cl | cyclopropyl | CH₃ | CH₃ | CH | |
| Ph | H | 0 | Cl | cyclopropyl | CH₃ | OCH₃ | CH | |
| Ph | H | 0 | Cl | cyloropyl | OCH₃ | OCH₃ | CH | |
| Ph | H | 0 | Cl | cyclopropyl | CH₃ | CH₃ | N | |
| Ph | H | 0 | Cl | cyclopropyl | CH₃ | OCH₃ | N | |
| Ph | H | 0 | Cl | cyclopropyl | OCH₃ | OCH₃ | N | |
| Ph | H | 0 | Cl | cyclopropyl | Cl | OCH₃ | CH | |
| Ph | H | 0 | Cl | cyclobutyl | CH₃ | CH₃ | CH | |
| Ph | H | 0 | Cl | cyclobutyl | CH₃ | OCH₃ | CH | |
| Ph | H | 0 | Cl | cyclobutyl | OCH₃ | OCH₃ | CH | |
| Ph | H | 0 | Cl | cyclobutyl | CH₃ | CH₃ | N | |
| Ph | H | 0 | Cl | cyclobutyl | CH₃ | OCH₃ | N | |
| Ph | H | 0 | Cl | cyclobutyl | OCH₃ | OCH₃ | N | |
| Ph | H | 0 | Cl | cyclobutyl | Cl | OCH₃ | CH | |
| Ph | H | 0 | Cl | cyclopentyl | CH₃ | CH₃ | CH | |
| Ph | H | 0 | Cl | cyclopentyl | CH₃ | OCH₃ | CH | |
| Ph | H | 0 | Cl | cyclopentyl | OCH₃ | OCH₃ | CH | |
| Ph | H | 0 | Cl | cyclopentyl | CH₃ | CH₃ | N | |
| Ph | H | 0 | Cl | cyclopentyl | CH₃ | OCH₃ | N | |
| Ph | H | 0 | Cl | cycloentyl | OCH₃ | OCH₃ | N | |
| Ph | H | 0 | Cl | cyclopentyl | Cl | OCH₃ | CH | |
| Ph | H | 0 | Cl | cyclopropyl | OCH₃ | OCH₂CH₃ | CH | |
| Ph | H | 0 | Cl | cyclopropyl | cyclopropyl | OCH₃ | CH | |
| Ph | H | 0 | Cl | cyclopropyl | OCH₃ | CH(OCH₃)₂ | CH | |
| Ph | H | 0 | Cl | cyclopropyl | NHCH₃ | OCH₂CH₃ | N | |
| Ph | H | 0 | Cl | cyclopropyl | NHCH₃ | OCH₃ | N | |
| Ph | H | 0 | Cl | cyclopropyl | OCH₃ | OCH₂CH₃ | N | |
| Ph | H | 0 | Cl | cyclopropyl | CH₂F | CH₃ | CH | |
| H | H | 0 | CH₃ | cyclopropyl | CH₃ | CH₃ | CH | |
| H | H | 0 | CH₃ | cyclopropyl | CH₃ | OCH₃ | CH | |
| H | H | 0 | CH₃ | cyclopropyl | OCH₃ | OCH₃ | CH | |
| H | H | 0 | CH₃ | cyclopropyl | CH₃ | CH₃ | N | |
| H | H | 0 | CH₃ | cyclopropyl | CH₃ | OCH₃ | N | |
| H | H | 0 | CH₃ | cyclopropyl | OCH₃ | OCH₃ | N | |
| H | H | 0 | CH₃ | cyclopropyl | Cl | OCH₃ | CH | |
| H | H | 0 | CH₃ | cyclobutyl | CH₃ | CH₃ | CH | |
| H | H | 0 | CH₃ | cyclobutyl | CH₃ | OCH₃ | CH | |
| H | H | 0 | CH₃ | cyclobutyl | OCH₃ | OCH₃ | CH | |
| H | H | 0 | CH₃ | cyclobutyl | CH₃ | CH₃ | N | |
| H | H | 0 | CH₃ | cyclobutyl | CH₃ | OCH₃ | N | |
| H | H | 0 | CH₃ | cyclobutyl | OCH₃ | OCH₃ | N | |
| H | H | 0 | CH₃ | cyclobutyl | Cl | OCH₃ | CH | |
| H | H | 0 | CH₃ | cyclopentyl | CH₃ | CH₃ | CH | |
| H | H | 0 | CH₃ | cyclopentyl | CH₃ | OCH₃ | CH | |
| H | H | 0 | CH₃ | cyclopentyl | OCH₃ | OCH₃ | CH | |
| H | H | 0 | CH₃ | cyclopentyl | CH₃ | CH₃ | N | |
| H | H | 0 | CH₃ | cyclopentyl | CH₃ | OCH₃ | N | |
| H | H | 0 | CH₃ | cyclopentyl | OCH₃ | OCH₃ | N | |
| H | H | 0 | CH₃ | cyclopentyl | Cl | OCH₃ | CH | |
| H | H | 0 | CH₃ | cyclopropyl | OCH₃ | OCH₂CH₃ | CH | |
| H | H | 0 | CH | cyclopropyl | cyclopropyl | OCH₃ | CH | |
| H | H | 0 | CH₃ | cyclopropyl | OCH₃ | CH(OCH₃)₂ | CH | |
| H | H | 0 | CH₃ | cyclopropyl | NHCH₃ | OCH₂CH₃ | N | |
| H | H | 0 | CH₃ | cyclopropyl | NHCH₃ | OCH₃ | N | |
| H | H | 0 | CH₃ | cyclopropyl | OCH₃ | OCH₂CH₃ | N | |
| H | H | 0 | CH₃ | cyclopropyl | CH₂F | CH₃ | CH | |
| CH₂CH₃ | H | 0 | CH₃ | cyclopropyl | CH₃ | CH₃ | CH | |
| CH₂CH₃ | H | 0 | CH₃ | cyclopropyl | CH₃ | OCH₃ | CH | |
| CH₂CH₃ | H | 0 | CH₃ | cyclopropyl | OCH₃ | OCH₃ | CH | |
| CH₂CH₃ | H | 0 | CH₃ | cyclopropyl | CH₃ | CH₃ | N | |
| CH₂CH₃ | H | 0 | CH₃ | cyclopropyl | CH₃ | OCH₃ | N | |
| CH₂CH₃ | H | 0 | CH₃ | cyclopropyl | OCH₃ | OH₃ | N | |
| CH₂CH₃ | H | 0 | CH₃ | cyclopropyl | Cl | OCH₃ | CH | |
| CH₂CH₃ | H | 0 | CH₃ | cyclobutyl | CH₃ | CH₃ | CH | |
| CH₂CH₃ | H | 0 | CH₃ | cyclobutyl | CH₃ | OCH₃ | CH | |
| CH₂CH₃ | H | 0 | CH₃ | cyclobutyl | OCH₃ | OCH₃ | CH | |

TABLE I-continued

| R | R₁ | n | R₂ | R' | X | Y | Z | m.p. (°C.) |
|---|---|---|---|---|---|---|---|---|
| CH₂CH₃ | H | 0 | CH₃ | cyclobutyl | CH₃ | CH₃ | N | |
| CH₂CH₃ | H | 0 | CH₃ | cyclobutyl | CH₃ | OCH₃ | N | |
| CH₂CH₃ | H | 0 | CH₃ | cyclobutyl | OCH₃ | OCH₃ | N | |
| CH₂CH₃ | H | 0 | CH₃ | cyclobutyl | Cl | OCH₃ | CH | |
| CH₂CH₃ | H | 0 | CH₃ | cyclopentyl | CH₃ | CH₃ | CH | |
| CH₂CH₃ | H | 0 | CH₃ | cyclopentyl | CH₃ | OCH₃ | CH | |
| CH₂CH₃ | H | 0 | CH₃ | cyclopentyl | OCH₃ | OCH₂CH₃ | CH | |
| CH₂CH₃ | H | 0 | CH₃ | cyclopentyl | CH₃ | CH₃ | N | |
| CH₂CH₃ | H | 0 | CH₃ | cyclopentyl | CH₃ | OCH₃ | N | |
| CH₂CH₃ | H | 0 | CH₃ | cyclopentyl | OCH₃ | OCH₃ | N | |
| CH₂CH₃ | H | 0 | CH₃ | cyclopentyl | Cl | OCH₃ | CH | |
| CH₂CH₃ | H | 0 | CH₃ | cyclopropyl | OCH₃ | OCH₂CH₃ | CH | |
| CH₂CH₃ | H | 0 | CH₃ | cyclopropyl | cyclopropyl | OCH₃ | CH | |
| CH₂CH₃ | H | 0 | CH₃ | cyclopropyl | OCH₃ | CH(OCH₃)₂ | CH | |
| CH₂CH₃ | H | 0 | CH₃ | cyclopropyl | NHCH₃ | OCH₂CH₃ | N | |
| CH₂CH₃ | H | 0 | CH₃ | cyclopropyl | NHCH₃ | OCH₃ | N | |
| CH₂CH₃ | H | 0 | CH₃ | cyclopropyl | OCH₃ | OCH₂CH₃ | N | |
| CH₂CH₃ | H | 0 | CH₃ | cyclopropyl | CH₂F | CH₃ | CH | |
| Ph | H | 0 | CH₃ | cyclopropyl | CH₃ | CH₃ | CH | |
| Ph | H | 0 | CH₃ | cyclopropyl | CH₃ | OCH₃ | CH | |
| Ph | H | 0 | CH₃ | cyclopropyl | OCH₃ | OCH₃ | CH | |
| Ph | H | 0 | CH₃ | cyclopropyl | CH₃ | CH₃ | N | |
| Ph | H | 0 | CH₃ | cyclopropyl | CH₃ | OCH₃ | N | |
| Ph | H | 0 | CH₃ | cyclopropyl | OCH₃ | OCH₃ | N | |
| Ph | H | 0 | CH₃ | cyclopropyl | OCH₃ | | CH | |
| Ph | H | 0 | CH₃ | cyclobutyl | CH₃ | CH₃ | CH | |
| Ph | H | 0 | CH₃ | cyclobutyl | CH₃ | OCH₃ | CH | |
| Ph | H | 0 | CH₃ | cyclobutyl | OCH₃ | OCH₃ CH | | |
| Ph | H | 0 | CH₃ | cyclobutyl | CH₃ | CH₃ | N | |
| Ph | H | 0 | CH₃ | cyclobutyl | CH₃ | OCH₃ | N | |
| Ph | H | 0 | CH₃ | cyclobutyl | OCH₃ | OCH₃ | N | |
| Ph | H | 0 | CH₃ | cyclobutyl | Cl | OCH₃ | CH | |
| Ph | H | 0 | CH₃ | cyclopentyl | CH₃ | CH₃ | CH | |
| Ph | H | 0 | CH₃ | cyclopentyl | CH₃ | OCH₃ | CH | |
| Ph | H | 0 | CH₃ | cyclopentyl | OCH₃ | OCH₃ | CH | |
| Ph | H | 0 | CH₃ | cyclopentyl | CH₃ | CH₃ | N | |
| Ph | H | 0 | CH₃ | cyclopentyl | CH₃ | OCH₃ | N | |
| Ph | H | 0 | CH₃ | cyclopentyl | OCH₃ | OCH₃ | N | |
| Ph | H | 0 | CH₃ | cyclopentyl | Cl | OCH₃ | CH | |
| Ph | H | 0 | CH₃ | cyclopropyl | OCH₃ | OCH₂CH₃ | CH | |
| Ph | H | 0 | CH₃ | cyclopropyl | cyclopropyl | OCH₃ | CH | |
| Ph | H | 0 | CH₃ | cyclopropyl | OCH₃ | CH(OCH₃)₂ | CH | |
| Ph | H | 0 | CH₃ | cyclopropyl | NHCH₃ | OCH₂CH₃ | N | |
| Ph | H | 0 | CH₃ | cyclopropyl | NHCH₃ | OCH₃ | N | |
| Ph | H | 0 | CH₃ | cyclopropyl | OCH₃ | OCH₂CH₃ | N | |
| Ph | H | 0 | CH₃ | cyclopropyl | CH₂F | CH₃ | CH | |
| CH₂CH=CH₂ | H | 0 | CH₃ | cyclopropyl | CH₃ | CH₃ | CH | |
| CH₂CH=CH₂ | H | 0 | CH₃ | cyclopropyl | CH₃ | OCH₃ | CH | |
| CH₂CH=CH₂ | H | 0 | CH₃ | cyclopropyl | OCH₃ | OCH₃ | CH | |
| CH₂CH=CH₂ | H | 0 | CH₃ | cyclopropyl | CH₃ | CH₃ | N | |
| CH₂CH=CH₂ | H | 0 | CH₃ | cyclopropyl | CH₃ | OCH₃ | N | |
| CH₂CH=CH₂ | H | 0 | CH₃ | cyclopropyl | OCH₃ | OCH₃ | N | |
| CH₂CH=CH₂ | H | 0 | CH₃ | cyclopropyl | Cl | OCH₃ | CH | |
| CH₂CH=CH₂ | H | 0 | CH₃ | cyclobutyl | CH₃ | CH₃ | CH | |
| CH₂CH=CH₂ | H | 0 | CH₃ | cyclobutyl | CH₃ | OCH₃ | CH | |
| CH₂CH=CH₂ | H | 0 | CH₃ | cyclobutyl | OCH₃ | OCH₃ | CH | |
| CH₂CH=CH₂ | H | 0 | CH₃ | cyclobutyl | CH₃ | CH₃ | N | |
| CH₂CH=CH₂ | H | 0 | CH₃ | cyclobutyl | CH₃ | OCH₃ | N | |
| CH₂CH=CH₂ | H | 0 | CH₃ | cyclobutyl | OCH₃ | OCH₃ | N | |
| CH₂CH=CH₂ | H | 0 | CH₃ | cyclobutyl | Cl | OCH₃ | CH | |
| CH₂CH=CH₂ | H | 0 | CH₃ | cyclopentyl | CH₃ | CH₃ | CH | |
| CH₂CH=CH₂ | H | 0 | CH₃ | cyclopentyl | CH₃ | OCH₃ | CH | |
| CH₂CH=CH₂ | H | 0 | CH₃ | cyclopentyl | OCH₃ | OCH₃ | CH | |
| CH₂CH=CH₂ | H | 0 | CH₃ | cyclopentyl | CH₃ | CH₃ | N | |
| CH₂CH=CH₂ | H | 0 | CH₃ | cyclopentyl | CH₃ | OCH₃ | N | |
| CH₂CH=CH₂ | H | 0 | CH₃ | cyclopentyl | OCH₃ | OCH₃ | N | |
| CH₂CH=CH₂ | H | 0 | CH₃ | cyclopentyl | Cl | OCH₃ | CH | |
| CH₂CH=CH₂ | H | 0 | CH₃ | cyclopropyl | OCH₃ | OCH₂CH₃ | CH | |
| CH₂CH=CH₂ | H | 0 | CH₃ | cyclopropyl | cyclopropyl | OCH₃ | CH | |
| CH₂CH=CH₂ | H | 0 | CH₃ | cyclopropyl | OCH₃ | CH(OCH₃)₂ | CH | |
| CH₂CH=CH₂ | H | 0 | CH₃ | cyclopropyl | NHCH₃ | OCH₂CH₃ | N | |
| CH₂CH=CH₂ | H | 0 | CH₃ | cyclopropyl | NHCH₃ | OCH₃ | N | |
| CH₂CH=CH₂ | H | 0 | CH₃ | cyclopropyl | OCH₃ | OCH₂CH₃ | N | |
| CH₂CH=CH₂ | H | 0 | CH₃ | cyclopropyl | CH₂F | CH₃ | CH | |
| CH₂Cl | H | 0 | CH₃ | cyclopropyl | CH₃ | CH₃ | CH | |
| CH₂Cl | H | 0 | CH₃ | cyclopropyl | CH₃ | OCH₃ | CH | |
| CH₂Cl | H | 0 | CH₃ | cyclopropyl | OCH₃ | OCH₃ | CH | |
| CH₂Cl | H | 0 | CH₃ | cyclopropyl | CH₃ | CH₃ | N | |
| CH₂Cl | H | 0 | CH₃ | cyclopropyl | CH₃ | OCH₃ | N | |
| CH₂Cl | H | 0 | CH₃ | cyclopropyl | OCH₃ | OCH₃ | N | |
| CH₂Cl | H | 0 | CH₃ | cyclopropyl | Cl | OCH₃ | CH | |

TABLE I-continued

| R | R₁ | n | R₂ | R' | X | Y | Z | m.p. (°C.) |
|---|---|---|---|---|---|---|---|---|
| CH₂Cl | H | 0 | CH₃ | cyclobutyl | CH₃ | CH₃ | CH | |
| CH₂Cl | H | 0 | CH₃ | cyclobutyl | CH₃ | OCH₃ | CH | |
| CH₂Cl | H | 0 | CH₃ | cyclobutyl | OCH₃ | OCH₃ | CH | |
| CH₂Cl | H | 0 | CH₃ | cyclobutyl | CH₃ | CH₃ | N | |
| CH₂Cl | H | 0 | CH₃ | cyclobutyl | CH₃ | OCH₃ | N | |
| CH₂Cl | H | 0 | CH₃ | cyclobutyl | OCH₃ | OCH₃ | N | |
| CH₂Cl | H | 0 | CH₃ | cyclobutyl | Cl | OCH₃ | CH | |
| CH₂Cl | H | 0 | CH₃ | cyclopentyl | CH₃ | CH₃ | CH | |
| CH₂Cl | H | 0 | CH₃ | cyclopentyl | CH₃ | OCH₃ | CH | |
| CH₂Cl | H | 0 | CH₃ | cyclopentyl | OCH₃ | OCH₃ | CH | |
| CH₂Cl | H | 0 | CH₃ | cyclopentyl | CH₃ | CH₃ | N | |
| CH₂Cl | H | 0 | CH₃ | cyclopentyl | CH₃ | OCH₃ | N | |
| CH₂Cl | H | 0 | CH₃ | cyclopentyl | OCH₃ | OCH₃ | N | |
| CH₂Cl | H | 0 | CH₃ | cyclopentyl | Cl | OCH₃ | CH | |
| CH₂Cl | H | 0 | CH₃ | cyclopropyl | OCH₃ | OCH₂CH₃ | CH | |
| CH₂Cl | H | 0 | CH₃ | cyclopropyl | cyclopropyl | OCH₃ | CH | |
| CH₂Cl | H | 0 | CH₃ | cyclopropyl | OCH₃ | CH(OCH₃)₂ | CH | |
| CH₂Cl | H | 0 | CH₃ | cyclopropyl | NHCH₃ | OCH₂CH₃ | N | |
| CH₂Cl | H | 0 | CH₃ | cyclopropyl | NHCH₃ | OCH₃ | N | |
| CH₂Cl | H | 0 | CH₃ | cyclopropyl | OCH₃ | OCH₂CH₃ | N | |
| CH₂Cl | H | 0 | CH₃ | cyclopropyl | CH₂F | CH₃ | CH | |
| CH₂C≡CH | H | 0 | CH₃ | cyclopropyl | CH₃ | CH₃ | CH | |
| CH₂C≡CH | H | 0 | CH₃ | cyclopropyl | CH₃ | OCH₃ | CH | |
| CH₂C≡CH | H | 0 | CH₃ | cyclopropyl | OCH₃ | OCH₃ | CH | |
| CH₂C≡CH | H | 0 | CH₃ | cyclopropyl | CH₃ | CH₃ | N | |
| CH₂C≡CH | H | 0 | CH₃ | cyclopropyl | CH₃ | OCH₃ | N | |
| CH₂C≡CH | H | 0 | CH₃ | cyclopropyl | OCH₃ | OCH₃ | N | |
| CH₂C≡CH | H | 0 | CH₃ | cyclopropyl | Cl | OCH₃ | CH | |
| CH₂C≡CH | H | 0 | CH₃ | cyclobutyl | CH₃ | CH₃ | CH | |
| CH₂C≡CH | H | 0 | CH₃ | cyclobutyl | CH₃ | OCH₃ | CH | |
| CH₂C≡CH | H | 0 | CH₃ | cyclobutyl | OCH₃ | OCH₃ | CH | |
| CH₂C≡CH | H | 0 | CH₃ | cyclobutyl | CH₃ | CH₃ | N | |
| CH₂C≡CH | H | 0 | CH₃ | cyclobutyl | CH₃ | OCH₃ | N | |
| CH₂C≡CH | H | 0 | CH₃ | cyclobutyl | OCH₃ | OCH₃ | N | |
| CH₂C≡CH | H | 0 | CH₃ | cyclobutyl | Cl | OCH₃ | CH | |
| CH₂C≡CH | H | 0 | CH₃ | cyclopentyl | CH₃ | CH₃ | CH | |
| CH₂C≡CH | H | 0 | CH₃ | cyclopentyl | CH₃ | OCH₃ | CH | |
| CH₂C≡CH | H | 0 | CH₃ | cyclopentyl | OCH₃ | OCH₃ | CH | |
| CH₂C≡CH | H | 0 | CH₃ | cyclopentyl | CH₃ | CH₃ | N | |
| CH₂C≡CH | H | 0 | CH₃ | cyclopentyl | CH₃ | OCH₃ | N | |
| CH₂C≡CH | H | 0 | CH₃ | cyclopentyl | OCH₃ | OCH₃ | N | |
| CH₂C≡CH | H | 0 | CH₃ | cyclopentyl | Cl | OCH₃ | CH | |
| CH₂C≡CH | H | 0 | CH₃ | cyclopropyl | OCH₃ | OCH₂CH₃ | CH | |
| CH₂C≡CH | H | 0 | CH₃ | cyclopropyl | cyclopropyl | OCH₃ | CH | |
| CH₂C≡CH | H | 0 | CH₃ | cyclopropyl | CH(OCH₃)₂ | CH | | |
| CH₂C≡CH | H | 0 | CH₃ | cyclopropyl | NHCH₃ | OCH₂CH₃ | N | |
| CH₂C≡CH | H | 0 | CH₃ | cyclopropyl | NHCH₃ | OCH₃ | N | |
| CH₂C≡CH | H | 0 | CH₃ | cyclopropyl | OCH₃ | OCH₂CH₃ | N | |
| CH₂C≡CH | H | 0 | CH₃ | cyclopropyl | CH₂F | CH₃ | CH | |
| CH₃ | H | 1 | H | cyclopropyl | CH₃ | CH₃ | CH | |
| CH₃ | H | 1 | H | cyclopropyl | CH₃ | OCH₃ | CH | |
| CH₃ | H | 1 | H | cyclopropyl | OCH₃ | OCH₃ | CH | |
| CH₃ | H | 1 | H | cyclopropyl | CH₃ | CH₃ | N | |
| CH₃ | H | 1 | H | cyclopropyl | CH₃ | OCH₃ | N | |
| CH₃ | H | 1 | H | cyclopropyl | OCH₃ | OCH₃ | N | |
| CH₃ | H | 1 | H | cyclopropyl | Cl | OCH₃ | CH | |
| CH₃ | H | 1 | H | cyclobutyl | CH₃ | CH₃ | CH | |
| CH₃ | H | 1 | H | cyclobutyl | CH₃ | OCH₃ | CH | |
| CH₃ | H | 1 | H | cyclobutyl | OCH₃ | OCH₃ | CH | |
| CH₃ | H | 1 | H | cyclobutyl | CH₃ | CH₃ | N | |
| CH₃ | H | 1 | H | cyclobutyl | CH₃ | OCH₃ | N | |
| CH₃ | H | 1 | H | cyclobutyl | OCH₃ | OCH₃ | N | |
| CH₃ | H | 1 | H | cyclobutyl | Cl | OCH₃ | CH | |
| CH₃ | H | 1 | H | cyclopentyl | CH₃ | CH₃ | CH | |
| CH₃ | H | 1 | H | cyclopentyl | CH₃ | OCH₃ | CH | |
| CH₃ | H | 1 | H | cyclopentyl | OCH₃ | OCH₃ | CH | |
| CH₃ | H | 1 | H | cyclopentyl | CH₃ | CH₃ | N | |
| CH₃ | H | 1 | H | cyclopentyl | CH₃ | OCH₃ | N | |
| CH₃ | H | 1 | H | cyclopentyl | OCH₃ | OCH₃ | N | |
| CH₃ | H | 1 | H | cyclopentyl | Cl | OCH₃ | CH | |
| CH₃ | H | 1 | H | cyclopropyl | OCH₃ | OCH₂CH₃ | CH | |
| CH₃ | H | 1 | H | cyclopropyl | cyclopropyl | OCH₃ | CH | |
| CH₃ | H | 1 | H | cyclopropyl | OCH₃ | CH(OCH₃)₂ | CH | |
| CH₃ | H | 1 | H | cycloproyl | NHCH₃ | OCH₂CH₃ | N | |
| CH₃ | H | 1 | H | cyclopropyl | NHCH₃ | OCH₃ | N | |
| CH₃ | H | 1 | H | cyclopropyl | OCH₃ | OCH₂CH₃ | N | |
| CH₃ | H | 1 | H | cyclopropyl | CH₂F | CH₃ | CH | |
| CH₃ | H | 1 | Cl | cyclopropyl | CH₃ | CH₃ | CH | |
| CH₃ | H | 1 | Cl | cyclopropyl | CH₃ | OCH₃ | CH | |
| CH₃ | H | 1 | Cl | cyclopropyl | OCH₃ | OCH₃ | CH | |
| CH₃ | H | 1 | Cl | cyclopropyl | CH₃ | CH₃ | N | |

TABLE I-continued

| R | R₁ | n | R₂ | R' | X | Y | Z | m.p. (°C.) |
|---|---|---|---|---|---|---|---|---|
| CH₃ | H | 1 | Cl | cyclopropyl | CH₃ | OCH₃ | N | |
| CH₃ | H | 1 | Cl | cyclopropyl | OCH₃ | OCH₃ | N | |
| CH₃ | H | 1 | Cl | cyclopropyl | Cl | OCH₃ | CH | |
| CH₃ | H | 1 | Cl | cyclobutyl | CH₃ | CH₃ | CH | |
| CH₃ | H | 1 | Cl | cyclobutyl | CH₃ | OCH₃ | CH | |
| CH₃ | H | 1 | Cl | cyclobutyl | OCH₃ | OCH₃ | CH | |
| CH₃ | H | 1 | Cl | cyclobutyl | CH₃ | CH₃ | N | |
| CH₃ | H | 1 | Cl | cyclobutyl | CH₃ | OCH₃ | N | |
| CH₃ | H | 1 | Cl | cyclobutyl | OCH₃ | OCH₃ | N | |
| CH₃ | H | 1 | Cl | cyclobutyl | Cl | OCH₃ | CH | |
| CH₃ | H | 1 | Cl | cyclopentyl | CH₃ | CH3 | CH | |
| CH₃ | H | 1 | Cl | cyclopentyl | CH₃ | OCH₃ | CH | |
| CH₃ | H | 1 | Cl | cyclopentyl | OCH₃ | OCH₃ | CH | |
| CH₃ | H | 1 | Cl | cyclopentyl | CH₃ | CH₃ | N | |
| CH₃ | H | 1 | Cl | cyclopentyl | CH₃ | OCH₃ | N | |
| CH₃ | H | 1 | Cl | cyclopentyl | OCH₃ | OCH₃ | N | |
| CH₃ | H | 1 | Cl | cyclopentyl | Cl | OCH₃ | CH | |
| CH₃ | H | 1 | Cl | cyclopropyl | OCH₃ | OCH₂CH₃ | CH | |
| CH₃ | H | 1 | Cl | cyclopropyl | cyclopropyl | OCH₃ | CH | |
| CH₃ | H | 1 | Cl | cyclopropyl | OCH₃ | CH(OCH₃)₂ | CH | |
| CH₃ | H | 1 | Cl | cyclopropyl | NHCH₃ | OCH₂CH₃ | N | |
| CH₃ | H | 1 | Cl | cyclopropyl | NHCH₃ | OCH₃ | N | |
| CH₃ | H | 1 | Cl | cyclpropyl | OCH₃ | OCH₂CH₃ | N | |
| CH₃ | H | 1 | Cl | cyclopropyl | CH₂F | CH₃ | CH | |
| CH₃ | H | 1 | CH₃ | cyclopropyl | CH₃ | CH₃ | CH | |
| CH₃ | H | 1 | CH₃ | cyclopropyl | CH₃ | OCH₃ | CH | |
| CH₃ | H | 1 | CH₃ | cyclopropyl | OCH₃ | OCH₃ | CH | |
| CH₃ | H | 1 | CH₃ | cyclopropyl | CH₃ | CH₃ | N | |
| CH₃ | H | 1 | CH₃ | cyclopropyl | CH₃ | OCH₃ | N | |
| CH₃ | H | 1 | CH₃ | cyclopropyl | OCH₃ | OCH₃ | N | |
| CH₃ | H | 1 | CH₃ | cyclopropyl | Cl | OCH₃ | CH | |
| CH₃ | H | 1 | CH₃ | cyclobutyl | CH₃ | CH₃ | CH | |
| CH₃ | H | 1 | CH₃ | cyclobutyl | CH₃ | OCH₃ | CH | |
| CH₃ | H | 1 | CH₃ | cyclobutyl | OCH₃ | OCH₃ | CH | |
| CH₃ | H | 1 | CH₃ | cyclobutyl | CH₃ | CH₃ | N | |
| CH₃ | H | 1 | CH₃ | cyclobutyl | CH₃ | OCH₃ | N | |
| CH₃ | H | 1 | CH₃ | cyclobutyl | OCH₃ | OCH₃ | N | |
| CH₃ | H | 1 | CH₃ | cyclobutyl | Cl | OCH₃ | CH | |
| CH₃ | H | 1 | CH₃ | cyclopentyl | CH₃ | CH₃ | CH | |
| CH₃ | H | 1 | CH₃ | cyclopentyl | CH₃ | OCH₃ | CH | |
| CH₃ | H | 1 | CH₃ | cyclopentyl | OCH₃ | OCH₃ | CH | |
| CH₃ | H | 1 | CH₃ | cyclopentyl | CH₃ | CH₃ | N | |
| CH₃ | H | 1 | CH₃ | cyclopentyl | CH₃ | OCH₃ | N | |
| CH₃ | H | 1 | CH₃ | cyclopentyl | OCH₃ | OCH₃ | N | |
| CH₃ | H | 1 | CH₃ | cyclopentyl | Cl | OCH₃ | CH | |
| CH₃ | H | 1 | CH₃ | cyclopropyl | OCH₃ | OCH₂CH₃ | CH | |
| CH₃ | H | 1 | CH₃ | cyclopropyl | cyclopropyl | OCH₃ | CH | |
| CH₃ | H | 1 | CH₃ | cyclopropyl | OCH₃ | CH(OCH₃)₂ | CH | |
| CH₃ | H | CH₃ | cyclopropyl | NHCH₃ | OCH₂CH₃ | N | | |
| CH₃ | H | 1 | CH₃ | cyclopropyl | NHCH₃ | OCH₃ | N | |
| CH₃ | H | 1 | CH₃ | cyclopropyl | OCH₃ | OCH₂CH₃ | N | |
| CH₃ | H | 1 | CH₃ | cyclopropyl | CH₂F | CH₃ | CH | |
| CH₃ | CH₃ | 0 | H | cyclopropyl | CH₃ | CH₃ | CH | |
| CH₃ | CH₃ | 0 | H | cyclopropyl | CH₃ | OCH₃ | CH | |
| CH₃ | CH₃ | 0 | H | cyclopropyl | OCH₃ | OCH₃ | CH | |
| CH₃ | CH₃ | 0 | H | cyclopropyl | CH₃ | CH₃ | N | |
| CH₃ | CH₃ | 0 | H | cyclopropyl | CH₃ | OCH₃ | N | |
| CH₃ | CH₃ | 0 | H | cyclopropyl | OCH₃ | OCH₃ | N | |
| CH₃ | CH₃ | 0 | H | cyclopropyl | Cl | OCH₃ | CH | |
| CH₃ | CH₃ | 0 | H | cyclobutyl | CH₃ | CH₃ | CH | |
| CH₃ | CH₃ | 0 | H | cyclobutyl | CH₃ | OCH₃ | CH | |
| CH₃ | CH₃ | 0 | H | cyclobutyl | OCH₃ | OCH₃ | CH | |
| CH₃ | CH₃ | 0 | H | cyclobutyl | CH₃ | CH₃ | N | |
| CH₃ | CH₃ | 0 | H | cyclobutyl | CH₃ | OCH₃ | N | |
| CH₃ | CH₃ | 0 | H | cyclobutyl | OCH₃ | OCH₃ | N | |
| CH₃ | CH₃ | 0 | H | cyclobutyl | Cl | OCH₃ | CH | |
| CH₃ | CH₃ | 0 | H | cyclopentyl | CH₃ | CH₃ | CH | |
| CH₃ | CH₃ | 0 | H | cyclopentyl | CH₃ | OCH₃ | CH | |
| CH₃ | CH₃ | 0 | H | cyclopentyl | OCH₃ | OCH₃ | CH | |
| CH₃ | CH₃ | 0 | H | cyclopentyl | CH₃ | CH₃ | N | |
| CH₃ | CH₃ | 0 | H | cyclopentyl | CH₃ | OCH₃ | N | |
| CH₃ | CH₃ | 0 | H | cyclopentyl | OCH₃ | OCH₃ | N | |
| CH₃ | CH₃ | 0 | H | cyclopentyl | Cl | OCH₃ | CH | |
| CH₃ | CH₃ | 0 | H | cyclopropyl | OCH₃ | OCH₂CH₃ | CH | |
| CH₃ | CH₃ | 0 | H | cyclopropyl | cyclopropyl | OCH₃ | CH | |
| CH₃ | CH₃ | 0 | H | cyclopropyl | OCH₃ | CH(OCH₃)₂ | CH | |
| CH₃ | CH₃ | 0 | H | cyclopropyl | NHCH₃ | OCH₂CH₃ | N | |
| CH₃ | CH₃ | 0 | H | cyclopropyl | NHCH₃ | OCH₃ | N | |
| CH₃ | CH₃ | 0 | H | cyclopropyl | OCH₃ | OCH₂CH₃ | N | |
| CH₃ | CH₃ | 0 | H | cyclopropyl | CH₂F | CH₃ | CH | |
| CH₃ | H | 0 | H | cyclopropyl | CH₂CH₃ | CH₃ | CH | |

TABLE I-continued

| R | R₁ | n | R₂ | R' | X | Y | Z | m.p. (°C.) |
|---|----|----|----|----|----|----|----|----|
| CH₃ | H | 0 | H | cyclopropyl | CH₂CH₃ | OCH₃ | CH | |
| CH₃ | H | 0 | H | cyclopropyl | CH₂F | CH₃ | CH | |
| CH₃ | H | 0 | H | cyclopropyl | OCF₂H | CH₃ | CH | |
| CH₃ | H | 0 | H | cyclopropyl | OCF₂H | OCH₃ | CH | |
| CH₃ | H | 0 | H | cyclopropyl | OCH₂CF₃ | OCH₃ | CH | |
| CH₃ | H | 0 | H | cyclopropyl | CH₂F | OCH₃ | CH | |
| CH₃ | H | 0 | H | cyclopropyl | CH₂Cl | OCH₃ | N | |
| CH₃ | H | 0 | H | cyclopropyl | SCH₃ | OCH₃ | CH | |
| CH₃ | H | 0 | H | cyclopropyl | SCH₂F | OCH₃ | CH | |
| CH₃ | H | 0 | H | cyclopropyl | Br | OCH₃ | CH | |
| CH₃ | H | 0 | H | cyclopropyl | CH₂OCH₃ | OCH₃ | N | |
| CH₃ | H | 0 | H | cyclopropyl | OCH₂OCH₃ | OCH₃ | CH | |
| CH₃ | H | 0 | H | cyclopropyl | OCH₂OCH₂CH₃ | CH₃ | CH | |
| CH₃ | H | 0 | H | cyclopropyl | N(CH₃)2 | OCH₃ | N | |
| CH₃ | H | 0 | H | cyclopropyl | NHCH₂CH₃ | CH₃ | N | |
| CH₃ | H | 0 | H | cyclopropyl | NHCH₃ | OCH₂CH₃ | N | |
| CH₃ | H | 0 | H | cyclopropyl | CH₃ | CH₂SCH₃ | CH | |
| CH₃ | H | 0 | H | cyclopropyl | OCH₃ | CH₂SO₂CH₃ | CH | |
| CH₃ | H | 0 | H | cyclopropyl | NH₂ | OCH₂CH₃ | | |
| CH₃ | H | 0 | H | cyclopropyl | CH₃ | OCH₂CH=CH₂ | CH | |
| CH₃ | H | 0 | H | cyclopropyl | CH₂CH₃ | OCF₂H | CH | |
| CH₃ | H | 0 | H | cyclopropyl | OCF₂H | OCF₂H | CH | |
| CH₃ | H | 0 | H | cyclopropyl | OCH₃ | OCH=CH₂ | CH | |
| CH₃ | H | 0 | H | cyclopropyl | OCH₃ | C(O)CH₃ | N | |
| CH₃ | H | 0 | H | cyclopropyl | CH₃ | N(OCH₃)CH₃ | N | |
| CH₃ | H | 0 | H | cyclopropyl | OCH(CH₃)2 | OCF₂H | CH | |
| CH₃ | H | 0 | H | cyclobutyl | CH₂CH₃ | CH₃ | CH | |
| CH₃ | H | 0 | H | cyclobutyl | CH₂CH₃ | OCH₃ | CH | |
| CH₃ | H | 0 | H | cyclobutyl | CH₂F | CH₃ | CH | |
| CH₃ | H | 0 | H | cyclobutyl | OCF₂H | CH₃ | CH | |
| CH₃ | H | 0 | H | cyclobutyl | OCF₂H | OCH₃ | CH | |
| CH₃ | H | 0 | H | cyclobutyl | OCH₂CF₃ | OCH₃ | CH | |
| CH₃ | H | 0 | H | cyclobutyl | CH₂F | OCH₃ | CH | |
| CH₃ | H | 0 | H | cyclobutyl | CH₂Cl | OCH₃ | N | |
| CH₃ | H | 0 | H | cyclobutyl | SCH₃ | OCH₃ | CH | |
| CH₃ | H | 0 | H | cyclobutyl | SCH₂F | OCH₃ | CH | |
| CH₃ | H | 0 | H | cyclobutyl | Br | OCH₃ | CH | |
| CH₃ | H | 0 | H | cyclobutyl | CH₂OCH₃ | OCH₃ | N | |
| CH₃ | H | 0 | H | cyclobutyl | OCH₂OCH₃ | OCH₃ | CH | |
| CH₃ | H | 0 | H | cyclobutyl | OCH₂OCH₂CH₃ | CH₃ | CH | |
| CH₃ | H | 0 | H | cyclobutyl | N(CH₃)2 | OCH₃ | N | |
| CH₃ | H | 0 | H | cyclobutyl | NHCH₂CH₃ | CH₃ | N | |
| CH₃ | H | 0 | H | cyclobutyl | NHCH₃ | OCH₂CH₃ | N | |
| CH₃ | H | 0 | H | cyclobutyl | CH₃ | CH₂SCH₃ | CH | |
| CH₃ | H | 0 | H | cyclobutyl | OCH₃ | CH₂SO₂CH₃ | CH | |
| CH₃ | H | 0 | H | cyclobutyl | NH₂ | OCH₂CH₃ | N | |
| CH₃ | H | 0 | H | cyclobutyl | CH₃ | OCH₂CH=CH₂ | CH | |
| CH₃ | H | 0 | H | cyclobutyl | CH₂CH₃ | OCF₂H | CH | |
| CH₃ | H | 0 | H | cyclobutyl | OCF₂H | OCF₂H | CH | |
| CH₃ | H | 0 | H | cyclobutyl | OCH₃ | OCH=CH₂ | CH | |
| CH₃ | H | 0 | H | cyclobutyl | OCH₃ | C(O)CH₃ | N | |
| CH₃ | H | 0 | H | cyclobutyl | CH₃ | N(OCH₃)CH₃ | N | |
| CH₃ | H | 0 | H | cyclobutyl | OCH(CH₃)2 | OCF₂H | CH | |

TABLE II

| R | R₁ | n | R₂ | R' | X | Y | Z | m.p.(°C.) |
|---|----|----|----|----|----|----|----|----|
| CH₃ | H | 0 | H | cyclopropyl | CH₃ | CH₃ | CH | |
| CH₃ | H | 0 | H | cyclopropyl | CH₃ | OCH₃ | CH | |
| CH₃ | H | 0 | H | cyclopropyl | OCH₃ | OCH₃ | CH | |
| CH₃ | H | 0 | H | cyclopropyl | CH₃ | CH₃ | N | |
| CH₃ | H | 0 | H | cyclopropyl | CH₃ | OCH₃ | N | |
| CH₃ | H | 0 | H | cyclopropyl | OCH₃ | OCH₃ | N | |
| CH₃ | H | 0 | H | cyclopropyl | Cl | OCH₃ | CH | |
| CH₃ | H | 0 | H | cyclobutyl | CH₃ | CH₃ | CH | |
| CH₃ | H | 0 | H | cyclobutyl | CH₃ | OCH₃ | CH | |
| CH₃ | H | 0 | H | cyclobutyl | OCH₃ | OCH₃ | CH | |
| CH₃ | H | 0 | H | cyclobutyl | CH₃ | CH₃ | N | |
| CH₃ | H | 0 | H | cyclobutyl | CH₃ | OCH₃ | N | |
| CH₃ | H | 0 | H | cyclobutyl | OCH₃ | OCH₃ | N | |
| CH₃ | H | 0 | H | cyclobutyl | Cl | OCH₃ | CH | |
| CH₃ | H | 0 | H | cyclopentyl | CH₃ | CH₃ | CH | |
| CH₃ | H | 0 | H | cyclopentyl | CH₃ | OCH₃ | CH | |
| CH₃ | H | 0 | H | cyclopentyl | OCH₃ | OCH₃ | CH | |
| CH₃ | H | 0 | H | cyclopentyl | CH₃ | CH₃ | N | |
| CH₃ | H | 0 | H | cyclopentyl | CH₃ | OCH₃ | N | |
| CH₃ | H | 0 | H | cyclopentyl | OCH₃ | OCH₃ | N | |
| CH₃ | H | 0 | H | cyclopentyl | Cl | OCH₃ | CH | |

TABLE II-continued

| R | R₁ | n | R₂ | R' | X | Y | Z | m.p.(°C.) |
|---|----|---|----|----|----|----|----|----|
| CH₃ | H | 0 | H | cyclopropyl | OCH₃ | OCH₂CH₃ | CH | |
| CH₃ | H | 0 | H | cyclopropyl | cyclopropyl | OCH₃ | CH | |
| CH₃ | H | 0 | H | cyclopropyl | OCH₃ | CH(OCH₃)₂ | CH | |
| CH₃ | H | 0 | H | cyclopropyl | NHCH₃ | OCH₂CH₃ | N | |
| CH₃ | H | 0 | H | cyclopropyl | NHCH₃ | OCH₃ | N | |
| CH₃ | H | 0 | H | cyclopropyl | OCH₃ | OCH₂CH₃ | N | |
| CH₃ | H | 0 | H | cyclopropyl | CH₂F | CH₃ | CH | |
| CH₃ | H | 0 | CH₃ | cyclopropyl | CH₃ | CH₃ | CH | |
| CH₃ | H | 0 | CH₃ | cyclopropyl | CH₃ | OCH₃ | CH | |
| CH₃ | H | 0 | CH₃ | cyclopropyl | OCH₃ | OCH₃ | CH | |
| CH₃ | H | 0 | CH₃ | cyclopropyl | CH₃ | CH₃ | N | |
| CH₃ | H | 0 | CH₃ | cyclopropyl | CH₃ | OCH₃ | N | |
| CH₃ | H | 0 | CH₃ | cyclopropyl | OCH₃ | OCH₃ | N | |
| CH₃ | H | 0 | CH₃ | cyclopropyl | Cl | OCH₃ | CH | |
| CH₃ | H | 0 | CH₃ | cyclobutyl | CH₃ | CH₃ | CH | |
| CH₃ | H | 0 | CH₃ | cyclobutyl | CH₃ | OCH₃ | CH | |
| CH₃ | H | 0 | CH₃ | cyclobutyl | OCH₃ | OCH₃ | CH | |
| CH₃ | H | 0 | CH₃ | cyclobutyl | CH₃ | CH₃ | N | |
| CH₃ | H | 0 | CH₃ | cyclobutyl | CH₃ | OCH₃ | N | |
| CH₃ | H | 0 | CH₃ | cyclobutyl | OCH₃ | OCH₃ | N | |
| CH₃ | H | 0 | CH₃ | cyclobutyl | Cl | OCH₃ | CH | |
| CH₃ | H | 0 | CH₃ | cyclopentyl | CH₃ | CH₃ | CH | |
| CH₃ | H | 0 | CH₃ | cyclopentyl | CH₃ | OCH₃ | CH | |
| CH₃ | H | 0 | CH₃ | cyclopentyl | OCH₃ | OCH₃ | CH | |
| CH₃ | H | 0 | CH₃ | cyclopentyl | CH₃ | CH₃ | N | |
| CH₃ | H | 0 | CH₃ | cyclopentyl | CH₃ | OCH₃ | N | |
| CH₃ | H | 0 | CH₃ | cyclopentyl | OCH₃ | OCH₃ | N | |
| CH₃ | H | 0 | CH₃ | cyclopentyl | Cl | OCH₃ | CH | |
| CH₃ | H | 0 | CH₃ | cyclopropyl | OCH₃ | OCH₂CH₃ | CH | |
| CH₃ | H | 0 | CH₃ | cyclopropyl | cyclopropyl | OCH₃ | CH | |
| CH₃ | H | 0 | CH₃ | cyclopropyl | OCH₃ | CH(OCH₃)₂ | CH | |
| CH₃ | H | 0 | CH₃ | cyclopropyl | NHCH₃ | OCH₂CH₃ | N | |
| CH₃ | H | 0 | CH₃ | cyclopropyl | NHCH₃ | OCH₃ | N | |
| CH₃ | H | 0 | CH₃ | cyclopropyl | OCH₃ | OCH₂CH₃ | N | |
| CH₃ | H | 0 | CH₃ | cyclopropyl | CH₂F | CH₃ | CH | |
| CH₃ | H | 0 | Cl | cyclopropyl | CH₃ | CH₃ | CH | |
| CH₃ | H | 0 | Cl | cyclopropyl | CH₃ | OCH₃ | CH | |
| CH₃ | H | 0 | Cl | cyclopropyl | OCH₃ | OCH₃ | CH | |
| CH₃ | H | 0 | Cl | cyclopropyl | CH₃ | CH₃ | N | |
| CH₃ | H | 0 | Cl | cyclopropyl | CH₃ | OCH₃ | N | |
| CH₃ | H | 0 | Cl | cyclopropyl | OCH₃ | OCH₃ | N | |
| CH₃ | H | 0 | Cl | cyclopropyl | Cl | OCH₃ | CH | |
| CH₃ | H | 0 | Cl | cyclobutyl | CH₃ | CH₃ | CH | |
| CH₃ | H | 0 | Cl | cyclobutyl | CH₃ | OCH₃ | CH | |
| CH₃ | H | 0 | Cl | cyclobutyl | OCH₃ | OCH₃ | CH | |
| CH₃ | H | 0 | Cl | cyclobutyl | CH₃ | CH₃ | N | |
| CH₃ | H | 0 | Cl | cyclobutyl | CH₃ | OCH₃ | N | |
| CH₃ | H | 0 | Cl | cyclobutyl | OCH₃ | OCH₃ | N | |
| CH₃ | H | 0 | Cl | cyclobutyl | Cl | OCH₃ | CH | |
| CH₃ | H | 0 | Cl | cyclopentyl | CH₃ | CH₃ | CH | |
| CH₃ | H | 0 | Cl | cyclopentyl | CH₃ | OCH₃ | CH | |
| CH₃ | H | 0 | Cl | cyclopentyl | OCH₃ | OCH₃ | CH | |
| CH₃ | H | 0 | Cl | cyclopentyl | CH₃ | CH₃ | N | |
| CH₃ | H | 0 | Cl | cyclopentyl | CH₃ | OCH₃ | N | |
| CH₃ | H | 0 | Cl | cyclopentyl | OCH₃ | OCH₃ | N | |
| CH₃ | H | 0 | Cl | cyclopentyl | Cl | OCH₃ | CH | |
| CH₃ | H | 0 | Cl | cyclopropyl | OCH₃ | OCH₂CH₃ | CH | |
| CH₃ | H | 0 | Cl | cyclopropyl | cyclopropyl | OCH₃ | CH | |
| CH₃ | H | 0 | Cl | cyclopropyl | OCH₃ | CH(OCH₃)₂ | CH | |
| CH₃ | H | 0 | Cl | cyclopropyl | NHCH₃ | OCH₂CH₃ | N | |
| CH₃ | H | 0 | Cl | cyclopropyl | NHCH₃ | OCH₃ | N | |
| CH₃ | H | 0 | Cl | cyclopropyl | OCH₃ | OCH₂CH₃ | N | |
| CH₃ | H | 0 | Cl | cyclopropyl | CH₂F | CH₃ | CH | |
| CH₃ | H | 0 | CH₂F | cyclopropyl | CH₃ | CH₃ | CH | |
| CH₃ | H | 0 | CH₂F | cyclopropyl | CH₃ | OCH₃ | CH | |
| CH₃ | H | 0 | CH₂F | cyclopropyl | OCH₃ | OCH₃ | CH | |
| CH₃ | H | 0 | CH₂F | cyclopropyl | CH₃ | CH₃ | N | |
| CH₃ | H | 0 | CH₂F | cyclopropyl | CH₃ | OCH₃ | N | |
| CH₃ | H | 0 | CH₂F | cyclopropyl | OCH₃ | OCH₃ | N | |
| CH₃ | H | 0 | CH₂F | cyclopropyl | Cl | OCH₃ | CH | |
| CH₃ | H | 0 | CH₂F | cyclobutyl | CH₃ | CH₃ | CH | |
| CH₃ | H | 0 | CH₂F | cyclobutyl | CH₃ | OCH₃ | CH | |
| CH₃ | H | 0 | CH₂F | cyclobutyl | OCH₃ | OCH₃ | CH | |
| CH₃ | H | 0 | CH₂F | cyclobutyl | CH₃ | CH₃ | N | |
| CH₃ | H | 0 | CH₂F | cyclobutyl | CH₃ | OCH₃ | N | |
| CH₃ | H | 0 | CH₂F | cyclobutyl | OCH₃ | OCH₃ | N | |
| CH₃ | H | 0 | CH₂F | cyclobutyl | Cl | OCH₃ | CH | |
| CH₃ | H | 0 | CH₂F | cyclopentyl | CH₃ | CH₃ | CH | |
| CH₃ | H | 0 | CH₂F | cyclopentyl | CH₃ | OCH₃ | CH | |
| CH₃ | H | 0 | CH₂F | cyclopentyl | OCH₃ | OCH₃ | CH | |
| CH₃ | H | 0 | CH₂F | cyclopentyl | CH₃ | CH₃ | N | |

TABLE II-continued

| R | $R_1$ | n | $R_2$ | R' | X | Y | Z | m.p.(°C.) |
|---|---|---|---|---|---|---|---|---|
| $CH_3$ | H | 0 | $CH_2F$ | cyclopentyl | $CH_3$ | $OCH_3$ | N | |
| $CH_3$ | H | 0 | $CH_2F$ | cyclopentyl | $OCH_3$ | $OCH_3$ | N | |
| $CH_3$ | H | 0 | $CH_2F$ | cyclopentyl | Cl | $OCH_3$ | CH | |
| $CH_3$ | H | 0 | $CH_2F$ | cyclopropyl | $OCH_3$ | $OCH_2CH_3$ | CH | |
| $CH_3$ | H | 0 | $CH_2F$ | cyclopropyl | cyclopropyl | $OCH_3$ | CH | |
| $CH_3$ | H | 0 | $CH_2F$ | cyclopropyl | $OCH_3$ | $CH(OCH_3)_2$ | CH | |
| $CH_3$ | H | 0 | $CH_2F$ | cyclopropyl | $NHCH_3$ | $OCH_2CH_3$ | N | |
| $CH_3$ | H | 0 | $CH_2F$ | cyclopropyl | $NHCH_3$ | $OCH_3$ | N | |
| $CH_3$ | H | 0 | $CH_2F$ | cyclopropyl | $OCH_3$ | $OCH_2CH_3$ | N | |
| $CH_3$ | H | 0 | $CH_2F$ | cyclopropyl | $CH_2F$ | $CH_3$ | CH | |
| $CH_3$ | H | 0 | $SO_2N(CH_3)_2$ | cyclopropyl | $CH_3$ | $CH_3$ | CH | |
| $CH_3$ | H | 0 | $SO_2N(CH_3)_2$ | cyclopropyl | $CH_3$ | $OCH_3$ | CH | |
| $CH_3$ | H | 0 | $SO_2N(CH_3)_2$ | cyclopropyl | $OCH_3$ | $OCH_3$ | CH | |
| $CH_3$ | H | 0 | $SO_2N(CH_3)_2$ | cyclopropyl | $CH_3$ | $CH_3$ | N | |
| $CH_3$ | H | 0 | $SO_2N(CH_3)_2$ | cyclopropyl | $CH_3$ | $OCH_3$ | N | |
| $CH_3$ | H | 0 | $SO_2N(CH_3)_2$ | cyclopropyl | $OCH_3$ | $OCH_3$ | N | |
| $CH_3$ | H | 0 | $SO_2N(CH_3)_2$ | cyclopropyl | Cl | $OCH_3$ | CH | |
| $CH_3$ | H | 0 | $SO_2N(CH_3)_2$ | cyclobutyl | $CH_3$ | $CH_3$ | CH | |
| $CH_3$ | H | 0 | $SO_2N(CH_3)_2$ | cyclobutyl | $CH_3$ | $OCH_3$ | CH | |
| $CH_3$ | H | 0 | $SO_2N(CH_3)_2$ | cyclobutyl | $OCH_3$ | $OCH_3$ | CH | |
| $CH_3$ | H | 0 | $SO_2N(CH_3)_2$ | cyclobutyl | $CH_3$ | $CH_3$ | N | |
| $CH_3$ | H | 0 | $SO_2N(CH_3)_2$ | cyclobutyl | $CH_3$ | $OCH_3$ | N | |
| $CH_3$ | H | 0 | $SO_2N(CH_3)_2$ | cyclobutyl | $OCH_3$ | $OCH_3$ | N | |
| $CH_3$ | H | 0 | $SO_2N(CH_3)_2$ | cyclobutyl | Cl | $OCH_3$ | CH | |
| $CH_3$ | H | 0 | $SO_2N(CH_3)_2$ | cyclopentyl | $CH_3$ | $CH_3$ | CH | |
| $CH_3$ | H | 0 | $SO_2N(CH_3)_2$ | cyclopentyl | $CH_3$ | $OCH_3$ | CH | |
| $CH_3$ | H | 0 | $SO_2N(CH_3)_2$ | cyclopentyl | $OCH_3$ | $OCH_3$ | CH | |
| $CH_3$ | H | 0 | $SO_2N(CH_3)_2$ | cyclopentyl | $CH_3$ | $CH_3$ | N | |
| $CH_3$ | H | 0 | $SO_2N(CH_3)_2$ | cyclopentyl | $CH_3$ | $OCH_3$ | N | |
| $CH_3$ | H | 0 | $SO_2N(CH_3)_2$ | cyclopentyl | $OCH_3$ | $OCH_3$ | N | |
| $CH_3$ | H | 0 | $SO_2N(CH_3)_2$ | cyclopentyl | Cl | $OCH_3$ | CH | |
| $CH_3$ | H | 0 | $SO_2N(CH_3)_2$ | cyclopropyl | $OCH_3$ | $OCH_2CH_3$ | CH | |
| $CH_3$ | H | 0 | $SO_2N(CH_3)_2$ | cyclopropyl | cyclopropyl | $OCH_3$ | CH | |
| $CH_3$ | H | 0 | $SO_2N(CH_3)_2$ | cyclopropyl | $OCH_3$ | $CH(OCH_3)_2$ | CH | |
| $CH_3$ | H | 0 | $SO_2N(CH_3)_2$ | cyclopropyl | $NHCH_3$ | $OCH_2CH_3$ | N | |
| $CH_3$ | H | 0 | $SO_2N(CH_3)_2$ | cyclopropyl | $NHCH_3$ | $OCH_3$ | N | |
| $CH_3$ | H | 0 | $SO_2N(CH_3)_2$ | cyclopropyl | $OCH_3$ | $OCH_2CH_3$ | N | |
| $CH_3$ | H | 0 | $SO_2N(CH_3)_2$ | cyclopropyl | $CH_2F$ | $CH_3$ | CH | |
| $CH_3$ | H | 0 | $SOCH_3$ | cyclopropyl | $CH_3$ | $CH_3$ | CH | |
| $CH_3$ | H | 0 | $SOCH_3$ | cyclopropyl | $CH_3$ | $OCH_3$ | CH | |
| $CH_3$ | H | 0 | $SOCH_3$ | cyclopropyl | $OCH_3$ | $OCH_3$ | CH | |
| $CH_3$ | H | 0 | $SOCH_3$ | cyclopropyl | $CH_3$ | $CH_3$ | N | |
| $CH_3$ | H | 0 | $SOCH_3$ | cyclopropyl | $CH_3$ | $OCH_3$ | N | |
| $CH_3$ | H | 0 | $SOCH_3$ | cyclopropyl | $OCH_3$ | $OCH_3$ | N | |
| $CH_3$ | H | 0 | $SOCH_3$ | cyclopropyl | Cl | $OCH_3$ | CH | |
| $CH_3$ | H | 0 | $SOCH_3$ | cyclobutyl | $CH_3$ | $CH_3$ | CH | |
| $CH_3$ | H | 0 | $SOCH_3$ | cyclobutyl | $CH_3$ | $OCH_3$ | CH | |
| $CH_3$ | H | 0 | $SOCH_3$ | cyclobutyl | $OCH_3$ | $OCH_3$ | CH | |
| $CH_3$ | H | 0 | $SOCH_3$ | cyclobutyl | $CH_3$ | $CH_3$ | N | |
| $CH_3$ | H | 0 | $SOCH_3$ | cyclobutyl | $CH_3$ | $OCH_3$ | N | |
| $CH_3$ | H | 0 | $SOCH_3$ | cyclobutyl | $OCH_3$ | $OCH_3$ | N | |
| $CH_3$ | H | 0 | $SOCH_3$ | cyclobutyl | Cl | $OCH_3$ | CH | |
| $CH_3$ | H | 0 | $SOCH_3$ | cyclopentyl | $CH_3$ | $CH_3$ | CH | |
| $CH_3$ | H | 0 | $SOCH_3$ | cyclopentyl | $CH_3$ | $OCH_3$ | CH | |
| $CH_3$ | H | 0 | $SOCH_3$ | cyclopentyl | $OCH_3$ | $OCH_3$ | CH | |
| $CH_3$ | H | 0 | $SOCH_3$ | cyclopentyl | $CH_3$ | $CH_3$ | N | |
| $CH_3$ | H | 0 | $SOCH_3$ | cyclopentyl | $CH_3$ | $OCH_3$ | N | |
| $CH_3$ | H | 0 | $SOCH_3$ | cyclopentyl | $OCH_3$ | $OCH_3$ | N | |
| $CH_3$ | H | 0 | $SOCH_3$ | cyclopentyl | Cl | $OCH_3$ | CH | |
| $CH_3$ | H | 0 | $SOCH_3$ | cyclopropyl | $OCH_3$ | $OCH_2CH_3$ | CH | |
| $CH_3$ | H | 0 | $SOCH_3$ | cyclopropyl | cyclopropyl | $OCH_3$ | CH | |
| $CH_3$ | H | 0 | $SOCH_3$ | cyclopropyl | $OCH_3$ | $CH(OCH_3)_2$ | CH | |
| $CH_3$ | H | 0 | $SOCH_3$ | cyclopropyl | $NHCH_3$ | $OCH_2CH_3$ | N | |
| $CH_3$ | H | 0 | $SOCH_3$ | cyclopropyl | $NHCH_3$ | $OCH_3$ | N | |
| $CH_3$ | H | 0 | $SOCH_3$ | cyclopropyl | $OCH_3$ | $OCH_2CH_3$ | N | |
| $CH_3$ | H | 0 | $SOCH_3$ | cyclopropyl | $CH_2F$ | $CH_3$ | CH | |
| $CH_3$ | H | 0 | CN | cyclopropyl | $CH_3$ | $CH_3$ | CH | |
| $CH_3$ | H | 0 | CN | cyclopropyl | $CH_3$ | $OCH_3$ | CH | |
| $CH_3$ | H | 0 | CN | cyclopropyl | $OCH_3$ | $OCH_3$ | CH | |
| $CH_3$ | H | 0 | CN | cyclopropyl | $CH_3$ | $CH_3$ | N | |
| $CH_3$ | H | 0 | CN | cyclopropyl | $CH_3$ | $OCH_3$ | N | |
| $CH_3$ | H | 0 | CN | cyclopropyl | $OCH_3$ | $OCH_3$ | N | |
| $CH_3$ | H | 0 | CN | cyclopropyl | Cl | $OCH_3$ | CH | |
| $CH_3$ | H | 0 | CN | cyclobutyl | $CH_3$ | $CH_3$ | CH | |
| $CH_3$ | H | 0 | CN | cyclobutyl | $CH_3$ | $OCH_3$ | CH | |
| $CH_3$ | H | 0 | CN | cyclobutyl | $OCH_3$ | $OCH_3$ | CH | |
| $CH_3$ | H | 0 | CN | cyclobutyl | $CH_3$ | $CH_3$ | N | |
| $CH_3$ | H | 0 | CN | cyclobutyl | $CH_3$ | $OCH_3$ | N | |
| $CH_3$ | H | 0 | CN | cyclobutyl | $OCH_3$ | $OCH_3$ | N | |
| $CH_3$ | H | 0 | CN | cyclobutyl | Cl | $OCH_3$ | CH | |
| $CH_3$ | H | 0 | CN | cyclopentyl | $CH_3$ | $CH_3$ | CH | |

TABLE II-continued

| R | R₁ | n | R₂ | R' | X | Y | Z | m.p.(°C.) |
|---|---|---|---|---|---|---|---|---|
| CH₃ | H | 0 | CN | cyclopentyl | CH₃ | OCH₃ | CH | |
| CH₃ | H | 0 | CN | cyclopentyl | OCH₃ | OCH₃ | CH | |
| CH₃ | H | 0 | CN | cyclopentyl | CH₃ | CH₃ | N | |
| CH₃ | H | 0 | CN | cyclopentyl | CH₃ | OCH₃ | N | |
| CH₃ | H | 0 | CN | cyclopentyl | OCH₃ | OCH₃ | N | |
| CH₃ | H | 0 | CN | cyclopentyl | Cl | OCH₃ | CH | |
| CH₃ | H | 0 | CN | cyclopropyl | OCH₃ | OCH₂CH₃ | CH | |
| CH₃ | H | 0 | CN | cyclopropyl | cyclopropyl | OCH₃ | CH | |
| CH₃ | H | 0 | CN | cyclopropyl | OCH₃ | CH(OCH₃)₂ | CH | |
| CH₃ | H | 0 | CN | cyclopropyl | NHCH₃ | OCH₂CH₃ | N | |
| CH₃ | H | 0 | CN | cyclopropyl | NHCH₃ | OCH₃ | N | |
| CH₃ | H | 0 | CN | cyclopropyl | OCH₃ | OCH₂CH₃ | N | |
| CH₃ | H | 0 | CN | cyclopropyl | CH₂F | CH₃ | CH | |
| CH₃ | H | 0 | N(CH₃)₂ | cyclopropyl | CH₃ | CH₃ | CH | |
| CH₃ | H | 0 | N(CH₃)₂ | cyclopropyl | CH₃ | OCH₃ | CH | |
| CH₃ | H | 0 | N(CH₃)₂ | cyclopropyl | OCH₃ | OCH₃ | CH | |
| CH₃ | H | 0 | N(CH₃)₂ | cyclopropyl | CH₃ | CH₃ | N | |
| CH₃ | H | 0 | N(CH₃)₂ | cyclopropyl | CH₃ | OCH₃ | N | |
| CH₃ | H | 0 | N(CH₃)₂ | cyclopropyl | OCH₃ | OCH₃ | N | |
| CH₃ | H | 0 | N(CH₃)₂ | cyclopropyl | Cl | OCH₃ | CH | |
| CH₃ | H | 0 | N(CH₃)₂ | cyclobutyl | CH₃ | CH₃ | CH | |
| CH₃ | H | 0 | N(CH₃)₂ | cyclobutyl | CH₃ | OCH₃ | CH | |
| CH₃ | H | 0 | N(CH₃)₂ | cyclobutyl | OCH₃ | OCH₃ | CH | |
| CH₃ | H | 0 | N(CH₃)₂ | cyclobutyl | CH₃ | CH₃ | N | |
| CH₃ | H | 0 | N(CH₃)₂ | cyclobutyl | CH₃ | OCH₃ | N | |
| CH₃ | H | 0 | N(CH₃)₂ | cyclobutyl | OCH₃ | OCH₃ | N | |
| CH₃ | H | 0 | N(CH₃)₂ | cyclobutyl | Cl | OCH₃ | CH | |
| CH₃ | H | 0 | N(CH₃)₂ | cyclopentyl | CH₃ | CH₃ | CH | |
| CH₃ | H | 0 | N(CH₃)₂ | cyclopentyl | CH₃ | OCH₃ | CH | |
| CH₃ | H | 0 | N(CH₃)₂ | cyclopentyl | OCH₃ | OCH₃ | CH | |
| CH₃ | H | 0 | N(CH₃)₂ | cyclopentyl | CH₃ | CH₃ | N | |
| CH₃ | H | 0 | N(CH₃)₂ | cyclopentyl | CH₃ | OCH₃ | N | |
| CH₃ | H | 0 | N(CH₃)₂ | cyclopentyl | OCH₃ | OCH₃ | N | |
| CH₃ | H | 0 | N(CH₃)₂ | cyclopentyl | Cl | OCH₃ | CH | |
| CH₃ | H | 0 | N(CH₃)₂ | cyclopropyl | OCH₃ | OCH₂CH₃ | CH | |
| CH₃ | H | 0 | N(CH₃)₂ | cyclopropyl | cyclopropyl | OCH₃ | CH | |
| CH₃ | H | 0 | N(CH₃)₂ | cyclopropyl | OCH₃ | CH(OCH₃)₂ | CH | |
| CH₃ | H | 0 | N(CH₃)₂ | cyclopropyl | NHCH₃ | OCH₂CH₃ | N | |
| CH₃ | H | 0 | N(CH₃)₂ | cyclopropyl | NHCH₃ | OCH₃ | N | |
| CH₃ | H | 0 | N(CH₃)₂ | cyclopropyl | OCH₃ | OCH₂CH₃ | N | |
| CH₃ | H | 0 | N(CH₃)₂ | cyclopropyl | CH₂F | CH₃ | CH | |
| CH₃ | H | 0 | CH₂OCH₃ | cyclopropyl | CH₃ | CH₃ | CH | |
| CH₃ | H | 0 | CH₂OCH₃ | cyclopropyl | CH₃ | OCH₃ | CH | |
| CH₃ | H | 0 | CH₂OCH₃ | cyclopropyl | OCH₃ | OCH₃ | CH | |
| CH₃ | H | 0 | CH₂OCH₃ | cyclopropyl | CH₃ | CH₃ | N | |
| CH₃ | H | 0 | CH₂OCH₃ | cyclopropyl | CH₃ | OCH₃ | N | |
| CH₃ | H | 0 | CH₂OCH₃ | cyclopropyl | OCH₃ | OCH₃ | N | |
| CH₃ | H | 0 | CH₂OCH₃ | cyclopropyl | Cl | OCH₃ | CH | |
| CH₃ | H | 0 | CH₂OCH₃ | cyclobutyl | CH₃ | CH₃ | CH | |
| CH₃ | H | 0 | CH₂OCH₃ | cyclobutyl | CH₃ | OCH₃ | CH | |
| CH₃ | H | 0 | CH₂OCH₃ | cyclobutyl | OCH₃ | OCH₃ | CH | |
| CH₃ | H | 0 | CH₂OCH₃ | cyclobutyl | CH₃ | CH₃ | N | |
| CH₃ | H | 0 | CH₂OCH₃ | cyclobutyl | CH₃ | OCH₃ | N | |
| CH₃ | H | 0 | CH₂OCH₃ | cyclobutyl | OCH₃ | OCH₃ | N | |
| CH₃ | H | 0 | CH₂OCH₃ | cyclobutyl | Cl | OCH₃ | CH | |
| CH₃ | H | 0 | CH₂OCH₃ | cyclopentyl | CH₃ | CH₃ | CH | |
| CH₃ | H | 0 | CH₂OCH₃ | cyclopentyl | CH₃ | OCH₃ | CH | |
| CH₃ | H | 0 | CH₂OCH₃ | cyclopentyl | CH₃ | CH₃ | N | |
| CH₃ | H | 0 | CH₂OCH₃ | cyclopentyl | CH₃ | OCH₃ | N | |
| CH₃ | H | 0 | CH₂OCH₃ | cyclopentyl | OCH₃ | OCH₃ | N | |
| CH₃ | H | 0 | CH₂OCH₃ | cyclopentyl | Cl | OCH₃ | CH | |
| CH₃ | H | 0 | CH₂OCH₃ | cyclopropyl | OCH₃ | OCH₂CH₃ | CH | |
| CH₃ | H | 0 | CH₂OCH₃ | cyclopropyl | cyclopropyl | OCH₃ | CH | |
| CH₃ | H | 0 | CH₂OCH₃ | cyclopropyl | OCH₃ | CH(OCH₃)₂ | CH | |
| CH₃ | H | 0 | CH₂OCH₃ | cyclopropyl | NHCH₃ | OCH₂CH₃ | N | |
| CH₃ | H | 0 | CH₂OCH₃ | cyclopropyl | NHCH₃ | OCH₃ | N | |
| CH₃ | H | 0 | CH₂OCH₃ | cyclopropyl | OCH₃ | OCH₂CH₃ | N | |
| CH₃ | H | 0 | CH₂OCH₃ | cyclopropyl | CH₂F | CH₃ | CH | |
| CH₂CH₃ | H | 0 | H | cyclopropyl | CH₃ | CH₃ | CH | |
| CH₂CH₃ | H | 0 | H | cyclopropyl | CH₃ | OCH₃ | CH | |
| CH₂CH₃ | H | 0 | H | cyclopropyl | OCH₃ | OCH₃ | CH | |
| CH₂CH₃ | H | 0 | H | cyclopropyl | CH₃ | CH₃ | N | |
| CH₂CH₃ | H | 0 | H | cyclopropyl | CH₃ | OCH₃ | N | |
| CH₂CH₃ | H | 0 | H | cyclopropyl | OCH₃ | OCH₃ | N | |
| CH₂CH₃ | H | 0 | H | cyclopropyl | Cl | OCH₃ | CH | |
| CH₂CH₃ | H | 0 | H | cyclobutyl | CH₃ | CH₃ | CH | |
| CH₂CH₃ | H | 0 | H | cyclobutyl | CH₃ | OCH₃ | CH | |
| CH₂CH₃ | H | 0 | H | cyclobutyl | OCH₃ | OCH₃ | CH | |
| CH₂CH₃ | H | 0 | H | cyclobutyl | CH₃ | CH₃ | N | |
| CH₂CH₃ | H | 0 | H | cyclobutyl | CH₃ | OCH₃ | N | |

TABLE II-continued

| R | R₁ | n | R₂ | R' | X | Y | Z | m.p.(°C.) |
|---|---|---|---|---|---|---|---|---|
| CH₂CH₃ | H | 0 | H | cyclobutyl | OCH₃ | OCH₃ | N | |
| CH₂CH₃ | H | 0 | H | cyclobutyl | Cl | OCH₃ | CH | |
| CH₂CH₃ | H | 0 | H | cyclopentyl | CH₃ | CH₃ | CH | |
| CH₂CH₃ | H | 0 | H | cyclopentyl | CH₃ | OCH₃ | CH | |
| CH₂CH₃ | H | 0 | H | cyclopentyl | OCH₃ | OCH₃ | CH | |
| CH₂CH₃ | H | 0 | H | cyclopentyl | CH₃ | CH₃ | N | |
| CH₂CH₃ | H | 0 | H | cyclopentyl | CH₃ | OCH₃ | N | |
| CH₂CH₃ | H | 0 | H | cyclopentyl | OCH₃ | OCH₃ | N | |
| CH₂CH₃ | H | 0 | H | cyclopentyl | Cl | OCH₃ | CH | |
| CH₂CH₃ | H | 0 | H | cyclopropyl | OCH₃ | OCH₂CH₃ | CH | |
| CH₂CH₃ | H | 0 | H | cyclopropyl | cyclopropyl | OCH₃ | CH | |
| CH₂CH₃ | H | 0 | H | cyclopropyl | OCH₃ | CH(OCH₃)₂ | CH | |
| CH₂CH₃ | H | 0 | H | cyclopropyl | NHCH₃ | OCH₂CH₃ | N | |
| CH₂CH₃ | H | 0 | H | cyclopropyl | NHCH₃ | OCH₃ | N | |
| CH₂CH₃ | H | 0 | H | cyclopropyl | OCH₃ | OCH₂CH₃ | N | |
| CH₂CH₃ | H | 0 | H | cyclopropyl | CH₂F | CH₃ | CH | |
| CO₂CH₃ | H | 0 | H | cyclopropyl | CH₃ | CH₃ | CH | |
| CO₂CH₃ | H | 0 | H | cyclopropyl | CH₃ | OCH₃ | CH | |
| CO₂CH₃ | H | 0 | H | cyclopropyl | OCH₃ | OCH₃ | CH | |
| CO₂CH₃ | H | 0 | H | cyclopropyl | CH₃ | CH₃ | N | |
| CO₂CH₃ | H | 0 | H | cyclopropyl | CH₃ | OCH₃ | N | |
| CO₂CH₃ | H | 0 | H | cyclopropyl | OCH₃ | OCH₃ | N | |
| CO₂CH₃ | H | 0 | H | cyclopropyl | Cl | OCH₃ | CH | |
| CO₂CH₃ | H | 0 | H | cyclobutyl | CH₃ | CH₃ | CH | |
| CO₂CH₃ | H | 0 | H | cyclobutyl | CH₃ | OCH₃ | CH | |
| CO₂CH₃ | H | 0 | H | cyclobutyl | OCH₃ | OCH₃ | CH | |
| CO₂CH₃ | H | 0 | H | cyclobutyl | CH₃ | CH₃ | N | |
| CO₂CH₃ | H | 0 | H | cyclobutyl | CH₃ | OCH₃ | N | |
| CO₂CH₃ | H | 0 | H | cyclobutyl | OCH₃ | OCH₃ | N | |
| CO₂CH₃ | H | 0 | H | cyclobutyl | Cl | OCH₃ | CH | |
| CO₂CH₃ | H | 0 | H | cyclopentyl | CH₃ | CH₃ | CH | |
| CO₂CH₃ | H | 0 | H | cyclopentyl | CH₃ | OCH₃ | CH | |
| CO₂CH₃ | H | 0 | H | cyclopentyl | OCH₃ | OCH₃ | CH | |
| CO₂CH₃ | H | 0 | H | cyclopentyl | CH₃ | CH₃ | N | |
| CO₂CH₃ | H | 0 | H | cyclopentyl | CH₃ | OCH₃ | N | |
| CO₂CH₃ | H | 0 | H | cyclopentyl | OCH₃ | OCH₃ | N | |
| CO₂CH₃ | H | 0 | H | cyclopentyl | Cl | OCH₃ | CH | |
| CO₂CH₃ | H | 0 | H | cyclopropyl | OCH₃ | OCH₂CH₃ | CH | |
| CO₂CH₃ | H | 0 | H | cyclopropyl | cyclopropyl | OCH₃ | CH | |
| CO₂CH₃ | H | 0 | H | cyclopropyl | OCH₃ | CH(OCH₃)₂ | CH | |
| CO₂CH₃ | H | 0 | H | cyclopropyl | NHCH₃ | OCH₂CH₃ | N | |
| CO₂CH₃ | H | 0 | H | cyclopropyl | NHCH₃ | OCH₃ | N | |
| CO₂CH₃ | H | 0 | H | cyclopropyl | OCH₃ | OCH₂CH₃ | N | |
| CO₂CH₃ | H | 0 | H | cyclopropyl | CH₂F | CH₃ | CH | |
| CH₂F | H | 0 | H | cyclopropyl | CH₃ | CH₃ | CH | |
| CH₂F | H | 0 | H | cyclopropyl | CH₃ | OCH₃ | CH | |
| CH₂F | H | 0 | H | cyclopropyl | OCH₃ | OCH₃ | CH | |
| CH₂F | H | 0 | H | cyclopropyl | CH₃ | CH₃ | N | |
| CH₂F | H | 0 | H | cyclopropyl | CH₃ | OCH₃ | N | |
| CH₂F | H | 0 | H | cyclopropyl | OCH₃ | OCH₃ | N | |
| CH₂F | H | 0 | H | cyclopropyl | Cl | OCH₃ | CH | |
| CH₂F | H | 0 | H | cyclobutyl | CH₃ | CH₃ | CH | |
| CH₂F | H | 0 | H | cyclobutyl | CH₃ | OCH₃ | CH | |
| CH₂F | H | 0 | H | cyclobutyl | OCH₃ | OCH₃ | CH | |
| CH₂F | H | 0 | H | cyclobutyl | CH₃ | CH₃ | N | |
| CH₂F | H | 0 | H | cyclobutyl | CH₃ | OCH₃ | N | |
| CH₂F | H | 0 | H | cyclobutyl | OCH₃ | OCH₃ | N | |
| CH₂F | H | 0 | H | cyclobutyl | Cl | OCH₃ | CH | |
| CH₂F | H | 0 | H | cyclopentyl | CH₃ | CH₃ | CH | |
| CH₂F | H | 0 | H | cyclopentyl | CH₃ | OCH₃ | CH | |
| CH₂F | H | 0 | H | cyclopentyl | OCH₃ | OCH₃ | CH | |
| CH₂F | H | 0 | H | cyclopentyl | CH₃ | CH₃ | N | |
| CH₂F | H | 0 | H | cyclopentyl | CH₃ | OCH₃ | N | |
| CH₂F | H | 0 | H | cyclopentyl | OCH₃ | OCH₃ | N | |
| CH₂F | H | 0 | H | cyclopentyl | Cl | OCH₃ | CH | |
| CH₂F | H | 0 | H | cyclopropyl | OCH₃ | OCH₂CH₃ | CH | |
| CH₂F | H | 0 | H | cyclopropyl | cyclopropyl | OCH₃ | CH | |
| CH₂F | H | 0 | H | cyclopropyl | OCH₃ | CH(OCH₃)₂ | CH | |
| CH₂F | H | 0 | H | cyclopropyl | NHCH₃ | OCH₂CH₃ | N | |
| CH₂F | H | 0 | H | cyclopropyl | NHCH₃ | OCH₃ | N | |
| CH₂F | H | 0 | H | cyclopropyl | OCH₃ | OCH₂CH₃ | N | |
| CH₂F | H | 0 | H | cyclopropyl | CH₂F | CH₃ | CH | |
| CH₂C≡CH | H | 0 | H | cyclopropyl | CH₃ | CH₃ | CH | |
| CH₂C≡CH | H | 0 | H | cyclopropyl | CH₃ | OCH₃ | CH | |
| CH₂C≡CH | H | 0 | H | cyclopropyl | OCH₃ | OCH₃ | CH | |
| CH₂C≡CH | H | 0 | H | cyclopropyl | CH₃ | CH₃ | N | |
| CH₂C≡CH | H | 0 | H | cyclopropyl | CH₃ | OCH₃ | N | |
| CH₂C≡CH | H | 0 | H | cyclopropyl | OCH₃ | OCH₃ | N | |
| CH₂C≡CH | H | 0 | H | cyclopropyl | Cl | OCH₃ | CH | |
| CH₂C≡CH | H | 0 | H | cyclobutyl | CH₃ | CH₃ | CH | |
| CH₂C≡CH | H | 0 | H | cyclobutyl | CH₃ | OCH₃ | CH | |

TABLE II-continued

| R | $R_1$ | n | $R_2$ | R' | X | Y | Z | m.p.(°C.) |
|---|---|---|---|---|---|---|---|---|
| $CH_2C\equiv CH$ | H | 0 | H | cyclobutyl | $OCH_3$ | $OCH_3$ | CH | |
| $CH_2C\equiv CH$ | H | 0 | H | cyclobutyl | $CH_3$ | $CH_3$ | N | |
| $CH_2C\equiv CH$ | H | 0 | H | cyclobutyl | $CH_3$ | $OCH_3$ | N | |
| $CH_2C\equiv CH$ | H | 0 | H | cyclobutyl | $OCH_3$ | $OCH_3$ | N | |
| $CH_2C\equiv CH$ | H | 0 | H | cyclobutyl | Cl | $OCH_3$ | CH | |
| $CH_2C\equiv CH$ | H | 0 | H | cyclopentyl | $CH_3$ | $CH_3$ | CH | |
| $CH_2C\equiv CH$ | H | 0 | H | cyclopentyl | $CH_3$ | $OCH_3$ | CH | |
| $CH_2C\equiv CH$ | H | 0 | H | cyclopentyl | $OCH_3$ | $OCH_3$ | CH | |
| $CH_2C\equiv CH$ | H | 0 | H | cyclopentyl | $CH_3$ | $CH_3$ | N | |
| $CH_2C\equiv CH$ | H | 0 | H | cyclopentyl | $CH_3$ | $OCH_3$ | N | |
| $CH_2C\equiv CH$ | H | 0 | H | cyclopentyl | $OCH_3$ | $OCH_3$ | N | |
| $CH_2C\equiv CH$ | H | 0 | H | cyclopentyl | Cl | $OCH_3$ | CH | |
| $CH_2C\equiv CH$ | H | 0 | H | cyclopropyl | $OCH_3$ | $OCH_2CH_3$ | CH | |
| $CH_2C\equiv CH$ | H | 0 | H | cyclopropyl | cyclopropyl | $OCH_3$ | CH | |
| $CH_2C\equiv CH$ | H | 0 | H | cyclopropyl | $OCH_3$ | $CH(OCH_3)_2$ | CH | |
| $CH_2C\equiv CH$ | H | 0 | H | cyclopropyl | $NHCH_3$ | $OCH_2CH_3$ | N | |
| $CH_2C\equiv CH$ | H | 0 | H | cyclopropyl | $NHCH_3$ | $OCH_3$ | N | |
| $CH_2C\equiv CH$ | H | 0 | H | cyclopropyl | $OCH_3$ | $OCH_2CH_3$ | N | |
| $CH_2C\equiv CH$ | H | 0 | H | cyclopropyl | $CH_2F$ | $CH_3$ | CH | |
| $CH_2CH_3$ | H | 0 | Cl | cyclopropyl | $CH_3$ | $CH_3$ | CH | |
| $CH_2CH_3$ | H | 0 | Cl | cyclopropyl | $CH_3$ | $OCH_3$ | CH | |
| $CH_2CH_3$ | H | 0 | Cl | cyclopropyl | $OCH_3$ | $OCH_3$ | CH | |
| $CH_2CH_3$ | H | 0 | Cl | cyclopropyl | $CH_3$ | $CH_3$ | N | |
| $CH_2CH_3$ | H | 0 | Cl | cyclopropyl | $CH_3$ | $OCH_3$ | N | |
| $CH_2CH_3$ | H | 0 | Cl | cyclopropyl | $OCH_3$ | $OCH_3$ | N | |
| $CH_2CH_3$ | H | 0 | Cl | cyclopropyl | Cl | $OCH_3$ | CH | |
| $CH_2CH_3$ | H | 0 | Cl | cyclobutyl | $CH_3$ | $CH_3$ | CH | |
| $CH_2CH_3$ | H | 0 | Cl | cyclobutyl | $CH_3$ | $OCH_3$ | CH | |
| $CH_2CH_3$ | H | 0 | Cl | cyclobutyl | $OCH_3$ | $OCH_3$ | CH | |
| $CH_2CH_3$ | H | 0 | Cl | cyclobutyl | $CH_3$ | $CH_3$ | N | |
| $CH_2CH_3$ | H | 0 | Cl | cyclobutyl | $CH_3$ | $OCH_3$ | N | |
| $CH_2CH_3$ | H | 0 | Cl | cyclobutyl | $OCH_3$ | $OCH_3$ | N | |
| $CH_2CH_3$ | H | 0 | Cl | cyclobutyl | Cl | $OCH_3$ | CH | |
| $CH_2CH_3$ | H | 0 | Cl | cyclopentyl | $CH_3$ | $CH_3$ | CH | |
| $CH_2CH_3$ | H | 0 | Cl | cyclopentyl | $CH_3$ | $OCH_3$ | CH | |
| $CH_2CH_3$ | H | 0 | Cl | cyclopentyl | $OCH_3$ | $OCH_3$ | CH | |
| $CH_2CH_3$ | H | 0 | Cl | cyclopentyl | $CH_3$ | $CH_3$ | N | |
| $CH_2CH_3$ | H | 0 | Cl | cyclopentyl | $CH_3$ | $OCH_3$ | N | |
| $CH_2CH_3$ | H | 0 | Cl | cyclopentyl | $OCH_3$ | $OCH_3$ | N | |
| $CH_2CH_3$ | H | 0 | Cl | cyclopentyl | Cl | $OCH_3$ | CH | |
| $CH_2CH_3$ | H | 0 | Cl | cyclopropyl | $OCH_3$ | $OCH_2CH_3$ | CH | |
| $CH_2CH_3$ | H | 0 | Cl | cyclopropyl | cyclopropyl | $OCH_3$ | CH | |
| $CH_2CH_3$ | H | 0 | Cl | cyclopropyl | $OCH_3$ | $CH(OCH_3)_2$ | CH | |
| $CH_2CH_3$ | H | 0 | Cl | cyclopropyl | $NHCH_3$ | $OCH_2CH_3$ | N | |
| $CH_2CH_3$ | H | 0 | Cl | cyclopropyl | $NHCH_3$ | $OCH_3$ | N | |
| $CH_2CH_3$ | H | 0 | Cl | cyclopropyl | $OCH_3$ | $OCH_2CH_3$ | N | |
| $CH_2CH_3$ | H | 0 | Cl | cyclopropyl | $CH_2F$ | $CH_3$ | CH | |
| $CH_2SO_2CH_3$ | H | 0 | Cl | cyclopropyl | $CH_3$ | $CH_3$ | CH | |
| $CH_2SO_2CH_3$ | H | 0 | Cl | cyclopropyl | $CH_3$ | $OCH_3$ | CH | |
| $CH_2SO_2CH_3$ | H | 0 | Cl | cyclopropyl | $OCH_3$ | $OCH_3$ | CH | |
| $CH_2SO_2CH_3$ | H | 0 | Cl | cyclopropyl | $CH_3$ | $CH_3$ | N | |
| $CH_2SO_2CH_3$ | H | 0 | Cl | cyclopropyl | $CH_3$ | $OCH_3$ | N | |
| $CH_2SO_2CH_3$ | H | 0 | Cl | cyclopropyl | $OCH_3$ | $OCH_3$ | N | |
| $CH_2SO_2CH_3$ | H | 0 | Cl | cyclopropyl | Cl | $OCH_3$ | CH | |
| $CH_2SO_2CH_3$ | H | 0 | Cl | cyclobutyl | $CH_3$ | $CH_3$ | CH | |
| $CH_2SO_2CH_3$ | H | 0 | Cl | cyclobutyl | $CH_3$ | $OCH_3$ | CH | |
| $CH_2SO_2CH_3$ | H | 0 | Cl | cyclobutyl | $OCH_3$ | $OCH_3$ | CH | |
| $CH_2SO_2CH_3$ | H | 0 | Cl | cyclobutyl | $CH_3$ | $CH_3$ | N | |
| $CH_2SO_2CH_3$ | H | 0 | Cl | cyclobutyl | $CH_3$ | $OCH_3$ | N | |
| $CH_2SO_2CH_3$ | H | 0 | Cl | cyclobutyl | $OCH_3$ | $OCH_3$ | N | |
| $CH_2SO_2CH_3$ | H | 0 | Cl | cyclobutyl | Cl | $OCH_3$ | CH | |
| $CH_2SO_2CH_3$ | H | 0 | Cl | cyclopentyl | $CH_3$ | $CH_3$ | CH | |
| $CH_2SO_2CH_3$ | H | 0 | Cl | cyclopentyl | $CH_3$ | $OCH_3$ | CH | |
| $CH_2SO_2CH_3$ | H | 0 | Cl | cyclopentyl | $OCH_3$ | $OCH_3$ | CH | |
| $CH_2SO_2CH_3$ | H | 0 | Cl | cyclopentyl | $CH_3$ | $CH_3$ | N | |
| $CH_2SO_2CH_3$ | H | 0 | Cl | cyclopentyl | $CH_3$ | $OCH_3$ | N | |
| $CH_2SO_2CH_3$ | H | 0 | Cl | cyclopentyl | $OCH_3$ | $OCH_3$ | N | |
| $CH_2SO_2CH_3$ | H | 0 | Cl | cyclopentyl | Cl | $OCH_3$ | CH | |
| $CH_2SO_2CH_3$ | H | 0 | Cl | cyclopropyl | $OCH_3$ | $OCH_2CH_3$ | CH | |
| $CH_2SO_2CH_3$ | H | 0 | Cl | cyclopropyl | cyclopropyl | $OCH_3$ | CH | |
| $CH_2SO_2CH_3$ | H | 0 | Cl | cyclopropyl | $OCH_3$ | $CH(OCH_3)_2$ | CH | |
| $CH_2SO_2CH_3$ | H | 0 | Cl | cyclopropyl | $NHCH_3$ | $OCH_2CH_3$ | N | |
| $CH_2SO_2CH_3$ | H | 0 | Cl | cyclopropyl | $NHCH_3$ | $OCH_3$ | N | |
| $CH_2SO_2CH_3$ | H | 0 | Cl | cyclopropyl | $OCH_3$ | $OCH_2CH_3$ | N | |
| $CH_2SO_2CH_3$ | H | 0 | Cl | cyclopropyl | $CH_2F$ | $CH_3$ | CH | |
| H | H | 0 | Cl | cyclopropyl | $CH_3$ | $CH_3$ | CH | |
| H | H | 0 | Cl | cyclopropyl | $CH_3$ | $OCH_3$ | CH | |
| H | H | 0 | Cl | cyclopropyl | $OCH_3$ | $OCH_3$ | CH | |
| H | H | 0 | Cl | cyclopropyl | $CH_3$ | $CH_3$ | N | |
| H | H | 0 | Cl | cyclopropyl | $CH_3$ | $OCH_3$ | N | |
| H | H | 0 | Cl | cyclopropyl | $OCH_3$ | $OCH_3$ | N | |

TABLE II-continued

| R | R₁ | n | R₂ | R' | X | Y | Z | m.p.(°C.) |
|---|---|---|---|---|---|---|---|---|
| H | H | 0 | Cl | cyclopropyl | Cl | OCH₃ | CH | |
| H | H | 0 | Cl | cyclobutyl | CH₃ | CH₃ | CH | |
| H | H | 0 | Cl | cyclobutyl | CH₃ | OCH₃ | CH | |
| H | H | 0 | Cl | cyclobutyl | OCH₃ | OCH₃ | CH | |
| H | H | 0 | Cl | cyclobutyl | CH₃ | CH₃ | N | |
| H | H | 0 | Cl | cyclobutyl | CH₃ | OCH₃ | N | |
| H | H | 0 | Cl | cyclobutyl | OCH₃ | OCH₃ | N | |
| H | H | 0 | Cl | cyclobutyl | Cl | OCH₃ | CH | |
| H | H | 0 | Cl | cyclopentyl | CH₃ | CH₃ | CH | |
| H | H | 0 | Cl | cyclopentyl | CH₃ | OCH₃ | CH | |
| H | H | 0 | Cl | cyclopentyl | OCH₃ | OCH₃ | CH | |
| H | H | 0 | Cl | cyclopentyl | CH₃ | CH₃ | N | |
| H | H | 0 | Cl | cyclopentyl | CH₃ | OCH₃ | N | |
| H | H | 0 | Cl | cyclopentyl | OCH₃ | OCH₃ | N | |
| H | H | 0 | Cl | cyclopentyl | Cl | OCH₃ | CH | |
| H | H | 0 | Cl | cyclopropyl | OCH₃ | OCH₂CH₃ | CH | |
| H | H | 0 | Cl | cyclopropyl | cyclopropyl | OCH₃ | CH | |
| H | H | 0 | Cl | cyclopropyl | OCH₃ | CH(OCH₃)₂ | CH | |
| H | H | 0 | Cl | cyclopropyl | NHCH₃ | OCH₂CH₃ | N | |
| H | H | 0 | Cl | cyclopropyl | NHCH₃ | OCH₃ | N | |
| H | H | 0 | Cl | cyclopropyl | OCH₃ | OCH₂CH₃ | N | |
| H | H | 0 | Cl | cyclopropyl | CH₂F | CH₃ | CH | |
| Ph | H | 0 | CH₃ | cyclopropyl | CH₃ | CH₃ | CH | |
| Ph | H | 0 | CH₃ | cyclopropyl | CH₃ | OCH₃ | CH | |
| Ph | H | 0 | CH₃ | cyclopropyl | OCH₃ | OCH₃ | CH | |
| Ph | H | 0 | CH₃ | cyclopropyl | CH₃ | CH₃ | N | |
| Ph | H | 0 | CH₃ | cyclopropyl | CH₃ | OCH₃ | N | |
| Ph | H | 0 | CH₃ | cyclopropyl | OCH₃ | OCH₃ | N | |
| Ph | H | 0 | CH₃ | cyclopropyl | Cl | OCH₃ | CH | |
| Ph | H | 0 | CH₃ | cyclobutyl | CH₃ | CH₃ | CH | |
| Ph | H | 0 | CH₃ | cyclobutyl | CH₃ | OCH₃ | CH | |
| Ph | H | 0 | CH₃ | cyclobutyl | OCH₃ | OCH₃ | CH | |
| Ph | H | 0 | CH₃ | cyclobutyl | CH₃ | CH₃ | N | |
| Ph | H | 0 | CH₃ | cyclobutyl | CH₃ | OCH₃ | N | |
| Ph | H | 0 | CH₃ | cyclobutyl | OCH₃ | OCH₃ | N | |
| Ph | H | 0 | CH₃ | cyclobutyl | Cl | OCH₃ | CH | |
| Ph | H | 0 | CH₃ | cyclopentyl | CH₃ | CH₃ | CH | |
| Ph | H | 0 | CH₃ | cyclopentyl | CH₃ | OCH₃ | CH | |
| Ph | H | 0 | CH₃ | cyclopentyl | OCH₃ | OCH₃ | CH | |
| Ph | H | 0 | CH₃ | cyclopentyl | CH₃ | CH₃ | N | |
| Ph | H | 0 | CH₃ | cyclopentyl | CH₃ | OCH₃ | N | |
| Ph | H | 0 | CH₃ | cyclopentyl | OCH₃ | OCH₃ | N | |
| Ph | H | 0 | CH₃ | cyclopentyl | Cl | OCH₃ | CH | |
| Ph | H | 0 | CH₃ | cyclopropyl | OCH₃ | OCH₂CH₃ | CH | |
| Ph | H | 0 | CH₃ | cyclopropyl | cyclopropyl | OCH₃ | CH | |
| Ph | H | 0 | CH₃ | cyclopropyl | OCH₃ | CH(OCH₃)₂ | CH | |
| Ph | H | 0 | CH₃ | cyclopropyl | NHCH₃ | OCH₂CH₃ | N | |
| Ph | H | 0 | CH₃ | cyclopropyl | NHCH₃ | OCH₃ | N | |
| Ph | H | 0 | CH₃ | cyclopropyl | OCH₃ | OCH₂CH₃ | N | |
| Ph | H | 0 | CH₃ | cyclopropyl | CH₂F | CH₃ | CH | |
| CH₂Cl | H | 0 | CH₃ | cyclopropyl | CH₃ | CH₃ | CH | |
| CH₂Cl | H | 0 | CH₃ | cyclopropyl | CH₃ | OCH₃ | CH | |
| CH₂Cl | H | 0 | CH₃ | cyclopropyl | OCH₃ | OCH₃ | CH | |
| CH₂Cl | H | 0 | CH₃ | cyclopropyl | CH₃ | CH₃ | N | |
| CH₂Cl | H | 0 | CH₃ | cyclopropyl | CH₃ | OCH₃ | N | |
| CH₂Cl | H | 0 | CH₃ | cyclopropyl | OCH₃ | OCH₃ | N | |
| CH₂Cl | H | 0 | CH₃ | cyclopropyl | Cl | OCH₃ | CH | |
| CH₂Cl | H | 0 | CH₃ | cyclobutyl | CH₃ | CH₃ | CH | |
| CH₂Cl | H | 0 | CH₃ | cyclobutyl | CH₃ | OCH₃ | CH | |
| CH₂Cl | H | 0 | CH₃ | cyclobutyl | OCH₃ | OCH₃ | CH | |
| CH₂Cl | H | 0 | CH₃ | cyclobutyl | CH₃ | CH₃ | N | |
| CH₂Cl | H | 0 | CH₃ | cyclobutyl | CH₃ | OCH₃ | N | |
| CH₂Cl | H | 0 | CH₃ | cyclobutyl | OCH₃ | OCH₃ | N | |
| CH₂Cl | H | 0 | CH₃ | cyclobutyl | Cl | OCH₃ | CH | |
| CH₂Cl | H | 0 | CH₃ | cyclopentyl | CH₃ | CH₃ | CH | |
| CH₂Cl | H | 0 | CH₃ | cyclopentyl | CH₃ | OCH₃ | CH | |
| CH₂Cl | H | 0 | CH₃ | cyclopentyl | OCH₃ | OCH₃ | CH | |
| CH₂Cl | H | 0 | CH₃ | cyclopentyl | CH₃ | CH₃ | N | |
| CH₂Cl | H | 0 | CH₃ | cyclopentyl | CH₃ | OCH₃ | N | |
| CH₂Cl | H | 0 | CH₃ | cyclopentyl | OCH₃ | OCH₃ | N | |
| CH₂Cl | H | 0 | CH₃ | cyclopentyl | Cl | OCH₃ | CH | |
| CH₂Cl | H | 0 | CH₃ | cyclopropyl | OCH₃ | OCH₂CH₃ | CH | |
| CH₂Cl | H | 0 | CH₃ | cyclopropyl | cyclopropyl | OCH₃ | CH | |
| CH₂Cl | H | 0 | CH₃ | cyclopropyl | OCH₃ | CH(OCH₃)₂ | CH | |
| CH₂Cl | H | 0 | CH₃ | cyclopropyl | NHCH₃ | OCH₂CH₃ | N | |
| CH₂Cl | H | 0 | CH₃ | cyclopropyl | NHCH₃ | OCH₃ | N | |
| CH₂Cl | H | 0 | CH₃ | cyclopropyl | OCH₃ | OCH₂CH₃ | N | |
| CH₂Cl | H | 0 | CH₃ | cyclopropyl | CH₂F | CH₃ | CH | |
| H | H | 0 | CH₃ | cyclopropyl | CH₃ | CH₃ | CH | |
| H | H | 0 | CH₃ | cyclopropyl | CH₃ | OCH₃ | CH | |
| H | H | 0 | CH₃ | cyclopropyl | OCH₃ | OCH₃ | CH | |

TABLE II-continued

| R | R$_1$ | n | R$_2$ | R' | X | Y | Z | m.p.(°C.) |
|---|---|---|---|---|---|---|---|---|
| H | H | 0 | CH$_3$ | cyclopropyl | CH$_3$ | CH$_3$ | N | |
| H | H | 0 | CH$_3$ | cyclopropyl | CH$_3$ | OCH$_3$ | N | |
| H | H | 0 | CH$_3$ | cyclopropyl | OCH$_3$ | OCH$_3$ | N | |
| H | H | 0 | CH$_3$ | cyclopropyl | Cl | OCH$_3$ | CH | |
| H | H | 0 | CH$_3$ | cyclobutyl | CH$_3$ | CH$_3$ | CH | |
| H | H | 0 | CH$_3$ | cyclobutyl | CH$_3$ | OCH$_3$ | CH | |
| H | H | 0 | CH$_3$ | cyclobutyl | OCH$_3$ | OCH$_3$ | CH | |
| H | H | 0 | CH$_3$ | cyclobutyl | CH$_3$ | CH$_3$ | N | |
| H | H | 0 | CH$_3$ | cyclobutyl | CH$_3$ | OCH$_3$ | N | |
| H | H | 0 | CH$_3$ | cyclobutyl | OCH$_3$ | OCH$_3$ | N | |
| H | H | 0 | CH$_3$ | cyclobutyl | Cl | OCH$_3$ | CH | |
| H | H | 0 | CH$_3$ | cyclopentyl | CH$_3$ | CH$_3$ | CH | |
| H | H | 0 | CH$_3$ | cyclopentyl | CH$_3$ | OCH$_3$ | CH | |
| H | H | 0 | CH$_3$ | cyclopentyl | OCH$_3$ | OCH$_3$ | CH | |
| H | H | 0 | CH$_3$ | cyclopentyl | CH$_3$ | CH$_3$ | N | |
| H | H | 0 | CH$_3$ | cyclopentyl | CH$_3$ | OCH$_3$ | N | |
| H | H | 0 | CH$_3$ | cyclopentyl | OCH$_3$ | OCH$_3$ | N | |
| H | H | 0 | CH$_3$ | cyclopentyl | Cl | OCH$_3$ | CH | |
| H | H | 0 | CH$_3$ | cyclopropyl | OCH$_3$ | OCH$_2$CH$_3$ | CH | |
| H | H | 0 | CH$_3$ | cyclopropyl | cyclopropyl | OCH$_3$ | CH | |
| H | H | 0 | CH$_3$ | cyclopropyl | OCH$_3$ | CH(OCH$_3$)$_2$ | CH | |
| H | H | 0 | CH$_3$ | cyclopropyl | NHCH$_3$ | OCH$_2$CH$_3$ | N | |
| H | H | 0 | CH$_3$ | cyclopropyl | NHCH$_3$ | OCH$_3$ | N | |
| H | H | 0 | CH$_3$ | cyclopropyl | OCH$_3$ | OCH$_2$CH$_3$ | N | |
| H | H | 0 | CH$_3$ | cyclopropyl | CH$_2$F | CH$_3$ | CH | |
| CH$_3$ | H | 1 | Cl | cyclopropyl | CH$_3$ | CH$_3$ | CH | |
| CH$_3$ | H | 1 | Cl | cyclopropyl | CH$_3$ | OCH$_3$ | CH | |
| CH$_3$ | H | 1 | Cl | cyclopropyl | OCH$_3$ | OCH$_3$ | CH | |
| CH$_3$ | H | 1 | Cl | cyclopropyl | CH$_3$ | CH$_3$ | N | |
| CH$_3$ | H | 1 | Cl | cyclopropyl | CH$_3$ | OCH$_3$ | N | |
| CH$_3$ | H | 1 | Cl | cyclopropyl | OCH$_3$ | OCH$_3$ | N | |
| CH$_3$ | H | 1 | Cl | cyclopropyl | Cl | OCH$_3$ | CH | |
| CH$_3$ | H | 1 | Cl | cyclobutyl | CH$_3$ | CH$_3$ | CH | |
| CH$_3$ | H | 1 | Cl | cyclobutyl | CH$_3$ | OCH$_3$ | CH | |
| CH$_3$ | H | 1 | Cl | cyclobutyl | OCH$_3$ | OCH$_3$ | CH | |
| CH$_3$ | H | 1 | Cl | cyclobutyl | CH$_3$ | CH$_3$ | N | |
| CH$_3$ | H | 1 | Cl | cyclobutyl | CH$_3$ | OCH$_3$ | N | |
| CH$_3$ | H | 1 | Cl | cyclobutyl | OCH$_3$ | OCH$_3$ | N | |
| CH$_3$ | H | 1 | Cl | cyclobutyl | Cl | OCH$_3$ | CH | |
| CH$_3$ | H | 1 | Cl | cyclopentyl | CH$_3$ | CH$_3$ | CH | |
| CH$_3$ | H | 1 | Cl | cyclopentyl | CH$_3$ | OCH$_3$ | CH | |
| CH$_3$ | H | 1 | Cl | cyclopentyl | OCH$_3$ | OCH$_3$ | CH | |
| CH$_3$ | H | 1 | Cl | cyclopentyl | CH$_3$ | CH$_3$ | N | |
| CH$_3$ | H | 1 | Cl | cyclopentyl | CH$_3$ | OCH$_3$ | N | |
| CH$_3$ | H | 1 | Cl | cyclopentyl | OCH$_3$ | OCH$_3$ | N | |
| CH$_3$ | H | 1 | Cl | cyclopentyl | Cl | OCH$_3$ | CH | |
| CH$_3$ | H | 1 | Cl | cyclopropyl | OCH$_3$ | OCH$_2$CH$_3$ | CH | |
| CH$_3$ | H | 1 | Cl | cyclopropyl | cyclopropyl | OCH$_3$ | CH | |
| CH$_3$ | H | 1 | Cl | cyclopropyl | OCH$_3$ | CH(OCH$_3$)$_2$ | CH | |
| CH$_3$ | H | 1 | Cl | cyclopropyl | NHCH$_3$ | OCH$_2$CH$_3$ | N | |
| CH$_3$ | H | 1 | Cl | cyclopropyl | NHCH$_3$ | OCH$_3$ | N | |
| CH$_3$ | H | 1 | Cl | cyclopropyl | OCH$_3$ | OCH$_2$CH$_3$ | N | |
| CH$_3$ | H | 1 | Cl | cyclopropyl | CH$_2$F | CH$_3$ | CH | |
| CH$_3$ | CH$_3$ | 0 | H | cyclopropyl | CH$_3$ | CH$_3$ | CH | |
| CH$_3$ | CH$_3$ | 0 | H | cyclopropyl | CH$_3$ | OCH$_3$ | CH | |
| CH$_3$ | CH$_3$ | 0 | H | cyclopropyl | OCH$_3$ | OCH$_3$ | CH | |
| CH$_3$ | CH$_3$ | 0 | H | cyclopropyl | CH$_3$ | CH$_3$ | N | |
| CH$_3$ | CH$_3$ | 0 | H | cyclopropyl | CH$_3$ | OCH$_3$ | N | |
| CH$_3$ | CH$_3$ | 0 | H | cyclopropyl | OCH$_3$ | OCH$_3$ | N | |
| CH$_3$ | CH$_3$ | 0 | H | cyclopropyl | Cl | OCH$_3$ | CH | |
| CH$_3$ | CH$_3$ | 0 | H | cyclobutyl | CH$_3$ | CH$_3$ | CH | |
| CH$_3$ | CH$_3$ | 0 | H | cyclobutyl | CH$_3$ | OCH$_3$ | CH | |
| CH$_3$ | CH$_3$ | 0 | H | cyclobutyl | OCH$_3$ | OCH$_3$ | CH | |
| CH$_3$ | CH$_3$ | 0 | H | cyclobutyl | CH$_3$ | CH$_3$ | N | |
| CH$_3$ | CH$_3$ | 0 | H | cyclobutyl | CH$_3$ | OCH$_3$ | N | |
| CH$_3$ | CH$_3$ | 0 | H | cyclobutyl | OCH$_3$ | OCH$_3$ | N | |
| CH$_3$ | CH$_3$ | 0 | H | cyclobutyl | Cl | OCH$_3$ | CH | |
| CH$_3$ | CH$_3$ | 0 | H | cyclopentyl | CH$_3$ | CH$_3$ | CH | |
| CH$_3$ | CH$_3$ | 0 | H | cyclopentyl | CH$_3$ | OCH$_3$ | CH | |
| CH$_3$ | CH$_3$ | 0 | H | cyclopentyl | OCH$_3$ | OCH$_3$ | CH | |
| CH$_3$ | CH$_3$ | 0 | H | cyclopentyl | CH$_3$ | CH$_3$ | N | |
| CH$_3$ | CH$_3$ | 0 | H | cyclopentyl | CH$_3$ | OCH$_3$ | N | |
| CH$_3$ | CH$_3$ | 0 | H | cyclopentyl | OCH$_3$ | OCH$_3$ | N | |
| CH$_3$ | CH$_3$ | 0 | H | cyclopentyl | Cl | OCH$_3$ | CH | |
| CH$_3$ | CH$_3$ | 0 | H | cyclopropyl | OCH$_3$ | OCH$_2$CH$_3$ | CH | |
| CH$_3$ | CH$_3$ | 0 | H | cyclopropyl | cyclopropyl | OCH$_3$ | CH | |
| CH$_3$ | CH$_3$ | 0 | H | cyclopropyl | OCH$_3$ | CH(OCH$_3$)$_2$ | CH | |
| CH$_3$ | CH$_3$ | 0 | H | cyclopropyl | NHCH$_3$ | OCH$_2$CH$_3$ | N | |
| CH$_3$ | CH$_3$ | 0 | H | cyclopropyl | NHCH$_3$ | OCH$_3$ | N | |
| CH$_3$ | CH$_3$ | 0 | H | cyclopropyl | OCH$_3$ | OCH$_2$CH$_3$ | N | |
| CH$_3$ | CH$_3$ | 0 | H | cyclopropyl | CH$_2$F | CH$_3$ | CH | |

TABLE II-continued

| R | R₁ | n | R₂ | R' | X | Y | Z | m.p.(°C.) |
|---|----|---|----|----|---|---|---|-----------|
| CH₃ | H | 0 | H | cyclobutyl | CH₂CH₃ | CH₃ | CH | |
| CH₃ | H | 0 | H | cyclobutyl | CH₂CH₃ | OCH₃ | CH | |
| CH₃ | H | 0 | H | cyclobutyl | CH₂F | CH₃ | CH | |
| CH₃ | H | 0 | H | cyclobutyl | OCF₂H | CH₃ | CH | |
| CH₃ | H | 0 | H | cyclobutyl | OCF₂H | OCH₃ | CH | |
| CH₃ | H | 0 | H | cyclobutyl | OCH₂CF₃ | OCH₃ | CH | |
| CH₃ | H | 0 | H | cyclobutyl | CH₂F | OCH₃ | CH | |
| CH₃ | H | 0 | H | cyclobutyl | CH₂Cl | OCH₃ | N | |
| CH₃ | H | 0 | H | cyclobutyl | SCH₃ | OCH₃ | CH | |
| CH₃ | H | 0 | H | cyclobutyl | SCH₂F | OCH₃ | CH | |
| CH₃ | H | 0 | H | cyclobutyl | Br | OCH₃ | CH | |
| CH₃ | H | 0 | H | cyclobutyl | CH₂OCH₃ | OCH₃ | N | |
| CH₃ | H | 0 | H | cyclobutyl | OCH₂OCH₃ | OCH₃ | CH | |
| CH₃ | H | 0 | H | cyclobutyl | OCH₂OCH₂CH₃ | CH₃ | CH | |
| CH₃ | H | 0 | H | cyclobutyl | N(CH₃)₂ | OCH₃ | N | |
| CH₃ | H | 0 | H | cyclobutyl | NHCH₂CH₃ | CH₃ | N | |
| CH₃ | H | 0 | H | cyclobutyl | NHCH₃ | OCH₂CH₃ | N | |
| CH₃ | H | 0 | H | cyclobutyl | CH₃ | CH₂SCH₃ | CH | |
| CH₃ | H | 0 | H | cyclobutyl | OCH₃ | CH₂SO₂CH₃ | CH | |
| CH₃ | H | 0 | H | cyclobutyl | NH₂ | OCH₂CH₃ | N | |
| CH₃ | H | 0 | H | cyclobutyl | CH₃ | OCH₂CH=CH₂ | CH | |
| CH₃ | H | 0 | H | cyclobutyl | CH₂CH₃ | OCF₂H | CH | |
| CH₃ | H | 0 | H | cyclobutyl | OCF₂H | OCF₂H | CH | |
| CH₃ | H | 0 | H | cyclobutyl | OCH₃ | OCH=CH₂ | CH | |
| CH₃ | H | 0 | H | cyclobutyl | OCH₃ | C(O)CH₃ | N | |
| CH₃ | H | 0 | H | cyclobutyl | CH₃ | N(OCH₃)CH₃ | N | |
| CH₃ | H | 0 | H | cyclobutyl | OCH(CH₃)₂ | OCF₂H | CH | |

TABLE III

| R | R₁ | n | R₂ | R' | X | Y | Z | m.p. (°C.) |
|---|----|---|----|----|---|---|---|------------|
| CH₃ | H | 0 | H | cyclopropyl | CH₃ | CH₃ | CH | 157–159 |
| CH₃ | H | 0 | H | cyclopropyl | CH₃ | OCH₃ | CH | 179–182 |
| CH₃ | H | 0 | H | cyclopropyl | OCH₃ | OCH₃ | CH | 159–161 |
| CH₃ | H | 0 | H | cyclopropyl | CH₃ | CH₃ | N | |
| CH₃ | H | 0 | H | cyclopropyl | CH₃ | OCH₃ | N | 185–187 |
| CH₃ | H | 0 | H | cyclopropyl | OCH₃ | OCH₃ | N | 196–198 |
| CH₃ | H | 0 | H | cyclopropyl | Cl | OCH₃ | CH | 202–205 |
| CH₃ | H | 0 | H | cyclobutyl | CH₃ | CH₃ | CH | |
| CH₃ | H | 0 | H | cyclobutyl | OCH₃ | OCH₃ | CH | |
| CH₃ | H | 0 | H | cyclobutyl | CH₃ | CH₃ | N | |
| CH₃ | H | 0 | H | cyclobutyl | CH₃ | OCH₃ | N | |
| CH₃ | H | 0 | H | cyclobutyl | OCH₃ | OCH₃ | N | |
| CH₃ | H | 0 | H | cyclobutyl | Cl | OCH₃ | CH | |
| CH₃ | H | 0 | H | cyclopentyl | CH₃ | CH₃ | CH | |
| CH₃ | H | 0 | H | cyclopentyl | CH₃ | OCH₃ | CH | |
| CH₃ | H | 0 | H | cyclopentyl | OCH₃ | OCH₃ | CH | |
| CH₃ | H | 0 | H | cyclopentyl | CH₃ | CH₃ | N | |
| CH₃ | H | 0 | H | cyclopentyl | CH₃ | OCH₃ | N | |
| CH₃ | H | 0 | H | cyclopentyl | OCH₃ | OCH₃ | N | |
| CH₃ | H | 0 | H | cyclopentyl | Cl | OCH₃ | CH | |
| CH₃ | H | 0 | H | cyclopropyl | OCH₃ | OCH₂CH₃ | CH | |
| CH₃ | H | 0 | H | cyclopropyl | cyclopropyl | OCH₃ | CH | |
| CH₃ | H | 0 | H | cyclopropyl | OCH₃ | CH(OCH₃)₂ | CH | |
| CH₃ | H | 0 | H | cyclopropyl | NHCH₃ | OCH₂CH₃ | N | |
| CH₃ | H | 0 | H | cyclopropyl | NHCH₃ | OCH₃ | N | |
| CH₃ | H | 0 | H | cyclopropyl | OCH₃ | OCH₂CH₃ | N | |
| CH₃ | H | 0 | H | cyclopropyl | CH₂F | CH₃ | CH | |
| CH₃ | H | 0 | CH₃ | cyclopropyl | CH₃ | CH₃ | CH | |
| CH₃ | H | 0 | CH₃ | cyclopropyl | OCH₃ | OCH₃ | CH | |
| CH₃ | H | 0 | CH₃ | cyclopropyl | CH₃ | CH₃ | N | |
| CH₃ | H | 0 | CH₃ | cyclopropyl | CH₃ | OCH₃ | N | |
| CH₃ | H | 0 | CH₃ | cyclopropyl | OCH₃ | OCH₃ | N | |
| CH₃ | H | 0 | CH₃ | cyclopropyl | Cl | OCH₃ | CH | |
| CH₃ | H | 0 | CH₃ | cyclobutyl | CH₃ | CH₃ | CH | |
| CH₃ | H | 0 | CH₃ | cyclobutyl | OCH₃ | OCH₃ | CH | |
| CH₃ | H | 0 | CH₃ | cyclobutyl | CH₃ | CH₃ | N | |
| CH₃ | H | 0 | CH₃ | cyclobutyl | CH₃ | OCH₃ | N | |
| CH₃ | H | 0 | CH₃ | cyclobutyl | OCH₃ | OCH₃ | N | |
| CH₃ | H | 0 | CH₃ | cyclobutyl | Cl | OCH₃ | CH | |
| CH₃ | H | 0 | CH₃ | cyclopentyl | CH₃ | CH₃ | CH | |
| CH₃ | H | 0 | CH₃ | cyclopentyl | CH₃ | OCH₃ | CH | |
| CH₃ | H | 0 | CH₃ | cyclopentyl | OCH₃ | OCH₃ | CH | |
| CH₃ | H | 0 | CH₃ | cyclopentyl | CH₃ | CH₃ | N | |
| CH₃ | H | 0 | CH₃ | cyclopentyl | CH₃ | OCH₃ | N | |
| CH₃ | H | 0 | CH₃ | cyclopentyl | OCH₃ | OCH₃ | N | |

TABLE III-continued

| R | R₁ | n | R₂ | R' | X | Y | Z | m.p. (°C.) |
|---|---|---|---|---|---|---|---|---|
| CH₃ | H | 0 | CH₃ | cyclopentyl | Cl | OCH₃ | CH | |
| CH₃ | H | 0 | CH₃ | cyclopropyl | OCH₃ | OCH₂CH₃ | CH | |
| CH₃ | H | 0 | CH₃ | cyclopropyl | cyclopropyl | OCH₃ | CH | |
| CH₃ | H | 0 | CH₃ | cyclopropyl | OCH₃ | CH(OCH₃)₂ | CH | |
| CH₃ | H | 0 | CH₃ | cyclopropyl | NHCH₃ | OCH₂CH₃ | N | |
| CH₃ | H | 0 | CH₃ | cyclopropyl | NHCH₃ | OCH₃ | N | |
| CH₃ | H | 0 | CH₃ | cyclopropyl | OCH₃ | OCH₂CH₃ | N | |
| CH₃ | H | 0 | CH₃ | cyclopropyl | CH₂F | CH₃ | CH | |
| CH₃ | H | 0 | Cl | cyclopropyl | CH₃ | CH₃ | CH | |
| CH₃ | H | 0 | Cl | cyclopropyl | CH₃ | OCH₃ | CH | |
| CH₃ | H | 0 | Cl | cyclopropyl | OCH₃ | OCH₃ | CH | |
| CH₃ | H | 0 | Cl | cyclopropyl | CH₃ | CH₃ | N | |
| CH₃ | H | 0 | Cl | cyclopropyl | CH₃ | OCH₃ | N | |
| CH₃ | H | 0 | Cl | cyclopropyl | OCH₃ | OCH₃ | N | |
| CH₃ | H | 0 | Cl | cyclopropyl | Cl | OCH₃ | CH | |
| CH₃ | H | 0 | Cl | cyclobutyl | CH₃ | CH₃ | CH | |
| CH₃ | H | 0 | Cl | cyclobutyl | CH₃ | OCH₃ | CH | |
| CH₃ | H | 0 | Cl | cyclobutyl | OCH₃ | OCH₃ | CH | |
| CH₃ | H | 0 | Cl | cyclobutyl | CH₃ | CH₃ | N | |
| CH₃ | H | 0 | Cl | cyclobutyl | CH₃ | OCH₃ | N | |
| CH₃ | H | 0 | Cl | cyclobutyl | OCH₃ | OCH₃ | N | |
| CH₃ | H | 0 | Cl | cyclobutyl | Cl | OCH₃ | CH | |
| CH₃ | H | 0 | Cl | cyclopentyl | CH₃ | CH₃ | CH | |
| CH₃ | H | 0 | Cl | cyclopentyl | CH₃ | OCH₃ | CH | |
| CH₃ | H | 0 | Cl | cyclopentyl | OCH₃ | OCH₃ | CH | |
| CH₃ | H | 0 | Cl | cyclopentyl | CH₃ | CH₃ | N | |
| CH₃ | H | 0 | Cl | cyclopentyl | CH₃ | OCH₃ | N | |
| CH₃ | H | 0 | Cl | cyclopentyl | OCH₃ | OCH₃ | N | |
| CH₃ | H | 0 | Cl | cyclopentyl | Cl | OCH₃ | CH | |
| CH₃ | H | 0 | Cl | cyclopropyl | OCH₃ | OCH₂CH₃ | CH | |
| CH₃ | H | 0 | Cl | cyclopropyl | cyclopropyl | OCH₃ | CH | |
| CH₃ | H | 0 | Cl | cyclopropyl | OCH₃ | CH(OCH₃)₂ | CH | |
| CH₃ | H | 0 | Cl | cyclopropyl | NHCH₃ | OCH₂CH₃ | N | |
| CH₃ | H | 0 | Cl | cyclopropyl | NHCH₃ | OCH₃ | N | |
| CH₃ | H | 0 | Cl | cyclopropyl | OCH₃ | OCH₂CH₃ | N | |
| CH₃ | H | 0 | Cl | cyclopropyl | CH₂F | CH₃ | CH | |
| CH₃ | H | 0 | Br | cyclopropyl | CH₃ | CH₃ | CH | |
| CH₃ | H | 0 | Br | cyclopropyl | CH₃ | OCH₃ | CH | |
| CH₃ | H | 0 | Br | cyclopropyl | OCH₃ | OCH₃ | CH | |
| CH₃ | H | 0 | Br | cyclopropyl | CH₃ | CH₃ | N | |
| CH₃ | H | 0 | Br | cyclopropyl | CH₃ | OCH₃ | N | |
| CH₃ | H | 0 | Br | cyclopropyl | OCH₃ | OCH₃ | N | |
| CH₃ | H | 0 | Br | cyclopropyl | Cl | OCH₃ | CH | |
| CH₃ | H | 0 | Br | cyclobutyl | CH₃ | CH₃ | CH | |
| CH₃ | H | 0 | Br | cyclobutyl | CH₃ | OCH₃ | CH | |
| CH₃ | H | 0 | Br | cyclobutyl | OCH₃ | OCH₃ | CH | |
| CH₃ | H | 0 | Br | cyclobutyl | CH₃ | CH₃ | N | |
| CH₃ | H | 0 | Br | cyclobutyl | CH₃ | OCH₃ | N | |
| CH₃ | H | 0 | Br | cyclobutyl | OCH₃ | OCH₃ | N | |
| CH₃ | H | 0 | Br | cyclobutyl | Cl | OCH₃ | CH | |
| CH₃ | H | 0 | Br | cyclopentyl | CH₃ | CH₃ | CH | |
| CH₃ | H | 0 | Br | cyclopentyl | OCH₃ | OCH₃ | CH | |
| CH₃ | H | 0 | Br | cyclopentyl | CH₃ | CH₃ | N | |
| CH₃ | H | 0 | Br | cyclopentyl | CH₃ | OCH₃ | N | |
| CH₃ | H | 0 | Br | cyclopentyl | OCH₃ | OCH₃ | N | |
| CH₃ | H | 0 | Br | cyclopentyl | Cl | OCH₃ | CH | |
| CH₃ | H | 0 | Br | cyclopropyl | OCH₃ | OCH₂CH₃ | CH | |
| CH₃ | H | 0 | Br | cyclopropyl | cyclopropyl | OCH₃ | CH | |
| CH₃ | H | 0 | Br | cyclopropyl | OCH₃ | CH(OCH₃)₂ | CH | |
| CH₃ | H | 0 | Br | cyclopropyl | NHCH₃ | OCH₂CH₃ | N | |
| CH₃ | H | 0 | Br | cyclopropyl | NHCH₃ | OCH₃ | N | |
| CH₃ | H | 0 | Br | cyclopropyl | OCH₃ | OCH₂CH₃ | N | |
| CH₃ | H | 0 | Br | cyclopropyl | CH₂F | CH₃ | CH | |
| CH₃ | H | 0 | OCH₃ | cyclopropyl | CH₃ | CH₃ | CH | |
| CH₃ | H | 0 | OCH₃ | cyclopropyl | CH₃ | OCH₃ | CH | |
| CH₃ | H | 0 | OCH₃ | cyclopropyl | OCH₃ | OCH₃ | CH | |
| CH₃ | H | 0 | OCH₃ | cyclopropyl | CH₃ | CH₃ | N | |
| CH₃ | H | 0 | OCH₃ | cyclopropyl | CH₃ | OCH₃ | N | |
| CH₃ | H | 0 | OCH₃ | cyclopropyl | OCH₃ | OCH₃ | N | |
| CH₃ | H | 0 | OCH₃ | cyclopropyl | Cl | OCH₃ | CH | |
| CH₃ | H | 0 | OCH₃ | cyclobutyl | CH₃ | CH₃ | CH | |
| CH₃ | H | 0 | OCH₃ | cyclobutyl | CH₃ | OCH₃ | CH | |
| CH₃ | H | 0 | OCH₃ | cyclobutyl | OCH₃ | OCH₃ | CH | |
| CH₃ | H | 0 | OCH₃ | cyclobutyl | CH₃ | CH₃ | N | |
| CH₃ | H | 0 | OCH₃ | cyclobutyl | CH₃ | OCH₃ | N | |
| CH₃ | H | 0 | OCH₃ | cyclobutyl | OCH₃ | OCH₃ | N | |
| CH₃ | H | 0 | OCH₃ | cyclobutyl | Cl | OCH₃ | CH | |
| CH₃ | H | 0 | OCH₃ | cyclopentyl | CH₃ | CH₃ | CH | |
| CH₃ | H | 0 | OCH₃ | cyclopentyl | CH₃ | OCH₃ | CH | |
| CH₃ | H | 0 | OCH₃ | cyclopentyl | OCH₃ | OCH₃ | CH | |

TABLE III-continued

| R | R₁ | n | R₂ | R' | X | Y | Z | m.p. (°C.) |
|---|---|---|---|---|---|---|---|---|
| CH₃ | H | 0 | OCH₃ | cyclopentyl | CH₃ | CH₃ | N | |
| CH₃ | H | 0 | OCH₃ | cyclopentyl | CH₃ | OCH₃ | N | |
| CH₃ | H | 0 | OCH₃ | cyclopentyl | OCH₃ | OCH₃ | N | |
| CH₃ | H | 0 | OCH₃ | cyclopentyl | Cl | OCH₃ | CH | |
| CH₃ | H | 0 | OCH₃ | cyclopropyl | OCH₃ | OCH₂CH₃ | CH | |
| CH₃ | H | 0 | OCH₃ | cyclopropyl | cyclopropyl | OCH₃ | CH | |
| CH₃ | H | 0 | OCH₃ | cyclopropyl | OCH₃ | CH(OCH₃)₂ | CH | |
| CH₃ | H | 0 | OCH₃ | cyclopropyl | NHCH₃ | OCH₂CH₃ | N | |
| CH₃ | H | 0 | OCH₃ | cyclopropyl | NHCH₃ | OCH₃ | N | |
| CH₃ | H | 0 | OCH₃ | cyclopropyl | OCH₃ | OCH₂CH₃ | N | |
| CH₃ | H | 0 | OCH₃ | cyclopropyl | CH₂F | CH₃ | CH | |
| CH₃ | H | 0 | SCH₃ | cyclopropyl | CH₃ | CH₃ | CH | |
| CH₃ | H | 0 | SCH₃ | cyclopropyl | CH₃ | OCH₃ | CH | |
| CH₃ | H | 0 | SCH₃ | cyclopropyl | OCH₃ | OCH₃ | CH | |
| CH₃ | H | 0 | SCH₃ | cyclopropyl | CH₃ | CH₃ | N | |
| CH₃ | H | 0 | SCH₃ | cyclopropyl | CH₃ | OCH₃ | N | |
| CH₃ | H | 0 | SCH₃ | cyclopropyl | OCH₃ | OCH₃ | N | |
| CH₃ | H | 0 | SCH₃ | cyclopropyl | Cl | OCH₃ | CH | |
| CH₃ | H | 0 | SCH₃ | cyclobutyl | CH₃ | CH₃ | CH | |
| CH₃ | H | 0 | SCH₃ | cyclobutyl | CH₃ | OCH₃ | CH | |
| CH₃ | H | 0 | SCH₃ | cyclobutyl | OCH₃ | OCH₃ | CH | |
| CH₃ | H | 0 | SCH₃ | cyclobutyl | CH₃ | CH₃ | N | |
| CH₃ | H | 0 | SCH₃ | cyclobutyl | CH₃ | OCH₃ | N | |
| CH₃ | H | 0 | SCH₃ | cyclobutyl | OCH₃ | OCH₃ | N | |
| CH₃ | H | 0 | SCH₃ | cyclobutyl | Cl | OCH₃ | CH | |
| CH₃ | H | 0 | SCH₃ | cyclopentyl | CH₃ | CH₃ | CH | |
| CH₃ | H | 0 | SCH₃ | cyclopentyl | CH₃ | OCH₃ | CH | |
| CH₃ | H | 0 | SCH₃ | cyclopentyl | OCH₃ | OCH₃ | CH | |
| CH₃ | H | 0 | SCH₃ | cyclopentyl | CH₃ | CH₃ | N | |
| CH₃ | H | 0 | SCH₃ | cyclopentyl | CH₃ | OCH₃ | N | |
| CH₃ | H | 0 | SCH₃ | cyclopentyl | OCH₃ | OCH₃ | N | |
| CH₃ | H | 0 | SCH₃ | cyclopentyl | Cl | OCH₃ | CH | |
| CH₃ | H | 0 | SCH₃ | cyclopropyl | OCH₃ | OCH₂CH₃ | CH | |
| CH₃ | H | 0 | SCH₃ | cyclopropyl | cyclopropyl | OCH₃ | CH | |
| CH₃ | H | 0 | SCH₃ | cyclopropyl | OCH₃ | CH(OCH₃)₂ | CH | |
| CH₃ | H | 0 | SCH₃ | cyclopropyl | NHCH₃ | OCH₂CH₃ | N | |
| CH₃ | H | 0 | SCH₃ | cyclopropyl | NHCH₃ | OCH₃ | N | |
| CH₃ | H | 0 | SCH₃ | cyclopropyl | OCH₃ | OCH₂CH₃ | N | |
| CH₃ | H | 0 | SCH₃ | cyclopropyl | CH₂F | CH₃ | CH | |
| CH₃ | H | 0 | SO₂CH₃ | cyclopropyl | CH₃ | CH₃ | CH | |
| CH₃ | H | 0 | SO₂CH₃ | cyclopropyl | CH₃ | OCH₃ | CH | |
| CH₃ | H | 0 | SO₂CH₃ | cyclopropyl | OCH₃ | OCH₃ | CH | |
| CH₃ | H | 0 | SO₂CH₃ | cyclopropyl | CH₃ | CH₃ | N | |
| CH₃ | H | 0 | SO₂CH₃ | cyclopropyl | CH₃ | OCH₃ | N | |
| CH₃ | H | 0 | SO₂CH₃ | cyclopropyl | OCH₃ | OCH₃ | N | |
| CH₃ | H | 0 | SO₂CH₃ | cyclopropyl | Cl | OCH₃ | CH | |
| CH₃ | H | 0 | SO₂CH₃ | cyclobutyl | CH₃ | CH₃ | CH | |
| CH₃ | H | 0 | SO₂CH₃ | cyclobutyl | CH₃ | OCH₃ | CH | |
| CH₃ | H | 0 | SO₂CH₃ | cyclobutyl | OCH₃ | OCH₃ | CH | |
| CH₃ | H | 0 | SO₂CH₃ | cyclobutyl | CH₃ | CH₃ | N | |
| CH₃ | H | 0 | SO₂CH₃ | cyclobutyl | CH₃ | OCH₃ | N | |
| CH₃ | H | 0 | SO₂CH₃ | cyclobutyl | OCH₃ | OCH₃ | N | |
| CH₃ | H | 0 | SO₂CH₃ | cyclobutyl | Cl | OCH₃ | CH | |
| CH₃ | H | 0 | SO₂CH₃ | cyclopentyl | CH₃ | CH₃ | CH | |
| CH₃ | H | 0 | SO₂CH₃ | cyclopentyl | CH₃ | OCH₃ | CH | |
| CH₃ | H | 0 | SO₂CH₃ | cyclopentyl | OCH₃ | OCH₃ | CH | |
| CH₃ | H | 0 | SO₂CH₃ | cyclopentyl | CH₃ | CH₃ | N | |
| CH₃ | H | 0 | SO₂CH₃ | cyclopentyl | CH₃ | OCH₃ | N | |
| CH₃ | H | 0 | SO₂CH₃ | cyclopentyl | OCH₃ | OCH₃ | N | |
| CH₃ | H | 0 | SO₂CH₃ | cyclopentyl | Cl | OCH₃ | CH | |
| CH₃ | H | 0 | SO₂CH₃ | cyclopropyl | OCH₃ | OCH₂CH₃ | CH | |
| CH₃ | H | 0 | SO₂CH₃ | cyclopropyl | cyclopropyl | OCH₃ | CH | |
| CH₃ | H | 0 | SO₂CH₃ | cyclopropyl | OCH₃ | CH(OCH₃)₂ | CH | |
| CH₃ | H | 0 | SO₂CH₃ | cyclopropyl | NHCH₃ | OCH₂CH₃ | N | |
| CH₃ | H | 0 | SO₂CH₃ | cyclopropyl | NHCH₃ | OCH₃ | N | |
| CH₃ | H | 0 | SO₂CH₃ | cyclopropyl | OCH₃ | OCH₂CH₃ | N | |
| CH₃ | H | 0 | SO₂CH₃ | cyclopropyl | CH₂F | CH₃ | CH | |
| CH₃ | H | 0 | CO₂CH₃ | cyclopropyl | CH₃ | CH₃ | CH | |
| CH₃ | H | 0 | CO₂CH₃ | cyclopropyl | CH₃ | OCH₃ | CH | |
| CH₃ | H | 0 | CO₂CH₃ | cyclopropyl | OCH₃ | OCH₃ | CH | |
| CH₃ | H | 0 | CO₂CH₃ | cyclopropyl | CH₃ | CH₃ | N | |
| CH₃ | H | 0 | CO₂CH₃ | cyclopropyl | CH₃ | OCH₃ | N | |
| CH₃ | H | 0 | CO₂CH₃ | cyclopropyl | OCH₃ | OCH₃ | N | |
| CH₃ | H | 0 | CO₂CH₃ | cyclopropyl | Cl | OCH₃ | CH | |
| CH₃ | H | 0 | CO₂CH₃ | cyclobutyl | CH₃ | CH₃ | CH | |
| CH₃ | H | 0 | CO₂CH₃ | cyclobutyl | CH₃ | OCH₃ | CH | |
| CH₃ | H | 0 | CO₂CH₃ | cyclobutyl | OCH₃ | OCH₃ | CH | |
| CH₃ | H | 0 | CO₂CH₃ | cyclobutyl | CH₃ | CH₃ | N | |
| CH₃ | H | 0 | CO₂CH₃ | cyclobutyl | CH₃ | OCH₃ | N | |
| CH₃ | H | 0 | CO₂CH₃ | cyclobutyl | OCH₃ | OCH₃ | N | |
| CH₃ | H | 0 | CO₂CH₃ | cyclobutyl | Cl | OCH₃ | CH | |

TABLE III-continued

| R | R₁ | n | R₂ | R' | X | Y | Z | m.p. (°C.) |
|---|---|---|---|---|---|---|---|---|
| CH₃ | H | 0 | CO₂CH₃ | cyclopentyl | CH₃ | CH₃ | CH | |
| CH₃ | H | 0 | CO₂CH₃ | cyclopentyl | CH₃ | OCH₃ | CH | |
| CH₃ | H | 0 | CO₂CH₃ | cyclopentyl | OCH₃ | OCH₃ | CH | |
| CH₃ | H | 0 | CO₂CH₃ | cyclopentyl | CH₃ | CH₃ | N | |
| CH₃ | H | 0 | CO₂CH₃ | cyclopentyl | CH₃ | OCH₃ | N | |
| CH₃ | H | 0 | CO₂CH₃ | cyclopentyl | OCH₃ | OCH₃ | N | |
| CH₃ | H | 0 | CO₂CH₃ | cyclopentyl | Cl | OCH₃ | CH | |
| CH₃ | H | 0 | CO₂CH₃ | cyclopropyl | OCH₃ | OCH₂CH₃ | CH | |
| CH₃ | H | 0 | CO₂CH₃ | cyclopropyl | cyclopropyl | OCH₃ | CH | |
| CH₃ | H | 0 | CO₂CH₃ | cyclopropyl | OCH₃ | CH(OCH₃)₂ | CH | |
| CH₃ | H | 0 | CO₂CH₃ | cyclopropyl | NHCH₃ | OCH₂CH₃ | N | |
| CH₃ | H | 0 | CO₂CH₃ | cyclopropyl | NHCH₃ | OCH₃ | N | |
| CH₃ | H | 0 | CO₂CH₃ | cyclopropyl | OCH₃ | OCH₂CH₃ | N | |
| CH₃ | H | 0 | CO₂CH₃ | cyclopropyl | CH₂F | CH₃ | CH | |
| CH₃ | H | 0 | CH₂CN | cyclopropyl | CH₃ | CH₃ | CH | |
| CH₃ | H | 0 | CH₂CN | cyclopropyl | CH₃ | OCH₃ | CH | |
| CH₃ | H | 0 | CH₂CN | cyclopropyl | OCH₃ | OCH₃ | CH | |
| CH₃ | H | 0 | CH₂CN | cyclopropyl | CH₃ | CH₃ | N | |
| CH₃ | H | 0 | CH₂CN | cyclopropyl | CH₃ | OCH₃ | N | |
| CH₃ | H | 0 | CH₂CN | cyclopropyl | OCH₃ | OCH₃ | N | |
| CH₃ | H | 0 | CH₂CN | cyclopropyl | Cl | OCH₃ | CH | |
| CH₃ | H | 0 | CH₂CN | cyclobutyl | CH₃ | CH₃ | CH | |
| CH₃ | H | 0 | CH₂CN | cyclobutyl | CH₃ | OCH₃ | CH | |
| CH₃ | H | 0 | CH₂CN | cyclobutyl | OCH₃ | OCH₃ | CH | |
| CH₃ | H | 0 | CH₂CN | cyclobutyl | CH₃ | CH₃ | N | |
| CH₃ | H | 0 | CH₂CN | cyclobutyl | CH₃ | OCH₃ | N | |
| CH₃ | H | 0 | CH₂CN | cyclobutyl | OCH₃ | OCH₃ | N | |
| CH₃ | H | 0 | CH₂CN | cyclobutyl | Cl | OCH₃ | CH | |
| CH₃ | H | 0 | CH₂CN | cyclopentyl | CH₃ | CH₃ | CH | |
| CH₃ | H | 0 | CH₂CN | cyclopentyl | CH₃ | OCH₃ | CH | |
| CH₃ | H | 0 | CH₂CN | cyclopentyl | OCH₃ | OCH₃ | CH | |
| CH₃ | H | 0 | CH₂CN | cyclopentyl | CH₃ | CH₃ | N | |
| CH₃ | H | 0 | CH₂CN | cyclopentyl | CH₃ | OCH₃ | N | |
| CH₃ | H | 0 | CH₂CN | cyclopentyl | OCH₃ | OCH₃ | N | |
| CH₃ | H | 0 | CH₂CN | cyclopentyl | Cl | OCH₃ | CH | |
| CH₃ | H | 0 | CH₂CN | cyclopropyl | OCH₃ | OCH₂CH₃ | CH | |
| CH₃ | H | 0 | CH₂CN | cyclopropyl | cyclopropyl | OCH₃ | CH | |
| CH₃ | H | 0 | CH₂CN | cyclopropyl | OCH₃ | CH(OCH₃)₂ | CH | |
| CH₃ | H | 0 | CH₂CN | cyclopropyl | NHCH₃ | OCH₂CH₃ | N | |
| CH₃ | H | 0 | CH₂CN | cyclopropyl | NHCH₃ | OCH₃ | N | |
| CH₃ | H | 0 | CH₂CN | cyclopropyl | OCH₃ | OCH₂CH₃ | N | |
| CH₃ | H | 0 | CH₂CN | cyclopropyl | CH₂F | CH₃ | CH | |
| CH₃ | H | 0 | CH(OH)CH₃ | cyclopropyl | CH₃ | CH₃ | CH | |
| CH₃ | H | 0 | CH(OH)CH₃ | cyclopropyl | CH₃ | OCH₃ | CH | |
| CH₃ | H | 0 | CH(OH)CH₃ | cyclopropyl | OCH₃ | OCH₃ | CH | |
| CH₃ | H | 0 | CH(OH)CH₃ | cyclopropyl | CH₃ | CH₃ | N | |
| CH₃ | H | 0 | CH(OH)CH₃ | cyclopropyl | CH₃ | OCH₃ | N | |
| CH₃ | H | 0 | CH(OH)CH₃ | cyclopropyl | OCH₃ | OCH₃ | N | |
| CH₃ | H | 0 | CH(OH)CH₃ | cyclopropyl | Cl | OCH₃ | CH | |
| CH₃ | H | 0 | CH(OH)CH₃ | cyclobutyl | CH₃ | CH₃ | CH | |
| CH₃ | H | 0 | CH(OH)CH₃ | cyclobutyl | CH₃ | OCH₃ | CH | |
| CH₃ | H | 0 | CH(OH)CH₃ | cyclobutyl | OCH₃ | OCH₃ | CH | |
| CH₃ | H | 0 | CH(OH)CH₃ | cyclobutyl | CH₃ | CH₃ | N | |
| CH₃ | H | 0 | CH(OH)CH₃ | cyclobutyl | CH₃ | OCH₃ | N | |
| CH₃ | H | 0 | CH(OH)CH₃ | cyclobutyl | OCH₃ | OCH₃ | N | |
| CH₃ | H | 0 | CH(OH)CH₃ | cyclobutyl | Cl | OCH₃ | CH | |
| CH₃ | H | 0 | CH(OH)CH₃ | cyclopentyl | CH₃ | CH₃ | CH | |
| CH₃ | H | 0 | CH(OH)CH₃ | cyclopentyl | CH₃ | OCH₃ | CH | |
| CH₃ | H | 0 | CH(OH)CH₃ | cyclopentyl | OCH₃ | OCH₃ | CH | |
| CH₃ | H | 0 | CH(OH)CH₃ | cyclopentyl | CH₃ | CH₃ | N | |
| CH₃ | H | 0 | CH(OH)CH₃ | cyclopentyl | CH₃ | OCH₃ | N | |
| CH₃ | H | 0 | CH(OH)CH₃ | cyclopentyl | OCH₃ | OCH₃ | N | |
| CH₃ | H | 0 | CH(OH)CH₃ | cyclopentyl | Cl | OCH₃ | CH | |
| CH₃ | H | 0 | CH(OH)CH₃ | cyclopropyl | OCH₃ | OCH₂CH₃ | CH | |
| CH₃ | H | 0 | CH(OH)CH₃ | cyclopropyl | cyclopropyl | OCH₃ | CH | |
| CH₃ | H | 0 | CH(OH)CH₃ | cyclopropyl | OCH₃ | CH(OCH₃)₂ | CH | |
| CH₃ | H | 0 | CH(OH)CH₃ | cyclopropyl | NHCH₃ | OCH₂CH₃ | N | |
| CH₃ | H | 0 | CH(OH)CH₃ | cyclopropyl | NHCH₃ | OCH₃ | N | |
| CH₃ | H | 0 | CH(OH)CH₃ | cyclopropyl | OCH₃ | OCH₂CH₃ | N | |
| CH₃ | H | 0 | CH(OH)CH₃ | cyclopropyl | CH₂F | CH₃ | CH | |
| Ph | H | 0 | H | cyclopropyl | CH₃ | CH₃ | CH | |
| Ph | H | 0 | H | cyclopropyl | CH₃ | OCH₃ | CH | |
| Ph | H | 0 | H | cyclopropyl | OCH₃ | OCH₃ | CH | |
| Ph | H | 0 | H | cyclopropyl | CH₃ | CH₃ | N | |
| Ph | H | 0 | H | cyclopropyl | CH₃ | OCH₃ | N | |
| Ph | H | 0 | H | cyclopropyl | OCH₃ | OCH₃ | N | |
| Ph | H | 0 | H | cyclopropyl | Cl | OCH₃ | CH | |
| Ph | H | 0 | H | cyclobutyl | CH₃ | CH₃ | CH | |
| Ph | H | 0 | H | cyclobutyl | CH₃ | OCH₃ | CH | |
| Ph | H | 0 | H | cyclobutyl | OCH₃ | OCH₃ | CH | |
| Ph | H | 0 | H | cyclobutyl | CH₃ | CH₃ | N | |

TABLE III-continued

| R | $R_1$ | n | $R_2$ | R' | X | Y | Z | m.p. (°C.) |
|---|---|---|---|---|---|---|---|---|
| Ph | H | 0 | H | cyclobutyl | $CH_3$ | $OCH_3$ | N | |
| Ph | H | 0 | H | cyclobutyl | $OCH_3$ | $OCH_3$ | N | |
| Ph | H | 0 | H | cyclobutyl | Cl | $OCH_3$ | CH | |
| Ph | H | 0 | H | cyclopentyl | $CH_3$ | $CH_3$ | CH | |
| Ph | H | 0 | H | cyclopentyl | $OCH_3$ | $OCH_3$ | CH | |
| Ph | H | 0 | H | cyclopentyl | $CH_3$ | $CH_3$ | N | |
| Ph | H | 0 | H | cyclopentyl | $CH_3$ | $OCH_3$ | N | |
| Ph | H | 0 | H | cyclopentyl | $OCH_3$ | $OCH_3$ | N | |
| Ph | H | 0 | H | cyclopentyl | Cl | $OCH_3$ | CH | |
| Ph | H | 0 | H | cyclopropyl | $OCH_3$ | $OCH_2CH_3$ | CH | |
| Ph | H | 0 | H | cyclopropyl | cyclopropyl | $OCH_3$ | CH | |
| Ph | H | 0 | H | cyclopropyl | $OCH_3$ | $CH(OCH_3)_2$ | CH | |
| Ph | H | 0 | H | cyclopropyl | $NHCH_3$ | $OCH_2CH_3$ | N | |
| Ph | H | 0 | H | cyclopropyl | $NHCH_3$ | $OCH_3$ | N | |
| Ph | H | 0 | H | cyclopropyl | $OCH_3$ | $OCH_2CH_3$ | N | |
| Ph | H | 0 | H | cyclopropyl | $CH_2F$ | $CH_3$ | CH | |
| $SO_2N(CH_3)_2$ | H | 0 | H | cyclopropyl | $CH_3$ | $CH_3$ | CH | |
| $SO_2N(CH_3)_2$ | H | 0 | H | cyclopropyl | $CH_3$ | $OCH_3$ | CH | |
| $SO_2N(CH_3)_2$ | H | 0 | H | cyclopropyl | $OCH_3$ | $OCH_3$ | CH | |
| $SO_2N(CH_3)_2$ | H | 0 | H | cyclopropyl | $CH_3$ | $CH_3$ | N | |
| $SO_2N(CH_3)_2$ | H | 0 | H | cyclopropyl | $CH_3$ | $OCH_3$ | N | |
| $SO_2N(CH_3)_2$ | H | 0 | H | cyclopropyl | $OCH_3$ | $OCH_3$ | N | |
| $SO_2N(CH_3)_2$ | H | 0 | H | cyclopropyl | Cl | $OCH_3$ | CH | |
| $SO_2N(CH_3)_2$ | H | 0 | H | cyclobutyl | $CH_3$ | $CH_3$ | CH | |
| $SO_2N(CH_3)_2$ | H | 0 | H | cyclobutyl | $CH_3$ | $OCH_3$ | CH | |
| $SO_2N(CH_3)_2$ | H | 0 | H | cyclobutyl | $OCH_3$ | $OCH_3$ | CH | |
| $SO_2N(CH_3)_2$ | H | 0 | H | cyclobutyl | $CH_3$ | $CH_3$ | N | |
| $SO_2N(CH_3)_2$ | H | 0 | H | cyclobutyl | $CH_3$ | $OCH_3$ | N | |
| $SO_2N(CH_3)_2$ | H | 0 | H | cyclobutyl | $OCH_3$ | $OCH_3$ | N | |
| $SO_2N(CH_3)_2$ | H | 0 | H | cyclobutyl | Cl | $OCH_3$ | CH | |
| $SO_2N(CH_3)_2$ | H | 0 | H | cyclopentyl | $CH_3$ | $CH_3$ | CH | |
| $SO_2N(CH_3)_2$ | H | 0 | H | cyclopentyl | $CH_3$ | $OCH_3$ | CH | |
| $SO_2N(CH_3)_2$ | H | 0 | H | cyclopentyl | $OCH_3$ | $OCH_3$ | CH | |
| $SO_2N(CH_3)_2$ | H | 0 | H | cyclopentyl | $CH_3$ | $CH_3$ | N | |
| $SO_2N(CH_3)_2$ | H | 0 | H | cyclopentyl | $CH_3$ | $OCH_3$ | N | |
| $SO_2N(CH_3)_2$ | H | 0 | H | cyclopentyl | $OCH_3$ | $OCH_3$ | N | |
| $SO_2N(CH_3)_2$ | H | 0 | H | cyclopentyl | Cl | $OCH_3$ | CH | |
| $SO_2N(CH_3)_2$ | H | 0 | H | cyclopropyl | $OCH_3$ | $OCH_2CH_3$ | CH | |
| $SO_2N(CH_3)_2$ | H | 0 | H | cyclopropyl | cyclopropyl | $OCH_3$ | CH | |
| $SO_2N(CH_3)_2$ | H | 0 | H | cyclopropyl | $OCH_3$ | $CH(OCH_3)_2$ | CH | |
| $SO_2N(CH_3)_2$ | H | 0 | H | cyclopropyl | $NHCH_3$ | $OCH_2CH_3$ | N | |
| $SO_2N(CH_3)_2$ | H | 0 | H | cyclopropyl | $NHCH_3$ | $OCH_3$ | N | |
| $SO_2N(CH_3)_2$ | H | 0 | H | cyclopropyl | $OCH_3$ | $OCH_2CH_3$ | N | |
| $SO_2N(CH_3)_2$ | H | 0 | H | cyclopropyl | $CH_2F$ | $CH_3$ | CH | |
| $CH_2CH=CH_2$ | H | 0 | H | cyclopropyl | $CH_3$ | $CH_3$ | CH | |
| $CH_2CH=CH_2$ | H | 0 | H | cyclopropyl | $CH_3$ | $OCH_3$ | CH | |
| $CH_2CH=CH_2$ | H | 0 | H | cyclopropyl | $OCH_3$ | $OCH_3$ | CH | |
| $CH_2CH=CH_2$ | H | 0 | H | cyclopropyl | $CH_3$ | $CH_3$ | N | |
| $CH_2CH=CH_2$ | H | 0 | H | cyclopropyl | $CH_3$ | $OCH_3$ | N | |
| $CH_2CH=CH_2$ | H | 0 | H | cyclopropyl | $OCH_3$ | $OCH_3$ | N | |
| $CH_2CH=CH_2$ | H | 0 | H | cyclopropyl | Cl | $OCH_3$ | CH | |
| $CH_2CH=CH_2$ | H | 0 | H | cyclobutyl | $CH_3$ | $CH_3$ | CH | |
| $CH_2CH=CH_2$ | H | 0 | H | cyclobutyl | $CH_3$ | $OCH_3$ | CH | |
| $CH_2CH=CH_2$ | H | 0 | H | cyclobutyl | $OCH_3$ | $OCH_3$ | CH | |
| $CH_2CH=CH_2$ | H | 0 | H | cyclobutyl | $CH_3$ | $CH_3$ | N | |
| $CH_2CH=CH_2$ | H | 0 | H | cyclobutyl | $CH_3$ | $OCH_3$ | N | |
| $CH_2CH=CH_2$ | H | 0 | H | cyclobutyl | $OCH_3$ | $OCH_3$ | N | |
| $CH_2CH=CH_2$ | H | 0 | H | cyclobutyl | Cl | $OCH_3$ | CH | |
| $CH_2CH=CH_2$ | H | 0 | H | cyclopentyl | $CH_3$ | $CH_3$ | CH | |
| $CH_2CH=CH_2$ | H | 0 | H | cyclopentyl | $CH_3$ | $OCH_3$ | CH | |
| $CH_2CH=CH_2$ | H | 0 | H | cyclopentyl | $OCH_3$ | $OCH_3$ | CH | |
| $CH_2CH=CH_2$ | H | 0 | H | cyclopentyl | $CH_3$ | $CH_3$ | N | |
| $CH_2CH=CH_2$ | H | 0 | H | cyclopentyl | $CH_3$ | $OCH_3$ | N | |
| $CH_2CH=CH_2$ | H | 0 | H | cyclopentyl | $OCH_3$ | $OCH_3$ | N | |
| $CH_2CH=CH_2$ | H | 0 | H | cyclopentyl | Cl | $OCH_3$ | CH | |
| $CH_2CH=CH_2$ | H | 0 | H | cyclopropyl | $OCH_3$ | $OCH_2CH_3$ | CH | |
| $CH_2CH=CH_2$ | H | 0 | H | cyclopropyl | cyclopropyl | $OCH_3$ | CH | |
| $CH_2CH=CH_2$ | H | 0 | H | cyclopropyl | $OCH_3$ | $CH(OCH_3)_2$ | CH | |
| $CH_2CH=CH_2$ | H | 0 | H | cyclopropyl | $NHCH_3$ | $OCH_2CH_3$ | N | |
| $CH_2CH=CH_2$ | H | 0 | H | cyclopropyl | $NHCH_3$ | $OCH_3$ | N | |
| $CH_2CH=CH_2$ | H | 0 | H | cyclopropyl | $OCH_3$ | $OCH_2CH_3$ | N | |
| $CH_2CH=CH_2$ | H | 0 | H | cyclopropyl | $CH_2F$ | $CH_3$ | CH | |
| H | H | 0 | H | cyclopropyl | $CH_3$ | $CH_3$ | CH | |
| H | H | 0 | H | cyclopropyl | $OCH_3$ | $OCH_3$ | CH | |
| H | H | 0 | H | cyclopropyl | $CH_3$ | $CH_3$ | N | |
| H | H | 0 | H | cyclopropyl | $CH_3$ | $OCH_3$ | N | |
| H | H | 0 | H | cyclopropyl | $OCH_3$ | $OCH_3$ | N | |
| H | H | 0 | H | cyclopropyl | Cl | $OCH_3$ | CH | |
| H | H | 0 | H | cyclobutyl | $CH_3$ | $CH_3$ | CH | |

TABLE III-continued

| R | R$_1$ | n | R$_2$ | R' | X | Y | Z | m.p. (°C.) |
|---|---|---|---|---|---|---|---|---|
| H | H | 0 | H | cyclobutyl | CH$_3$ | OCH$_3$ | CH | |
| H | H | 0 | H | cyclobutyl | OCH$_3$ | OCH$_3$ | CH | |
| H | H | 0 | H | cyclobutyl | CH$_3$ | CH$_3$ | N | |
| H | H | 0 | H | cyclobutyl | CH$_3$ | OCH$_3$ | N | |
| H | H | 0 | H | cyclobutyl | OCH$_3$ | OCH$_3$ | N | |
| H | H | 0 | H | cyclobutyl | Cl | OCH$_3$ | CH | |
| H | H | 0 | H | cyclopentyl | CH$_3$ | CH$_3$ | CH | |
| H | H | 0 | H | cyclopentyl | CH$_3$ | OCH$_3$ | CH | |
| H | H | 0 | H | cyclopentyl | OCH$_3$ | OCH$_3$ | CH | |
| H | H | 0 | H | cyclopentyl | CH$_3$ | CH$_3$ | N | |
| H | H | 0 | H | cyclopentyl | CH$_3$ | OCH$_3$ | N | |
| H | H | 0 | H | cyclopentyl | OCH$_3$ | OCH$_3$ | N | |
| H | H | 0 | H | cyclopentyl | Cl | OCH$_3$ | CH | |
| H | H | 0 | H | cyclopropyl | OCH$_3$ | OCH$_2$CH$_3$ | CH | |
| H | H | 0 | H | cyclopropyl | cyclopropyl | OCH$_3$ | CH | |
| H | H | 0 | H | cyclopropyl | OCH$_3$ | CH(OCH$_3$)$_2$ | CH | |
| H | H | 0 | H | cyclopropyl | NHCH$_3$ | OCH$_2$CH$_3$ | N | |
| H | H | 0 | H | cyclopropyl | NHCH$_3$ | OCH$_3$ | N | |
| H | H | 0 | H | cyclopropyl | OCH$_3$ | OCH$_2$CH$_3$ | N | |
| H | H | 0 | H | cyclopropyl | CH$_2$F | CH$_3$ | CH | |
| CH$_2$CH$_2$CH$_3$ | H | 0 | Cl | cyclopropyl | CH$_3$ | CH$_3$ | CH | |
| CH$_2$CH$_2$CH$_3$ | H | 0 | Cl | cyclopropyl | CH$_3$ | OCH$_3$ | CH | |
| CH$_2$CH$_2$CH$_3$ | H | 0 | Cl | cyclopropyl | OCH$_3$ | OCH$_3$ | CH | |
| CH$_2$CH$_2$CH$_3$ | H | 0 | Cl | cyclopropyl | CH$_3$ | CH$_3$ | N | |
| CH$_2$CH$_2$CH$_3$ | H | 0 | Cl | cyclopropyl | CH$_3$ | OCH$_3$ | N | |
| CH$_2$CH$_2$CH$_3$ | H | 0 | Cl | cyclopropyl | OCH$_3$ | OCH$_3$ | N | |
| CH$_2$CH$_2$CH$_3$ | H | 0 | Cl | cyclopropyl | Cl | OCH$_3$ | CH | |
| CH$_2$CH$_2$CH$_3$ | H | 0 | Cl | cyclobutyl | CH$_3$ | CH$_3$ | CH | |
| CH$_2$CH$_2$CH$_3$ | H | 0 | Cl | cyclobutyl | CH$_3$ | OCH$_3$ | CH | |
| CH$_2$CH$_2$CH$_3$ | H | 0 | Cl | cyclobutyl | OCH$_3$ | OCH$_3$ | CH | |
| CH$_2$CH$_2$CH$_3$ | H | 0 | Cl | cyclobutyl | CH$_3$ | CH$_3$ | N | |
| CH$_2$CH$_2$CH$_3$ | H | 0 | Cl | cyclobutyl | CH$_3$ | OCH$_3$ | N | |
| CH$_2$CH$_2$CH$_3$ | H | 0 | Cl | cyclobutyl | OCH$_3$ | OCH$_3$ | N | |
| CH$_2$CH$_2$CH$_3$ | H | 0 | Cl | cyclobutyl | Cl | OCH$_3$ | CH | |
| CH$_2$CH$_2$CH$_3$ | H | 0 | Cl | cyclopentyl | CH$_3$ | CH$_3$ | CH | |
| CH$_2$CH$_2$CH$_3$ | H | 0 | Cl | cyclopentyl | CH$_3$ | OCH$_3$ | CH | |
| CH$_2$CH$_2$CH$_3$ | H | 0 | Cl | cyclopentyl | OCH$_3$ | OCH$_3$ | CH | |
| CH$_2$CH$_2$CH$_3$ | H | 0 | Cl | cyclopentyl | CH$_3$ | CH$_3$ | N | |
| CH$_2$CH$_2$CH$_3$ | H | 0 | Cl | cyclopentyl | CH$_3$ | OCH$_3$ | N | |
| CH$_2$CH$_2$CH$_3$ | H | 0 | Cl | cyclopentyl | OCH$_3$ | OCH$_3$ | N | |
| CH$_2$CH$_2$CH$_3$ | H | 0 | Cl | cyclopentyl | Cl | OCH$_3$ | CH | |
| CH$_2$CH$_2$CH$_3$ | H | 0 | Cl | cyclopropyl | OCH$_3$ | OCH$_2$CH$_3$ | CH | |
| CH$_2$CH$_2$CH$_3$ | H | 0 | Cl | cyclopropyl | cyclopropyl | OCH$_3$ | CH | |
| CH$_2$CH$_2$CH$_3$ | H | 0 | Cl | cyclopropyl | OCH$_3$ | CH(OCH$_3$)$_2$ | CH | |
| CH$_2$CH$_2$CH$_3$ | H | 0 | Cl | cyclopropyl | NHCH$_3$ | OCH$_2$CH$_3$ | N | |
| CH$_2$CH$_2$CH$_3$ | H | 0 | Cl | cyclopropyl | NHCH$_3$ | OCH$_3$ | N | |
| CH$_2$CH$_2$CH$_3$ | H | 0 | Cl | cyclopropyl | OCH$_3$ | OCH$_2$CH$_3$ | N | |
| CH$_2$CH$_2$CH$_3$ | H | 0 | Cl | cyclopropyl | CH$_2$F | CH$_3$ | CH | |
| Ph | H | 0 | Cl | cyclopropyl | CH$_3$ | CH$_3$ | CH | |
| Ph | H | 0 | Cl | cyclopropyl | CH$_3$ | OCH$_3$ | CH | |
| Ph | H | 0 | Cl | cyclopropyl | OCH$_3$ | OCH$_3$ | CH | |
| Ph | H | 0 | Cl | cyclopropyl | CH$_3$ | CH$_3$ | N | |
| Ph | H | 0 | Cl | cyclopropyl | CH$_3$ | OCH$_3$ | N | |
| Ph | H | 0 | Cl | cyclopropyl | OCH$_3$ | OCH$_3$ | N | |
| Ph | H | 0 | Cl | cyclopropyl | Cl | OCH$_3$ | CH | |
| Ph | H | 0 | Cl | cyclobutyl | CH$_3$ | CH$_3$ | CH | |
| Ph | H | 0 | Cl | cyclobutyl | CH$_3$ | OCH$_3$ | CH | |
| Ph | H | 0 | Cl | cyclobutyl | OCH$_3$ | OCH$_3$ | CH | |
| Ph | H | 0 | Cl | cyclobutyl | CH$_3$ | CH$_3$ | N | |
| Ph | H | 0 | Cl | cyclobutyl | CH$_3$ | OCH$_3$ | N | |
| Ph | H | 0 | Cl | cyclobutyl | OCH$_3$ | OCH$_3$ | N | |
| Ph | H | 0 | Cl | cyclobutyl | Cl | OCH$_3$ | CH | |
| Ph | H | 0 | Cl | cyclopentyl | CH$_3$ | CH$_3$ | CH | |
| Ph | H | 0 | Cl | cyclopentyl | CH$_3$ | OCH$_3$ | CH | |
| Ph | H | 0 | Cl | cyclopentyl | OCH$_3$ | OCH$_3$ | CH | |
| Ph | H | 0 | Cl | cyclopentyl | CH$_3$ | CH$_3$ | N | |
| Ph | H | 0 | Cl | cyclopentyl | CH$_3$ | OCH$_3$ | N | |
| Ph | H | 0 | Cl | cyclopentyl | OCH$_3$ | OCH$_3$ | N | |
| Ph | H | 0 | Cl | cyclopentyl | Cl | OCH$_3$ | CH | |
| Ph | H | 0 | Cl | cyclopropyl | OCH$_3$ | OCH$_2$CH$_3$ | CH | |
| Ph | H | 0 | Cl | cyclopropyl | cyclopropyl | OCH$_3$ | CH | |
| Ph | H | 0 | Cl | cyclopropyl | OCH$_3$ | CH(OCH$_3$)$_2$ | CH | |
| Ph | H | 0 | Cl | cyclopropyl | NHCH$_3$ | OCH$_2$CH$_3$ | N | |
| Ph | H | 0 | Cl | cyclopropyl | NHCH$_3$ | OCH$_3$ | N | |
| Ph | H | 0 | Cl | cyclopropyl | OCH$_3$ | OCH$_2$CH$_3$ | N | |
| Ph | H | 0 | Cl | cyclopropyl | CH$_2$F | CH$_3$ | CH | |
| CH$_2$CH$_3$ | H | 0 | CH$_3$ | cyclopropyl | CH$_3$ | CH$_3$ | CH | |
| CH$_2$CH$_3$ | H | 0 | CH$_3$ | cyclopropyl | CH$_3$ | OCH$_3$ | CH | |
| CH$_2$CH$_3$ | H | 0 | CH$_3$ | cyclopropyl | OCH$_3$ | OCH$_3$ | CH | |
| CH$_2$CH$_3$ | H | 0 | CH$_3$ | cyclopropyl | CH$_3$ | CH$_3$ | N | |
| CH$_2$CH$_3$ | H | 0 | CH$_3$ | cyclopropyl | CH$_3$ | OCH$_3$ | N | |

TABLE III-continued

| R | $R_1$ | n | $R_2$ | R' | X | Y | Z | m.p. (°C.) |
|---|---|---|---|---|---|---|---|---|
| $CH_2CH_3$ | H | 0 | $CH_3$ | cyclopropyl | $OCH_3$ | $OCH_3$ | N | |
| $CH_2CH_3$ | H | 0 | $CH_3$ | cyclopropyl | Cl | $OCH_3$ | CH | |
| $CH_2CH_3$ | H | 0 | $CH_3$ | cyclobutyl | $CH_3$ | $CH_3$ | CH | |
| $CH_2CH_3$ | H | 0 | $CH_3$ | cyclobutyl | $CH_3$ | $OCH_3$ | CH | |
| $CH_2CH_3$ | H | 0 | $CH_3$ | cyclobutyl | $OCH_3$ | $OCH_3$ | CH | |
| $CH_2CH_3$ | H | 0 | $CH_3$ | cyclobutyl | $CH_3$ | $CH_3$ | N | |
| $CH_2CH_3$ | H | 0 | $CH_3$ | cyclobutyl | $CH_3$ | $OCH_3$ | N | |
| $CH_2CH_3$ | H | 0 | $CH_3$ | cyclobutyl | $OCH_3$ | $OCH_3$ | N | |
| $CH_2CH_3$ | H | 0 | $CH_3$ | cyclobutyl | Cl | $OCH_3$ | CH | |
| $CH_2CH_3$ | H | 0 | $CH_3$ | cyclopentyl | $CH_3$ | $CH_3$ | CH | |
| $CH_2CH_3$ | H | 0 | $CH_3$ | cyclopentyl | $CH_3$ | $OCH_3$ | CH | |
| $CH_2CH_3$ | H | 0 | $CH_3$ | cyclopentyl | $OCH_3$ | $OCH_3$ | CH | |
| $CH_2CH_3$ | H | 0 | $CH_3$ | cyclopentyl | $CH_3$ | $CH_3$ | N | |
| $CH_2CH_3$ | H | 0 | $CH_3$ | cyclopentyl | $CH_3$ | $OCH_3$ | N | |
| $CH_2CH_3$ | H | 0 | $CH_3$ | cyclopentyl | $OCH_3$ | $OCH_3$ | N | |
| $CH_2CH_3$ | H | 0 | $CH_3$ | cyclopentyl | Cl | $OCH_3$ | CH | |
| $CH_2CH_3$ | H | 0 | $CH_3$ | cyclopropyl | $OCH_3$ | $OCH_2CH_3$ | CH | |
| $CH_2CH_3$ | H | 0 | $CH_3$ | cyclopropyl | cyclopropyl | $OCH_3$ | CH | |
| $CH_2CH_3$ | H | 0 | $CH_3$ | cyclopropyl | $OCH_3$ | $CH(OCH_3)_2$ | CH | |
| $CH_2CH_3$ | H | 0 | $CH_3$ | cyclopropyl | $NHCH_3$ | $OCH_2CH_3$ | N | |
| $CH_2CH_3$ | H | 0 | $CH_3$ | cyclopropyl | $NHCH_3$ | $OCH_3$ | N | |
| $CH_2CH_3$ | H | 0 | $CH_3$ | cyclopropyl | $OCH_3$ | $OCH_2CH_3$ | N | |
| $CH_2CH_3$ | H | 0 | $CH_3$ | cyclopropyl | $CH_2F$ | $CH_3$ | CH | |
| $CH_2CH=CH_2$ | H | 0 | $CH_3$ | cyclopropyl | $CH_3$ | $CH_3$ | CH | |
| $CH_2CH=CH_2$ | H | 0 | $CH_3$ | cyclopropyl | $CH_3$ | $OCH_3$ | CH | |
| $CH_2CH=CH_2$ | H | 0 | $CH_3$ | cyclopropyl | $OCH_3$ | $OCH_3$ | CH | |
| $CH_2CH=CH_2$ | H | 0 | $CH_3$ | cyclopropyl | $CH_3$ | $CH_3$ | N | |
| $CH_2CH=CH_2$ | H | 0 | $CH_3$ | cyclopropyl | $CH_3$ | $OCH_3$ | N | |
| $CH_2CH=CH_2$ | H | 0 | $CH_3$ | cyclopropyl | $OCH_3$ | $OCH_3$ | N | |
| $CH_2CH=CH_2$ | H | 0 | $CH_3$ | cyclopropyl | Cl | $OCH_3$ | CH | |
| $CH_2CH=CH_2$ | H | 0 | $CH_3$ | cyclobutyl | $CH_3$ | $CH_3$ | CH | |
| $CH_2CH=CH_2$ | H | 0 | $CH_3$ | cyclobutyl | $CH_3$ | $OCH_3$ | CH | |
| $CH_2CH=CH_2$ | H | 0 | $CH_3$ | cyclobutyl | $OCH_3$ | $OCH_3$ | CH | |
| $CH_2CH=CH_2$ | H | 0 | $CH_3$ | cyclobutyl | $CH_3$ | $CH_3$ | N | |
| $CH_2CH=CH_2$ | H | 0 | $CH_3$ | cyclobutyl | $CH_3$ | $OCH_3$ | N | |
| $CH_2CH=CH_2$ | H | 0 | $CH_3$ | cyclobutyl | $OCH_3$ | $OCH_3$ | N | |
| $CH_2CH=CH_2$ | H | 0 | $CH_3$ | cyclobutyl | Cl | $OCH_3$ | CH | |
| $CH_2CH=CH_2$ | H | 0 | $CH_3$ | cyclopentyl | $CH_3$ | $CH_3$ | CH | |
| $CH_2CH=CH_2$ | H | 0 | $CH_3$ | cyclopentyl | $CH_3$ | $OCH_3$ | CH | |
| $CH_2CH=CH_2$ | H | 0 | $CH_3$ | cyclopentyl | $OCH_3$ | $OCH_3$ | CH | |
| $CH_2CH=CH_2$ | H | 0 | $CH_3$ | cyclopentyl | $CH_3$ | $CH_3$ | N | |
| $CH_2CH=CH_2$ | H | 0 | $CH_3$ | cyclopentyl | $CH_3$ | $OCH_3$ | N | |
| $CH_2CH=CH_2$ | H | 0 | $CH_3$ | cyclopentyl | $OCH_3$ | $OCH_3$ | N | |
| $CH_2CH=CH_2$ | H | 0 | $CH_3$ | cyclopentyl | Cl | $OCH_3$ | CH | |
| $CH_2CH=CH_2$ | H | 0 | $CH_3$ | cyclopropyl | $OCH_3$ | $OCH_2CH_3$ | CH | |
| $CH_2CH=CH_2$ | H | 0 | $CH_3$ | cyclopropyl | cyclopropyl | $OCH_3$ | CH | |
| $CH_2CH=CH_2$ | H | 0 | $CH_3$ | cyclopropyl | $OCH_3$ | $CH(OCH_3)_2$ | CH | |
| $CH_2CH=CH_2$ | H | 0 | $CH_3$ | cyclopropyl | $NHCH_3$ | $OCH_2CH_3$ | N | |
| $CH_2CH=CH_2$ | H | 0 | $CH_3$ | cyclopropyl | $NHCH_3$ | $OCH_3$ | N | |
| $CH_2CH=CH_2$ | H | 0 | $CH_3$ | cyclopropyl | $OCH_3$ | $OCH_2CH_3$ | N | |
| $CH_2CH=CH_2$ | H | 0 | $CH_3$ | cyclopropyl | $CH_2F$ | $CH_3$ | CH | |
| $CH_2C\equiv CH$ | H | 0 | $CH_3$ | cyclopropyl | $CH_3$ | $CH_3$ | CH | |
| $CH_2C\equiv CH$ | H | 0 | $CH_3$ | cyclopropyl | $CH_3$ | $OCH_3$ | CH | |
| $CH_2C\equiv CH$ | H | 0 | $CH_3$ | cyclopropyl | $OCH_3$ | $OCH_3$ | CH | |
| $CH_2C\equiv CH$ | H | 0 | $CH_3$ | cyclopropyl | $CH_3$ | $CH_3$ | N | |
| $CH_2C\equiv CH$ | H | 0 | $CH_3$ | cyclopropyl | $CH_3$ | $OCH_3$ | N | |
| $CH_2C\equiv CH$ | H | 0 | $CH_3$ | cyclopropyl | $OCH_3$ | $OCH_3$ | N | |
| $CH_2C\equiv CH$ | H | 0 | $CH_3$ | cyclopropyl | Cl | $OCH_3$ | CH | |
| $CH_2C\equiv CH$ | H | 0 | $CH_3$ | cyclobutyl | $CH_3$ | $CH_3$ | CH | |
| $CH_2C\equiv CH$ | H | 0 | $CH_3$ | cyclobutyl | $CH_3$ | $OCH_3$ | CH | |
| $CH_2C\equiv CH$ | H | 0 | $CH_3$ | cyclobutyl | $OCH_3$ | $OCH_3$ | CH | |
| $CH_2C\equiv CH$ | H | 0 | $CH_3$ | cyclobutyl | $CH_3$ | $CH_3$ | N | |
| $CH_2C\equiv CH$ | H | 0 | $CH_3$ | cyclobutyl | $CH_3$ | $OCH_3$ | N | |
| $CH_2C\equiv CH$ | H | 0 | $CH_3$ | cyclobutyl | $OCH_3$ | $OCH_3$ | N | |
| $CH_2C\equiv CH$ | H | 0 | $CH_3$ | cyclobutyl | Cl | $OCH_3$ | CH | |
| $CH_2C\equiv CH$ | H | 0 | $CH_3$ | cyclopentyl | $CH_3$ | $CH_3$ | CH | |
| $CH_2C\equiv CH$ | H | 0 | $CH_3$ | cyclopentyl | $CH_3$ | $OCH_3$ | CH | |
| $CH_2C\equiv CH$ | H | 0 | $CH_3$ | cyclopentyl | $OCH_3$ | $OCH_3$ | CH | |
| $CH_2C\equiv CH$ | H | 0 | $CH_3$ | cyclopentyl | $CH_3$ | $CH_3$ | N | |
| $CH_2C\equiv CH$ | H | 0 | $CH_3$ | cyclopentyl | $CH_3$ | $OCH_3$ | N | |
| $CH_2C\equiv CH$ | H | 0 | $CH_3$ | cyclopentyl | $OCH_3$ | $OCH_3$ | N | |
| $CH_2C\equiv CH$ | H | 0 | $CH_3$ | cyclopentyl | Cl | $OCH_3$ | CH | |
| $CH_2C\equiv CH$ | H | 0 | $CH_3$ | cyclopropyl | $OCH_3$ | $OCH_2CH_3$ | CH | |
| $CH_2C\equiv CH$ | H | 0 | $CH_3$ | cyclopropyl | cyclopropyl | $OCH_3$ | CH | |
| $CH_2C\equiv CH$ | H | 0 | $CH_3$ | cyclopropyl | $OCH_3$ | $CH(OCH_3)_2$ | CH | |
| $CH_2C\equiv CH$ | H | 0 | $CH_3$ | cyclopropyl | $NHCH_3$ | $OCH_2CH_3$ | N | |
| $CH_2C\equiv CH$ | H | 0 | $CH_3$ | cyclopropyl | $NHCH_3$ | $OCH_3$ | N | |
| $CH_2C\equiv CH$ | H | 0 | $CH_3$ | cyclopropyl | $OCH_3$ | $OCH_2CH_3$ | N | |
| $CH_2C\equiv CH$ | H | 0 | $CH_3$ | cyclopropyl | $CH_2F$ | $CH_3$ | CH | |
| $CH_3$ | H | 1 | H | cyclopropyl | $CH_3$ | $CH_3$ | CH | |
| $CH_3$ | H | 1 | H | cyclopropyl | $CH_3$ | $OCH_3$ | CH | |

TABLE III-continued

| R | R$_1$ | n | R$_2$ | R' | X | Y | Z | m.p. (°C.) |
|---|---|---|---|---|---|---|---|---|
| CH$_3$ | H | 1 | H | cyclopropyl | OCH$_3$ | OCH$_3$ | CH | |
| CH$_3$ | H | 1 | H | cyclopropyl | CH$_3$ | CH$_3$ | N | |
| CH$_3$ | H | 1 | H | cyclopropyl | CH$_3$ | OCH$_3$ | N | |
| CH$_3$ | H | 1 | H | cyclopropyl | OCH$_3$ | OCH$_3$ | N | |
| CH$_3$ | H | 1 | H | cyclopropyl | Cl | OCH$_3$ | CH | |
| CH$_3$ | H | 1 | H | cyclobutyl | CH$_3$ | CH$_3$ | CH | |
| CH$_3$ | H | 1 | H | cyclobutyl | CH$_3$ | OCH$_3$ | CH | |
| CH$_3$ | H | 1 | H | cyclobutyl | OCH$_3$ | OCH$_3$ | CH | |
| CH$_3$ | H | 1 | H | cyclobutyl | CH$_3$ | CH$_3$ | N | |
| CH$_3$ | H | 1 | H | cyclobutyl | CH$_3$ | OCH$_3$ | N | |
| CH$_3$ | H | 1 | H | cyclobutyl | OCH$_3$ | OCH$_3$ | N | |
| CH$_3$ | H | 1 | H | cyclobutyl | Cl | OCH$_3$ | CH | |
| CH$_3$ | H | 1 | H | cyclopentyl | CH$_3$ | CH$_3$ | CH | |
| CH$_3$ | H | 1 | H | cyclopentyl | CH$_3$ | OCH$_3$ | CH | |
| CH$_3$ | H | 1 | H | cyclopentyl | OCH$_3$ | OCH$_3$ | CH | |
| CH$_3$ | H | 1 | H | cyclopentyl | CH$_3$ | CH$_3$ | N | |
| CH$_3$ | H | 1 | H | cyclopentyl | CH$_3$ | OCH$_3$ | N | |
| CH$_3$ | H | 1 | H | cyclopentyl | OCH$_3$ | OCH$_3$ | N | |
| CH$_3$ | H | 1 | H | cyclopentyl | Cl | OCH$_3$ | CH | |
| CH$_3$ | H | 1 | H | cyclopropyl | OCH$_3$ | OCH$_2$CH$_3$ | CH | |
| CH$_3$ | H | 1 | H | cyclopropyl | cyclopropyl | OCH$_3$ | CH | |
| CH$_3$ | H | 1 | H | cyclopropyl | OCH$_3$ | CH(OCH$_3$)$_2$ | CH | |
| CH$_3$ | H | 1 | H | cyclopropyl | NHCH$_3$ | OCH$_2$CH$_3$ | N | |
| CH$_3$ | H | 1 | H | cyclopropyl | NHCH$_3$ | OCH$_3$ | N | |
| CH$_3$ | H | 1 | H | cyclopropyl | OCH$_3$ | OCH$_2$CH$_3$ | N | |
| CH$_3$ | H | 1 | H | cyclopropyl | CH$_2$F | CH$_3$ | CH | |
| CH$_3$ | H | 1 | CH$_3$ | cyclopropyl | CH$_3$ | CH$_3$ | CH | |
| CH$_3$ | H | 1 | CH$_3$ | cyclopropyl | CH$_3$ | OCH$_3$ | CH | |
| CH$_3$ | H | 1 | CH$_3$ | cyclopropyl | OCH$_3$ | OCH$_3$ | CH | |
| CH$_3$ | H | 1 | CH$_3$ | cyclopropyl | CH$_3$ | CH$_3$ | N | |
| CH$_3$ | H | 1 | CH$_3$ | cyclopropyl | CH$_3$ | OCH$_3$ | N | |
| CH$_3$ | H | 1 | CH$_3$ | cyclopropyl | OCH$_3$ | OCH$_3$ | N | |
| CH$_3$ | H | 1 | CH$_3$ | cyclopropyl | Cl | OCH$_3$ | CH | |
| CH$_3$ | H | 1 | CH$_3$ | cyclobutyl | CH$_3$ | CH$_3$ | CH | |
| CH$_3$ | H | 1 | CH$_3$ | cyclobutyl | CH$_3$ | OCH$_3$ | CH | |
| CH$_3$ | H | 1 | CH$_3$ | cyclobutyl | OCH$_3$ | OCH$_3$ | CH | |
| CH$_3$ | H | 1 | CH$_3$ | cyclobutyl | CH$_3$ | CH$_3$ | N | |
| CH$_3$ | H | 1 | CH$_3$ | cyclobutyl | CH$_3$ | OCH$_3$ | N | |
| CH$_3$ | H | 1 | CH$_3$ | cyclobutyl | OCH$_3$ | OCH$_3$ | N | |
| CH$_3$ | H | 1 | CH$_3$ | cyclobutyl | Cl | OCH$_3$ | CH | |
| CH$_3$ | H | 1 | CH$_3$ | cyclopentyl | CH$_3$ | CH$_3$ | CH | |
| CH$_3$ | H | 1 | CH$_3$ | cyclopentyl | CH$_3$ | OCH$_3$ | CH | |
| CH$_3$ | H | 1 | CH$_3$ | cyclopentyl | OCH$_3$ | OCH$_3$ | CH | |
| CH$_3$ | H | 1 | CH$_3$ | cyclopentyl | CH$_3$ | CH$_3$ | N | |
| CH$_3$ | H | 1 | CH$_3$ | cyclopentyl | CH$_3$ | OCH$_3$ | N | |
| CH$_3$ | H | 1 | CH$_3$ | cyclopentyl | OCH$_3$ | OCH$_3$ | N | |
| CH$_3$ | H | 1 | CH$_3$ | cyclopentyl | Cl | OCH$_3$ | CH | |
| CH$_3$ | H | 1 | CH$_3$ | cyclopropyl | OCH$_3$ | OCH$_2$CH$_3$ | CH | |
| CH$_3$ | H | 1 | CH$_3$ | cyclopropyl | cyclopropyl | OCH$_3$ | CH | |
| CH$_3$ | H | 1 | CH$_3$ | cyclopropyl | OCH$_3$ | CH(OCH$_3$)$_2$ | CH | |
| CH$_3$ | H | 1 | CH$_3$ | cyclopropyl | NHCH$_3$ | OCH$_2$CH$_3$ | N | |
| CH$_3$ | H | 1 | CH$_3$ | cyclopropyl | NHCH$_3$ | OCH$_3$ | N | |
| CH$_3$ | H | 1 | CH$_3$ | cyclopropyl | OCH$_3$ | OCH$_2$CH$_3$ | N | |
| CH$_3$ | H | 1 | CH$_3$ | cyclopropyl | CH$_2$F | CH$_3$ | CH | |
| CH$_3$ | H | 0 | H | cyclopropyl | CH$_2$CH$_3$ | CH$_3$ | CH | |
| CH$_3$ | H | 0 | H | cyclopropyl | CH$_2$CH$_3$ | OCH$_3$ | CH | |
| CH$_3$ | H | 0 | H | cyclopropyl | CH$_2$F | CH$_3$ | CH | |
| CH$_3$ | H | 0 | H | cyclopropyl | OCF$_2$H | CH$_3$ | CH | |
| CH$_3$ | H | 0 | H | cyclopropyl | OCF$_2$H | OCH$_3$ | CH | |
| CH$_3$ | H | 0 | H | cyclopropyl | OCH$_2$CF$_3$ | OCH$_3$ | CH | |
| CH$_3$ | H | 0 | H | cyclopropyl | CH$_2$F | OCH$_3$ | CH | |
| CH$_3$ | H | 0 | H | cyclopropyl | CH$_2$Cl | OCH$_3$ | N | |
| CH$_3$ | H | 0 | H | cyclopropyl | SCH$_3$ | OCH$_3$ | CH | |
| CH$_3$ | H | 0 | H | cyclopropyl | SCH$_2$F | OCH$_3$ | CH | |
| CH$_3$ | H | 0 | H | cyclopropyl | Br | OCH$_3$ | CH | |
| CH$_3$ | H | 0 | H | cyclopropyl | CH$_2$OCH$_3$ | OCH$_3$ | N | |
| CH$_3$ | H | 0 | H | cyclopropyl | OCH$_2$OCH$_3$ | OCH$_3$ | CH | |
| CH$_3$ | H | 0 | H | cyclopropyl | OCH$_2$OCH$_2$CH$_3$ | CH$_3$ | CH | |
| CH$_3$ | H | 0 | H | cyclopropyl | N(CH$_3$)$_2$ | OCH$_3$ | N | |
| CH$_3$ | H | 0 | H | cyclopropyl | NHCH$_2$CH$_3$ | CH$_3$ | N | |
| CH$_3$ | H | 0 | H | cyclopropyl | NHCH$_3$ | OCH$_2$CH$_3$ | N | |
| CH$_3$ | H | 0 | H | cyclopropyl | CH$_3$ | CH$_2$SCH$_3$ | CH | |
| CH$_3$ | H | 0 | H | cyclopropyl | OCH$_3$ | CH$_2$SO$_2$CH$_3$ | CH | |
| CH$_3$ | H | 0 | H | cyclopropyl | NH$_2$ | OCH$_2$CH$_3$ | N | |
| CH$_3$ | H | 0 | H | cyclopropyl | CH$_3$ | OCH$_2$CH=CH$_2$ | CH | |
| CH$_3$ | H | 0 | H | cyclopropyl | CH$_2$CH$_3$ | OCF$_2$H | CH | |
| CH$_3$ | H | 0 | H | cyclopropyl | OCF$_2$H | OCF$_2$H | CH | |
| CH$_3$ | H | 0 | H | cyclopropyl | OCH$_3$ | OCH=CH$_2$ | CH | |
| CH$_3$ | H | 0 | H | cyclopropyl | OCH$_3$ | C(O)CH$_3$ | N | |
| CH$_3$ | H | 0 | H | cyclopropyl | CH$_3$ | N(OCH$_3$)CH$_3$ | N | |

TABLE III-continued

| R | R₁ | n | R₂ | R' | X | Y | Z | m.p. (°C.) |
|---|---|---|---|---|---|---|---|---|
| CH₃ | H | 0 | H | cyclopropyl | OCH(CH₃)₂ | OCF₂H | CH | |

TABLE IV

| R | R₁ | n | R₂ | R' | X | Y | Z | m.p. (°C.) |
|---|---|---|---|---|---|---|---|---|
| CH₃ | H | 0 | H | cyclopropyl | CH₃ | CH₃ | CH | |
| CH₃ | H | 0 | H | cyclopropyl | CH₃ | OCH₃ | CH | |
| CH₃ | H | 0 | H | cyclopropyl | OCH₃ | OCH₃ | CH | |
| CH₃ | H | 0 | H | cyclopropyl | CH₃ | CH₃ | N | |
| CH₃ | H | 0 | H | cyclopropyl | CH₃ | OCH₃ | N | |
| CH₃ | H | 0 | H | cyclopropyl | OCH₃ | OCH₃ | N | |
| CH₃ | H | 0 | H | cyclopropyl | Cl | OCH₃ | CH | |
| CH₃ | H | 0 | H | cyclobutyl | CH₃ | CH₃ | CH | |
| CH₃ | H | 0 | H | cyclobutyl | CH₃ | OCH₃ | CH | |
| CH₃ | H | 0 | H | cyclobutyl | OCH₃ | OCH₃ | CH | |
| CH₃ | H | 0 | H | cyclobutyl | CH₃ | CH₃ | N | |
| CH₃ | H | 0 | H | cyclobutyl | CH₃ | OCH₃ | N | |
| CH₃ | H | 0 | H | cyclobutyl | OCH₃ | OCH₃ | N | |
| CH₃ | H | 0 | H | cyclobutyl | Cl | OCH₃ | CH | |
| CH₃ | H | 0 | H | cyclopentyl | CH₃ | CH₃ | CH | |
| CH₃ | H | 0 | H | cyclopentyl | CH₃ | OCH₃ | CH | |
| CH₃ | H | 0 | H | cyclopentyl | OCH₃ | OCH₃ | CH | |
| CH₃ | H | 0 | H | cyclopentyl | CH₃ | CH₃ | N | |
| CH₃ | H | 0 | H | cyclopentyl | CH₃ | OCH₃ | N | |
| CH₃ | H | 0 | H | cyclopentyl | OCH₃ | OCH₃ | N | |
| CH₃ | H | 0 | H | cyclopentyl | Cl | OCH₃ | CH | |
| CH₃ | H | 0 | H | cyclopropyl | OCH₃ | OCH₂CH₃ | CH | |
| CH₃ | H | 0 | H | cyclopropyl | cyclopropyl | OCH₃ | CH | |
| CH₃ | H | 0 | H | cyclopropyl | OCH₃ | CH(OCH₃)₂ | CH | |
| CH₃ | H | 0 | H | cyclopropyl | NHCH₃ | OCH₂CH₃ | N | |
| CH₃ | H | 0 | H | cyclopropyl | NHCH₃ | OCH₃ | N | |
| CH₃ | H | 0 | H | cyclopropyl | OCH₃ | OCH₂CH₃ | N | |
| CH₃ | H | 0 | H | cyclopropyl | CH₂F | CH₃ | CH | |
| CH₃ | H | 0 | CH₃ | cyclopropyl | CH₃ | CH₃ | CH | |
| CH₃ | H | 0 | CH₃ | cyclopropyl | CH₃ | OCH₃ | CH | |
| CH₃ | H | 0 | CH₃ | cyclopropyl | OCH₃ | OCH₃ | CH | |
| CH₃ | H | 0 | CH₃ | cyclopropyl | CH₃ | CH₃ | N | |
| CH₃ | H | 0 | CH₃ | cyclopropyl | CH₃ | OCH₃ | N | |
| CH₃ | H | 0 | CH₃ | cyclopropyl | OCH₃ | OCH₃ | N | |
| CH₃ | H | 0 | CH₃ | cyclopropyl | Cl | OCH₃ | CH | |
| CH₃ | H | 0 | CH₃ | cyclobutyl | CH₃ | CH₃ | CH | |
| CH₃ | H | 0 | CH₃ | cyclobutyl | CH₃ | OCH₃ | CH | |
| CH₃ | H | 0 | CH₃ | cyclobutyl | OCH₃ | OCH₃ | CH | |
| CH₃ | H | 0 | CH₃ | cyclobutyl | CH₃ | CH₃ | N | |
| CH₃ | H | 0 | CH₃ | cyclobutyl | CH₃ | OCH₃ | N | |
| CH₃ | H | 0 | CH₃ | cyclobutyl | OCH₃ | OCH₃ | N | |
| CH₃ | H | 0 | CH₃ | cyclobutyl | Cl | OCH₃ | CH | |
| CH₃ | H | 0 | CH₃ | cyclopentyl | CH₃ | CH₃ | CH | |
| CH₃ | H | 0 | CH₃ | cyclopentyl | CH₃ | OCH₃ | CH | |
| CH₃ | H | 0 | CH₃ | cyclopentyl | OCH₃ | OCH₃ | CH | |
| CH₃ | H | 0 | CH₃ | cyclopentyl | CH₃ | CH₃ | N | |
| CH₃ | H | 0 | CH₃ | cyclopentyl | CH₃ | OCH₃ | N | |
| CH₃ | H | 0 | CH₃ | cyclopentyl | OCH₃ | OCH₃ | N | |
| CH₃ | H | 0 | CH₃ | cyclopentyl | Cl | OCH₃ | CH | |
| CH₃ | H | 0 | CH₃ | cyclopropyl | OCH₃ | OCH₂CH₃ | CH | |
| CH₃ | H | 0 | CH₃ | cyclopropyl | cyclopropyl | OCH₃ | CH | |
| CH₃ | H | 0 | CH₃ | cyclopropyl | OCH₃ | CH(OCH₃)₂ | CH | |
| CH₃ | H | 0 | CH₃ | cyclopropyl | NHCH₃ | OCH₂CH₃ | N | |
| CH₃ | H | 0 | CH₃ | cyclopropyl | NHCH₃ | OCH₃ | N | |
| CH₃ | H | 0 | CH₃ | cyclopropyl | OCH₃ | OCH₂CH₃ | N | |
| CH₃ | H | 0 | CH₃ | cyclopropyl | CH₂F | CH₃ | CH | |
| CH₃ | H | 0 | Cl | cyclopropyl | CH₃ | CH₃ | CH | |
| CH₃ | H | 0 | Cl | cyclopropyl | CH₃ | OCH₃ | CH | |
| CH₃ | H | 0 | Cl | cyclopropyl | OCH₃ | OCH₃ | CH | |
| CH₃ | H | 0 | Cl | cyclopropyl | CH₃ | CH₃ | N | |
| CH₃ | H | 0 | Cl | cyclopropyl | CH₃ | OCH₃ | N | |
| CH₃ | H | 0 | Cl | cyclopropyl | OCH₃ | OCH₃ | N | |
| CH₃ | H | 0 | Cl | cyclopropyl | Cl | OCH₃ | CH | |
| CH₃ | H | 0 | Cl | cyclobutyl | CH₃ | CH₃ | CH | |
| CH₃ | H | 0 | Cl | cyclobutyl | CH₃ | OCH₃ | CH | |
| CH₃ | H | 0 | Cl | cyclobutyl | OCH₃ | OCH₃ | CH | |
| CH₃ | H | 0 | Cl | cyclobutyl | CH₃ | CH₃ | N | |
| CH₃ | H | 0 | Cl | cyclobutyl | CH₃ | OCH₃ | N | |
| CH₃ | H | 0 | Cl | cyclobutyl | OCH₃ | OCH₃ | N | |
| CH₃ | H | 0 | Cl | cyclobutyl | Cl | OCH₃ | CH. | |
| CH₃ | H | 0 | Cl | cyclopentyl | CH₃ | CH₃ | CH | |
| CH₃ | H | 0 | Cl | cyclopentyl | CH₃ | OCH₃ | CH | |
| CH₃ | H | 0 | Cl | cyclopentyl | OCH₃ | OCH₃ | CH | |
| CH₃ | H | 0 | Cl | cyclopentyl | CH₃ | CH₃ | N | |

TABLE IV-continued

| R | R₁ | n | R₂ | R' | X | Y | Z | m.p. (°C.) |
|---|---|---|---|---|---|---|---|---|
| CH₃ | H | 0 | Cl | cyclopentyl | CH₃ | OCH₃ | N | |
| CH₃ | H | 0 | Cl | cyclopentyl | OCH₃ | OCH₃ | N | |
| CH₃ | H | 0 | Cl | cyclopentyl | Cl | OCH₃ | CH | |
| CH₃ | H | 0 | Cl | cyclopropyl | OCH₃ | OCH₂CH₃ | CH | |
| CH₃ | H | 0 | Cl | cyclopropyl | cyclopropyl | OCH₃ | CH | |
| CH₃ | H | 0 | Cl | cyclopropyl | OCH₃ | CH(OCH₃)₂ | CH | |
| CH₃ | H | 0 | Cl | cyclopropyl | NHCH₃ | OCH₂CH₃ | N | |
| CH₃ | H | 0 | Cl | cyclopropyl | NHCH₃ | OCH₃ | N | |
| CH₃ | H | 0 | Cl | cyclopropyl | OCH₃ | OCH₂CH₃ | N | |
| CH₃ | H | 0 | Cl | cyclopropyl | CH₂F | CH₃ | CH | |
| CH₃ | H | 0 | CH₂F | cyclopropyl | CH₃ | CH₃ | CH | |
| CH₃ | H | 0 | CH₂F | cyclopropyl | CH₃ | OCH₃ | CH | |
| CH₃ | H | 0 | CH₂F | cyclopropyl | OCH₃ | OCH₃ | CH | |
| CH₃ | H | 0 | CH₂F | cyclopropyl | CH₃ | CH₃ | N | |
| CH₃ | H | 0 | CH₂F | cyclopropyl | CH₃ | OCH₃ | N | |
| CH₃ | H | 0 | CH₂F | cyclopropyl | OCH₃ | OCH₃ | N | |
| CH₃ | H | 0 | CH₂F | cyclopropyl | Cl | OCH₃ | CH | |
| CH₃ | H | 0 | CH₂F | cyclobutyl | CH₃ | CH₃ | CH | |
| CH₃ | H | 0 | CH₂F | cyclobutyl | CH₃ | OCH₃ | CH | |
| CH₃ | H | 0 | CH₂F | cyclobutyl | OCH₃ | OCH₃ | CH | |
| CH₃ | H | 0 | CH₂F | cyclobutyl | CH₃ | CH₃ | N | |
| CH₃ | H | 0 | CH₂F | cyclobutyl | CH₃ | OCH₃ | N | |
| CH₃ | H | 0 | CH₂F | cyclobutyl | OCH₃ | OCH₃ | N | |
| CH₃ | H | 0 | CH₂F | cyclobutyl | Cl | OCH₃ | CH | |
| CH₃ | H | 0 | CH₂F | cyclopentyl | CH₃ | CH₃ | CH | |
| CH₃ | H | 0 | CH₂F | cyclopentyl | CH₃ | OCH₃ | CH | |
| CH₃ | H | 0 | CH₂F | cyclopentyl | OCH₃ | OCH₃ | CH | |
| CH₃ | H | 0 | CH₂F | cyclopentyl | CH₃ | CH₃ | N | |
| CH₃ | H | 0 | CH₂F | cyclopentyl | CH₃ | OCH₃ | N | |
| CH₃ | H | 0 | CH₂F | cyclopentyl | OCH₃ | OCH₃ | N | |
| CH₃ | H | 0 | CH₂F | cyclopentyl | Cl | OCH₃ | CH | |
| CH₃ | H | 0 | CH₂F | cyclopropyl | OCH₃ | OCH₂CH₃ | CH | |
| CH₃ | H | 0 | CH₂F | cyclopropyl | cyclopropyl | OCH₃ | CH | |
| CH₃ | H | 0 | CH₂F | cyclopropyl | OCH₃ | CH(OCH₃)₂ | CH | |
| CH₃ | H | 0 | CH₂F | cyclopropyl | NHCH₃ | OCH₂CH₃ | N | |
| CH₃ | H | 0 | CH₂F | cyclopropyl | NHCH₃ | OCH₃ | N | |
| CH₃ | H | 0 | CH₂F | cyclopropyl | OCH₃ | OCH₂CH₃ | N | |
| CH₃ | H | 0 | CH₂F | cyclopropyl | CH₂F | CH₃ | CH | |
| CH₃ | H | 0 | SO₂N(CH₃)₂ | cyclopropyl | CH₃ | CH₃ | CH | |
| CH₃ | H | 0 | SO₂N(CH₃)₂ | cyclopropyl | CH₃ | OCH₃ | CH | |
| CH₃ | H | 0 | SO₂N(CH₃)₂ | cyclopropyl | OCH₃ | OCH₃ | CH | |
| CH₃ | H | 0 | SO₂N(CH₃)₂ | cyclopropyl | CH₃ | CH₃ | N | |
| CH₃ | H | 0 | SO₂N(CH₃)₂ | cyclopropyl | CH₃ | OCH₃ | N | |
| CH₃ | H | 0 | SO₂N(CH₃)₂ | cyclopropyl | OCH₃ | OCH₃ | N | |
| CH₃ | H | 0 | SO₂N(CH₃)₂ | cyclopropyl | Cl | OCH₃ | CH | |
| CH₃ | H | 0 | SO₂N(CH₃)₂ | cyclobutyl | CH₃ | CH₃ | CH | |
| CH₃ | H | 0 | SO₂N(CH₃)₂ | cyclobutyl | CH₃ | OCH₃ | CH | |
| CH₃ | H | 0 | SO₂N(CH₃)₂ | cyclobutyl | OCH₃ | OCH₃ | CH | |
| CH₃ | H | 0 | SO₂N(CH₃)₂ | cyclobutyl | CH₃ | CH₃ | N | |
| CH₃ | H | 0 | SO₂N(CH₃)₂ | cyclobutyl | CH₃ | OCH₃ | N | |
| CH₃ | H | 0 | SO₂N(CH₃)₂ | cyclobutyl | OCH₃ | OCH₃ | N | |
| CH₃ | H | 0 | SO₂N(CH₃)₂ | cyclobutyl | Cl | OCH₃ | CH | |
| CH₃ | H | 0 | SO₂N(CH₃)₂ | cyclopentyl | CH₃ | CH₃ | CH | |
| CH₃ | H | 0 | SO₂N(CH₃)₂ | cyclopentyl | CH₃ | OCH₃ | CH | |
| CH₃ | H | 0 | SO₂N(CH₃)₂ | cyclopentyl | OCH₃ | OCH₃ | CH | |
| CH₃ | H | 0 | SO₂N(CH₃)₂ | cyclopentyl | CH₃ | CH₃ | N | |
| CH₃ | H | 0 | SO₂N(CH₃)₂ | cyclopentyl | CH₃ | OCH₃ | N | |
| CH₃ | H | 0 | SO₂N(CH₃)₂ | cyclopentyl | OCH₃ | OCH₃ | N | |
| CH₃ | H | 0 | SO₂N(CH₃)₂ | cyclopentyl | Cl | OCH₃ | CH | |
| CH₃ | H | 0 | SO₂N(CH₃)₂ | cyclopropyl | OCH₃ | OCH₂CH₃ | CH | |
| CH₃ | H | 0 | SO₂N(CH₃)₂ | cyclopropyl | cyclopropyl | OCH₃ | CH | |
| CH₃ | H | 0 | SO₂N(CH₃)₂ | cyclopropyl | OCH₃ | CH(OCH₃)₂ | CH | |
| CH₃ | H | 0 | SO₂N(CH₃)₂ | cyclopropyl | NHCH₃ | OCH₂CH₃ | N | |
| CH₃ | H | 0 | SO₂N(CH₃)₂ | cyclopropyl | NHCH₃ | OCH₃ | N | |
| CH₃ | H | 0 | SO₂N(CH₃)₂ | cyclopropyl | OCH₃ | OCH₂CH₃ | N | |
| CH₃ | H | 0 | SO₂N(CH₃)₂ | cyclopropyl | CH₂F | CH₃ | CH | |
| CH₃ | H | 0 | SOCH₃ | cyclopropyl | CH₃ | CH₃ | CH | |
| CH₃ | H | 0 | SOCH₃ | cyclopropyl | CH₃ | OCH₃ | CH | |
| CH₃ | H | 0 | SOCH₃ | cyclopropyl | OCH₃ | OCH₃ | CH | |
| CH₃ | H | 0 | SOCH₃ | cyclopropyl | CH₃ | CH₃ | N | |
| CH₃ | H | 0 | SOCH₃ | cyclopropyl | CH₃ | OCH₃ | N | |
| CH₃ | H | 0 | SOCH₃ | cyclopropyl | OCH₃ | OCH₃ | N | |
| CH₃ | H | 0 | SOCH₃ | cyclopropyl | Cl | OCH₃ | CH | |
| CH₃ | H | 0 | SOCH₃ | cyclobutyl | CH₃ | CH₃ | CH | |
| CH₃ | H | 0 | SOCH₃ | cyclobutyl | CH₃ | OCH₃ | CH | |
| CH₃ | H | 0 | SOCH₃ | cyclobutyl | OCH₃ | OCH₃ | CH | |
| CH₃ | H | 0 | SOCH₃ | cyclobutyl | CH₃ | CH₃ | N | |
| CH₃ | H | 0 | SOCH₃ | cyclobutyl | CH₃ | OCH₃ | N | |
| CH₃ | H | 0 | SOCH₃ | cyclobutyl | OCH₃ | OCH₃ | N | |
| CH₃ | H | 0 | SOCH₃ | cyclobutyl | Cl | OCH₃ | CH | |
| CH₃ | H | 0 | SOCH₃ | cyclopentyl | CH₃ | CH₃ | CH | |

TABLE IV-continued

| R | R₁ | n | R₂ | R' | X | Y | Z | m.p. (°C.) |
|---|---|---|---|---|---|---|---|---|
| CH₃ | H | 0 | SOCH₃ | cyclopentyl | CH₃ | OCH₃ | CH | |
| CH₃ | H | 0 | SOCH₃ | cyclopentyl | OCH₃ | OCH₃ | CH | |
| CH₃ | H | 0 | SOCH₃ | cyclopentyl | CH₃ | CH₃ | N | |
| CH₃ | H | 0 | SOCH₃ | cyclopentyl | CH₃ | OCH₃ | N | |
| CH₃ | H | 0 | SOCH₃ | cyclopentyl | OCH₃ | OCH₃ | N | |
| CH₃ | H | 0 | SOCH₃ | cyclopentyl | Cl | OCH₃ | CH | |
| CH₃ | H | 0 | SOCH₃ | cyclopropyl | OCH₃ | OCH₂CH₃ | CH | |
| CH₃ | H | 0 | SOCH₃ | cyclopropyl | cyclopropyl | OCH₃ | CH | |
| CH₃ | H | 0 | SOCH₃ | cyclopropyl | OCH₃ | CH(OCH₃)₂ | CH | |
| CH₃ | H | 0 | SOCH₃ | cyclopropyl | NHCH₃ | OCH₂CH₃ | N | |
| CH₃ | H | 0 | SOCH₃ | cyclopropyl | NHCH₃ | OCH₃ | N | |
| CH₃ | H | 0 | SOCH₃ | cyclopropyl | OCH₃ | OCH₂CH₃ | N | |
| CH₃ | H | 0 | SOCH₃ | cyclopropyl | CH₂F | CH₃ | CH | |
| CH₃ | H | 0 | CN | cyclopropyl | CH₃ | CH₃ | CH | |
| CH₃ | H | 0 | CN | cyclopropyl | CH₃ | OCH₃ | CH | |
| CH₃ | H | 0 | CN | cyclopropyl | OCH₃ | OCH₃ | CH | |
| CH₃ | H | 0 | CN | cyclopropyl | CH₃ | CH₃ | N | |
| CH₃ | H | 0 | CN | cyclopropyl | CH₃ | OCH₃ | N | |
| CH₃ | H | 0 | CN | cyclopropyl | OCH₃ | OCH₃ | N | |
| CH₃ | H | 0 | CN | cyclopropyl | Cl | OCH₃ | CH | |
| CH₃ | H | 0 | CN | cyclobutyl | CH₃ | CH₃ | CH | |
| CH₃ | H | 0 | CN | cyclobutyl | CH₃ | OCH₃ | CH | |
| CH₃ | H | 0 | CN | cyclobutyl | OCH₃ | OCH₃ | CH | |
| CH₃ | H | 0 | CN | cyclobutyl | CH₃ | CH₃ | N | |
| CH₃ | H | 0 | CN | cyclobutyl | CH₃ | OCH₃ | N | |
| CH₃ | H | 0 | CN | cyclobutyl | OCH₃ | OCH₃ | N | |
| CH₃ | H | 0 | CN | cyclobutyl | Cl | OCH₃ | CH | |
| CH₃ | H | 0 | CN | cyclopentyl | CH₃ | CH₃ | CH | |
| CH₃ | H | 0 | CN | cyclopentyl | CH₃ | OCH₃ | CH | |
| CH₃ | H | 0 | CN | cyclopentyl | OCH₃ | OCH₃ | CH | |
| CH₃ | H | 0 | CN | cyclopentyl | CH₃ | CH₃ | N | |
| CH₃ | H | 0 | CN | cyclopentyl | CH₃ | OCH₃ | N | |
| CH₃ | H | 0 | CN | cyclopentyl | OCH₃ | OCH₃ | N | |
| CH₃ | H | 0 | CN | cyclopentyl | Cl | OCH₃ | CH | |
| CH₃ | H | 0 | CN | cyclopropyl | OCH₃ | OCH₂CH₃ | CH | |
| CH₃ | H | 0 | CN | cyclopropyl | cyclopropyl | OCH₃ | CH | |
| CH₃ | H | 0 | CN | cyclopropyl | OCH₃ | CH(OCH₃)₂ | CH | |
| CH₃ | H | 0 | CN | cyclopropyl | NHCH₃ | OCH₂CH₃ | N | |
| CH₃ | H | 0 | CN | cyclopropyl | NHCH₃ | OCH₃ | N | |
| CH₃ | H | 0 | CN | cyclopropyl | OCH₃ | OCH₂CH₃ | N | |
| CH₃ | H | 0 | CN | cyclopropyl | CH₂F | CH₃ | CH | |
| CH₃ | H | 0 | N(CH₃)₂ | cyclopropyl | CH₃ | CH₃ | CH | |
| CH₃ | H | 0 | N(CH₃)₂ | cyclopropyl | CH₃ | OCH₃ | CH | |
| CH₃ | H | 0 | N(CH₃)₂ | cyclopropyl | OCH₃ | OCH₃ | CH | |
| CH₃ | H | 0 | N(CH₃)₂ | cyclopropyl | CH₃ | CH₃ | N | |
| CH₃ | H | 0 | N(CH₃)₂ | cyclopropyl | CH₃ | OCH₃ | N | |
| CH₃ | H | 0 | N(CH₃)₂ | cyclopropyl | OCH₃ | OCH₃ | N | |
| CH₃ | H | 0 | N(CH₃)₂ | cyclopropyl | Cl | OCH₃ | CH | |
| CH₃ | H | 0 | N(CH₃)₂ | cyclobutyl | CH₃ | CH₃ | CH | |
| CH₃ | H | 0 | N(CH₃)₂ | cyclobutyl | CH₃ | OCH₃ | CH | |
| CH₃ | H | 0 | N(CH₃)₂ | cyclobutyl | OCH₃ | OCH₃ | CH | |
| CH₃ | H | 0 | N(CH₃)₂ | cyclobutyl | CH₃ | CH₃ | N | |
| CH₃ | H | 0 | N(CH₃)₂ | cyclobutyl | CH₃ | OCH₃ | N | |
| CH₃ | H | 0 | N(CH₃)₂ | cyclobutyl | OCH₃ | OCH₃ | N | |
| CH₃ | H | 0 | N(CH₃)₂ | cyclobutyl | Cl | OCH₃ | CH | |
| CH₃ | H | 0 | N(CH₃)₂ | cyclopentyl | CH₃ | CH₃ | CH | |
| CH₃ | H | 0 | N(CH₃)₂ | cyclopentyl | CH₃ | OCH₃ | CH | |
| CH₃ | H | 0 | N(CH₃)₂ | cyclopentyl | OCH₃ | OCH₃ | CH | |
| CH₃ | H | 0 | N(CH₃)₂ | cyclopentyl | CH₃ | CH₃ | N | |
| CH₃ | H | 0 | N(CH₃)₂ | cyclopentyl | CH₃ | OCH₃ | N | |
| CH₃ | H | 0 | N(CH₃)₂ | cyclopentyl | OCH₃ | OCH₃ | N | |
| CH₃ | H | 0 | N(CH₃)₂ | cyclopentyl | Cl | OCH₃ | CH | |
| CH₃ | H | 0 | N(CH₃)₂ | cyclopropyl | OCH₃ | OCH₃ | CH | |
| CH₃ | H | 0 | N(CH₃)₂ | cyclopropyl | cyclopropyl | OCH₃ | CH | |
| CH₃ | H | 0 | N(CH₃)₂ | cyclopropyl | OCH₃ | CH(OCH₃)₂ | CH | |
| CH₃ | H | 0 | N(CH₃)₂ | cyclopropyl | NHCH₃ | OCH₂CH₃ | N | |
| CH₃ | H | 0 | N(CH₃)₂ | cyclopropyl | NHCH₃ | OCH₃ | N | |
| CH₃ | H | 0 | N(CH₃)₂ | cyclopropyl | OCH₃ | OCH₂CH₃ | N | |
| CH₃ | H | 0 | N(CH₃)₂ | cyclopropyl | CH₂F | CH₃ | CH | |
| CH₃ | H | 0 | CH₂OCH₃ | cyclopropyl | CH₃ | CH₃ | CH | |
| CH₃ | H | 0 | CH₂OCH₃ | cyclopropyl | CH₃ | OCH₃ | CH | |
| CH₃ | H | 0 | CH₂OCH₃ | cyclopropyl | OCH₃ | OCH₃ | CH | |
| CH₃ | H | 0 | CH₂OCH₃ | cyclopropyl | CH₃ | CH₃ | N | |
| CH₃ | H | 0 | CH₂OCH₃ | cyclopropyl | CH₃ | OCH | N | |
| CH₃ | H | 0 | CH₂OCH₃ | cyclopropyl | OCH₃ | OCH₃ | N | |
| CH₃ | H | 0 | CH₂OCH₃ | cyclopropyl | Cl | OCH₃ | CH | |
| CH₃ | H | 0 | CH₂OCH₃ | cyclobutyl | CH₃ | CH₃ | CH | |
| CH₃ | H | 0 | CH₂OCH₃ | cyclobutyl | CH₃ | OCH₃ | CH | |
| CH₃ | H | 0 | CH₂OCH₃ | cyclobutyl | OCH₃ | OCH₃ | CH | |
| CH₃ | H | 0 | CH₂OCH₃ | cyclobutyl | CH₃ | CH₃ | N | |
| CH₃ | H | 0 | CH₂OCH₃ | cyclobutyl | CH₃ | OCH₃ | N | |

TABLE IV-continued

| R | R₁ | n | R₂ | R' | X | Y | Z | m.p. (°C.) |
|---|---|---|---|---|---|---|---|---|
| CH₃ | H | 0 | CH₂OCH₃ | cyclobutyl | OCH₃ | OCH₃ | N | |
| CH₃ | H | 0 | CH₂OCH₃ | cyclobutyl | Cl | OCH₃ | CH | |
| CH₃ | H | 0 | CH₂OCH₃ | cyclopentyl | CH₃ | CH₃ | CH | |
| CH₃ | H | 0 | CH₂OCH₃ | cyclopentyl | CH₃ | OCH₃ | CH | |
| CH₃ | H | 0 | CH₂OCH₃ | cyclopentyl | OCH₃ | OCH₃ | CH | |
| CH₃ | H | 0 | CH₂OCH₃ | cyclopentyl | CH₃ | CH₃ | N | |
| CH₃ | H | 0 | CH₂OCH₃ | cyclopentyl | CH₃ | OCH₃ | N | |
| CH₃ | H | 0 | CH₂OCH₃ | cyclopentyl | OCH₃ | OCH₃ | N | |
| CH₃ | H | 0 | CH₂OCH₃ | cyclopentyl | Cl | OCH₃ | CH | |
| CH₃ | H | 0 | CH₂OCH₃ | cyclopropyl | OCH₃ | OCH₂CH₃ | CH | |
| CH₃ | H | 0 | CH₂OCH₃ | cyclopropyl | cyclopropyl | OCH₃ | CH | |
| CH₃ | H | 0 | CH₂OCH₃ | cyclopropyl | OCH₃ | CH(OCH₃)₂ | CH | |
| CH₃ | H | 0 | CH₂OCH₃ | cyclopropyl | NHCH₃ | OCH₂CH₃ | N | |
| CH₃ | H | 0 | CH₂OCH₃ | cyclopropyl | NHCH₃ | OCH₃ | N | |
| CH₃ | H | 0 | CH₂OCH₃ | cyclopropyl | OCH₃ | OCH₂CH₃ | N | |
| CH₃ | H | 0 | CH₂OCH₃ | cyclopropyl | CH₂F | CH₃ | CH | |
| CH₂CH₃ | H | 0 | H | cyclopropyl | CH₃ | CH₃ | CH | |
| CH₂CH₃ | H | 0 | H | cyclopropyl | CH₃ | OCH₃ | CH | |
| CH₂CH₃ | H | 0 | H | cyclopropyl | OCH₃ | OCH₃ | CH | |
| CH₂CH₃ | H | 0 | H | cyclopropyl | CH₃ | CH₃ | N | |
| CH₂CH₃ | H | 0 | H | cyclopropyl | CH₃ | OCH₃ | N | |
| CH₂CH₃ | H | 0 | H | cyclopropyl | OCH₃ | OCH₃ | N | |
| CH₂CH₃ | H | 0 | H | cyclopropyl | Cl | OCH₃ | CH | |
| CH₂CH₃ | H | 0 | H | cyclobutyl | CH₃ | CH₃ | CH | |
| CH₂CH₃ | H | 0 | H | cyclobutyl | CH₃ | OCH₃ | CH | |
| CH₂CH₃ | H | 0 | H | cyclobutyl | OCH₃ | OCH₃ | CH | |
| CH₂CH₃ | H | 0 | H | cyclobutyl | CH₃ | CH₃ | N | |
| CH₂CH₃ | H | 0 | H | cyclobutyl | CH₃ | OCH₃ | N | |
| CH₂CH₃ | H | 0 | H | cyclobutyl | OCH₃ | OCH₃ | N | |
| CH₂CH₃ | H | 0 | H | cyclobutyl | Cl | OCH₃ | CH | |
| CH₂CH₃ | H | 0 | H | cyclopentyl | CH₃ | CH₃ | CH | |
| CH₂CH₃ | H | 0 | H | cyclopentyl | CH₃ | OCH₃ | CH | |
| CH₂CH₃ | H | 0 | H | cyclopentyl | OCH₃ | OCH₃ | CH | |
| CH₂CH₃ | H | 0 | H | cyclopentyl | CH₃ | CH₃ | N | |
| CH₂CH₃ | H | 0 | H | cyclopentyl | CH₃ | OCH₃ | N | |
| CH₂CH₃ | H | 0 | H | cyclopentyl | OCH₃ | OCH₃ | N | |
| CH₂CH₃ | H | 0 | H | cyclopentyl | Cl | OCH | CH | |
| CH₂CH₃ | H | 0 | H | cyclopropyl | OCH₃ | OCH₂CH₃ | CH | |
| CH₂CH₃ | H | 0 | H | cyclopropyl | cyclopropyl | OCH₃ | CH | |
| CH₂CH₃ | H | 0 | H | cyclopropyl | OCH₃ | CH(OCH₃)₂ | CH | |
| CH₂CH₃ | H | 0 | H | cyclopropyl | NHCH₃ | OCH₂CH₃ | N | |
| CH₂CH₃ | H | 0 | H | cyclopropyl | NHCH₃ | OCH₃ | N | |
| CH₂CH₃ | H | 0 | H | cyclopropyl | OCH₃ | OCH₂CH₃ | N | |
| CH₂CH₃ | H | 0 | H | cyclopropyl | CH₂F | CH₃ | CH | |
| CO₂CH₃ | H | 0 | H | cyclopropyl | CH₃ | CH₃ | CH | |
| CO₂CH₃ | H | 0 | H | cyclopropyl | CH₃ | OCH₃ | CH | |
| CO₂CH₃ | H | 0 | H | cyclopropyl | OCH₃ | OCH₃ | CH | |
| CO₂CH₃ | H | 0 | H | cyclopropyl | CH₃ | CH₃ | N | |
| CO₂CH₃ | H | 0 | H | cyclopropyl | CH₃ | OCH₃ | N | |
| CO₂CH₃ | H | 0 | H | cyclopropyl | OCH₃ | OCH₃ | N | |
| CO₂CH₃ | H | 0 | H | cyclopropyl | Cl | OCH₃ | CH | |
| CO₂CH₃ | H | 0 | H | cyclobutyl | CH₃ | CH₃ | CH | |
| CO₂CH₃ | H | 0 | H | cyclobutyl | CH₃ | OCH₃ | CH | |
| CO₂CH₃ | H | 0 | H | cyclobutyl | OCH₃ | OCH₃ | CH | |
| CO₂CH₃ | H | 0 | H | cyclobutyl | CH₃ | CH₃ | N | |
| CO₂CH₃ | H | 0 | H | cyclobutyl | CH₃ | OCH₃ | N | |
| CO₂CH₃ | H | 0 | H | cyclobutyl | OCH₃ | OCH₃ | N | |
| CO₂CH₃ | H | 0 | H | cyclobutyl | Cl | OCH₃ | CH | |
| CO₂CH₃ | H | 0 | H | cyclopentyl | CH₃ | CH₃ | CH | |
| CO₂CH₃ | H | 0 | H | cyclopentyl | CH₃ | OCH₃ | CH | |
| CO₂CH₃ | H | 0 | H | cyclopentyl | OCH₃ | OCH₃ | CH | |
| CO₂CH₃ | H | 0 | H | cyclopentyl | CH₃ | CH₃ | N | |
| CO₂CH₃ | H | 0 | H | cyclopentyl | CH₃ | OCH₃ | N | |
| CO₂CH₃ | H | 0 | H | cyclopentyl | OCH₃ | OCH₃ | N | |
| CO₂CH₃ | H | 0 | H | cyclopentyl | Cl | OCH₃ | CH | |
| CO₂CH₃ | H | 0 | H | cyclopropyl | OCH₃ | OCH₂CH₃ | CH | |
| CO₂CH₃ | H | 0 | H | cyclopropyl | cyclopropyl | OCH₃ | CH | |
| CO₂CH₃ | H | 0 | H | cyclopropyl | OCH₃ | CH(OCH₃)₂ | CH | |
| CO₂CH₃ | H | 0 | H | cyclopropyl | NHCH₃ | OCH₂CH₃ | N | |
| CO₂CH₃ | H | 0 | H | cyclopropyl | NHCH₃ | OCH₃ | N | |
| CO₂CH₃ | H | 0 | H | cyclopropyl | OCH₃ | OCH₂CH₃ | N | |
| CO₂CH₃ | H | 0 | H | cyclopropyl | CH₂F | CH₃ | CH | |
| CH₂F | H | 0 | H | cyclopropyl | CH₃ | CH₃ | CH | |
| CH₂F | H | 0 | H | cyclopropyl | CH₃ | OCH₃ | CH | |
| CH₂F | H | 0 | H | cyclopropyl | OCH₃ | OCH₃ | CH | |
| CH₂F | H | 0 | H | cyclopropyl | CH₃ | CH₃ | N | |
| CH₂F | H | 0 | H | cyclopropyl | CH₃ | OCH₃ | N | |
| CH₂F | H | 0 | H | cyclopropyl | OCH₃ | OCH₃ | N | |
| CH₂F | H | 0 | H | cyclopropyl | Cl | OCH₃ | CH | |
| CH₂F | H | 0 | H | cyclobutyl | CH₃ | CH₃ | CH | |
| CH₂F | H | 0 | H | cyclobutyl | CH₃ | OCH₃ | CH | |

TABLE IV-continued

| R | R₁ | n | R₂ | R' | X | Y | Z | m.p. (°C.) |
|---|---|---|---|---|---|---|---|---|
| CH₂F | H | 0 | H | cyclobutyl | OCH₃ | OCH₃ | CH | |
| CH₂F | H | 0 | H | cyclobutyl | CH₃ | CH₃ | N | |
| CH₂F | H | 0 | H | cyclobutyl | CH₃ | OCH₃ | N | |
| CH₂F | H | 0 | H | cyclobutyl | OCH₃ | OCH₃ | N | |
| CH₂F | H | 0 | H | cyclobutyl | Cl | OCH₃ | CH | |
| CH₂F | H | 0 | H | cyclopentyl | CH₃ | CH₃ | CH | |
| CH₂F | H | 0 | H | cyclopentyl | CH₃ | OCH₃ | CH | |
| CH₂F | H | 0 | H | cyclopentyl | OCH₃ | OCH₃ | CH | |
| CH₂F | H | 0 | H | cyclopentyl | CH₃ | CH₃ | N | |
| CH₂F | H | 0 | H | cyclopentyl | CH₃ | OCH₃ | N | |
| CH₂F | H | 0 | H | cyclopentyl | OCH₃ | OCH₃ | N | |
| CH₂F | H | 0 | H | cyclopentyl | Cl | OCH₃ | CH | |
| CH₂F | H | 0 | H | cyclopropyl | OCH₃ | OCH₂CH₃ | CH | |
| CH₂F | H | 0 | H | cyclopropyl | cyclopropyl | OCH₃ | CH | |
| CH₂F | H | 0 | H | cyclopropyl | OCH₃ | CH(OCH₃)₂ | CH | |
| CH₂F | H | 0 | H | cyclopropyl | NHCH₃ | OCH₂CH₃ | N | |
| CH₂F | H | 0 | H | cyclopropyl | NHCH₃ | OCH₃ | N | |
| CH₂F | H | 0 | H | cyclopropyl | OCH₃ | OCH₂CH₃ | N | |
| CH₂F | H | 0 | H | cyclopropyl | CH₂F | CH₃ | CH | |
| CH₂C≡CH | H | 0 | H | cyclopropyl | CH₃ | CH₃ | CH | |
| CH₂C≡CH | H | 0 | H | cyclopropyl | CH₃ | OCH₃ | CH | |
| CH₂C≡CH | H | 0 | H | cyclopropyl | OCH₃ | OCH₃ | CH | |
| CH₂C≡CH | H | 0 | H | cyclopropyl | CH₃ | CH₃ | N | |
| CH₂C≡CH | H | 0 | H | cyclopropyl | CH₃ | OCH₃ | N | |
| CH₂C≡CH | H | 0 | H | cyclopropyl | OCH₃ | OCH₃ | N | |
| CH₂C≡CH | H | 0 | H | cyclopropyl | Cl | OCH₃ | CH | |
| CH₂C≡CH | H | 0 | H | cyclobutyl | CH₃ | CH₃ | CH | |
| CH₂C≡CH | H | 0 | H | cyclobutyl | CH₃ | OCH₃ | CH | |
| CH₂C≡CH | H | 0 | H | cyclobutyl | OCH₃ | OCH₃ | CH | |
| CH₂C≡CH | H | 0 | H | cyclobutyl | CH₃ | CH₃ | N | |
| CH₂C≡CH | H | 0 | H | cyclobutyl | CH₃ | OCH₃ | N | |
| CH₂C≡CH | H | 0 | H | cyclobutyl | OCH₃ | OCH₃ | N | |
| CH₂C≡CH | H | 0 | H | cyclobutyl | Cl | OCH₃ | CH | |
| CH₂C≡CH | H | 0 | H | cyclopentyl | CH₃ | CH₃ | CH | |
| CH₂C≡CH | H | 0 | H | cyclopentyl | CH₃ | OCH₃ | CH | |
| CH₂C≡CH | H | 0 | H | cyclopentyl | OCH₃ | OCH₃ | CH | |
| CH₂C≡CH | H | 0 | H | cyclopentyl | CH₃ | CH₃ | N | |
| CH₂C≡CH | H | 0 | H | cyclopentyl | CH₃ | OCH₃ | N | |
| CH₂C≡CH | H | 0 | H | cyclopentyl | OCH₃ | OCH₃ | N | |
| CH₂C≡CH | H | 0 | H | cyclopentyl | Cl | OCH₃ | CH | |
| CH₂C≡CH | H | 0 | H | cyclopropyl | OCH₃ | OCH₂CH₃ | CH | |
| CH₂C≡CH | H | 0 | H | cyclopropyl | cyclopropyl | OCH₃ | CH | |
| CH₂C≡CH | H | 0 | H | cyclopropyl | OCH₃ | CH(OCH₃)₂ | CH | |
| CH₂C≡CH | H | 0 | H | cyclopropyl | NHCH₃ | OCH₂CH₃ | N | |
| CH₂C≡CH | H | 0 | H | cyclopropyl | NHCH₃ | OCH₃ | N | |
| CH₂C≡CH | H | 0 | H | cyclopropyl | OCH₃ | OCH₂CH₃ | N | |
| CH₂C≡CH | H | 0 | H | cyclopropyl | CH₂F | CH₃ | CH | |
| CH₂CH₃ | H | 0 | Cl | cyclopropyl | CH₃ | CH₃ | CH | |
| CH₂CH₃ | H | 0 | Cl | cyclopropyl | CH₃ | OCH₃ | CH | |
| CH₂CH₃ | H | 0 | Cl | cyclopropyl | OCH₃ | OCH₃ | CH | |
| CH₂CH₃ | H | 0 | Cl | cyclopropyl | CH₃ | CH₃ | N | |
| CH₂CH₃ | H | 0 | Cl | cyclopropyl | CH₃ | OCH₃ | N | |
| CH₂CH₃ | H | 0 | Cl | cyclopropyl | OCH₃ | OCH₃ | N | |
| CH₂CH₃ | H | 0 | Cl | cyclopropyl | Cl | OCH₃ | CH | |
| CH₂CH₃ | H | 0 | Cl | cyclobutyl | CH₃ | CH₃ | CH | |
| CH₂CH₃ | H | 0 | Cl | cyclobutyl | CH₃ | OCH₃ | CH | |
| CH₂CH₃ | H | 0 | Cl | cyclobutyl | OCH₃ | OCH₃ | CH | |
| CH₂CH₃ | H | 0 | Cl | cyclobutyl | CH₃ | CH₃ | N | |
| CH₂CH₃ | H | 0 | Cl | cyclobutyl | CH₃ | OCH₃ | N | |
| CH₂CH₃ | H | 0 | Cl | cyclobutyl | OCH₃ | OCH₃ | N | |
| CH₂CH₃ | H | 0 | Cl | cyclobutyl | Cl | OCH₃ | CH | |
| CH₂CH₃ | H | 0 | Cl | cyclopentyl | CH₃ | CH₃ | CH | |
| CH₂CH₃ | H | 0 | Cl | cyclopentyl | CH₃ | OCH₃ | CH | |
| CH₂CH₃ | H | 0 | Cl | cyclopentyl | OCH₃ | OCH₃ | CH | |
| CH₂CH₃ | H | 0 | Cl | cyclopentyl | CH₃ | CH₃ | N | |
| CH₂CH₃ | H | 0 | Cl | cyclopentyl | CH₃ | OCH₃ | N | |
| CH₂CH₃ | H | 0 | Cl | cyclopentyl | OCH₃ | OCH₃ | N | |
| CH₂CH₃ | H | 0 | Cl | cyclopentyl | Cl | OCH₃ | CH | |
| CH₂CH₃ | H | 0 | Cl | cyclopropyl | OCH₃ | OCH₂CH₃ | CH | |
| CH₂CH₃ | H | 0 | Cl | cyclopropyl | cyclopropyl | OCH₃ | CH | |
| CH₂CH₃ | H | 0 | Cl | cyclopropyl | OCH₃ | CH(OCH₃)₂ | CH | |
| CH₂CH₃ | H | 0 | Cl | cyclopropyl | NHCH₃ | OCH₂CH₃ | N | |
| CH₂CH₃ | H | 0 | Cl | cyclopropyl | NHCH₃ | OCH₃ | N | |
| CH₂CH₃ | H | 0 | Cl | cyclopropyl | OCH₃ | OCH₂CH₃ | N | |
| CH₂CH₃ | H | 0 | Cl | cyclopropyl | CH₂F | CH₃ | CH | |
| CH₂SO₂CH₃ | H | 0 | Cl | cyclopropyl | CH₃ | CH₃ | CH | |
| CH₂SO₂CH₃ | H | 0 | Cl | cyclopropyl | CH₃ | OCH₃ | CH | |
| CH₂SO₂CH₃ | H | 0 | Cl | cyclopropyl | OCH₃ | OCH₃ | CH | |
| CH₂SO₂CH₃ | H | 0 | Cl | cyclopropyl | CH₃ | CH₃ | N | |
| CH₂SO₂CH₃ | H | 0 | Cl | cyclopropyl | CH₃ | OCH₃ | N | |
| CH₂SO₂CH₃ | H | 0 | Cl | cyclopropyl | OCH₃ | OCH₃ | N | |

TABLE IV-continued

| R | $R_1$ | n | $R_2$ | R' | X | Y | Z | m.p. (°C.) |
|---|---|---|---|---|---|---|---|---|
| $CH_2SO_2CH_3$ | H | 0 | Cl | cyclopropyl | Cl | $OCH_3$ | CH | |
| $CH_2SO_2CH_3$ | H | 0 | Cl | cyclobutyl | $CH_3$ | $CH_3$ | CH | |
| $CH_2SO_2CH_3$ | H | 0 | Cl | cyclobutyl | $CH_3$ | $OCH_3$ | CH | |
| $CH_2SO_2CH_3$ | H | 0 | Cl | cyclobutyl | $OCH_3$ | $OCH_3$ | CH | |
| $CH_2SO_2CH_3$ | H | 0 | Cl | cyclobutyl | $CH_3$ | $CH_3$ | N | |
| $CH_2SO_2CH_3$ | H | 0 | Cl | cyclobutyl | $CH_3$ | $OCH_3$ | N | |
| $CH_2SO_2CH_3$ | H | 0 | Cl | cyclobutyl | $OCH_3$ | $OCH_3$ | N | |
| $CH_2SO_2CH_3$ | H | 0 | Cl | cyclobutyl | Cl | $OCH_3$ | CH | |
| $CH_2SO_2CH_3$ | H | 0 | Cl | cyclopentyl | $CH_3$ | $CH_3$ | CH | |
| $CH_2SO_2CH_3$ | H | 0 | Cl | cyclopentyl | $CH_3$ | $OCH_3$ | CH | |
| $CH_2SO_2CH_3$ | H | 0 | Cl | cyclopentyl | $OCH_3$ | $OCH_3$ | CH | |
| $CH_2SO_2CH_3$ | H | 0 | Cl | cyclopentyl | $CH_3$ | $CH_3$ | N | |
| $CH_2SO_2CH_3$ | H | 0 | Cl | cyclopentyl | $CH_3$ | $OCH_3$ | N | |
| $CH_2SO_2CH_3$ | H | 0 | Cl | cyclopentyl | $OCH_3$ | $OCH_3$ | N | |
| $CH_2SO_2CH_3$ | H | 0 | Cl | cyclopentyl | Cl | $OCH_3$ | CH | |
| $CH_2SO_2CH_3$ | H | 0 | Cl | cyclopropyl | $OCH_3$ | $OCH_2CH_3$ | CH | |
| $CH_2SO_2CH_3$ | H | 0 | Cl | cyclopropyl | cyclopropyl | $OCH_3$ | CH | |
| $CH_2SO_2CH_3$ | H | 0 | Cl | cyclopropyl | $OCH_3$ | $CH(OCH_3)_2$ | CH | |
| $CH_2SO_2CH_3$ | H | 0 | Cl | cyclopropyl | $NHCH_3$ | $OCH_2CH_3$ | N | |
| $CH_2SO_2CH_3$ | H | 0 | Cl | cyclopropyl | $NHCH_3$ | $OCH_3$ | N | |
| $CH_2SO_2CH_3$ | H | 0 | Cl | cyclopropyl | $OCH_3$ | $OCH_2CH_3$ | N | |
| $CH_2SO_2CH_3$ | H | 0 | Cl | cyclopropyl | $CH_2F$ | $CH_3$ | CH | |
| H | H | 0 | Cl | cyclopropyl | $CH_3$ | $CH_3$ | CH | |
| H | H | 0 | Cl | cyclopropyl | $CH_3$ | $OCH_3$ | CH | |
| H | H | 0 | Cl | cyclopropyl | $OCH_3$ | $OCH_3$ | CH | |
| H | H | 0 | Cl | cyclopropyl | $CH_3$ | $CH_3$ | N | |
| H | H | 0 | Cl | cyclopropyl | $CH_3$ | $OCH_3$ | N | |
| H | H | 0 | Cl | cyclopropyl | $OCH_3$ | $OCH_3$ | N | |
| H | H | 0 | Cl | cyclopropyl | Cl | $OCH_3$ | CH | |
| H | H | 0 | Cl | cyclobutyl | $CH_3$ | $CH_3$ | CH | |
| H | H | 0 | Cl | cyclobutyl | $CH_3$ | $OCH_3$ | CH | |
| H | H | 0 | Cl | cyclobutyl | $OCH_3$ | $OCH_3$ | CH | |
| H | H | 0 | Cl | cyclobutyl | $CH_3$ | $CH_3$ | N | |
| H | H | 0 | Cl | cyclobutyl | $CH_3$ | $OCH_3$ | N | |
| H | H | 0 | Cl | cyclobutyl | $OCH_3$ | $OCH_3$ | N | |
| H | H | 0 | Cl | cyclobutyl | Cl | $OCH_3$ | CH | |
| H | H | 0 | Cl | cyclopentyl | $CH_3$ | $CH_3$ | CH | |
| H | H | 0 | Cl | cyclopentyl | $CH_3$ | $OCH_3$ | CH | |
| H | H | 0 | Cl | cyclopentyl | $OCH_3$ | $OCH_3$ | CH | |
| H | H | 0 | Cl | cyclopentyl | $CH_3$ | $CH_3$ | N | |
| H | H | 0 | Cl | cyclopentyl | $CH_3$ | $OCH_3$ | N | |
| H | H | 0 | Cl | cyclopentyl | $OCH_3$ | $OCH_3$ | N | |
| H | H | 0 | Cl | cyclopentyl | Cl | $OCH_3$ | CH | |
| H | H | 0 | Cl | cyclopropyl | $OCH_3$ | $OCH_2CH_3$ | CH | |
| H | H | 0 | Cl | cyclopropyl | cyclopropyl | $OCH_3$ | CH | |
| H | H | 0 | Cl | cyclopropyl | $OCH_3$ | $CH(OCH_3)_2$ | CH | |
| H | H | 0 | Cl | cyclopropyl | $NHCH_3$ | $OCH_2CH_3$ | N | |
| H | H | 0 | Cl | cyclopropyl | $NHCH_3$ | $OCH_3$ | N | |
| H | H | 0 | Cl | cyclopropyl | $OCH_3$ | $OCH_2CH_3$ | N | |
| H | H | 0 | Cl | cyclopropyl | $CH_2F$ | $CH_3$ | CH | |
| Ph | H | 0 | $CH_3$ | cyclopropyl | $CH_3$ | $CH_3$ | CH | |
| Ph | H | 0 | $CH_3$ | cyclopropyl | $CH_3$ | $OCH_3$ | CH | |
| Ph | H | 0 | $CH_3$ | cyclopropyl | $OCH_3$ | $OCH_3$ | CH | |
| Ph | H | 0 | $CH_3$ | cyclopropyl | $CH_3$ | $CH_3$ | N | |
| Ph | H | 0 | $CH_3$ | cyclopropyl | $CH_3$ | $OCH_3$ | N | |
| Ph | H | 0 | $CH_3$ | cyclopropyl | $OCH_3$ | $OCH_3$ | N | |
| Ph | H | 0 | $CH_3$ | cyclopropyl | Cl | $OCH_3$ | CH | |
| Ph | H | 0 | $CH_3$ | cyclobutyl | $CH_3$ | $CH_3$ | CH | |
| Ph | H | 0 | $CH_3$ | cyclobutyl | $CH_3$ | $OCH_3$ | CH | |
| Ph | H | 0 | $CH_3$ | cyclobutyl | $OCH_3$ | $OCH_3$ | CH | |
| Ph | H | 0 | $CH_3$ | cyclobutyl | $CH_3$ | $CH_3$ | N | |
| Ph | H | 0 | $CH_3$ | cyclobutyl | $CH_3$ | $OCH_3$ | N | |
| Ph | H | 0 | $CH_3$ | cyclobutyl | $OCH_3$ | $OCH_3$ | N | |
| Ph | H | 0 | $CH_3$ | cyclobutyl | Cl | $OCH_3$ | CH | |
| Ph | H | 0 | $CH_3$ | cyclopentyl | $CH_3$ | $CH_3$ | CH | |
| Ph | H | 0 | $CH_3$ | cyclopentyl | $CH_3$ | $OCH_3$ | CH | |
| Ph | H | 0 | $CH_3$ | cyclopentyl | $OCH_3$ | $OCH_3$ | CH | |
| Ph | H | 0 | $CH_3$ | cyclopentyl | $CH_3$ | $CH_3$ | N | |
| Ph | H | 0 | $CH_3$ | cyclopentyl | $CH_3$ | $OCH_3$ | N | |
| Ph | H | 0 | $CH_3$ | cyclopentyl | $OCH_3$ | $OCH_3$ | N | |
| Ph | H | 0 | $CH_3$ | cyclopentyl | Cl | $OCH_3$ | CH | |
| Ph | H | 0 | $CH_3$ | cyclopropyl | $OCH_3$ | $OCH_2CH_3$ | CH | |
| Ph | H | 0 | $CH_3$ | cyclopropyl | cyclopropyl | $OCH_3$ | CH | |
| Ph | H | 0 | $CH_3$ | cyclopropyl | $OCH_3$ | $CH(OCH_3)_2$ | CH | |
| Ph | H | 0 | $CH_3$ | cyclopropyl | $NHCH_3$ | $OCH_2CH_3$ | N | |
| Ph | H | 0 | $CH_3$ | cyclopropyl | $NHCH_3$ | $OCH_3$ | N | |
| Ph | H | 0 | $CH_3$ | cyclopropyl | $OCH_3$ | $OCH_2CH_3$ | N | |
| Ph | H | 0 | $CH_3$ | cyclopropyl | $CH_2F$ | $CH_3$ | CH | |
| $CH_2Cl$ | H | 0 | $CH_3$ | cyclopropyl | $CH_3$ | $CH_3$ | CH | |
| $CH_2Cl$ | H | 0 | $CH_3$ | cyclopropyl | $CH_3$ | $OCH_3$ | $CH_3$ | |
| $CH_2Cl$ | H | 0 | $CH_3$ | cyclopropyl | $OCH_3$ | $OCH_3$ | CH | |

TABLE IV-continued

| R | R₁ | n | R₂ | R' | X | Y | Z | m.p. (°C.) |
|---|---|---|---|---|---|---|---|---|
| CH₂Cl | H | 0 | CH₃ | cyclopropyl | CH₃ | CH₃ | N | |
| CH₂Cl | H | 0 | CH₃ | cyclopropyl | CH₃ | OCH₃ | N | |
| CH₂Cl | H | 0 | CH₃ | cyclopropyl | OCH₃ | OCH₃ | N | |
| CH₂Cl | H | 0 | CH₃ | cyclopropyl | Cl | OCH₃ | CH | |
| CH₂Cl | H | 0 | CH₃ | cyclobutyl | CH₃ | CH₃ | CH | |
| CH₂Cl | H | 0 | CH₃ | cyclobutyl | CH₃ | OCH₃ | CH | |
| CH₂Cl | H | 0 | CH₃ | cyclobutyl | OCH₃ | OCH₃ | CH | |
| CH₂Cl | H | 0 | CH₃ | cyclobutyl | CH₃ | CH₃ | N | |
| CH₂Cl | H | 0 | CH₃ | cyclobutyl | CH₃ | OCH₃ | N | |
| CH₂Cl | H | 0 | CH₃ | cyclobutyl | OCH₃ | OCH₃ | N | |
| CH₂Cl | H | 0 | CH₃ | cyclobutyl | Cl | OCH₃ | CH | |
| CH₂Cl | H | 0 | CH₃ | cyclopentyl | CH₃ | CH₃ | CH | |
| CH₂Cl | H | 0 | CH₃ | cyclopentyl | CH₃ | OCH₃ | CH | |
| CH₂Cl | H | 0 | CH₃ | cyclopentyl | OCH₃ | OCH₃ | CH | |
| CH₂Cl | H | 0 | CH₃ | cyclopentyl | CH₃ | CH₃ | N | |
| CH₂Cl | H | 0 | CH₃ | cyclopentyl | CH₃ | OCH₃ | N | |
| CH₂Cl | H | 0 | CH₃ | cyclopentyl | OCH₃ | OCH₃ | N | |
| CH₂Cl | H | 0 | CH₃ | cyclopentyl | Cl | OCH₃ | CH | |
| CH₂Cl | H | 0 | CH₃ | cyclopropyl | OCH₃ | OCH₂CH₃ | CH | |
| CH₂Cl | H | 0 | CH₃ | cyclopropyl | cyclopropyl | OCH₃ | CH | |
| CH₂Cl | H | 0 | CH₃ | cyclopropyl | OCH₃ | CH(OCH₃)₂ | CH | |
| CH₂Cl | H | 0 | CH₃ | cyclopropyl | NHCH₃ | OCH₂CH₃ | N | |
| CH₂Cl | H | 0 | CH₃ | cyclopropyl | NHCH₃ | OCH₃ | N | |
| CH₂Cl | H | 0 | CH₃ | cyclopropyl | OCH₃ | OCH₂CH₃ | N | |
| CH₂Cl | H | 0 | CH₃ | cyclopropyl | CH₂F | CH₃ | CH | |
| H | H | 0 | CH₃ | cyclopropyl | CH₃ | CH₃ | CH | |
| H | H | 0 | CH₃ | cyclopropyl | CH₃ | OCH₃ | CH | |
| H | H | 0 | CH₃ | cyclopropyl | OCH₃ | OCH₃ | CH | |
| H | H | 0 | CH₃ | cyclopropyl | CH₃ | CH₃ | N | |
| H | H | 0 | CH₃ | cyclopropyl | CH₃ | OCH₃ | N | |
| H | H | 0 | CH₃ | cyclopropyl | OCH₃ | OCH₃ | N | |
| H | H | 0 | CH₃ | cyclopropyl | Cl | OCH₃ | CH | |
| H | H | 0 | CH₃ | cyclobutyl | CH₃ | CH₃ | CH | |
| H | H | 0 | CH₃ | cyclobutyl | CH₃ | OCH₃ | CH | |
| H | H | 0 | CH₃ | cyclobutyl | OCH₃ | OCH₃ | CH | |
| H | H | 0 | CH₃ | cyclobutyl | CH₃ | CH₃ | N | |
| H | H | 0 | CH₃ | cyclobutyl | CH₃ | OCH₃ | N | |
| H | H | 0 | CH₃ | cyclobutyl | OCH₃ | OCH₃ | N | |
| H | H | 0 | CH₃ | cyclobutyl | Cl | OCH₃ | CH | |
| H | H | 0 | CH₃ | cyclopentyl | CH₃ | CH₃ | CH | |
| H | H | 0 | CH₃ | cyclopentyl | CH₃ | OCH₃ | CH | |
| H | H | 0 | CH₃ | cyclopentyl | OCH₃ | OCH₃ | CH | |
| H | H | 0 | CH₃ | cyclopentyl | CH₃ | CH₃ | N | |
| H | H | 0 | CH₃ | cyclopentyl | CH₃ | OCH₃ | N | |
| H | H | 0 | CH₃ | cyclopentyl | OCH₃ | OCH₃ | N | |
| H | H | 0 | CH₃ | cyclopentyl | Cl | OCH₃ | CH | |
| H | H | 0 | CH₃ | cyclopropyl | OCH₃ | OCH₂CH₃ | CH | |
| H | H | 0 | CH₃ | cyclopropyl | cyclopropyl | OCH₃ | CH | |
| H | H | 0 | CH₃ | cyclopropyl | OCH₃ | CH(OCH₃)₂ | CH | |
| H | H | 0 | CH₃ | cyclopropyl | NHCH₃ | OCH₂CH₃ | N | |
| H | H | 0 | CH₃ | cyclopropyl | NHCH₃ | OCH₃ | N | |
| H | H | 0 | CH₃ | cyclopropyl | OCH₃ | OCH₂CH₃ | N | |
| H | H | 0 | CH₃ | cyclopropyl | CH₂F | CH₃ | CH | |
| CH₃ | H | 1 | Cl | cyclopropyl | CH₃ | CH₃ | CH | |
| CH₃ | H | 1 | Cl | cyclopropyl | CH₃ | OCH₃ | CH | |
| CH₃ | H | 1 | Cl | cyclopropyl | OCH₃ | OCH₃ | CH | |
| CH₃ | H | 1 | Cl | cyclopropyl | CH₃ | CH₃ | N | |
| CH₃ | H | 1 | Cl | cyclopropyl | CH₃ | OCH₃ | N | |
| CH₃ | H | 1 | Cl | cyclopropyl | OCH₃ | OCH₃ | N | |
| CH₃ | H | 1 | Cl | cyclopropyl | Cl | OCH₃ | CH | |
| CH₃ | H | 1 | Cl | cyclobutyl | CH₃ | CH₃ | CH | |
| CH₃ | H | 1 | Cl | cyclobutyl | CH₃ | OCH₃ | CH | |
| CH₃ | H | 1 | Cl | cyclobutyl | OCH₃ | OCH₃ | CH | |
| CH₃ | H | 1 | Cl | cyclobutyl | CH₃ | CH₃ | N | |
| CH₃ | H | 1 | Cl | cyclobutyl | CH₃ | OCH₃ | N | |
| CH₃ | H | 1 | Cl | cyclobutyl | OCH₃ | OCH₃ | N | |
| CH₃ | H | 1 | Cl | cyclobutyl | Cl | OCH₃ | CH | |
| CH₃ | H | 1 | Cl | cyclopentyl | CH₃ | CH₃ | CH | |
| CH₃ | H | 1 | Cl | cyclopentyl | CH₃ | OCH₃ | CH | |
| CH₃ | H | 1 | Cl | cyclopentyl | OCH₃ | OCH₃ | CH | |
| CH₃ | H | 1 | Cl | cyclopentyl | CH₃ | CH₃ | N | |
| CH₃ | H | 1 | Cl | cyclopentyl | CH₃ | OCH₃ | N | |
| CH₃ | H | 1 | Cl | cyclopentyl | OCH₃ | OCH₃ | N | |
| CH₃ | H | 1 | Cl | cyclopentyl | Cl | OCH₃ | CH | |
| CH₃ | H | 1 | Cl | cyclopropyl | OCH₃ | OCH₂CH₃ | CH | |
| CH₃ | H | 1 | Cl | cyclopropyl | cyclopropyl | OCH₃ | CH | |
| CH₃ | H | 1 | Cl | cyclopropyl | OCH₃ | CH(OCH₃)₂ | CH | |
| CH₃ | H | 1 | Cl | cyclopropyl | NHCH₃ | OCH₂CH₃ | N | |
| CH₃ | H | 1 | Cl | cyclopropyl | NHCH₃ | OCH₃ | N | |
| CH₃ | H | 1 | Cl | cyclopropyl | OCH₃ | OCH₂CH₃ | N | |
| CH₃ | H | 1 | Cl | cyclopropyl | CH₂F | CH₃ | CH | |

TABLE IV-continued

| R | R₁ | n | R₂ | R' | X | Y | Z | m.p. (°C.) |
|---|---|---|---|---|---|---|---|---|
| CH₃ | CH | 0 | H | cylopropyl | CH₃ | CH₃ | CH | |
| CH₃ | CH | 0 | H | cyclopropyl | CH₃ | OCH₃ | CH | |
| CH₃ | CH | 0 | H | cyclopropyl | OCH₃ | OCH₃ | CH | |
| CH₃ | CH | 0 | H | cyclopropyl | CH₃ | CH₃ | N | |
| CH₃ | CH | 0 | H | cyclopropyl | CH₃ | OCH₃ | N | |
| CH₃ | CH | 0 | H | cyclopropyl | OCH₃ | OCH₃ | N | |
| CH₃ | CH | 0 | H | cyclopropyl | Cl | OCH₃ | CH | |
| CH₃ | CH | 0 | H | cyclobutyl | CH₃ | CH₃ | CH | |
| CH₃ | CH | 0 | H | cyclobutyl | CH₃ | OCH₃ | CH | |
| CH₃ | CH | 0 | H | cyclobutyl | OCH₃ | OCH₃ | CH | |
| CH₃ | CH | 0 | H | cyclobutyl | CH₃ | CH₃ | N | |
| CH₃ | CH | 0 | H | cyclobutyl | CH₃ | OCH₃ | N | |
| CH₃ | CH | 0 | H | cyclobutyl | OCH₃ | OCH₃ | N | |
| CH₃ | CH | 0 | H | cyclobutyl | Cl | OCH₃ | CH | |
| CH₃ | CH | 0 | H | cyclopentyl | CH₃ | CH₃ | CH | |
| CH₃ | CH | 0 | H | cyclopentyl | CH₃ | OCH₃ | CH | |
| CH₃ | CH | 0 | H | cyclopentyl | OCH₃ | OCH₃ | CH | |
| CH₃ | CH | 0 | H | cyclopentyl | CH₃ | CH₃ | N | |
| CH₃ | CH | 0 | H | cyclopentyl | CH₃ | OCH₃ | N | |
| CH₃ | CH | 0 | H | cyclopentyl | OCH₃ | OCH₃ | N | |
| CH₃ | CH | 0 | H | cyclopentyl | Cl | OCH₃ | CH | |
| CH₃ | CH | 0 | H | cyclopropyl | OCH₃ | OCH₂CH₃ | CH | |
| CH₃ | CH | 0 | H | cyclopropyl | cyclopropyl | OCH₃ | CH | |
| CH₃ | CH | 0 | H | cyclopropyl | OCH₃ | CH(OCH₃)₂ | CH | |
| CH₃ | CH | 0 | H | cyclopropyl | NHCH₃ | OCH₂CH₃ | N | |
| CH₃ | CH | 0 | H | cyclopropyl | NHCH₃ | OCH₃ | N | |
| CH₃ | CH | 0 | H | cyclopropyl | OCH₃ | OCH₂CH₃ | N | |
| CH₃ | CH | 0 | H | cyclopropyl | CH₂F | CH₃ | CH | |
| CH₃ | H | 0 | H | cyclobutyl | CH₂CH₃ | CH₃ | CH | |
| CH₃ | H | 0 | H | cyclobutyl | CH₂CH₃ | OCH₃ | CH | |
| CH₃ | H | 0 | H | cyclobutyl | CH₂F | CH₃ | CH | |
| CH₃ | H | 0 | H | cyclobutyl | OCF₂H | CH₃ | CH | |
| CH₃ | H | 0 | H | cyclobutyl | OCF₂H | OCH₃ | CH | |
| CH₃ | H | 0 | H | cyclobutyl | OCH₂CH₃ | OCH₃ | CH | |
| CH₃ | H | 0 | H | cyclobutyl | CH₂F | OCH₃ | CH | |
| CH₃ | H | 0 | H | cyclobutyl | CH₂Cl | OCH₃ | N | |
| CH₃ | H | 0 | H | cyclobutyl | SCH₃ | OCH₃ | CH | |
| CH₃ | H | 0 | H | cyclobutyl | SCH₂F | OCH₃ | CH | |
| CH₃ | H | 0 | H | cyclobutyl | Br | OCH₃ | CH | |
| CH₃ | H | 0 | H | cyclobutyl | CH₂OCH₃ | OCH₃ | N | |
| CH₃ | H | 0 | H | cyclobutyl | OCH₂OCH₃ | OCH₃ | CH | |
| CH₃ | H | 0 | H | cyclobutyl | OCH₂OCH₂CH₃ | CH₃ | CH | |
| CH₃ | H | 0 | H | cyclobutyl | N(CH₃)₂ | OCH₃ | N | |
| CH₃ | H | 0 | H | cyclobutyl | NHCH₂CH₃ | CH₃ | N | |
| CH₃ | H | 0 | H | cyclobutyl | NHCH₃ | OCH₂CH₃ | N | |
| CH₃ | H | 0 | H | cyclobutyl | CH₃ | CH₂SCH₃ | CH | |
| CH₃ | H | 0 | H | cyclobutyl | OCH₃ | CH₂SO₂CH₃ | CH | |
| CH₃ | H | 0 | H | cyclobutyl | NH₂ | OCH₂CH₃ | N | |
| CH₃ | H | 0 | H | cyclobutyl | CH₃ | OCH₂CH=CH₂ | CH | |
| CH₃ | H | 0 | H | cyclobutyl | CH₂CH₃ | OCF₂H | CH | |
| CH₃ | H | 0 | H | cyclobutyl | OCF₂H | OCF₂H | CH | |
| CH₃ | H | 0 | H | cyclobutyl | OCH₃ | OCH=CH₂ | CH | |
| CH₃ | H | 0 | H | cyclobutyl | OCH₃ | C(O)CH₃ | N | |
| CH₃ | H | 0 | H | cyclobutyl | CH₃ | N(OCH₃)CH₃ | N | |
| CH₃ | H | 0 | H | cyclobutyl | OCH(CH₃)₂ | OCF₂H | CH | |

TABLE V

| R | R₁ | R₂ | R' | n | A | X₁ | Y₁ | X₂ | Y₂ | X₃ | Y₃ | m.p. (°C.) |
|---|---|---|---|---|---|---|---|---|---|---|---|---|
| CH₃ | H | H | cyclopropyl | 0 | A-2 | CH₃ | O | — | — | — | — | |
| CH₃ | H | H | cyclopropyl | 0 | A-2 | OCH₃ | O | — | — | — | — | |
| CH₃ | H | H | cyclopropyl | 0 | A-2 | OCH₃ | CH₂ | — | — | — | — | |
| CH₃ | H | H | cyclopropyl | 0 | A-2 | OCH₂CH₃ | O | — | — | — | — | |
| CH₃ | H | H | cyclopropyl | 0 | A-3 | CH₃ | — | — | — | — | — | |
| CH₃ | H | H | cyclopropyl | 0 | A-3 | OCH₃ | — | — | — | — | — | |
| CH₃ | H | H | cyclopropyl | 0 | A-3 | OCH₂CH₃ | — | — | — | — | — | |
| CH₃ | H | H | cyclopropyl | 0 | A-3 | OCF₂H | — | — | — | — | — | |
| CH₃ | H | H | cyclopropyl | 0 | A-4 | CH₃ | — | — | — | — | H | |
| CH₃ | H | H | cyclopropyl | 0 | A-4 | CH₃ | — | — | — | — | CH₃ | |
| CH₃ | H | H | cyclopropyl | 0 | A-4 | OCH₃ | — | — | — | — | H | |
| CH₃ | H | H | cyclopropyl | 0 | A-4 | OCH₃ | — | — | — | — | CH₃ | |
| CH₃ | H | H | cyclopropyl | 0 | A-4 | OCF₂H | — | — | — | — | H | |
| CH₃ | H | H | cyclopropyl | 0 | A-5 | — | — | CH₃ | OCH₃ | — | — | |
| CH₃ | H | H | cyclopropyl | 0 | A-5 | — | — | CH₃ | OCH₂CH₃ | — | — | |
| CH₃ | H | H | cyclopropyl | 0 | A-5 | — | — | CH₃ | SCH₃ | — | — | |
| CH₃ | H | H | cyclopropyl | 0 | A-5 | — | — | CH₂CH₃ | OCH₃ | — | — | |
| CH₃ | H | H | cyclopropyl | 0 | A-6 | — | — | — | — | CH₃ | — | |
| CH₃ | H | H | cyclopropyl | 0 | A-6 | — | — | — | — | OCH₃ | — | |

TABLE V-continued

| R | $R_1$ | $R_2$ | R' | n | A | $X_4$ | $Y_4$ | $Z_1$ | m.p. (°C.) |
|---|---|---|---|---|---|---|---|---|---|
| $CH_3$ | H | H | cyclopropyl | 0 | A-7 | $CH_3$ | $CH_3$ | CH | |

| R | $R_1$ | $R_2$ | R' | n | A | $X_1$ | $Y_1$ | $X_2$ | $Y_2$ | $X_3$ | $Y_3$ | m.p. (°C.) |
|---|---|---|---|---|---|---|---|---|---|---|---|---|
| $CH_3$ | H | $CH_3$ | cyclopropyl | 0 | A-2 | $CH_3$ | O | — | — | — | — | |
| $CH_3$ | H | $CH_3$ | cyclopropyl | 0 | A-2 | $OCH_3$ | O | — | — | — | — | |
| $CH_3$ | H | $CH_3$ | cyclopropyl | 0 | A-2 | $OCH_3$ | $CH_2$ | — | — | — | — | |
| $CH_3$ | H | $CH_3$ | cyclopropyl | 0 | A-2 | $OCH_2CH_3$ | O | — | — | — | — | |
| $CH_3$ | H | $CH_3$ | cyclopropyl | 0 | A-3 | $CH_3$ | — | — | — | — | — | |
| $CH_3$ | H | $CH_3$ | cyclopropyl | 0 | A-3 | $OCH_3$ | — | — | — | — | — | |
| $CH_3$ | H | $CH_3$ | cyclopropyl | 0 | A-3 | $OCH_2CH_3$ | — | — | — | — | — | |
| $CH_3$ | H | $CH_3$ | cyclopropyl | 0 | A-3 | $OCF_2H$ | — | — | — | — | — | |
| $CH_3$ | H | $CH_3$ | cyclopropyl | 0 | A-4 | $CH_3$ | — | — | — | — | H | |
| $CH_3$ | H | $CH_3$ | cyclopropyl | 0 | A-4 | $CH_3$ | — | — | — | — | $CH_3$ | |
| $CH_3$ | H | $CH_3$ | cyclopropyl | 0 | A-4 | $OCH_3$ | — | — | — | — | H | |
| $CH_3$ | H | $CH_3$ | cyclopropyl | 0 | A-4 | $OCH_3$ | — | — | — | — | $CH_3$ | |
| $CH_3$ | H | $CH_3$ | cyclopropyl | 0 | A-4 | $OCF_2H$ | — | — | — | — | H | |
| $CH_3$ | H | $CH_3$ | cyclopropyl | 0 | A-5 | — | — | $CH_3$ | $OCH_3$ | — | — | |
| $CH_3$ | H | $CH_3$ | cyclopropyl | 0 | A-5 | — | — | $CH_3$ | $OCH_2CH_3$ | — | — | |
| $CH_3$ | H | $CH_3$ | cyclopropyl | 0 | A-5 | — | — | $CH_3$ | $SCH_3$ | — | — | |
| $CH_3$ | H | $CH_3$ | cyclopropyl | 0 | A-5 | — | — | $CH_2CH_3$ | $OCH_3$ | — | — | |
| $CH_3$ | H | $CH_3$ | cyclopropyl | 0 | A-6 | — | — | — | — | $CH_3$ | — | |
| $CH_3$ | H | $CH_3$ | cyclopropyl | 0 | A-6 | — | — | — | — | $OCH_3$ | — | |
| $CH_3$ | H | H | cyclobutyl | 0 | A-2 | $CH_3$ | O | — | — | — | — | |
| $CH_3$ | H | H | cyclobutyl | 0 | A-2 | $OCH_3$ | O | — | — | — | — | |
| $CH_3$ | H | H | cyclobutyl | 0 | A-2 | $OCH_3$ | $CH_2$ | — | — | — | — | |
| $CH_3$ | H | H | cyclobutyl | 0 | A-2 | $OCH_2CH_3$ | O | — | — | — | — | |
| $CH_3$ | H | H | cyclobutyl | 0 | A-3 | $CH_3$ | — | — | — | — | — | |
| $CH_3$ | H | H | cyclobutyl | 0 | A-3 | $OCH_3$ | — | — | — | — | — | |
| $CH_3$ | H | H | cyclobutyl | 0 | A-3 | $OCH_2CH_3$ | — | — | — | — | — | |
| $CH_3$ | H | H | cyclobutyl | 0 | A-3 | $OCF_2H$ | — | — | — | — | — | |
| $CH_3$ | H | H | cyclobutyl | 0 | A-4 | $CH_3$ | — | — | — | — | H | |
| $CH_3$ | H | H | cyclobutyl | 0 | A-4 | $CH_3$ | — | — | — | — | $CH_3$ | |
| $CH_3$ | H | H | cyclobutyl | 0 | A-4 | $OCH_3$ | — | — | — | — | H | |
| $CH_3$ | H | H | cyclobutyl | 0 | A-4 | $OCH_3$ | — | — | — | — | $CH_3$ | |
| $CH_3$ | H | H | cyclobutyl | 0 | A-4 | $OCF_2H$ | — | — | — | — | H | |
| $CH_3$ | H | H | cyclobutyl | 0 | A-5 | — | — | $CH_3$ | $OCH_3$ | — | — | |
| $CH_3$ | H | H | cyclobutyl | 0 | A-5 | — | — | $CH_3$ | $OCH_2CH_3$ | — | — | |
| $CH_3$ | H | H | cyclobutyl | 0 | A-5 | — | — | $CH_3$ | $SCH_3$ | — | — | |
| $CH_3$ | H | H | cyclobutyl | 0 | A-5 | — | — | $CH_2CH_3$ | $OCH_3$ | — | — | |
| $CH_3$ | H | H | cyclobutyl | 0 | A-6 | — | — | — | — | $CH_3$ | — | |
| $CH_3$ | H | H | cyclobutyl | 0 | A-6 | — | — | — | — | $OCH_3$ | — | |

TABLE VI

| R | $R_1$ | n | $R_2$ | R' | X | Y | Z | m.p. (°C.) |
|---|---|---|---|---|---|---|---|---|
| $CH_3$ | H | 0 | H | cyclopropyl | $CH_3$ | $CH_3$ | CH | |
| $CH_3$ | H | 0 | H | cyclopropyl | $CH_3$ | $OCH_3$ | CH | |
| $CH_3$ | H | 0 | H | cyclopropyl | $OCH_3$ | $OCH_3$ | CH | |
| $CH_3$ | H | 0 | H | cyclopropyl | $CH_3$ | $CH_3$ | N | |
| $CH_3$ | H | 0 | H | cyclopropyl | $CH_3$ | $OCH_3$ | N | |
| $CH_3$ | H | 0 | H | cyclopropyl | $OCH_3$ | $OCH_3$ | N | |
| $CH_3$ | H | 0 | H | cyclopropyl | Cl | $OCH_3$ | CH | |
| $CH_3$ | H | 0 | H | cyclobutyl | $CH_3$ | $CH_3$ | CH | |
| $CH_3$ | H | 0 | H | cyclobutyl | $CH_3$ | $OCH_3$ | CH | |
| $CH_3$ | H | 0 | H | cyclobutyl | $OCH_3$ | $OCH_3$ | CH | |
| $CH_3$ | H | 0 | H | cyclobutyl | $CH_3$ | $CH_3$ | N | |
| $CH_3$ | H | 0 | H | cyclobutyl | $CH_3$ | $OCH_3$ | N | |
| $CH_3$ | H | 0 | H | cyclobutyl | $OCH_3$ | $OCH_3$ | N | |
| $CH_3$ | H | 0 | H | cyclobutyl | Cl | $OCH_3$ | CH | |
| $CH_3$ | H | 0 | H | cyclopentyl | $CH_3$ | $CH_3$ | CH | |
| $CH_3$ | H | 0 | H | cyclopentyl | $CH_3$ | $OCH_3$ | CH | |
| $CH_3$ | H | 0 | H | cyclopentyl | $OCH_3$ | $OCH_3$ | CH | |
| $CH_3$ | H | 0 | H | cyclopentyl | $CH_3$ | $CH_3$ | N | |
| $CH_3$ | H | 0 | H | cyclopentyl | $CH_3$ | $OCH_3$ | N | |
| $CH_3$ | H | 0 | H | cyclopentyl | $OCH_3$ | $OCH_3$ | N | |
| $CH_3$ | H | 0 | H | cyclopentyl | Cl | $OCH_3$ | CH | |
| $CH_3$ | H | 0 | H | cyclopropyl | $OCH_3$ | $OCH_2CH_3$ | CH | |
| $CH_3$ | H | 0 | H | cyclopropyl | cyclopropyl | $OCH_3$ | CH | |
| $CH_3$ | H | 0 | H | cyclopropyl | $OCH_3$ | $CH(OCH_3)_2$ | CH | |
| $CH_3$ | H | 0 | H | cyclopropyl | $NHCH_3$ | $OCH_2CH_3$ | N | |
| $CH_3$ | H | 0 | H | cyclopropyl | $NHCH_3$ | $OCH_3$ | N | |
| $CH_3$ | H | 0 | H | cyclopropyl | $OCH_3$ | $OCH_2CH_3$ | N | |
| $CH_3$ | H | 0 | H | cyclopropyl | $CH_2F$ | $CH_3$ | CH | |

TABLE VII

| R | $R_1$ | n | $R_2$ | R' | X | Y | Z | m.p. (°C.) |
|---|---|---|---|---|---|---|---|---|
| $CH_3$ | H | 0 | H | cyclopropyl | $CH_3$ | $CH_3$ | CH | |

TABLE VII-continued

| R | R₁ | n | R₂ | R' | X | Y | Z | m.p. (°C.) |
|---|---|---|---|---|---|---|---|---|
| CH₃ | H | 0 | H | cyclopropyl | CH₃ | OCH₃ | CH | |
| CH₃ | H | 0 | H | cyclopropyl | OCH₃ | OCH₃ | CH | |
| CH₃ | H | 0 | H | cyclopropyl | CH₃ | CH₃ | N | |
| CH₃ | H | 0 | H | cyclopropyl | CH₃ | OCH₃ | N | |
| CH₃ | H | 0 | H | cyclopropyl | OCH₃ | OCH₃ | N | |
| CH₃ | H | 0 | H | cyclopropyl | Cl | OCH₃ | CH | |
| CH₃ | H | 0 | H | cyclobutyl | CH₃ | CH₃ | CH | |
| CH₃ | H | 0 | H | cyclobutyl | CH₃ | OCH₃ | CH | |
| CH₃ | H | 0 | H | cyclobutyl | OCH₃ | OCH₃ | CH | |
| CH₃ | H | 0 | H | cyclobutyl | CH₃ | CH₃ | N | |
| CH₃ | H | 0 | H | cyclobutyl | CH₃ | OCH₃ | N | |
| CH₃ | H | 0 | H | cyclobutyl | OCH₃ | OCH₃ | N | |
| CH₃ | H | 0 | H | cyclobutyl | Cl | OCH₃ | CH | |
| CH₃ | H | 0 | H | cyclopentyl | CH₃ | CH₃ | CH | |
| CH₃ | H | 0 | H | cyclopentyl | CH₃ | OCH₃ | CH | |
| CH₃ | H | 0 | H | cyclopentyl | OCH₃ | OCH₃ | CH | |
| CH₃ | H | 0 | H | cyclopentyl | CH₃ | CH₃ | N | |
| CH₃ | H | 0 | H | cyclopentyl | CH₃ | OCH₃ | N | |
| CH₃ | H | 0 | H | cyclopentyl | OCH₃ | OCH₃ | N | |
| CH₃ | H | 0 | H | cyclopentyl | Cl | OCH₃ | CH | |
| CH₃ | H | 0 | H | cyclopropyl | OCH₃ | OCH₂CH₃ | CH | |
| CH₃ | H | 0 | H | cyclopropyl | cyclopropyl | OCH₃ | CH | |
| CH₃ | H | 0 | H | cyclopropyl | OCH₃ | CH(OCH₃)₂ | CH | |
| CH₃ | H | 0 | H | cyclopropyl | NHCH₃ | OCH₂CH₃ | N | |
| CH₃ | H | 0 | H | cyclopropyl | NHCH₃ | OCH₃ | N | |
| CH₃ | H | 0 | H | cyclopropyl | OCH₃ | OCH₂CH₃ | N | |
| CH₃ | H | 0 | H | cyclopropyl | CH₂F | CH₃ | CH | |

Formulations

Useful formulations of the compounds of Formula I can be prepared in conventional ways. They include dusts, granules, pellets, solutions, suspensions, emulsions, wettable powders, emulsifiable concentrates and the like. Many of these may be applied directly. Sprayable formulations can be extended in suitable media and used at spray volumes of from a few liters to several hundred liters per hectare. High strength compositions are primarily used as intermediates for further formulation. The formulations, broadly, contain about 0.1% to 99% by weight of active ingredient(s) and at least one of (a) about 0.1% to 20% surfactant(s) and (b) about 1% to 99.9% solid or liquid inert diluent(s). More specifically, they will contain these ingredients in the following approximate proportions:

| | Active Ingredient | Weight Percent* Diluent(s) | Surfactant(s) |
|---|---|---|---|
| Wettable Powders | 20-90 | 0-74 | 1-10 |
| Oil Suspensions, Emulsions, Solutions, (including Emulsifiable Concentrates) | 3-50 | 40-95 | 0-15 |
| Aqueous Suspension | 10-50 | 40-84 | 1-20 |
| Dusts | 1-25 | 70-99 | 0-5 |
| Granules and Pellets | 0.1-95 | 5-99.9 | 0-15 |
| High Strength Compositions | 90-99 | 0-10 | 0-2 |

*Active ingredient plus at least one of a Surfactant or a Diluent equals 100 weight percent.

Lower or higher levels of active ingredient can, of course, be present depending on the intended use and the physical properties of the compound. Higher ratios of surfactant to active ingredient are sometimes, desirable, and are achieved by incorporation into the formulation or by tank mixing.

Typical solid diluents are described in Watkins, et al., "Handbook of Insecticide Dust Diluents and Carriers", 2nd Ed., Dorland Books, Caldwell, N.J., but other solids, either mined or manufactured, may be used. The more absorptive diluents are preferred for wettable powders and the denser ones for dusts. Typical liquid diluents and solvents are described in Marsden, "Solvents Guide," 2nd Ed., Interscience, New York, 1950. Solubility under 0.1% is preferred for suspension concentrates; solution concentrates are preferably stable against phase separation at 0° C. "McCutcheon's Detergents and Emulsifiers Annual", MC Publishing Corp., Ridgewood, N.J., as well as Sisely and Wood, "Encyclopedia of Surface Active Agents", Chemical Publishing Co., Inc., New York, 1964, lists surfactants and recommended uses. All formulations can contain minor amounts of additives to reduce foaming, caking, corrosion, microbiological growth, etc.

The methods of making such compositions are well known. Solutions are prepared by simply mixing the ingredients. Fine solid compositions are made by blending and, usually, grinding as in a hammer or fluid energy mill. Suspensions ae prepared by wet milling (see, for example, Littler, U.S. Pat. No. 3,060,084). Granules and pellets may be made by spraying the active material upon preformed granular carriers or by agglomeration techniques. See J. E. Browning, "Agglomeration", *Chemical Engineering,* Dec. 4, 1967, pp. 147ff. and "Perry's Chemical Engineer's Handbook", 5th Ed., McGraw-Hill, New York, 1973, pp. 8-57ff.

For further information regarding the art of formulation, see for example:

H. M. Loux, U.S. Pat. No. 3,235,361, Feb. 15, 1966, Col. 6, line 16 through Col. 7, line 19 and Examples 10 through 41;

R. W. Luckenbaugh, U.S. Pat. No. 3,309,192, Mar. 14, 1967, Col. 5, line 43 through Col. 7, line 62 and Examples 8, 12, 15, 39, 41, 52, 53, 58, 132, 138-140, 162-164, 166, 167 and 169-182;

H. Gysin and E. Knusli, U.S. Pat. No. 2,891,855, June 23, 1959, Col. 3, line 66 through Col. 5, line 17 and Examples 1-4;

G. C. Klingman, "Weed Control as a Science", John Wiley and Sons, Inc., New York, 1961, pp. 81-96; and J. D. Fryer and S. A. Evans, "Weed Control Handbook", 5th Ed., Blackwell Scientific Publications, Oxford, 1968, pp. 101–103.

In the following Examples, all parts are by weight unless otherwise indicated.

EXAMPLE 4

Wettable Powder 4-(Cyclopropylcarbonyl)-N-[(4,6-dimethoxypyrimidin 2-yl)aminocarbonyl]-1-methyl-1H-pyrazole-5-sulfonamide: 80%
sodium alkylnaphthalenesulfonate: 2%
sodium ligninsulfonate: 2%
synthetic amorphous silica: 3%
kaolinite: 13%

The ingredients are blended, hammer-milled until all the solids are essentially under 50 microns, reblended, and packaged.

EXAMPLE 5

Wettable Powder 4-(Cyclopropylcarbonyl)-N-[(4,6-dimethoxypyrimidin 2-yl)aminocarbonyl]-1-methyl-1H-pyrazole-5-sulfonamide: 50%
sodium alkylnaphthalenesulfonate: 2%
low viscosity methyl cellulose: 2%
diatomaceous earth: 46%

The ingredients are blended, coarsely hammer-milled and then air-milled to produce particles essentially all below 10 microns in diameter. The product is reblended before packaging.

EXAMPLE 6

Granule

Wettable Powder of Example 4: 5% attapulgite granules (U.S.S. 20 to 40 mesh; 0.84–0.42 mm): 95%

A slurry of wettable powder containing 25% solids is sprayed on the surface of attapulgite granules in a double-cone blender. The granules are dried and packaged.

EXAMPLE 7

Extruded Pellet 4-(Cyclopropylcarbonyl)-N-[(4,6-dimethoxypyrimidin 2-yl)aminocarbonyl]-1-methyl-1-H-pyrazole-5-sulfonamide: 25%
anhydrous sodium sulfate: 10%
crude calcium ligninsulfonate: 5%
sodium alkylnaphthalenesulfonate: 1%
calcium/magnesium bentonite: 59%

The ingredients are blended, hammer-milled and then moistened with about 12% water. The mixture is extruded as cylinders about 3 mm diameter which are cut to produce pellets about 3 mm long. These may be used directly after drying, or the dried pellets may be crushed to pass a U.S.S. No. 20 sieve (0.84 mm openings). The granules held on a U.S.S. No. 40 sieve (0.42 mm openings) may be packaged for use and the fines recycled.

EXAMPLE 8

Low Strength Granule 4-(Cyclopropylcarbonyl)-N-[(4,6-dimethoxypyrimidin 2-yl)aminocarbonyl]-1-methyl-1-H-pyrazole-5-sulfonamide: 0.1%
attapulgite granules (U.S.S. 20 to 40 mesh): 99.9%

The active ingredient is dissolved in a solvent and the solution is sprayed upon dedusted granules in a double-cone blender. After spraying of the solution has been completed, the material is warmed to evaporate the solvent. The material is allowed to cool and then packaged.

EXAMPLE 9

Granule 4-(Cyclopropylcarbonyl)-N-[(4,6-dimethoxypyrimidin 2-yl)aminocarbonyl]-1-methyl-1-H-pyrazole-5-sulfonamide: 80%
wetting agent: 1%
crude ligninsulfonate salt (containing 5 to 20% of the natural sugars): 10%
attapulgite clay: 9%

The ingredients are blended and milled to pass through a 100 mesh screen. This material is then added to a fluid bed granulator, the air flow is adjusted to gently fluidize the material, and a fine spray of water is sprayed onto the fluidized material. The fluidization and spraying are continued until granules of the desired size range are made. The spraying is stopped, but fluidization is continued, optionally with heat, until the water content is reduced to the desired level, generally less than 1%. The material is then discharged, screened to the desired size range, generally 14 to 100 mesh (1410 to 149 microns), and packaged for use.

EXAMPLE 10

Low Strength Granule 4-(Cyclopropylcarbonyl)-N-[(4,6-dimethoxypyrimidin 2-yl)aminocarbonyl]-1-methyl-1-H-pyrazole-5-sulfonamide: 1%
N,N-dimethylformamide: 9%
attapulgite granules (U.S.S. 20 to 40 sieve): 90%

The active ingredient is dissolved in the solvent and the solution is sprayed upon dedusted granules in a double cone blender. After spraying of the solution has been completed, the blender is allowed to run for a short period and then the granules are packaged.

EXAMPLE 11

Aqueous Suspension 4-(Cyclopropylcarbonyl)-N-[(4,6-dimethoxypyrimidin 2-yl)aminocarbonyl]-1-methyl-1-H-pyrazole-5-sulfonamide: 40%
polyacrylic acid thickener: 0.3%
dodecylphenol polyethylene glycol ether: 0.5%
disodium phosphate: 1%
monosodium phosphate: 0.5%
polyvinyl alcohol: 1.0%
water: 56.7%

The ingredients are blended and ground together in a sand mill to produce particles essentially all under 5 microns in size.

EXAMPLE 12

Solution 4-(Cyclopropylcarbonyl)-N-[(4,6-dimethoxypyrimidin 2-yl)aminocarbonyl]-1-methyl-1-H-pyrazole-5-sulfonamide: 5%
water: 95%

The salt is added directly to the water with stirring to produce the solution, which may then be packaged for use.

EXAMPLE 13

High Strength Concentrate 4-(Cyclopropylcarbonyl)-N-[(4,6-dimethoxypyrimidin 2-yl)aminocarbonyl]-1-methyl-1-H-pyrazole-5-sulfonamide: 99%
silica aerogel: 0.5%
synthetic amorphous silica: 0.5%

The ingredients are blended and ground in a hammer-mill to produce a material essentially all passing a U.S.S. No. 50 screen (0.3 mm opening). The concentrate may be formulated further if necessary.

EXAMPLE 14

Wettable Powder 4-(Cyclopropylcarbonyl)-N-[4,6-dimethoxyprimidin 2-yl)aminocarbonyl]-1-methyl-1-H-pyrazole-5-sulfonamide: 90%
dioctyl sodium sulfosuccinate: 0.1%
synthetic fine silica: 9.9%

The ingredients are blended and ground in a hammer-mill to produce particles essentially all below 100 microns. The material is sifted through a U.S.S. No. 50 screen and then packaged.

EXAMPLE 15

Wettable Powder 4-(Cyclopropylcarbonyl)-N-[(4,6-dimethoxypyrimidin 2-yl)aminocarbonyl]-1-methyl-1-H-pyrazole-5-sulfonamide: 40%
sodium ligninsulfonate: 20%
montmorillonite clay: 40%

The ingredients are thoroughly blended, coarsely hammer-milled and then air-milled to produce particles essentially all below 10 microns in size. The material is reblended and then packaged.

EXAMPLE 16

Oil Suspension 4-(Cyclopropylcarbonyl)-N-[(4,6-dimethoxypyrimidin 2-yl)aminocarbonyl]-1-methyl-1-H-pyrazole-5-sulfonamide: 35%
blend of polyalcohol carboxylic esters and oil soluble petroleum sulfonates: 6%
xylene: 59%

The ingredients are combined and ground together in a sand mill to produce particles essentially all below 5 microns. The product can be used directly, extended with oils, or emulsified in water.

EXAMPLE 17

Dust 4-(Cyclopropylcarbonyl)-N-[(4,6-dimethoxypyrimidin 2-yl)aminocarbonyl]-1-methyl-1-H-pyrazole-5-sulfonamide: 10%
attapulgite: 10%
Pyrophyllite: 80%

The active ingredient is blended with attapulgite and then passed through a hammer-mill to produce particles substantially all below 200 microns. The ground concentrate is then blended with powdered pyrophyllite until homogeneous.

Utility

Test results indicate that the compounds of the present invention are highly active preemergent or postemergent herbicides or plant growth regulants. Many of them have utility for broad-spectrum pre-and/or postemergence weed control in areas where complete control of all vegetation is desired, such as around fuel shortage tanks, ammunition depots, industrial storage areas, parking lots, drive-in theaters, around billboards, highway and railroad structures. Some of the compounds have utility for selective weed control in crops such as rice, wheat, barley, soybeans and corn. Some compounds of the invention are especially selective to wheat and rice. Alternatively, the subject compounds are useful to modify plant growth.

The rates of application for the compounds of the invention are determined by a number of factors, including their use as plant growth modifiers or as herbicides, the crop species involved, the types of weeds to be controlled, weather and climate, formulations selected, mode of application, amount of foliage present, etc. In general terms, the subject compounds should be applied at levels of around 0.001 to 10 kg/ha, the lower rates being suggested for use or lighter soils and/or those having a low organic matter content, for plant growth modification or for situations where only short-term persistence is required.

The compounds of the invention may be used in combination with any other commercial herbicide, examples of which are those of the triazine, triazole, imidazolinone, uracil, urea, amide, diphenylether, carbamate and bipyridylium types as well as other sulfonylureas. The compound of this invention is also especially useful in combination with the following herbicides.

| Common Name | Chemical Name |
|---|---|
| alachlor | 2-chloro-2',6'-diethyl-N—(methoxymethyl)-acetanilide |
| atrazine | 2-chloro-4-(ethylamino)-6-(isopropylamino)-s-triazine |
| butylate | S—ethyl-diisobutylthiocarbamate |
| cyanazine | 2-[[4-chloro-6-(ethylamino)-s-triazin-2-yl]amino]-2-methylpropionitrile |
| dicamba | 3,6-dichloro-o-anisic acid |
| EPTC | S—ethyl dipropylthiocarbamate |
| linuron | 3-(3,4-dichlorophenyl)-1-methoxy-1-methylurea |
| metolachlor | 2-chloro-N—(2-ethyl-6-methylphenyl)-N—(2-methoxy-1-methylethyl)acetamide |
| metribuzin | 4-amino-6-tert-butyl-3-(methylthio)-as-triazine-5(4H)—one |
| tridiphane | 2-(3,5-dichlorophenyl)-2-(2,2,2-trichloroethyl)oxirane |
| 2,4-D | (2,4-dichlorophenoxy)acetic acid |
| thiobencarb | S—4-chlorobenzyldiethylthiocarbamate |
| molinate | S—ethyl N,N—hexamethylenethiocarbamate |
| butachlor | N—(butoxymethyl-2-chloro-2',6'-diethylacetanilide |
| naproanilide | N—phenyl-2-(1-naphthyloxy)propionamide |
| pyrazolate | 4-(2,4-dichlorobenzoyl)-1,3-dimethylpyrazol-5-yl-4-toluenesulfonate |
| pretilachlor | 2-chloro-2',6'-diethyl-N—(n-propoxyethyl)acetanilide |
| oxidiazon | 3-[2,4-dichloro-5-(1-methylethoxy)phenyl]-5-(1,1-dimethylethyl)-1,3,4-oxadizol-2(3H)—one |
| Trade Name or Code Number | |
| Harmony ® | 3-[[(4-methoxy-6-methyl-1,3,5-triazin-2-yl)aminocarbonyl]aminosulfonyl]-2-thiophenecarboxylic acid, methyl ester |
| Cinch ® | exo-1-methyl-4-(1-methylethyl)-2-[(2-methylphenyl)methoxy]-7-oxabicyclo-[2.2.1]heptane |
| MY-93 | S—(1-methyl-1-phenethyl)piperidine-1-carbothioate |

-continued

| | Chemical Name |
|---|---|
| CH-83 | S—(2-methylpropyl)-hexanhydro-1H—azepine-1-carbothioic acid, ester |
| X-52 | 2,4-dichlorophenyl-3-methoxy-4-nitrophenyl ether |
| SC-2957 | S—benzyl-N— ethyl-N—propylthiocarbamate |
| HW-52 | N—(2,3-dichlorophenyl)-4-(ethoxymethoxy)benzamide |
| NTN-801 | 2-(benzothiazol-2-yl)-N—methyl-N—phenylacetamide |
| SL-49 | 2-[4-[(2,4-dichlorophenyl)carbonyl]-1,3-dimethyl-1H—pyrazol-5-yloxy]-1-phenylethanone |
| BAS-514 | 3,7-dichloro-8-quinoline carboxylic acid |

The herbicidal properties of the subject compounds were discovered in a number of greenhouse tests. The test procedures and results follow.

| Compound Number | X | Y | Z |
|---|---|---|---|
| 1 | CH₃ | CH₃ | CH |
| 2 | CH₃ | OCH₃ | CH |
| 3 | OCH₃ | OCH₃ | CH |
| 4 | CH₃ | OCH₃ | N |
| 5 | OCH₃ | OCH₃ | N |
| 6 | Cl | OCH₃ | CH |

| 7 | CH₃ | CH₃ | CH |
| 8 | CH₃ | OCH₃ | CH |
| 9 | OCH₃ | OCH₃ | CH |
| 10 | CH₃ | OCH₃ | N |

| Compound Number | X | Y | Z |
|---|---|---|---|
| 11 | OCH₃ | OCH₃ | N |
| 12 | Cl | OCH₃ | CH |

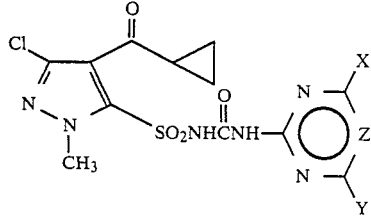

| 13 | CH₃ | CH₃ | CH |
| 14 | OCH₃ | CH₃ | CH |
| 15 | OCH₃ | OCH₃ | CH |

Test A

Seeds of crabgrass (Digitaria spp.), barnyard-grass (Echinochloa crusgalli), giant foxtail (Setaria faberi), wild oats (Avena fatua), cheatgrass (Bromus secalinus), velvetleaf (Abutilon theophrasti), morningglory (Ipomoea spp.), cockelbur (Xanthium pennsylvanicum), sorghum, corn soybean, sugarbeet, cotton, rice, wheat, barley and purple nutsedge (Cyperus rotundus) tubers were planted and treated preemergence with the test chemicals dissolved in a non-phytotoxic solvent. At the same time these crop and weed species were treated with a soil/foliage application. At the time of treatment, the plants ranged in height from 2 to 18 cm. Treated plants and controls were maintained in a greenhouse for sixteen days, after which all species were compared to controls and visually rated for response to treatment. The ratings, summarized in Table A, are based on a numerical scale extending from 0=no injury, to 10=complete kill. The accompanying descriptive symbols have the following meanings:

C=chlorosis/necrosis
B=burn
D=defoliation
E=emergence inhibition
G=growth retardation
H=formative effect
U=unusual pigmentation
X=axillary stimulation
S=albinism
6Y=abscised buds or flowers

TABLE A

| | Compound 1 | | Compound 2 | | Compound 3 | | Compound 4 | | Compound 5 | |
|---|---|---|---|---|---|---|---|---|---|---|
| Rate kg/ha | 0.05 | 0.01 | 0.05 | 0.01 | 0.05 | 0.01 | 0.05 | 0.01 | 0.05 | 0.01 |
| POSTEMERGENCE | | | | | | | | | | |
| MORNINGGLORY | 9C | 3C,8G | 10C | 10C | 10C | 10C | 9C | 3C,8G | 5C,9G | 3C,8H |
| COCKLEBUR | 9C | 5C,9G | 10C | 10C | 10C | 10C | 9C | 4C,9G | 9H | 3C,9H |
| VELVETLEAF | 10C | 9C | 10C | 10C | 10C | 10C | 9C | 3C,7H | 2G | 0 |
| NUTSEDGE | 9G | 3C,8G | 5C,9G | 9G | 9G | 9G | 9G | 2C,5G | 9G | 0 |
| CRABGRASS | 3G | 0 | 2G | 0 | 2C,5G | 2G | 2C,5G | 0 | 4G | 0 |
| BARNYARDGRASS | 3H | 0 | 5C,9H | 3C,5H | 5C,9H | 6C,9H | 3C,8H | 0 | 9H | 2H |
| CHEATGRASS | 3C,7G | 0 | 3C,9G | 8G | 2C,8G | 7G | 9G | 0 | 3C,9G | 0 |
| WILD OATS | 0 | 0 | 2C,2G | 0 | 0 | 0 | 0 | 0 | 0 | 0 |
| SICKLEPOD | — | — | — | — | — | — | — | — | — | — |
| WHEAT | 0 | 0 | 0 | 0 | 2G | 0 | 3G | 0 | 0 | 0 |
| CORN | 0 | 0 | 9H | 2C,6G | 9H | 9H | 3C,7H | 3C,7H | 3C,9H | 2H |
| SOYBEAN | 3H | 0 | 3C,6H | 3H | 3C,5H | 5H | 3C,6H | 2H | 3C,6H | 3C,3H |
| RICE | 3G | 0 | 3G | 0 | 3G | 0 | 3G | 0 | 5C,9G | 0 |
| SORGHUM | 9G | 3C,9H | 4C,9G | 4C,9G | 9H | 5H | 2C,9H | 2C,8G | 4C,9G | 3C,7H |
| SUGAR BEET | 9C | 10C | 9C | 10C | 9C | 9C | 5C,9H | 4C,8H | 4C,9H | 4C,8G |

TABLE A-continued

| | | | | | | | | | | |
|---|---|---|---|---|---|---|---|---|---|---|
| COTTON | 10C | 3C,9H | 10C | 10C | 10C | 9C | 4C,9G | 8H | 10C | 5C,9G |

PREEMERGENCE

| | | | | | | | | | | |
|---|---|---|---|---|---|---|---|---|---|---|
| MORNINGGLORY | 8H | 0 | 3C,7H | 5G | 9G | 7G | 9G | 7H | 3C,8G | 2C,5H |
| COCKLEBUR | 7H | 2C,3H | 9H | 7H | 9H | — | 7H | — | 7H | 2C |
| VELVETLEAF | 7H | 0 | 5C,9G | 5H | 9G | 2H | 2C,5H | 2H | 0 | 0 |
| NUTSEDGE | 10E | 3C,8G | 10E | 10E | 10E | 10E | 8G | 5G | 9G | 9G |
| CRABGRASS | 0 | 0 | 3C | 0 | 3G | 0 | 2C,3G | 0 | 0 | 0 |
| BARNYARDGRASS | 2G | 0 | 3C,7G | 3G | 9H | 7H | 4G | 2H | 3H | 0 |
| CHEATGRASS | 7G | 0 | 9G | 8G | 9H | 7G | 7G | 0 | 5G | 0 |
| WILD OATS | 0 | 0 | 1C | 0 | 0 | 0 | 0 | 0 | 0 | 0 |
| SICKLEPOD | — | — | — | — | — | — | — | — | — | — |
| WHEAT | 0 | 2G | 0 | 0 | 0 | 0 | 0 | 0 | 0 | 0 |
| CORN | 3G | 0 | 2C,9G | 3C,7G | 9G | 5G | 9H | 3C,9H | 9H | 2C,8H |
| SOYBEAN | 1H | 0 | 3C,6H | 2C,3H | 2C,5H | 0 | 3C,6H | 3C,5H | 3C,6H | 3C,3H |
| RICE | 6G | 5G | 5G | 2G | 2G | 0 | 6G | 1C | 3C,9H | 5G |
| SORGHUM | 3C,9H | 3C,8G | 9G | 8H | 2C,9H | 2G | 9H | 3C,9H | 3C,9H | 2C,8G |
| SUGAR BEET | 3C,9G | 3C,7H | 4C,9G | 4C,9G | 9G | 7G | 5C,9G | 8H | 9G | 8H |
| COTTON | 8G | 0 | 9G | 7H | 9G | 7G | 2C,7H | 2C,2G | 3C,7H | 0 |

| | Compound 6 | | CMPD 7 | | CMPD 8 | | CMPD 9 | | CMPD 10 | |
|---|---|---|---|---|---|---|---|---|---|---|
| Rate kg/ha | 0.05 | 0.01 | 0.01 | 0.05 | 0.01 | 0.05 | 0.01 | 0.05 | 0.01 | 0.05 |

POSTEMERGENCE

| | | | | | | | | | | |
|---|---|---|---|---|---|---|---|---|---|---|
| MORNINGGLORY | 10C | 2C,4G | 5C,9G | 10C | 10C | 10C | 2C,6G | 10C | 3C,7H | 10C |
| COCKLEBUR | 9C | 2C,8H | 3C,6G | 10C | 10C | 10C | 10C | 10C | 10C | 10C |
| VELVETLEAF | 9C | 3C,7H | 4C,9H | 9C | 10C | 10C | 9C | 10C | 3C,7H | 6C,9H |
| NUTSEDGE | 9G | 9G | 3C,7G | 9C | 9C | 9C | 8G | 9C | 7G | 9C |
| CRABGRASS | 0 | 0 | 2G | 3C,7G | 7G | 4C,9G | 4G | 3C,9G | 3C,8G | 9C |
| BARNYARDGRASS | 2C,5H | 0 | 4C,9H | 9C | 4C,9H | 9C | 9H | 9C | 9C | 9C |
| CHEATGRASS | 2C,5G | 0 | 9C | 10C | 10C | 9C | 9C | 10C | 9C | 5C,9G |
| WILD OATS | 0 | 0 | 3C,5G | 3C,9G | 2C,3G | 4C,9G | 2C,5G | 2C,8G | 4C,8G | 4C,9G |
| SICKLEPOD | — | — | | | | | | | | |
| WHEAT | 0 | 0 | 7G | 9G | 5G | 9G | 2G | 6G | 2C,8G | 5C,9G |
| CORN | 2G | 0 | 3C,7H | 3C,9G | 4C,9H | 6C,9G | 9G | 5C,9G | 5C,9G | 9C |
| SOYBEAN | 2C | 0 | 4C,9G | 5C,9G | 4C,9G | 9C | 9C | 5C,9G | 4C,9G | 9C |
| RICE | 0 | 0 | 9C | 9C | 4C,8G | 9C | 4C,9G | 5C,9G | 9C | 9C |
| SORGHUM | 3C,8H | 2G | 3C,9G | 9C | 5C,9G | 9C | 9G | 5C,9G | 9C | 10C |
| SUGAR BEET | 5C,9G | 8G | 9C | 9C | 10C | 9C | 10C | 9C | 9C | 10C |
| COTTON | 9C | 7G | 4C,9G | 10C | 5C,9G | 10C | 4C,9G | 10C | 2C,9H | 10C |
| GIANT FOXTAIL | | | 3C,6G | 4C,9G | 4C,8G | 5C,9G | 3C,7G | 5C,9G | 6C,9G | 9C |
| BARLEY | | | 3C,6G | 2C,8G | 3C,7G | 6C,9G | 2C,4G | 3C,7G | 2C,6G | 4C,9G |

PREEMERGENCE

| | | | | | | | | | | |
|---|---|---|---|---|---|---|---|---|---|---|
| MORNINGGLORY | 2C,5H | 0 | 7H | 9H | 3C,8H | 8H | 7G | 8G | 2C,5H | 9G |
| COCKLEBUR | 2C,5H | 0 | | 9H | 3C,5G | 3C,7H | 1H | 8H | | |
| VELVETLEAF | 3C,7G | 0 | 3C,6H | 3C,5G | 3C,9G | 7H | 4C,9G | 7H | 3C,9G | |
| NUTSEDGE | 10E | 0 | 3C,8G | 10E | 10E | 10E | 9G | 10E | 4C,9G | 10E |
| CRABGRASS | 0 | 0 | 3G | 3G | 6G | 4C,9G | 3G | 6G | 4C,9G | 9H |
| BARNYARDGRASS | 5G | 0 | 3C,6G | 4C,9H | 3C,8G | 9H | 3C,7H | 9H | 4C,9H | 4C,9H |
| CHEATGRASS | 3G | 0 | 3C,7G | 9G | 9H | 10E | 8G | 9H | 9H | 10E |
| WILD OATS | 0 | 0 | 2C,4G | 4C,8G | 3C,3G | 3C,7G | 0 | 6G | 3C,7H | 4C,8H |
| SICKLEPOD | — | — | | | | | | | | |
| WHEAT | 0 | 0 | 3G | 3C,8H | 2G | 7G | 0 | 2G | 7G | 2C,9H |
| CORN | 2C,6G | 2G | 3C,4G | 4C,9H | 3C,7G | 3C,9H | 3C,7G | 8G | 2C,8G | 9G |
| SOYBEAN | 0 | 0 | 3C,5G | 3C,7H | 4C,8H | 9H | 2C,4G | 9H | 3C,7H | 9H |
| RICE | 2G | 0 | 9H | 10E | 9H | 10H | 9H | 9H | 5C,9H | 10E |
| SORGHUM | 2C,7H | 0 | 3C,8H | 10E | 3C,9H | 10H | 3C,8G | 9H | 9H | 10H |
| SUGAR BEET | 9G | 5G | 7G | 9G | 4C,9G | 4C,9G | 9G | 9C | 9G | 5C,9G |
| COTTON | 3G | 0 | 3C,6G | 9G | 3C,7H | 9G | 2G | 6G | 5G | 9G |
| GIANT FOXTAIL | | | 3C,5G | 4C,8H | 3C,8G | 9H | 3C,5G | 9H | 4C,9G | 4C,9H |
| BARLEY | | | 3C,7G | 9G | 3C,8G | 9G | 2C,4G | 7G | 9G | 4C,9H |

| | CMPD 11 | | CMPD 12 | | COMPD 13 | | COMPD 14 | | COMPD 15 | |
|---|---|---|---|---|---|---|---|---|---|---|
| Rate kg/ha | 0.01 | 0.05 | 0.01 | 0.05 | 0.01 | 0.05 | 0.01 | 0.05 | 0.01 | 0.05 |

POSTEMERGENCE

| | | | | | | | | | | |
|---|---|---|---|---|---|---|---|---|---|---|
| BARLEY | 7G | 9C | 0 | 2C,3G | 0 | 2G | 0 | 3G | 0 | 0 |
| BARNYARDGRASS | 5C,9H | 10C | 3C,7G | 4C,9H | 0 | 0 | 2H | 2C,5G | 3G | 2C,7G |
| CHEATGRASS | 6C,9G | 9C | 7G | 9C | 3G | 8G | 8G | 8G | 6G | 4C,9G |
| COCKLEBUR | 3C,8H | 10C | 10C | 10C | 5C,9G | 10C | 10C | 10C | 10C | 10C |
| CORN | 9C | 9C | 2G | 3C,7H | 0 | 0 | 0 | 0 | 0 | 2C,2H |
| COTTON | 5C,9H | 5C,9G | 4C,9G | 10C | 7G | 4C,9G | 9C | 5C,9G | 5C,9G | 5C,9G |
| CRABGRASS | 5C,8G | 9C | 2G | 2C,5G | 0 | 0 | 0 | 0 | 2G | 3C,7G |
| GIANT FOXTAIL | 5C,9G | 9C | 3C,3G | 4C,8H | 0 | 3G | 0 | 3G | 3G | 4C,7G |
| MORNINGGLORY | 3C,7H | 10C | 4C,8G | 9C | 2C,5G | 3C,8G | 3C,8G | 9C | 6G | 10C |
| NUTSEDGE | 4G | 5G | 4C,9G | 5C,9G | 3C,7G | 4C,9G | 9G | 10C | 4C,9G | 10C |
| RICE | 9C | 9C | 6G | 9C | 0 | 5G | 0 | 2G | 0 | 2G |
| SORGHUM | 9C | 9C | 3C,9H | 9G | 0 | 0 | 0 | 2G | 0 | 0 |
| SOYBEAN | 5C,9G | 6C,9G | 3C,5H | 4C,9G | 1H | 5H | 2C,5H | 3C,7H | 3C,8H | 5C,9G |
| SUGAR BEETS | 9CF | 10C | 9C | 9C | 9C | 10C | 4C,9G | 9C | 10C | 10C |
| VELVETLEAF | 6G | 7G | 9C | 10C | 4C,8H | 10C | 9C | 10C | 10C | 10C |
| WHEAT | 3C,9G | 6C,9G | 0 | 2C,4G | 0 | 2G | 0 | 5G | 0 | 0 |
| WILD OATS | 6C,9G | 5C,9G | 0 | 2C,2G | 0 | 2G | 0 | 3C,7G | 0 | 0 |

PREEMERGENCE

TABLE A-continued

| | | | | | | | | | | |
|---|---|---|---|---|---|---|---|---|---|---|
| BARLEY | 9G | 9G | 4G | 3C,5G | 0 | 2G | 0 | 0 | 0 | 2G |
| BARNYARDGRASS | 3C,7H | 9H | 4H | 9H | 0 | 2C,2H | 0 | 5G | 0 | 5G |
| CHEATGRASS | 8H | 10E | 8G | 9H | 0 | 7G | 0 | 8G | 4G | 9G |
| COCKLEBUR | 2C | 3C,7H | 0 | | 3C,3H | — | 2C,3H | 9H | 2C,4H | 7H |
| CORN | 3C,9G | 3C,9G | 2C | 3C,9G | 0 | 2G | 0 | 3G | 0 | 2G |
| COTTON | 4H | 7H | 4G | 8G | 0 | 7H | 0 | 8G | — | 4H |
| CRABGRASS | 3C,8G | 4C,8G | 0 | 7G | 0 | 0 | 0 | 2G | 2C,3G | 2C,5G |
| GIANT FOXTAIL | 3C,8H | 4C,9H | 3G | 9H | 0 | 2G | 0 | 3G | 0 | 3G |
| MORNINGGLORY | 3C,3H | 8G | 3C,5G | 5H | 2G | 8G | 5G | 9G | 7G | 8G |
| NUTSEDGE | 2C | 10E | 9G | 10E | 0 | 9G | 10E | 10E | 5G | 10E |
| RICE | 9H | 10E | 8H | 9H | 0 | 0 | 0 | 0 | 0 | 0 |
| SORGHUM | 5C,9H | 10H | 3C,8H | 5C,9H | 0 | 0 | 0 | 0 | 0 | 0 |
| SOYBEAN | 3C,7H | 9H | 3C,4H | 3C,7H | 0 | 0 | 0 | 6H | 0 | 6H |
| SUGAR BEETS | 3G | 3C,8G | 8G | 8G | 7G | 9G | 7G | 9G | 9C | 9G |
| VELVETLEAF | 0 | 5H | 2H | 5H | 0 | 3C,8H | 5H | 4C,9G | 3H | 8G |
| WHEAT | 7G | 9H | 0 | 3G | 0 | 3G | 0 | 4G | 0 | 0 |
| WILD OATS | 3C,6G | 3C,7G | 0 | 3G | 0 | 3G | 0 | 3G | 0 | 0 |

Test B

Postemergence

Three round pans (25 cm diameter by 12.5 cm deep) were filled with Sassafras sandy loam soil. One pan was planted with nutsedge (Cyperus rotundus) tubers, crabgrass (Digitaria sanguinalis), sicklepod (Cassia obtusifolia), jimsonweed (Datura stramonium), velvetleaf (Abutilon theophrasti), lambsquarters (Chenopodium album), rice (Oryza sativa), and teaweed (Sida spinosa). The second pot was planted with green foxtail (Setaria viridis), cocklebur (Xanthium pensylvanicum), morningglory (Ipomoea hederacea), cotton (Gossypium hirsutum), johnsongrass (Sorghum halepense), barnyardgrass (Echinochloa crusgalli), corn (Zea mays), soybean (Glycine max), and giant foxtail (Setaria faberi). The third pot was planted with wheat (Triticum aestivum), barley (Hordeum vulgare), wild buckwheat (Polygonum convolvulus L.), cheatgrass (Bromus secalinus L.), sugarbeet (Beta vulgaris), wild oat (Avena fatua L.), viola (Viola arvensis), blackgrass (Alopecurus myosuroides), and rape (Brassica napus). The plants were grown for approximately fourteen days, then sprayed post-emergence with the chemicals dissolved in a non-phytotoxic solvent.

Premergence

Three round pans (25 cm diameter by 12.5 cm deep) were filled with Sassafras sandy loam soil. One pan was planted with nutsedge tubers, crabgrass, sicklepod, jimsonweed, velvetleaf, lambsquarters, rice and teaweed. The second pot was planted with green foxtail, cocklebur, morningglory, cotton, johnsongrass, barnyardgrass, corn soybean, and giant foxtail. The third pot was planted with wheat, barley, wild buckwheat, cheatgrass, sugarbeet, wild oat, viola, blackgrass, and rape. The three pans were sprayed preemergence with the chemicals dissolved in a non-phytotoxic solvent.

Treated plants and controls were maintained in the greenhouse for approximatly 24 days, then all rated plants were compared to controls and visually rated for plant response.

Response ratings are based on a scale of 0 to 100 where 0=no effect, and 100=complete control. A dash (-) response means no test.

Response ratings are contained in Table B.

TABLE B

| | CMPD 3 | | | | CMPD 10 | | | |
|---|---|---|---|---|---|---|---|---|
| RATE RATE = G/HA | 0001. | 0004. | 0016. | 0062. | 0.25 | 0001. | 0004. | 0016. |
| POSTEMERGENCE | | | | | | | | |
| GIANT FOXTAIL | 0 | 30 | 60 | 80 | 0 | 20 | 50 | 80 |
| VELVETLEAF | 60 | 100 | 100 | 100 | 30 | 40 | 60 | 80 |
| SUGAR BEETS | 100 | 100 | 100 | | 70 | 80 | 90 | 100 |
| CRABGRASS | 0 | 30 | 50 | 70 | 0 | 0 | 60 | 60 |
| TEAWEED | 30 | 50 | 70 | 90 | 60 | 60 | 70 | 80 |
| JIMSONWEED | 30 | 50 | 70 | 100 | 0 | 40 | 70 | 80 |
| RICE | 0 | 0 | 0 | 100 | 30 | 50 | 80 | 100 |
| COCKLEBUR | 100 | 100 | 100 | 100 | 40 | 50 | 80 | 100 |
| COTTON | 30 | 60 | 100 | 100 | 0 | 20 | 80 | 80 |
| SOYBEAN | 0 | 0 | 20 | | | 60 | 70 | 100 |
| BARNYARDGRASS | 0 | 0 | 60 | 100 | 20 | 60 | 70 | 100 |
| WILD OATS | 0 | 0 | 0 | | 0 | 50 | 80 | 90 |
| MORNINGGLORY | 30 | 50 | 70 | 90 | 0 | 30 | 70 | 80 |
| WHEAT | 0 | 0 | 0 | | 0 | 20 | 50 | 90 |
| CASSIA | 0 | 30 | 50 | 70 | 60 | | 80 | 90 |
| JOHNSONGRASS | 0 | 0 | 0 | 50 | 30 | 70 | 90 | 100 |
| NUTSEDGE | 100 | 100 | 100 | 100 | 20 | 40 | 60 | 60 |
| CORN | 0 | 30 | 50 | | 0 | 40 | 90 | 90 |
| WILD BUCKWHEAT | 30 | 50 | 70 | | 0 | 50 | 90 | 90 |
| BLACK GRASS | 0 | 30 | 50 | | 20 | 70 | 80 | 100 |
| RAPESEED | 100 | 100 | 100 | | 40 | 80 | 90 | 100 |
| BARLEY | 0 | 0 | 0 | | 20 | 60 | 90 | 100 |
| GREEN FOXTAIL | 0 | 0 | 30 | 60 | 30 | 60 | 70 | 90 |
| CHEAT GRASS BUCKWHEAT | 0 | 0 | 30 | | 0 | 30 | 60 | 70 |
| VIOLA | 70 | 90 | 100 | | 0 | 40 | 90 | 100 |
| LAMBSQUARTER | 50 | 70 | 90 | 100 | 40 | 70 | 90 | 100 |
| | CMPD 3 | | | | CMPD 4 | | | |

TABLE B-continued

| RATE = G/HA | 0004. | 0016. | 0062. | 0.250 | 0001. | 0004. | 0016. | 0062. |
|---|---|---|---|---|---|---|---|---|
| | | PREEMERGENCE | | | | | | |
| GIANT FOXTAIL | 30 | 60 | 100 | 100 | 50 | 70 | 80 | 90 |
| VELVETLEAF | 50 | 70 | 80 | 100 | 30 | 50 | 70 | 90 |
| SUGAR BEETS | 60 | 70 | 80 | 90 | 70 | 90 | 100 | 100 |
| CRABGRASS | 30 | 50 | 80 | 100 | 50 | 70 | 80 | 100 |
| TEAWEED | 30 | 50 | 70 | 90 | 40 | 50 | 70 | 80 |
| JIMSONWEED | 40 | 70 | 80 | 90 | 50 | 70 | 80 | 90 |
| RICE | 0 | 0 | 30 | 80 | 90 | 100 | 100 | 100 |
| COCKLEBUR | 50 | 70 | 60 | 90 | 60 | 70 | 80 | 90 |
| COTTON | 0 | 30 | 60 | 80 | 20 | 40 | 60 | 80 |
| SOYBEAN | 0 | 20 | 50 | 70 | 20 | 40 | 70 | 90 |
| BARNYARDGRASS | 0 | 40 | 70 | 90 | 30 | 60 | 90 | 100 |
| WILD OATS | 0 | 0 | 0 | 0 | 40 | 50 | 70 | 90 |
| MORNINGGLORY | 30 | 70 | 80 | 90 | 30 | 50 | 60 | 70 |
| WHEAT | 0 | 0 | 0 | 0 | 20 | 30 | 60 | 100 |
| CASSIA | 30 | 50 | 60 | 80 | 80 | 90 | 100 | 100 |
| JOHNSONGRASS | 30 | 50 | 70 | 90 | 70 | 80 | 90 | 100 |
| NUTSEDGE | 100 | 100 | 100 | 100 | 0 | 30 | 60 | 90 |
| CORN | 0 | 20 | 60 | 80 | 0 | 60 | 80 | 100 |
| WILD BUCKWHEAT | 50 | 70 | 80 | 90 | 30 | 60 | 80 | 90 |
| BLACK GRASS | 0 | 30 | 60 | 90 | 50 | 70 | 80 | 100 |
| RAPESEED | 80 | 90 | 100 | 100 | 60 | 70 | 80 | 90 |
| BARLEY | 0 | 0 | 0 | 0 | 20 | 40 | 90 | 100 |
| GREEN FOXTAIL | 30 | 50 | 100 | 100 | 60 | 80 | 100 | 100 |
| CHEAT GRASS BUCKWHEAT | 0 | 30 | 60 | 90 | 50 | 80 | 100 | 100 |
| VIOLA | 70 | 90 | 100 | 100 | 60 | 70 | 80 | 100 |
| LAMBSQUARTER | 80 | 100 | 100 | 100 | 70 | 80 | 90 | 100 |

Test C

Sixteen cm diameter Wagner pots, equipped with a stoppered drain opening near the bottom of the side wall, were partially filled with Woodstown sandy loam. About 1500 mls of water were added to each pot to bring the water level to a point 3 cm above the soil surface. Japonica and Indica rice seedlings were transplanted as described in Test E. Also, a number of barnyardgrass (Echinochloa crusgalli) seeds were added to each pot. At the same time, seedlings or tubers of the following species were transplanted into the muddy soil: water plantain (Alisma trivale). Scirpus (Scirpus mucranatus), and Cyperus (Cyperus difformis). The weed species selected for this test are of economic importance in major rice-growning areas. The chemical treatments were applied directly to the paddy water after being formulated in a non-phytotoxic solvent within hours after transplanting of two additional species: water chestnut (Eleocharis spp.) and arrowhead (Saqittaria latifolia). Shortly after treatment, the drain hole was opened to drop the water level by two cm. Water was then added to restore the water level to its original height. The following day the draining and refilling process was repeated. The pots were then maintained in the greenhouse. Rates of application and plant response ratings made 21 days after treatment are summarized in Table C.

In the subsequent tables, LS is used as an abbreciation for leaf stage.

TABLE C

| | CMPD 3 | | |
|---|---|---|---|
| RATE RATE = G/HA | 0004. | 0008. | 0016. |
| SOIL | | | |
| BARNYARD GRASS | 45 | 60 | 65 |
| WATER CHESTNUT | 75 | 95 | 92 |
| ARROWHEAD | 85 | 90 | 95 |
| SCIRPUS (SEDGE) | 82 | 85 | 92 |
| CYPRESS (SEDGE) | 92 | 95 | 100 |
| WATER PLANTAIN | 87 | 100 | 100 |
| RICE JAP EFF | | 0 | 5 | 10 |

TABLE C-continued

| | CMPD 3 | | |
|---|---|---|---|
| RATE RATE = G/HA | 0004. | 0008. | 0016. |
| RICE INDICA EFF | 0 | 0 | 5 |

What is claimed is:

1. A compound of the formula

wherein
J is

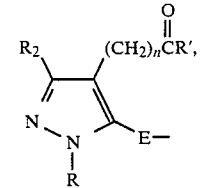

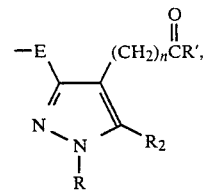

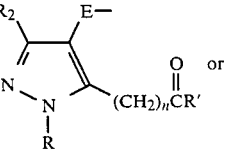

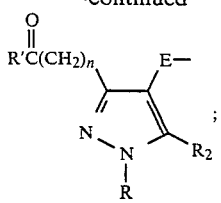

R is H, $C_1$–$C_3$ alkyl, phenyl, $SO_2NR_aR_b$, $C_1$–$C_2$ haloalkyl, $C_2$–$C_4$ alkoxyalkyl, $C_2$–$C_3$ cyanoalkyl, $C_2$–$C_4$ alkylthioalkyl, $C_2$–$C_4$ alkylsulfinylalkyl, $C_2$–$C_4$ alkylsulfonylalkyl, $CO_2C_1$–$C_2$ alkyl, $C_1$–$C_4$ alkylcarbonyl, $C_1$–$C_2$ alkylsulfonyl, $C_3$–$C_4$ alkenyl, $C_3$–$C_4$ alkynyl or $C_1$–$C_2$ alkyl substituted with $CO_2C_1$–$C_2$ alkyl;

$R_1$ is H or $CH_3$;

$R_2$ is H, $C_1$–$C_3$ alkyl, $C_1$–$C_3$ haloalkyl, halogen, nitro, $C_1$–$C_3$ alkoxy, $SO_2NR_cR_d$, $C_1$–$C_3$ alkylthio, $C_1$–$C_3$ alkylsulfinyl, $C_1$–$C_3$ alkylsulfonyl, CN, $CO_2R_e$, $C_1$–$C_3$ haloalkoxy, $C_1$–$C_3$ haloalkylthio, amino, $C_1$–$C_2$ alkylamino, di($C_1$–$C_3$ alkyl)amino or $C_1$–$C_2$ alkyl substituted with $C_1$–$C_2$ alkoxy, $C_1$–$C_2$ haloalkoxy, $C_1$–$C_2$ alkylthio, $C_1$–$C_2$ haloalkylthio, CN, OH or SH;

$R_a$ and $R_b$ are independently $C_1$–$C_2$ alkyl;

$R_c$ is H, $C_1$–$C_4$ alkyl, $C_2$–$C_3$ cyanoalkyl, methoxy or ethoxy;

$R_d$ is H, $C_1$–$C_4$ alkyl or $C_3$–$C_4$ alkenyl; or $R_c$ and $R_d$ may be taken together as —$(CH_2)_3$—, —$(CH_2)_4$—, —$(CH_2)_5$— or —$CH_2CH_2OCH_2CH_2$—;

$R_e$ is $C_1$–$C_4$ alkyl, $C_3$–$C_4$ alkenyl, $C_3$–$C_4$ alkynyl, $C_2$–$C_4$ haloalkyl, $C_2$–$C_3$ cyanoalkyl, $C_5$–$C_6$ cycloalkyl, $C_4$–$C_7$ cycloalkylalkyl or $C_2$–$C_4$ alkoxyalkyl;

R' is $C_3$–$C_5$ cycloalkyl;

E is a single bond or $CH_2$;

W is O or S;

n is 0 or 1;

A is

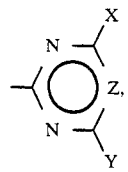

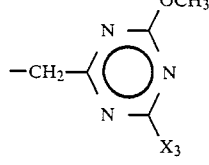

X is H, $C_1$–$C_4$ alkyl, $C_1$–$C_4$ alkoxy, $C_1$–$C_4$ haloalkoxy, $C_1$–$C_4$ haloalkyl, $C_1$–$C_4$ haloalkylthio, $C_1$–$C_4$ alkylthio, $C_2$–$C_5$ alkoxyalkyl, $C_2$–$C_5$ alkoxyalkoxy, amino, $C_1$–$C_3$ alkylamino, di($C_1$–$C_3$ alkyl)amino or $C_3$–$C_5$ cycloalkyl;

Y is H, $C_1$–$C_4$ alkyl, $C_1$–$C_4$ alkoxy, $C_1$–$C_4$ haloalkoxy, $C_1$–$C_4$ haloalkylthio, $C_1$–$C_4$ alkylthio, $C_2$–$C_5$ alkoxyalkyl, $C_2$–$C_5$ alkoxyalkoxy, amino, $C_1$–$C_3$ alkylamino, di($C_1$–$C_3$ alkyl)amino, $C_3$–$C_4$ alkenyloxy, $C_3$–$C_4$ alkynyloxy, $C_2$–$C_5$ alkylthioalkyl, $C_1$–$C_4$ haloalkyl, $C_2$–$C_4$ alkynyl, azido, cyano, $C_2$–$C_5$ alkylsulfinylalkyl, $C_2$–$C_5$ alkylsulfonylalkyl,

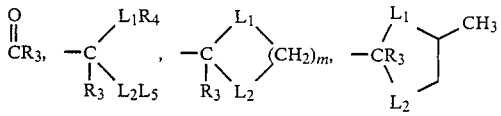

or $N(OCH_3)CH_3$;

m is 2 or 3;

$L_1$ and $L_2$ are independently O or S;

$R_3$ is H or $C_1$–$C_3$ alkyl;

$R_4$ and $R_5$ are independently $C_1$–$C_3$ alkyl;

Z is N;

$X_3$ is $CH_3$ or $OCH_3$;

and their agriculturally suitable salts; provided that (a) when W is S, then $R_1$ is H, A is A-1 and Y is $CH_3$, $OCH_3$, $OC_2H_5$, $CH_2OCH_3$, $C_2H_5$, $CF_3$, $SCH_3$, $OCH_2CH=CH_2$, $OCH_2C\equiv CH$, $OCH_2CH_2OCH_3$, $CH(OCH_3)_2$ or 1,3-dioxolan-2-yl;

(b) when the total number of carbons of X and Y is greater than four, then the number of carbons of R must be less than or equal to two;

(c) X or Y are not $C_1$ haloalkoxy.

2. Compounds of claim 1 where
E is a single bond; and
W is O.

3. Compounds of claim 1 where
E is $CH_2$; and
W is O.

4. Compounds of claim 2 where
$R_2$ is H, $C_1$–$C_3$ alkyl, halogen, $C_1$–$C_3$ alkyl substituted with 1 to 3 halogen atoms selected from 1 to 3 Cl, 1 to 3 F or 1 Br, $OCH_3$, $SO_2NHCH_3$, $SO_2N(CH_3)_2$, $S(O)_nCH_3$, $CO_2CH_3$, $CO_2CH_2CH_3$, $OCF_2H$, $CH_2OCH_3$ or $CH_2CN$;

X is $C_1$–$C_2$ alkyl, $C_1$–$C_2$ alkoxy, $CH_2F$, $CF_3$, $OCH_2CH_2F$, $OCH_2CHF_2$, $OCH_2CF_3$, $CH_2Cl$ or $CH_2Br$; and Y is H, $C_1$–$C_2$ alkyl, $C_1$–$C_2$ alkoxy, $CH_2OCH_3$, $CH_2OCH_2CH_3$, $NHCH_3$, $N(OCH_3)CH_3$, $N(CH_3)_2$, $CF_3$, $SCH_3$, $OCH_2CH=CH_2$, $OCH_2C\equiv CH$, $OCH_2CH_2OCH_3$,

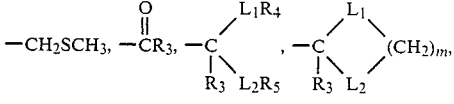

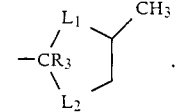

$SCF_2H$, $C\equiv CH$ or $C\equiv CCH_3$.

5. Compounds of claim 4 where
R is H, $C_1$–$C_3$ alkyl, phenyl, $CH_2CF_3$ or $CH_2CH_2CH=CH_2$;
X is $CH_3$; $OCH_3$, or $OCH_2CH_3$ and
Y is $CH_3$, $OCH_3$, $C_2H_5$, $CH_2OCH_3$, $NHCH_3$, or $CH(OCH_3)_2$.

6. Compounds of claim 5 where
A is A-1;
$R_2$ is H, Cl, Br, $OCH_3$ or $CH_3$; and
n is 0.

7. Compounds of claim 6 where J is J-1.

8. Compounds of claim 6 where J is J-2.

9. Compounds of claim 6 where J is J-3.

10. Compounds of claim 6 where J is J-4.

11. Compounds of claim 3 where
R is H, $C_1$-$C_3$ alkyl, phenyl, $CH_2CF_3$ or $CH_2CH=CH_2$;
$R_2$ is H, Cl, Br, $OCH_3$ or $CH_3$;
n is 0;
A is A-1;
X is $CH_3$, $OCH_3$, or $OCH_2CH_3$ and
Y is $CH_3$, $OCH_3$, $C_2H_5$, $CH_2OCH_3$, $NHCH_3$, or $CH(OCH_3)_2$.

12. An agriculturally suitable composition for controlling the growth of undesired vegetation comprises an effective amount of a compound of claim 1 and at least one of the following; surfactant, solid or liquid diluent.

13. An agriculturally suitable composition for controlling the growth of undesired vegetation comprises an effective amount of a compound of claim 2 and at least one of the following; surfactant, solid or liquid diluent.

14. An agriculturally suitable composition for controlling the growth of undesired vegetation comprises an effective amount of a compound of claim 3 and at least one of the following; surfactant, solid or liquid diluent.

15. An agriculturally suitable composition for controlling the growth of undesired vegetation comprises an effective amount of a compound of claim 4 and at least one of the following; surfactant, solid or liquid diluent.

16. An agriculturally suitable composition for controlling the growth of undesired vegetation comprises an effective amount of a compound of claim 5 and at least one of the following; surfactant, solid or liquid diluent.

17. An agriculturally suitable composition for controlling the growth of undesired vegetation comprises an effective amount of a compound of claim 6 and at least one of the following; surfactant, solid or liquid diluent.

18. An agriculturally suitable composition for controlling the growth of undesired vegetation comprises an effective amount of a compound of claim 7 and at least one of the following; surfactant, solid or liquid diluent.

19. An agriculturally suitable composition for controlling the growth of undesired vegetation comprises an effective amount of a compound of claim 8 and at least one of the following; surfactant, solid or liquid diluent.

20. An agriculturally suitable composition for controlling the growth of undesired vegetation comprises an effective amount of a compound of claim 9 and at least one of the following; surfactant, solid or liquid diluent.

21. An agriculturally suitable composition for controlling the growth of undesired vegetation comprises an effective amount of a compound of claim 10 and at least one of the following; surfactant, solid or liquid diluent.

22. An agriculturally suitable composition for controlling the growth of undesired vegetation comprises an effective amount of a compound of claim 11 and at least one of the following; surfactant, solid or liquid diluent.

23. A method for controlling the growth of desired vegetation which comprises applying to the locus to be protected an effective amount of a compound of claim 1.

24. A method for controlling the growth of desired vegetation which comprises applying to the locus to be protected an effective amount of a compound of claim 2.

25. A method for controlling the growth of desired vegetation which comprises applying to the locus to be protected an effective amount of a compound of claim 3.

26. A method for controlling the growth of desired vegetation which comprises applying to the locus to be protected an effective amount of a compound of claim 4.

27. A method for controlling the growth of desired vegetation which comprises applying to the locus to be protected an effective amount of a compound of claim 5.

28. A method for controlling the growth of desired vegetation which comprises applying to the locus to be protected an effective amount of a compound of claim 6.

29. A method for controlling the growth of desired vegetation which comprises applying to the locus to be protected an effective amount of a compound of claim 7.

30. A method for controlling the growth of desired vegetation which comprises applying to the locus to be protected an effective amount of a compound of claim 8.

31. A method for controlling the growth of desired vegetation which comprises applying to the locus to be protected an effective amount of a compound of claim 9.

32. A method for controlling the growth of desired vegetation which comprises applying to the locus to be protected an effective amount of a compound of claim 10.

33. A method for controlling the growth of desired vegetation which comprises applying to the locus to be protected an effective amount of a compound of claim 11.

* * * * *